US008916548B2

(12) United States Patent
Wunberg et al.

(10) Patent No.: US 8,916,548 B2
(45) Date of Patent: Dec. 23, 2014

(54) 5-ALKYNYL-PYRIMIDINES

(75) Inventors: Tobias Wunberg, Hinterbruehl (AT); Ralph Brueckner, Hallstadt (AT); Dirk Kessler, Vienna (AT); Oliver Kraemer, Vienna (AT); Darryl McConnell, Vienna (AT); Siegfried Schneider, Vienna (AT); Lars van der Veen, Alsbach-Haehnlein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 475 days.

(21) Appl. No.: 13/055,949

(22) PCT Filed: Jul. 28, 2009

(86) PCT No.: PCT/EP2009/059763
§ 371 (c)(1),
(2), (4) Date: Apr. 8, 2011

(87) PCT Pub. No.: WO2010/012740
PCT Pub. Date: Feb. 4, 2010

(65) Prior Publication Data
US 2011/0281838 A1    Nov. 17, 2011

(30) Foreign Application Priority Data
Jul. 29, 2008    (EP) ..................... 08161369

(51) Int. Cl.
C07D 239/48    (2006.01)
C07D 401/04    (2006.01)
C07D 403/06    (2006.01)

(52) U.S. Cl.
USPC .................................... 514/210.2

(58) Field of Classification Search
USPC .................................... 514/210.2
See application file for complete search history.

(56) References Cited

U.S. PATENT DOCUMENTS

| 5,091,386 | A * | 2/1992 | Kesseler et al. ............ 514/277 |
| 5,622,954 | A | 4/1997 | Henrie, II et al. |
| 2011/0281838 | A1 | 11/2011 | Wunberg et al. |
| 2012/0028952 | A1 | 2/2012 | Schneider et al. |

FOREIGN PATENT DOCUMENTS

| EP | 0361273 A2 | 4/1990 |
| WO | 9414780 A1 | 7/1994 |
| WO | 9820878 A1 | 5/1998 |
| WO | 0162233 A2 | 8/2001 |
| WO | 0208205 A1 | 1/2002 |
| WO | 2005060969 A1 | 7/2005 |
| WO | 2006044823 A2 | 4/2006 |
| WO | 2006082371 A1 | 8/2006 |
| WO | 2006082373 A1 | 8/2006 |
| WO | 2006103449 A2 | 10/2006 |
| WO | 2006106721 A1 | 10/2006 |
| WO | 2008023180 A1 | 2/2008 |
| WO | 2008067389 A2 | 6/2008 |
| WO | 2008080965 A2 | 7/2008 |
| WO | 2008155140 A1 | 12/2008 |
| WO | 2010012740 A1 | 2/2010 |

OTHER PUBLICATIONS

Wilberg, Substituent effects. 3. A comparison of ethyl, vinyl, isopropyl, and cyclopropyl derivatives, J. Org. Chem., 57:5092-5101, 1992.*
International Search Report, Form PCT/ISA/210, for corresponding PCT/EP2009/059114; date of mailing: Oct. 2, 2009.
Banker et al "Prodrugs" Modern Pharmaceutics, (1996) 3rd Edition, pp. 451 and 596.
Bundgaard, Hans "Design of Prodrugs" 1985, p. 1.
Douglas, Jr., R. Gordon. "Introduction to Viral Diseases" Cecil Textbook of Medicine, (1996) 20th Edition, vol. 2, pp. 1739-1742.
Fry, Michael John "Phosphoinositide 3-kinase signalling in breast cancer: how big a role might it play?" Breast Cancer Research (2001) vol. 3, No. 5, pp. 304-312.
Gura, Trisha "Cancer Models: Systems for Identifying New Drugs are Often Faulty" Science (1997) vol. 278, No. 5340 pp. 1041-1042.
Hannah, Duncan R. et al. "Structural Studies on Bioactive Compounds. Part 29: Palladium Catalysed Arylations and Alkynylations of Sterically Hindered Immunomodulatory 2-Amino-5-halo-4,6-(disubstituted) pyrimidines" Bioorganic & Medicinal Chemistry (2000) vol. 8, pp. 739-750.
International Search Report for PCT/EP2011/051061 mailed on Mar. 22, 2011.
International Search Report PCT/EP2011/051060 mailed Apr. 26, 2011.
Johnson, Ji et al. "Relationships between drug activity in NCI preclinical in vitro and in vivo models and early clinical trials" British Journal of Cancer (2001) 84(10, pp. 1424-1431.

(Continued)

Primary Examiner — Jeffery S. Lundgren
Assistant Examiner — Zenab Olabowale
(74) Attorney, Agent, or Firm — Michael P. Morris; Mary-Ellen Devlin; Usha R. Patel

(57) ABSTRACT

The present invention encompasses compounds of general Formula (1) wherein $R^1$ to $R^4$ are defined as in claim 1, which are suitable for the treatment of diseases characterized by excessive or abnormal cell proliferation, and the use thereof for preparing a medicament having the above-mentioned properties.

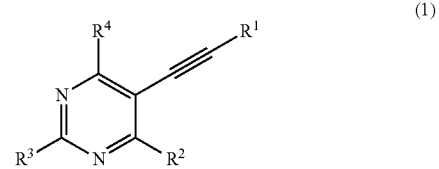

(1)

7 Claims, No Drawings

(56) References Cited

OTHER PUBLICATIONS

Jones, Michael L. et al. "Inhibitors of Dihydrofolate Reductase: Design, Synthesis and Antimicrobial Activities of 2,4- Diamino-6-methyl-5-ethynylpyrimidines" Journal of Heterocylic Chemistry (1999) vol. 36, pp. 145-148.

Liu, Pixu et al. "Targeting the phosphoinositide 3-kinase pathway in cancer" (2009) Nature Reviews vol. 8, pp. 627-644.

Matulenko, Mark et al. "4-Amino-5-aryl-6-arylethynylpyrimidines: Structure-activity relationships of non-nucleoside adenosine kinase inhibitors" Bioorganic & Medicinal Chemistry (2007) vol. 15, pp. 1586-1605.

Pal, Manojit et al. "Alkynylation of halo pyrimidines under Pd/C-copper catalysis: regioselective synthesis of 4- and 5-alkynylpyrimidinee" Tetrahedron Letters (2006) vol. 47, pp. 3923-3928.

Pearce, Homer L. et al. "Failure modes in anticancer drug discovery and development" Cancer Drug Design and Discovery (2008) Chapter 18, pp. 424-435.

Pelphrey, Phillip M. et al. "Highly Efficient Ligands for Dihydrofolate Reductase from Cryptosporidium hominis and Toxoplasma gondii Inspired by Structural Analysis" Journal of Medicinal Chemistry (2007) vol. 50 pp. 940-950.

Petricci, Elena et al. "Microwave-enhanced Sonogashira coupling reaction of substituted pyrimidinones and pyrimidine nucleosides" Tetrahedron Letters, (2003) vol. 44, pp. 9181-9184.

Rodriguez, Alain Louis et al. "Verstile Indole Synthesis by a 5-endo-dig Cyclization Mediated by Potassium or Cesium Bases**" Angew Chem. Int. Ed. (2000) vol. 39, No. 14 pp. 2488-2490.

Silverman, Richard B. "The Organic Chemistry of Drug Design and Drug Action" Prodrugs and Drug Delivery Systems (1992) pp. 352-399.

Simone, Joseph V. "Oncology: Introduction" Cecil Textbook of Medicine, (1996) 20th Edition, vol. 1, pp. 1004-1010.

Testa, Bernard et al. "Prodrug Design" Encyclopedia of Pharmaceutical Technology, (J Swarbrick ed., 3rd ed, 2007) pp. 3008-3014.

Wolff, Manfred E. "Some Considerations for Prodrug Design" Burger's Medicinal Chemistry and Drug Discovery, 5th Edition vol. 1: Principles and Practice (1995) pp. 975-977.

* cited by examiner

5-ALKYNYL-PYRIMIDINES

The present invention relates to new 5-alkynyl-pyrimidines of general formula (1)

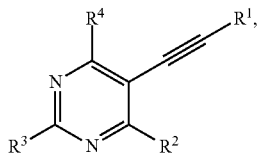

wherein the groups $R^1$ to $R^4$ have the meanings given in the claims and specification, the isomers thereof, processes for preparing these alkynyl-pyrimidines and their use as medicaments.

BACKGROUND TO THE INVENTION

A number of protein kinases have already proved to be suitable target molecules for therapeutic intervention in a variety of indications, e.g. cancer and inflammatory and autoimmune diseases. Since a high percentage of the genes involved in the development of cancer which have been identified thus far encode kinases, these enzymes are attractive target molecules for the therapy of cancer in particular.

Phosphatidylinositol-3-kinases (PI3-kinases) are a subfamily of the lipid kinases which catalyse the transfer of a phosphate group to the 3'-position of the inositol ring of phosphoinositides.

They play an important role in numerous cell processes such as e.g. cell growth and differentiation processes, the control of cytoskeletal changes and the regulation of intracellular transport processes. On the basis of their in vitro specificity for certain phosphoinositide substrates the PI3-kinases can be divided into different categories.

5-Alkynyl-pyrimidines are described for example as protein kinases inhibiting compounds in WO2006044823.

DETAILED DESCRIPTION OF THE INVENTION

It has now surprisingly been found that compounds of general formula (1), wherein the groups $R^1$ to $R^4$ have the meanings given below, act as inhibitors of kinases. Thus, the compounds according to the invention may be used for example for the treatment of diseases connected with the activity of kinases and characterised by excessive or abnormal cell proliferation.

The present invention relates to compounds of general formula (1)

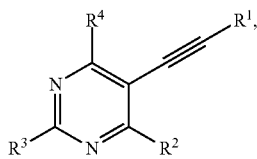

wherein
$R^1$ denotes a group selected from among $C_{3-8}$cycloalkyl, 3-8 membered heterocycloalkyl, $C_{6-10}$aryl and 5-12 membered heteroaryl, optionally substituted by one or more identical or different $R^5$; and $R^2$ denotes a group selected from among $C_{3-8}$cycloalkyl, 3-8 membered heterocycloalkyl, $C_{6-10}$aryl and 5-12 membered heteroaryl, optionally substituted by one or more identical or different $R^5$ and $R^3$ denotes hydrogen or a group selected from among halogen, $—OR^e$, $—NR^eR^e$, $—CF_3$, $—CN$, $—NC$, $—NO_2$ and $C_{1-6}$alkyl; and $R^4$ denotes a group selected from among $C_{1-3}$alkyl, $C_{3-8}$cycloalkyl, 3-8 membered heterocycloalkyl, halogen, $—OR^e$, $—NR^eR^e$, $—CF_3$, $—CN$, $—NC$ and $—NO_2$, and each $R^5$ denotes a group selected from among $R^a$, $R^b$ and $R^a$ substituted by one or more identical or different $R^b$ and/or $R^e$; and each $R^a$ independently of one another denotes hydrogen or a group optionally substituted by one or more identical or different $R^b$ and/or $R^c$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^b$ denotes a suitable group and is selected independently of one another from among $=O$, $—OR^c$, $C_{1-3}$haloalkyloxy, $—OCF_3$, $=S$, $—SR^c$, $=NR^c$, $=NOR^c$, $=NNR^cR^c$, $=NN(R^g)C(O)NR^cR^c$, $—NR^cR^c$, $—ONR^cR^c$, $—N(OR^c)R^c$, $—N(R^g)NR^cR^c$, halogen, $—CF_3$, $—CN$, $—NC$, $—OCN$, $—SCN$, $—NO$, $—NO_2$, $=N_2$, $—N_3$, $—S(O)R^c$, $—S(O)OR^c$, $—S(O)_2R^c$, $—S(O)_2OR^c$, $—S(O)NR^cR^c$, $—S(O)_2NR^cR^c$, $—OS(O)R^c$, $—OS(O)_2R^c$, $—OS(O)_2OR^c$, $—OS(O)NR^cR^c$, $—OS(O)_2NR^cR^c$, $—C(O)R^c$, $—C(O)OR^c$, $—C(O)SR^c$, $—C(O)NR^cR^c$, $—C(O)N(R^g)NR^cR^c$, $—C(O)N(R^g)OR^c$, $—C(NR^g)NR^cR^c$, $—C(NOH)R^c$, $—C(NOH)NR^cR^c$, $—OC(O)R^c$, $—OC(O)OR^c$, $—OC(O)SR^c$, $—OC(O)NR^cR^c$, $—OC(NR^g)NR^cR^c$, $—SC(O)R^c$, $—SC(O)OR^c$, $—SC(O)NR^cR^c$, $—SC(NR^g)NR^cR^c$, $—N(R^g)C(O)R^c$, $—N[C(O)R^c]_2$, $—N(OR^g)C(O)R^c$, $—N(R^g)C(NR^g)R^c$, $—N(R^g)N(R^g)C(O)R^c$, $—N[C(O)R^c]NR^cR^c$, $—N(R^g)C(S)R^c$, $—N(R^g)S(O)R^c$, $—N(R^g)S(O)OR^c$, $—N(R^g)S(O)_2R^c$, $—N[S(O)_2R^c]_2$, $—N(R^g)S(O)_2OR^c$, $—N(R^g)S(O)_2NR^cR^c$, $—N(R^g)[S(O)_2]_2R^c$, $—N(R^g)C(O)OR^c$, $—N(R^g)C(O)SR^c$, $—N(R^g)C(O)NR^cR^c$, $—N(R^g)C(O)NR^gNR^cR^c$, $—N(R^g)N(R^g)C(O)NR^cR^c$, $—N(R^g)C(S)NR^cR^c$, $—[N(R^g)C(O)]_2R^c$, $—N(R^g)[C(O)]_2R^c$, $—N\{[C(O)]_2R^c\}_2$, $—N(R^g)$ $[C(O)]_2OR^c$, $—N(R^g)[C(O)]_2NR^cR^c$, $—N\{[C(O)]_2 OR^c\}_2$, $—N\{[C(O)]_2NR^cR^c\}_2$, $—[N(R^g)C(O)]_2OR^c$, $—N(R^g)C(NR^g)OR^c$, $—N(R^g)C(NOH)R^c$, $—N(R^g)C(NR^g)SR^c$, $—N(R^g)C(NR^g)NR^cR^c$ and $—N=C(R^g)NR^cR^c$ and each $R^c$ independently of one another denotes hydrogen or a group optionally substituted by one or more identical or different $R^d$ and/or $R^e$, selected from among $C_{1-6}$alkyl, 2-6 membered heteroalkyl, $C_{1-6}$halo alkyl, $C_{3-10}$cycloalkyl, $C_{4-16}$cycloalkylalkyl, $C_{6-10}$aryl, $C_{7-16}$arylalkyl, 5-12 membered hetero-aryl, 6-18 membered heteroarylalkyl, 3-14 membered heterocycloalkyl and 4-14 membered heterocycloalkylalkyl, and each $R^d$ denotes a suitable group and is selected independently of one another from among $=O$, $—OR^e$, $C_{1-3}$haloalkyloxy, $—OCF_3$, $=S$, $—SR^e$, $=NR^e$, $=NOR^e$, $=NNR^eR^e$, $=NN(R^g)C(O)NR^eR^e$, $—NR^eR^e$, $—ONR^e$ $R^e$, $—N(R^g)NR^eR^e$, halogen, $—CF_3$, $—CN$, $—NC$, $—OCN$, $—SCN$, $—NO$, $—NO_2$, $=N_2$, $—N_3$, $—S(O)R^e$, $—S(O)OR^e$, $—S(O)_2R^e$, $—S(O)_2OR^e$, $—S(O)NR^eR^e$, $—S(O)_2NR^eR^e$, $—OS(O)R^e$, $—OS(O)_2R^e$, $—OS(O)_2 OR^e$, $—OS(O)NR^eR^e$, $—OS(O)_2NR^eR^e$, $—C(O)R^e$, $—C(O)OR^e$, $—C(O)SR^e$, $—C(O)NR^eR^e$, $—C(O)N(R^g)$ —NR$^e$R$^e$, —C(O)N(R$^g$)OR$^e$, —C(NR$^g$)NR$^e$R$^e$, —C(NOH)R$^e$, —C(NOH)NR$^e$R$^e$, —OC(O)R$^e$, —OC(O)OR$^e$, —OC(O)SR$^e$, —OC(O)NR$^e$R$^e$, —OC(NR$^g$)NR$^e$R$^e$, —SC(O)R$^e$, —SC(O)OR$^e$, —SC(O)NR$^e$R$^e$, —SC(NR$^g$)NR$^e$R$^e$, —N(R$^g$)C(O)R$^e$, —N[C(O)R$^e$]$_2$, —N(OR$^g$)C(O)R$^e$, —N(R$^g$)C(NR$^g$)R$^e$, —N(R$^g$)N(R$^g$)C(O)R$^e$, —N[C(O)R$^e$]NR$^e$R$^e$, —N(R$^g$)C(S)R$^e$, —N(R$^g$)S(O)R$^e$, —N(R$^g$)S(O)OR$^e$—N(R$^g$)S(O)$_2$R$^e$, —N[S(O)$_2$R$^e$]$_2$, —N(R$^g$)S(O)$_2$OR$^e$, —N(R$^g$)S(O)$_2$NR$^e$R$^e$, —N(R$^g$)[S(O)$_2$]$_2$R$^e$, —N(R$^g$)C(O)OR$^e$, —N(R$^g$)C(O)SR$^e$, —N(R$^g$)C(O)NR$^e$R$^e$, —N(R$^g$)C(O)NR$^g$NR$^e$R$^e$, —N(R$^g$)N(R$^g$)C(O)NR$^e$R$^e$, —N(R$^g$)C(S)NR$^e$R$^e$, —[N(R$^g$)C(O)]$_2$R$^e$, —N(R$^g$)[C(O)]$_2$R$^e$, —N{[C(O)]$_2$R$^e$}$_2$, —N(R$^g$)[C(O)]$_2$OR$^e$, —N(R$^g$)[C(O)]$_2$NR$^e$R$^e$, —N{[C(O)]$_2$OR$^e$}$_2$, —N{[C(O)]$_2$NR$^e$R$^e$}$_2$, —[N(R$^g$)C(O)]$_2$OR$^e$, —N(R$^g$)C(NR$^g$)OR$^e$, —N(R$^g$)C(NOH)R$^e$, —N(R$^g$)C(NR$^g$)SR$^e$, —N(R$^g$)C(NR$^g$)NR$^e$R$^e$ and —N=C(R$^g$)NR$^e$R$^e$ each R$^e$ independently of one another denotes hydrogen or a group optionally substituted by one or more identical or different R$^f$ and/or R$^g$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero-aryl, 6-18 membered heteroarylalkyl, 3-14 membered heterocycloalkyl and 4-14 membered heterocycloalkylalkyl, and each R$^f$ denotes a suitable group and in each case is selected independently of one another from among =O, —OR$^g$, C$_{1-3}$haloalkyloxy, —OCF$_3$, =S, —SR$^g$, =NR$^g$, =NOR$^g$, =NNR$^g$R$^g$, =NN(R$^h$)C(O)NR$^g$R$^g$, —NR$^g$R$^g$, —ONR$^g$R$^g$, —N(R$^h$)NR$^g$R$^g$, halogen, —CF$_3$, —CN, —NC, —OCN, —SCN, —NO, —NO$_2$, =N$_2$, —N$_3$, —S(O)R$^g$, —S(O)OR$^g$, —S(O)$_2$R$^g$, —S(O)$_2$OR$^g$, —S(O)NR$^g$R$^g$, —S(O)$_2$NR$^g$R$^g$, —OS(O)R$^g$, —OS(O)$_2$R$^g$, —OS(O)$_2$OR$^g$, —OS(O)NR$^g$R$^g$, —OS(O)$_2$NR$^g$R$^g$, —C(O)R$^g$, —C(O)OR$^g$, —C(O)SR$^g$, —C(O)NR$^g$R$^g$, —C(O)N(R$^h$)NR$^g$R$^g$, —C(O)N(R$^h$)OR$^g$, —C(NR$^h$)NR$^g$R$^g$, —C(NOH)R$^g$, —C(NOH)NR$^g$R$^g$, —OC(O)R$^g$, —OC(O)OR$^g$, —OC(O)SR$^g$, —OC(O)NR$^g$R$^g$, —OC(NR$^h$)NR$^g$R$^g$, —SC(O)R$^g$, —SC(O)OR$^g$, —SC(O)NR$^g$R$^g$, —SC(NR$^h$)NR$^g$R$^g$, —N(R$^h$)C(O)R$^g$, —N[C(O)R$^g$]$_2$, —N(OR$^h$)C(O)R$^g$, —N(R$^h$)C(NR$^h$)R$^g$, —N(R$^h$)N(R$^h$)C(O)R$^g$, —N[C(O)R$^g$]NR$^g$R$^g$, —N(R$^h$)C(S)R$^g$, —N(R$^h$)S(O)R$^g$, —N(R$^h$)S(O)OR$^g$, —N(R$^h$)S(O)$_2$R$^g$, —N[S(O)$_2$R$^g$]$_2$, —N(R$^h$)S(O)$_2$OR$^g$, —N(R$^h$)S(O)$_2$NR$^g$R$^g$, —N(R$^h$)[S(O)$_2$]$_2$R$^g$, —N(R$^h$)C(O)OR$^g$, —N(R$^h$)C(O)SR$^g$, —N(R$^h$)C(O)NR$^g$R$^g$, —N(R$^h$)C(O)NR$^h$NR$^g$R$^g$, —N(R$^h$)N(R$^h$)C(O)NR$^g$R$^g$, —N(R$^h$)C(S)NR$^g$R$^g$, —[N(R$^h$)C(O)]$_2$R$^g$, —N(R$^h$)[C(O)]$_2$R$^g$, —N{[C(O)]$_2$R$^g$}$_2$, —N(R$^h$)[C(O)]$_2$OR$^g$, —N(R$^h$)[C(O)]$_2$NR$^g$R$^g$, —N{[C(O)]$_2$OR$^g$}$_2$, —N{[C(O)]$_2$NR$^g$R$^g$}$_2$, —[N(R$^h$)C(O)]$_2$OR$^g$, —N(R$^h$)C(NR$^h$)OR$^g$, —N(R$^h$)C(NOH)R$^g$, —N(R$^h$)C(NR$^h$)SR$^g$, —N(R$^h$)C(NR$^h$)NR$^g$R$^g$; and —N=C(R$^h$)NR$^h$R$^h$; and each R$^g$ independently of one another denotes hydrogen or a group optionally substituted by one or more identical or different R$^h$, selected from among C$_{1-6}$alkyl, 2-6 membered heteroalkyl, C$_{1-6}$haloalkyl, C$_{3-10}$cycloalkyl, C$_{4-10}$cycloalkylalkyl, C$_{6-10}$aryl, C$_{7-10}$arylalkyl, 5-12 membered hetero-aryl, 6-18 membered heteroarylalkyl, 3-14 membered heterocycloalkyl and 4-14 membered heterocycloalkylalkyl; and each R$^h$ is selected independently of one another from among hydrogen, C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl, optionally in the form of the prodrugs, the tautomers, the racemates, the enantiomers, the diastereomers, the prodrugs and the mixtures thereof, and optionally the pharmacologically acceptable salts thereof.

One aspect of the invention relates to compounds of general formulae (1), wherein R$^4$ denotes —CH$_3$ or —CH$_2$CH$_3$.

Another aspect of the invention relates to compounds of general formula (1), wherein R$^3$ denotes hydrogen or —NR$^e$R$^e$.

Another aspect of the invention relates to compounds of general formula (1), wherein R$^3$ denotes —NH$_2$.

Another aspect of the invention relates to compounds of general formula (1), wherein R$^2$ denotes phenyl or pyridyl, optionally substituted by one or more identical or different R$^5$.

Another aspect of the invention relates to compounds of general formula (1), wherein R$^2$ denotes heterocyclo alkyl, optionally substituted by one or more identical or different R$^5$.

Another aspect of the invention relates to compounds of general formula (1), wherein R$^1$ denotes phenyl, pyridyl or pyrimidinyl, optionally substituted by one or more identical or different R$^5$.

One aspect of the invention relates to compounds of general formula (1), or the pharmacologically effective salts thereof, as medicaments.

One aspect of the invention relates to compounds of general formula (1), or the pharmacologically effective salts thereof, for preparing a medicament with an antiproliferative activity.

One aspect of the invention is a pharmaceutical preparations, containing as active substance one or more compounds of general formula (1), or the pharmacologically effective salts thereof, optionally in combination with conventional excipients and/or carriers.

One aspect of the invention is the use of compounds of general formula (1) for preparing a medicament for the treatment and/or prevention of cancer, infections, inflammatory and autoimmune diseases.

One aspect of the invention is a pharmaceutical preparation comprising a compound of general formula (1) and at least one other cytostatic or cytotoxic active substance, different from formula (1), optionally in the form of the tautomers, the racemates, the enantiomers, the diastereomers and the mixtures thereof, as well as optionally the pharmacologically acceptable salts thereof.

Definitions

As used herein the following definitions apply, unless stated otherwise.

By alkyl substituents are meant in each case saturated, unsaturated, straight-chain or branched aliphatic hydrocarbon groups (alkyl group) and this includes both saturated alkyl groups and unsaturated alkenyl and alkynyl groups. Alkenyl substituents are in each case straight-chain or branched, unsaturated alkyl groups, which have at least one double bond. By alkynyl substituents are meant in each case straight-chain or branched, unsaturated alkyl groups, which have at least one triple bond.

The term heteroalkyl refers to groups which can be derived from alkyl as defined above in its broadest sense by replacing one or more of the groups —CH$_3$ in the hydrocarbon chains independently of one another by the groups —OH, —SH or —NH$_2$, one or more of the groups —CH$_2$— independently of one another by the groups —O—, —S— or —NH—, one or more of the groups by the group

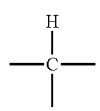

one or more of the groups ═CH— by the group ═N—, one or more of the groups ═CH₂ by the group ═NH or one or more of the groups ≡CH by the group ≡N, while in all only a maximum of three heteroatoms may be present in a heteroalkyl, there must be at least one carbon atom between two oxygen and between two sulphur atoms or between one oxygen and one sulphur atom and the group as a whole must have chemical stability.

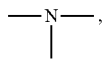

It flows from the indirect definition/derivation from alkyl that heteroalkyl is made up of the sub-groups of saturated hydrocarbon chains with hetero-atom(s), heteroalkenyl and heteroalkynyl, while further subdivision into straight-chain (unbranched) and branched may be carried out. If a heteroalkyl is supposed to be substituted, the substitution may take place independently of one another, in each case mono- or polysubstituted, at all the hydrogen-carrying oxygen, sulphur, nitrogen and/or carbon atoms. Heteroalkyl itself may be linked to the molecule as substituent both through a carbon atom and through a heteroatom.

By way of example, the following representative compounds are listed: dimethylaminomethyl; dimethylaminoethyl (1-dimethylaminoethyl; 2-dimethyl-aminoethyl); dimethylaminopropyl (1-dimethylaminopropyl, 2-dimethylaminopropyl, 3-dimethylaminopropyl); diethylaminomethyl; diethylaminoethyl (1-diethylaminoethyl, 2-diethylaminoethyl); diethylaminopropyl (1-diethylaminopropyl, 2-diethylamino-propyl, 3-diethylaminopropyl); diisopropylaminoethyl (1-diisopropylaminoethyl, 2-di-isopropylaminoethyl); bis-2-methoxyethylamino; [2-(dimethylamino-ethyl)-ethyl-amino]-methyl; 3-[2-(dimethylamino-ethyl)-ethyl-amino]-propyl; hydroxymethyl; 2-hydroxyethyl; 3-hydroxypropyl; methoxy; ethoxy; propoxy; methoxymethyl; 2-methoxyethyl etc.

Haloalkyl relates to alkyl groups, wherein one or more hydrogen atoms are replaced by halogen atoms. Haloalkyl includes both saturated alkyl groups and unsaturated alkenyl and alkynyl groups, such as for example —CF₃, —CHF₂, —CH₂F, —CF₂CF₃, —CHFCF₃, —CH₂CF₃, —CF₂CH₃, —CHFCH₃, —CF₂CF₂CF₃, —CF₂CH₂CH₃, —CF═CF₂, —CCl═CH₂, —CBr═CH₂, —CI═CH₂, —C≡C—CF₃, —CHFCH₂CH₃ and —CHFCH₂CF₃.

Halogen refers to fluorine, chlorine, bromine and/or iodine atoms.

By cycloalkyl is meant a mono or bicyclic ring, while the ring system may be a saturated ring or, however, an unsaturated, non-aromatic ring, which may optionally also contain double bonds, such as for example cyclopropyl, cyclopropenyl, cyclobutyl, cyclobutenyl, cyclopentyl, cyclopentenyl, cyclohexyl, cyclohexenyl, norbornyl and norbornenyl.

Cycloalkylalkyl includes a non-cyclic alkyl group wherein a hydrogen atom bound to a carbon atom, usually to a terminal C atom, is replaced by a cycloalkyl group.

Aryl relates to monocyclic or bicyclic aromatic rings with 6-10 carbon atoms such as phenyl and naphthyl, for example.

Arylalkyl includes a non-cyclic alkyl group wherein a hydrogen atom bound to a carbon atom, usually to a terminal C atom, is replaced by an aryl group.

By heteroaryl are meant mono- or bicyclic aromatic rings, which instead of one or more carbon atoms contain one or more, identical or different hetero atoms, such as e.g. nitrogen, sulphur or oxygen atoms. Examples include furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heteroaryl groups are indolyl, isoindolyl, benzofuryl, benzothienyl, benzoxazolyl, benzothiazolyl, benzisoxazolyl, benzisothiazolyl, benzimidazolyl, benzopyrazolyl, indazolyl, isoquinolinyl, quinolinyl, quinoxalinyl, cinnolinyl, phthalazinyl, quinazolinyl and benzotriazinyl, indolizinyl, oxazolopyridyl, imidazopyridyl, naphthyridinyl, indolinyl, isochromanyl, chromanyl, tetrahydroisoquinolinyl, isoindolinyl, isobenzotetrahydrofuryl, isobenzotetrahydrothienyl, isobenzothienyl, benzoxazolyl, pyridopyridyl, benzotetrahydrofuryl, benzotetrahydrothienyl, purinyl, benzodioxolyl, triazinyl, phenoxazinyl, phenothiazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridyl-N-oxide tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl-N-oxide, pyrimidinyl-N-oxide, pyridazinyl-N-oxide, pyrazinyl-N-oxide, quinolinyl-N-oxide, indolyl-N-oxide, indolinyl-N-oxide, isoquinolyl-N-oxide, quinazolinyl-N-oxide, quinoxalinyl-N-oxide, phthalazinyl-N-oxide, imidazolyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, tetrazolyl-N-oxide, benzothiopyranyl-S-oxide and benzothiopyranyl-S,S-dioxide.

Heteroarylalkyl encompasses a non-cyclic alkyl group wherein a hydrogen atom bound to a carbon atom, usually to a terminal C atom, is replaced by a heteroaryl group.

Heterocycloalkyl relates to saturated or unsaturated, non-aromatic mono-, bicyclic or bridged bicyclic rings comprising 3-12 carbon atoms, which instead of one or more carbon atoms carry heteroatoms, such as nitrogen, oxygen or sulphur. Examples of such heterocycloalkyl groups are tetrahydrofuryl, pyrrolidinyl, pyrrolinyl, imidazolidinyl, imidazolinyl, pyrazolidinyl, pyrazolinyl, piperidinyl, piperazinyl, indolinyl, isoindolinyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, tetrahydropyranyl, tetrahydrothienyl, homothiomorpholinyl-S,S-dioxide, oxazolidinonyl, dihydropyrazolyl, dihydropyrrolyl, dihydropyrazinyl, dihydropyridyl, dihydropyrimidinyl, dihydrofuryl, dihydropyranyl, tetrahydrothienyl-S-oxide, tetrahydrothienyl-S,S-dioxide, homothiomorpholinyl-S-oxide, 2-oxa-5-azabicyclo[2,2,1]heptane, 8-oxa-3-aza-bicyclo[3.2.1]octane, 3,8-diaza-bicyclo[3.2.1]octane, 2,5-diaza-bicyclo[2.2.1]heptane, 3,8-diaza-bicyclo[3.2.1]octane, 3,9-diaza-bicyclo[4.2.1]nonane and 2,6-diaza-bicyclo[3.2.2]nonane.

Heterocycloalkylalkyl relates to a non-cyclic alkyl group wherein a hydrogen atom bound to a carbon atom, usually to a terminal C atom, is replaced by a heterocycloalkyl group.

The following Examples illustrate the present invention without restricting its scope.

General Procedure 1 (GP1): Iodination of Pyrimidines or Pyridines

A solution of the pyrimidine or pyridine (1.0 eq.) in acetic acid is cooled to 0° C. and N-iodosuccinimide (1.0 eq.) is added in one portion. The reaction mixture is stirred at RT until conversion of the starting material is completed (2-6 h). The mixture is poured on ice-cooled water and treated with a mixture of 5% $Na_2S_2O_3$ and 10% $NaHCO_3$. The precipitate is filtered off, intensely washed with water and dried under vacuum at 40° C. The crude product can be used without further purification or is further purified by chromatography on silica gel using a $CH_2Cl_2$/MeOH gradient.

General Procedure 2 (GP2): Sonogashira Reaction

The halide (1.0 eq.) is dissolved in DMF or THF and $PdCl_2(PPh_3)_2$ (0.1 eq.) and CuI (0.1 eq.) are added. Subsequently, triethylamine (10.0 eq.) and finally the alkyne (1.5 eq.) are added and the reaction mixture is stirred at 65° C. The reaction is monitored by LC-MS. If the iodide is not completed converted after 4 h, additional amounts of alkyne are added in small portions. The product either precipitates from the reaction mixture (and is filtered off and if necessary re-crystallized) and/or, after removal of the solvent, is purified by preparative RP-HPLC.

General Procedure 3 (GP3): Desilylation of Alkynes

The TMS-alkyne (1.0 eq.) is dissolved in MeOH, $K_2CO_3$ (0.5 eq.) is added in one portion and the reaction mixture is stirred at RT until conversion is complete (3-16 h). The solvent is removed in vacuo, the crude product is dissolved in ethyl acetate and the organic phase is extracted with water. The organic phase is dried, filtered off and the solvent removed in vacuo. The product is either used without further purification or purified by chromatography on silica gel using a DCM/MeOH or (cyclo-)hexane/ethyl acetate.

General Procedure 4 (GP4): Suzuki Coupling

The 4-chloropyrimidine (1.0 eq.) is dissolved in DME/water (20:1 v/v), boronic acid (1.3 eq.), $K_2CO_3$ (2.0 eq.) and $Pd(PPh_3)_4$ (0.2 eq.) are added and the reaction mixture is stirred for 4 h under reflux. In case the conversion of the starting material is not complete, additional amounts of boronic acid and Pd-catalyst are added and the reaction is run over night under reflux. After cooling to RT water is added. The precipitate is filtered off. In cases where the product is not precipitated it is extracted with diethylether, the organic phase is dried, filtered off, and the solvent removed under reduced pressure. The obtained product can either be used without further purification or is purified by chromatography.

General Procedure 5 (GP5): Oxidation of a Thioalkyl Group

The 2-methylsulfanyl-pyrimidine (1.0 eq.) is taken up in DCM, meta-chloroperbenzoic acid (2.5 eq.) is added and the reaction mixture is stirred for one day. The reaction mixture is filtered, washed with water and concentrated in vacuo. The crude product can be used without further purification.

General Procedure 6 (GP6): Nucleophilic Substitution of 2-Sulfonylpyrimidines with Amines The starting material is dissolved in NMP, an excess of amine is added and the reaction mixture is heated in the microwave at 120-150° C. After cooling to RT the product is purified by NP-HPLC.

General Procedure 7 (GP7): Nucleophilic Substitution of 4-Chloropyrimidines with Amines The starting material is dissolved in NMP, an excess of amine is added and the reaction mixture is heated in the microwave at 120-150° C. After cooling to RT the product is purified by NP-HPLC.

General Procedure 8 (GP8): Saponification of Esters

The ester is taken up in either THF or dioxane, 1.1-1.5 eq. of 1N NaOH are added and the mixture is heated under reflux until reaction control shows complete conversion of the starting material. The product either precipitates from the reaction mixture and is used without additional purification steps or can further be purified by chromatography.

General Procedure 9 (GP9): Amide Formation with Amines

To a mixture of 0.21 mmol starting material, 0.31 mmol TBTU or HATU and 0.42 mmol Huenig's base in 2 mL DMSO is stirred for 5 min. 0.31 mmol of amine is added and the resultant mixture is stirred at room temp. over night. Purification is performed via preparative RP-HPLC yielding after evaporation of the solvent the desired product.

General Procedure 10 (GP10) Amide Formation with Acid Chlorides

To a mixture of 0.13 mmol of starting material and 67 µL Huenig's base in 2 mL THF is added 0.26 mmol acid chloride. The reaction mixture is stirred over night at RT. The solvent is evaporated and the residue is taken up in 1 mL DMSO insoluble material is filtered off and the resulting solution is purified via preparative RP-HPLC yielding after evaporation of the solvent the desired product.

General Procedure 11 (GP11): Urea Formation with Isocyanates

To a mixture of 0.16 mmol of starting material and 64.4 µL Huenig's base in 2 mL THF is added 0.49 mmol isocyanate. The reaction mixture is stirred over night at RT. The solvent is evaporated and the residue is taken up in 1 mL DMSO insoluble material is filtered off and the resulting solution is purified via preparative RP-HPLC yielding after evaporation of the solvent the desired product.

General Procedure 12 (GP12): Urea Formation via Pre-activation of the Amine.

To a mixture of 0.34 mmol amine and 0.34 mmol N,N'-carbonyldiimidazole and 0.34 mmol 1,8-diazabicyclo[5.4.0]undec-7-ene is stirred for 10 min at RT. 0.32 mmol of starting material are added in one portion. The reaction mixture is heated at 100° C. for 1 h in the microwave. The solvent is evaporated and the residue is taken up in 1 mL DMSO insoluble material is filtered off and the resulting solution is purified via preparative RP-HPLC yielding the desired product.

General Procedure 13 (GP13): Amide formation with Carbonic Acids

To a mixture of 0.62 mmol carbonic acid, 0.93 mmol TBTU and 1.2 mmol Huenig's base in 2 mL DMSO is stirred for 5 min. 0.31 mmol of starting material is added and the resultant mixture is stirred at RT over night. Purification is performed via preparative RP-HPLC yielding after evaporation of the solvent the desired product.

INTERMEDIATES A

A-1) 5-Iodo-3-trifluoromethyl-pyridin-2-ylamine

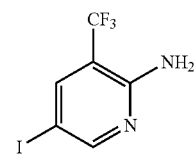

The title compound is synthesized according to general procedure GP1 starting from 5.0 g (31 mmol) 3-trifluoro-2-amino pyridine and 6.9 g (31 mmol) NIS. Yield after precipitation from the reaction mixture: 6.78 g (76%).

A-2) 5-Trifluoromethyl-3-(tert-butyl-oxyxcarbonyl) amino-phenylboronic acid

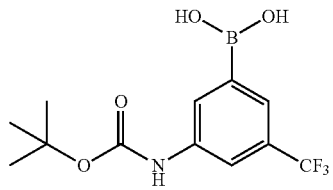 [SMILES: CC(C)(C)OC(=O)Nc1cc(B(O)O)cc(C(F)(F)F)c1]

A solution of 1.5 g (4.4 mmol) 3-bromo-5-trifluoromethyl-tert.-butyl-oxyxcarbonyl-aniline and 1.2 mL (5.3 mmol) tri-isopropylborate in a mixture of 4.5 mL dry THF/10.5 mL dry toluene is cooled to −70° C. under an inert atmosphere before 6.9 mL of a 1.6 M solution of n-BuLi in hexane are added dropwise (syringe pump) over 30 min. The reaction mixture is stirred for additional 50 min at −70° C. before the reaction temperature is allowed to rise to −20° C. After addition of 4.4 mL of 2.2 M HCl the reaction mixture warmed to RT and the layers are separated. The organic phase is diluted with ethyl acetate, washed with brine (pH of the aqueous phase <3), dried over $Na_2SO_4$, filtered off and the solvent is removed under reduced pressure. The product is purified by PR-HPLC using an ACN/water gradient. Yield: 635 mg (47%).

A-3) 4-Chloro-5-iodo-6-methyl-pyrimidin-2-ylamine

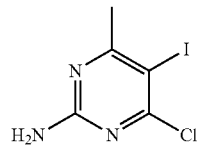

The title compound is synthesized according to general procedure GP1 starting from 10 g (70 mmol) 2-amino-4-chloro-6-methylpyrimidine and 16 g NIS (70 mmol). Yield: 18 g (95%). The crude product is used in next steps without further purification.

A-4) 2-Methyl-5-trimethylsilanylethynyl-pyridine

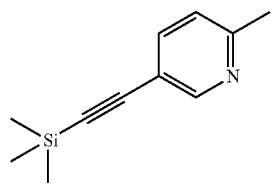

The title compound is synthesized according to general procedure GP2 starting from 2.0 g (11.6 mmol) 5-bromo-2-methyl-pyridine and 2.3 mL (16.3 mmol) 1-trimethylsilyl-ethyne using 68 mg (0.36 mmol) CuI, 305 mg (1.2 mmol) triphenylphosphine, 213 mg (0.30 mmol) $PdCl_2(PPh_3)_2$ and 18 mL (127 mmol) triethylamine in 18 mL dry THF. For the work-up the reaction mixture is diluted with ethyl acetate, the organic phase is extracted with water and brine. The product is purified by chromatography on silica gel using a hexane/ethyl acetate gradient. Yield: 1.5 g (68%).

A-5) 5-Trimethylsilanylethynyl-pyridin-2-ylamine

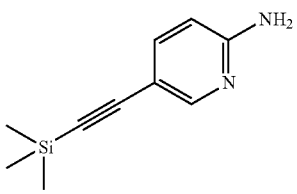

The title compound is synthesized according to general procedure GP2 starting from 5.0 g (28.9 mmol) 5-bromo-2-amino-pyridine and 5.7 mL (40.5 mmol) 1-trimethylsilyl-ethyne using 168 mg (0.88 mmol) CuI, 758 mg (2.9 mmol) triphenylphosphine, 533 mg (0.76 mmol) $PdCl_2(PPh_3)_2$ and 40 mL (288 mmol) triethylamine in 40 mL dry THF. For the work-up the reaction mixture is diluted with ethyl acetate and small amounts of cyclohexane, the organic phase is extracted with water and brine. The product is purified by chromatography on silica gel using hexane/ethyl acetate (10/1 v/v). Yield: 5.0 g (91%).

A-6) Methyl-(5-trimethylsilanylethynyl-pyridin-2-yl)-amine

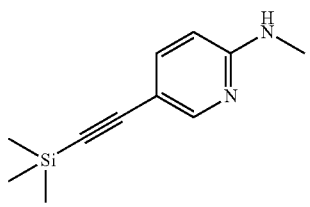

The title compound is synthesized according to general procedure GP2 starting from 4.3 g (23.0 mmol) 5-bromo-2-methylamino-pyridine and 4.5 mL (32.2 mmol) 1-trimethyl-silyl-ethyne using 134 mg (0.71 mmol) CuI, 601 mg (2.3 mmol) triphenylphosphine, 420 mg (0.60 mmol) $PdCl_2(PPh_3)_2$ and 32 mL (101 mmol) triethylamine in 40 mL dry THF. For the work-up the reaction mixture is diluted with ethyl acetate and small amounts of cyclohexane, the organic phase is extracted with water and brine. The product is purified by chromatography on silica gel using a hexane/ethyl acetate gradient. Yield: 4.0 g (85%).

A-7) Ethyl-(5-trimethylsilanylethynyl-pyridin-2-yl)-amine

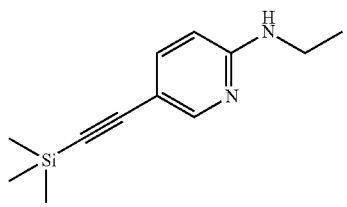

The title compound is synthesized according to general procedure GP2 starting from 909 mg (4.5 mmol) 5-bromo-2-ethylamino-pyridine and 0.89 mL (6.3 mmol) 1-trimethylsilyl-ethyne using 26 mg (0.13 mmol) CuI, 118 mg (0.45 mmol) triphenylphosphine, 82 mg (0.12 mmol) PdCl$_2$(PPh$_3$)$_2$ and 6.3 mL (45.0 mmol) triethylamine in 7 mL dry THF. For the work-up the reaction mixture is diluted with ethyl acetate and small amounts of cyclohexane, the organic phase is extracted with water and brine. The product is purified by chromatography on silica gel using a hexane/ethyl acetate gradient. Yield: 980 mg (99%).

A-8) 5-Trimethylsilanylethynyl-pyridin-3-ol

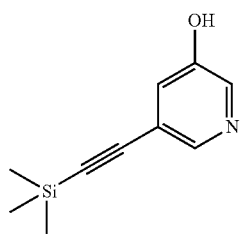

The title compound is synthesized according to general procedure GP2 starting from 2.0 g (11.6 mmol) 5-bromo-3-hydroxy-pyridine and 2.3 mL (16.2 mmol) 1-trimethylsilyl-ethyne using 66 mg (0.3 mmol) CuI, 303 mg (1.2 mmol) triphenylphosphine, 243 mg (0.3 mmol) PdCl$_2$(PPh$_3$)$_2$ and 19 mL (139 mmol) triethylamine in 20 mL dry THF. For the work-up the reaction mixture is diluted with ethyl acetate and small amounts of cyclohexane, the organic phase is extracted with water and brine. The product is purified by chromatography on silica gel using a DCM/MeOH gradient. Yield: 2.0 g (91%).

A-9) 5-Trimethylsilanylethynyl-pyridin-3-ylamine

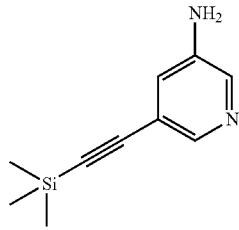

The title compound is synthesized according to general procedure GP2 starting from 2.0 g (11.6 mmol) 5-bromo-3-amino-pyridine and 2.3 mL (16.2 mmol) 1-trimethylsilyl-ethyne using 66 mg (0.3 mmol) CuI, 303 mg (1.2 mmol) triphenylphosphine, 243 mg (0.3 mmol) PdCl$_2$(PPh$_3$)$_2$ and 19 mL (139 mmol) triethylamine in 20 mL dry THF. For the work-up the reaction mixture is diluted with ethyl acetate and small amounts of cyclohexane, the organic phase is extracted with water and brine. The product is purified by chromatography on silica gel using a DCM/MeOH gradient. The product precipitated on the column and was subsequently extracted from the silica gel with pure MeOH. Yield: 2.0 g (91%).

A-10) 5-Trimethylsilanylethynyl-1H-pyrazolo[3,4-b]pyridine

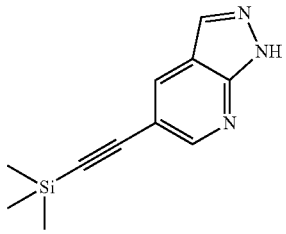

The title compound is synthesized according to general procedure GP2 starting from 1.0 g (5.1 mmol) 5-bromo-1H-pyrazolo[4,5-b]pyridine and 1.0 mL (7.1 mmol) 1-trimethylsilyl-ethyne using 29 mg (0.15 mmol) CuI, 133 mg (0.51 mmol) triphenylphosphine, 106 mg (0.15 mmol) PdCl$_2$(PPh$_3$)$_2$ and 8.4 mL (60.6 mmol) triethylamine in 8 mL dry THF. The formed precipitate is filtered off and the product is purified by RP-HPLC using an ACN/H$_2$O gradient. Yield: 542 mg (50%).

A-11) 5-Trimethylsilanylethynyl-1H-pyrrolo[2,3-b]pyridine

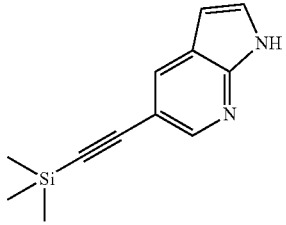

The title compound is synthesized according to general procedure GP2 starting from 3.0 g (15.2 mmol) 5-bromo-1H-pyrrolo[2,3-B]pyridine and 3.0 mL (21.3 mmol) 1-trimethylsilyl-ethyne using 87 mg (0.46 mmol) CuI, 400 mg (1.5 mmol) triphenylphosphine, 312 mg (0.46 mmol) PdCl$_2$(PPh$_3$)$_2$ and 25.4 mL (182 mmol) triethylamine in 25 mL dry THF. The formed precipitate is filtered off and the product is purified by chromatography on silica gel using a DCM/MeOH gradient. Yield: 3.05 g (94%).

A-12) 6-Trimethylsilanylethynyl-3H-imidazo[4,5-b]pyridine

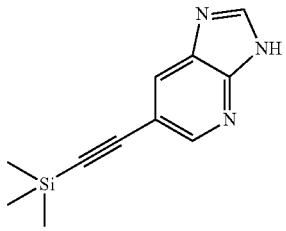

The title compound is synthesized according to general procedure GP2 starting from 1.2 g (6.1 mmol) 5-bromo-3H-imidazo[4,5-b]pyridine and 1.2 mL (8.4 mmol) 1-trimethylsilyl-ethyne using 34 mg (0.18 mmol) CuI, 159 mg (0.61 mmol) triphenylphosphine, 128 mg (0.18 mmol) PdCl$_2$(PPh$_3$)$_2$ and 10.1 mL (72.7 mmol) triethylamine in 10 mL dry THF. The formed precipitate is filtered off and the product is purified by RP-HPLC using an ACN/H$_2$O gradient. Yield: 606 mg (46%).

A-13) 5-Ethynyl-2-methyl-pyridine

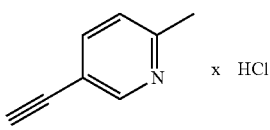

The title compound is synthesized according to general procedure GP3 starting from 2.2 g (12 mmol) 2-methyl-5-trimethylsilanylethynyl-pyridine (A4) and 0.80 g (5.8 mmol) K$_2$CO$_3$ in 13 mL MeOH. The crude product is purified by chromatography on silica gel using a cyclohexane/ethyl acetate gradient. The product is extracted from the organic phase with 1 N HCl and isolated as the hydrochloride after lyophilization. Yield: 1.3 g (73%).

A-14) 5-Ethynyl-2-amino-pyridine

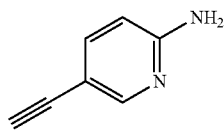

The title compound is synthesized according to general procedure GP3 starting from 5.5 g (29 mmol) 5-trimethylsilanylethynyl-pyridin-2-ylamine (A5) and 2.0 g (14 mmol) K$_2$CO$_3$ in 30 mL MeOH. The product is purified by chromatography on silica gel using a hexane/ethyl acetate gradient. Yield: 2.9 g (85%).

A-15) (5-Ethynyl-pyridin-2-yl)-methyl-amine

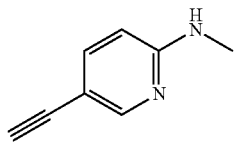

The title compound is synthesized according to general procedure GP3 starting from 1.5 g (7.3 mmol) methyl-(5-trimethylsilanylethynyl-pyridin-2-yl)-amine (A6) and 507 mg (3.7 mmol) K$_2$CO$_3$ in 10 mL MeOH. Yield: 698 mg (56%) after chromatography on silica gel.

A-16) (5-Ethynyl-pyridin-2-yl)-ethyl-amine

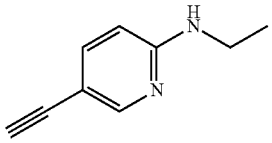

The title compound is synthesized according to general procedure GP3 starting from 980 mg (4.5 mmol) TMS-alkyne and 310 mg (2.3 mmol) K$_2$CO$_3$ in 6 mL MeOH. Yield: 388 mg (59%) after chromatography on silica gel.

A-17) 5-Ethynyl-pyridin-3-ol

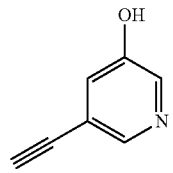

The title compound is synthesized according to general procedure GP3 starting from 2.0 g (10.5 mmol) TMS-alkyne and 722 mg (5.2 mmol) K$_2$CO$_3$ in 10 mL MeOH. Yield: 804 mg (49%) after chromatography on silica gel.

A-18) 5-Ethynyl-pyridin-3-ylamine

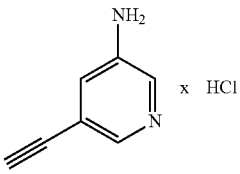

The title compound is synthesized according to general procedure GP3 starting from 2.0 g (11 mmol) TMS-alkyne and 722 mg (5.2 mmol) K$_2$CO$_3$ in 10 mL MeOH. Yield: 1.2 g (74%) after chromatography on silica gel and precipitation from dioxane/HCl.

A-19) 5-Ethynyl-1H-pyrazolo[3,4-b]pyridine

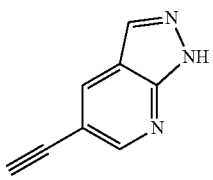

The title compound is synthesized according to general procedure GP3 starting from 542 mg (2.5 mmol) TMS-alkyne and 174 mg (1.3 mmol) K$_2$CO$_3$ in 6 mL MeOH. Yield: 330 mg (92%) after extraction.

A-20) 5-Ethynyl-1H-pyrrolo[2,3-b]pyridine

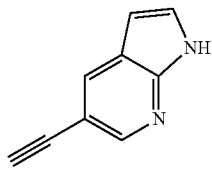

The title compound is synthesized according to general procedure GP3 starting from 3.1 g (14 mmol) TMS-alkyne and 983 mg (7.1 mmol) $K_2CO_3$ in 15 mL MeOH. Yield: 1.2 g (61%) after chromatography on silica gel.

A-21) 6-Ethynyl-3H-imidazo[4,5-b]pyridine

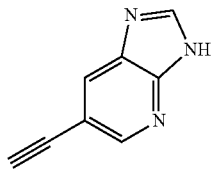

The title compound is synthesized according to general procedure GP3 starting from 706 mg (3.3 mmol) TMS-alkyne and 227 mg (1.6 mmol) $K_2CO_3$ in 6 mL MeOH. Yield: 491 mg (94%) after extraction.

A-22) 4-Methyl-6-(3-trifluoromethyl-phenyl)-pyrimidin-2-ylamine

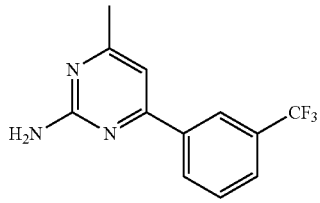 [SMILES: Cc1cc(-c2cccc(C(F)(F)F)c2)nc(N)n1]

The title compound is synthesized according to general procedure GP4 starting from 2.0 g (14 mmol) 2-amino-4-chloro-6-methylpyrimidine and 3.4 g (18 mmol) 3-trifluoromethyl-phenyl boronic acid. Yield after extraction: 5.0 g (99%).

A-23) 4-Methyl-6-(3-cyano-phenyl)-pyrimidin-2-ylamine

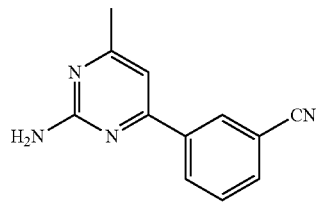 [SMILES: Cc1cc(-c2cccc(C#N)c2)nc(N)n1]

The title compound is synthesized according to general procedure GP4 starting from 2.0 g (14 mmol) 2-amino-4-chloro-6-methylpyrimidine and 2.7 g (18 mmol) 3-cyano-phenyl boronic acid. Yield after extraction and crystallization from diethylether: 3.2 g (100%).

A-24) 4-Methyl-6-(3-methyl-phenyl)-pyrimidin-2-ylamine

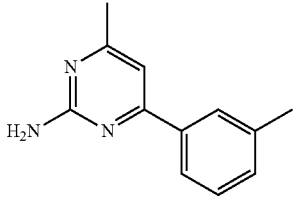

The title compound is synthesized according to general procedure GP4 starting from 2.0 g (14 mmol) 2-amino-4-chloro-6-methylpyrimidine and 2.5 g (18 mmol) 3-methyl-phenyl boronic acid. Yield after extraction and re-crystallization from diethylether: 4.1 g (>100%, approximately 70% pure).

A-25) 4-Methyl-6-(3,5-dimethyl-phenyl)-pyrimidin-2-ylamine

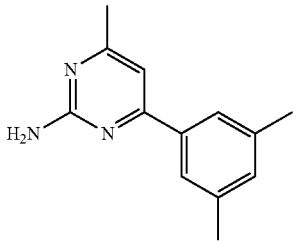 [SMILES: Cc1cc(C)cc(-c2cc(C)nc(N)n2)c1]

The title compound is synthesized according to general procedure GP4 starting from 2.0 g (14 mmol) 2-amino-4-chloro-6-methylpyrimidine and 2.7 g (18 mmol) 3,5-dimethyl-phenyl boronic acid. Yield after extraction and crystallization from diethylether: 3.2 g (75%, approximately 70% pure).

A-26) 4-Methyl-6-(4-methanesulfonyl-phenyl)-pyrimidin-2-ylamine

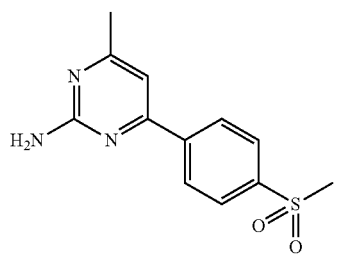 [SMILES: Cc1cc(-c2ccc(S(C)(=O)=O)cc2)nc(N)n1]

The title compound is synthesized according to general procedure GP4 (A) starting from 1.5 g (10 mmol) 2-amino-4-chloro-6-methylpyrimidine and 2.7 g (14 mmol) 4-sulfonyl-phenyl boronic acid. After treatment of the precipitated product with diethyl ether 2.3 g (75%) of the desired product are obtained.

A-27) 5-Iodo-4-methyl-6-(3-trifluoromethyl-phenyl)-pyrimidin-2-ylamine

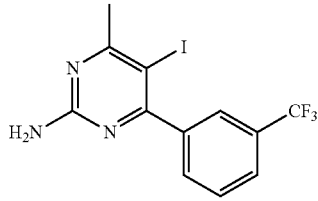 [SMILES: Cc1nc(N)nc(-c2cccc(C(F)(F)F)c2)c1I]

The title compound is synthesized according to general procedure GP1 starting from 5.0 g (14 mmol) 4-methyl-6-(3-trifluoromethyl-phenyl)-pyrimidin-2-ylamine and 3.3 g (15 mmol) NIS. Yield after chromatography on silica gel with DCM/MeOH: 3.8 g (73%).

A-28) 5-Iodo-4-methyl-6-(3-cyano-phenyl)-pyrimidin-2-ylamine

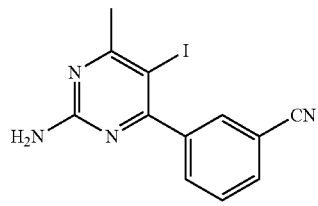 [SMILES: Cc1nc(N)nc(-c2cccc(C#N)c2)c1I]

The title compound is synthesized according to general procedure GP1 starting from 3.2 g (12 mmol) 4-methyl-6-(3-cyano-phenyl)-pyrimidin-2-ylamine and 2.8 g (13 mmol) NIS. Yield after chromatography on silica gel with DCM/MeOH: 3.5 g (78%).

A-29) 5-Iodo-4-methyl-6-(3,5-dimethyl-phenyl)-pyrimidin-2-ylamine

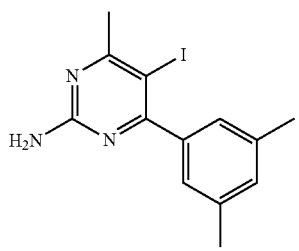 [SMILES: Cc1cc(C)cc(-c2nc(N)nc(C)c2I)c1]

The title compound is synthesized according to general procedure GP1 starting from 3.2 g (11 mmol) 4-methyl-6-(3,5-dimethyl-phenyl)-pyrimidin-2-ylamine and 2.5 g (11 mmol) NIS. Yield after chromatography on silica gel with DCM/MeOH: 1.1 g (31%).

A-30) 5-Iodo-4-methyl-6-(4-methanesulfonyl-phenyl)-pyrimidin-2-ylamine

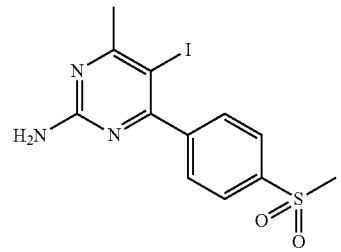 [SMILES: Cc1nc(N)nc(-c2ccc(S(C)(=O)=O)cc2)c1I]

The title compound is synthesized according to general procedure GP1 starting from 2.3 g (7.9 mmol) 4-methyl-6-(4-sulfonyl-phenyl)-pyrimidin-2-ylamine and 1.8 g (7.9 mmol) NIS. Yield after precipitation from the reaction mixture with water: 3.1 g (91%).

A-31) 4-Chloro-6-methyl-5-pyridin-2-ylethynyl-pyrimidin-2-ylamine

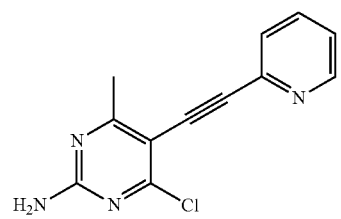 [SMILES: Cc1nc(N)nc(Cl)c1C#Cc1ccccn1]

The title compound is synthesized according to general procedure GP2 starting from 1.5 g (5.6 mmol) 4-chloro-5-iodo-6-methyl-pyrimidin-2-ylamine (GP3) and 0.84 mL (8.4 mmol) 2-ethynyl-pyridine using 106 mg (0.57 mmol) CuI, 390 mg (0.56 mmol) $PdCl_2(PPh_3)_2$ and 7.8 mL (56 mmol) triethylamine in 10 mL dry DMF. Additional amounts are added after 24 h and 48 h reaction time, respectively. For the work-up the solvent is removed in vacuo and the product is purified by chromatography on silica gel using a DCM/MeOH gradient. Yield: 2.0 g (>100%, approximately 70% pure).

A-32) 4-Chloro-6-methyl-5-pyridin-3-ylethynyl-pyrimidin-2-ylamine

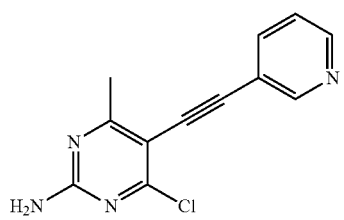 [SMILES: Cc1nc(N)nc(Cl)c1C#Cc1cccnc1]

The title compound is synthesized according to general procedure GP2 starting from 4.0 g (15 mmol) 4-chloro-5-iodo-6-methyl-pyrimidin-2-ylamine (GP3) and 2.0 g (19 mmol) 3-ethynyl-pyridine using 282 mg (1.5 mmol) CuI, 1.0 g (1.5 mmol) $PdCl_2(PPh_3)_2$ and 21 mL (148 mmol) triethylamine in 200 mL dry DMF. For the work-up the reaction mixture is concentrated in vacuo before water is added. The precipitate is collected, dried at 40° C. and crystallized from MeOH/$H_2O$. Yield: 3.0 g (83%).

A-33) 5-(6-Amino-pyridin-3-ylethynyl)-4-chloro-6-methyl-pyrimidin-2-ylamine

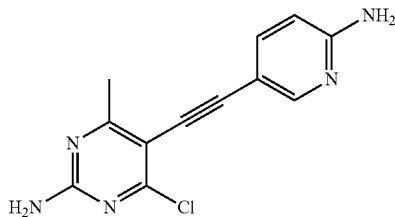 [SMILES: Cc1nc(N)nc(Cl)c1C#Cc1ccc(N)nc1]

The title compound is synthesized according to general procedure GP2 starting from 1.5 g (5.7 mmol) 4-chloro-5-iodo-6-methyl-pyrimidin-2-ylamine (GP3) and 1.7 g (15 mmol) 2-amino-5-ethynyl-pyridine (GP15) using 106 mg (0.56 mmol) CuI, 390 mg (0.56 mmol) PdCl$_2$(PPh$_3$)$_2$ and 8 mL (55 mmol) triethylamine in 12 mL dry DMF. For the work-up water is added to the reaction mixture. The precipitate is collected, dried at 40° C. and re-crystallized from MeOH. Yield: 1.5 g (83%, approximately 80% pure).

A-34) 3-(2-Amino-4-chloro-6-methyl-pyrimidin-5-ylethynyl)-phenol

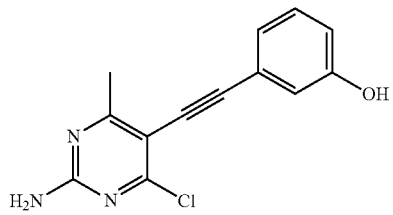 [SMILES: Cc1nc(N)nc(Cl)c1C#Cc1cccc(O)c1]

The title compound is synthesized according to general procedure GP2 starting from 1.5 g (5.7 mmol) 4-chloro-5-iodo-6-methyl-pyrimidin-2-ylamine (GP3) and 986 mg (8.4 mmol) 3-ethynyl-phenol using 106 mg (0.56 mmol) CuI, 390 mg (0.56 mmol) PdCl$_2$(PPh$_3$)$_2$ and 8 mL (55 mmol) triethylamine in 12 mL dry DMF. For the work-up the solvent is removed in vacuo and the product is purified by chromatography on silica gel (DCM/MeOH gradient) and subsequently RP-HPLC (ACN/H$_2$O gradient). Yield: 419 mg (29%).

A-35) 4-Chloro-6-methyl-5-trimethylsilanylethynyl-pyrimidin-2-ylamine

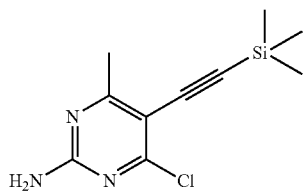

The title compound is synthesized according to general procedure GP2 starting from 5.0 g (19 mmol) 4-chloro-5-iodo-6-methyl-pyrimidin-2-ylamine (GP3) and 3.6 mL (26 mmol) trimethylsilylethyne using 352 mg (1.9 mmol) CuI, 485 mg triphenylphosphine (1.9 mmol), 1.3 g (1.9 mmol) PdCl$_2$(PPh$_3$)$_2$ and 26 mL (185 mmol) triethylamine in 100 mL dry DMF. For the work-up the solvent is removed in vacuo and the product is purified by RP-MPLC (ACN/H$_2$O gradient). Yield: 1.6 g (38%).

A-36) 4-(3-Trifluoromethyl-phenyl)-6-methyl-5-trimethylsilanylethynyl-pyrimidin-2-ylamine

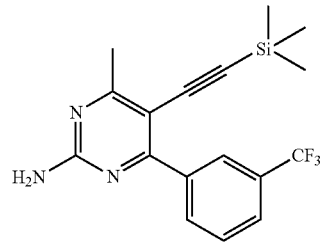 [SMILES: Cc1nc(N)nc(-c2cccc(C(F)(F)F)c2)c1C#C[Si](C)(C)C]

The title compound is synthesized according to general procedure GP2 starting from 1.7 g (7.0 mmol) 4-chloro-6-methyl-5-trimethylsilanylethynyl-pyrimidin-2-ylamine (A-35) and 2.7 g (14 mmol) 3-trifluorophenylboronic acid using 571 mg (0.70 mmol) PdCl$_2$(dppf)$_2$ and 3.4 g (11 mmol) Cs$_2$CO$_3$ in a mixture of 36 mL THF/3.3 mL water. For the work-up the solvent is removed in vacuo and the product is purified by chromatography on silica (DCM/MeOH gradient). Yield: 1.23 g (50%).

A-37) 5-Ethynyl-4-(3-trifluoromethyl-phenyl)-6-methyl-pyrimidin-2-ylamine

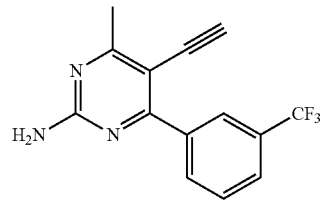 [SMILES: C#Cc1c(C)nc(N)nc1-c1cccc(C(F)(F)F)c1]

The title compound is synthesized according to general procedure GP3 starting from 1.2 g (3.5 mmol) 4-(3-trifluoromethyl-phenyl)-6-methyl-5-trimethylsilanylethynyl-pyrimidin-2-ylamine (A-36) and 120 mg (0.87 mmol) potassium carbonate in 5 mL MeOH. After stirring for 2 h at RT, the reaction mixture is diluted with DCM and the organic phase is extracted with water. The organic phase is dried over NGP$_2$SO$_4$ and the solvent is removed in vacuo. Yield: 523 mg (54%).

A-38) 4-(4-Methanesulfonyl-phenyl)-6-methyl-5-trimethylsilanylethynyl-pyrimidin-2-ylamine

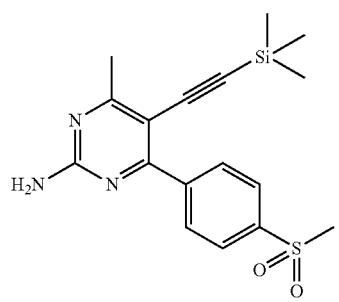 [SMILES: Cc1nc(N)nc(-c2ccc(S(C)(=O)=O)cc2)c1C#C[Si](C)(C)C]

The title compound is synthesized according to general procedure GP2 starting from 3.0 g (7.7 mmol) 5-iodo-4-methyl-6-(4-methanesulfonyl-phenyl)-pyrimidin-2-ylamine (A-33) and 1.6 mL (12 mmol) trimethylsilylethyne using 147 mg (0.77 mmol) CuI, 541 mg (0.77 mmol) PdCl$_2$(PPh$_3$)$_2$ and 11 mL (7.7 mmol) triethylamine in 18 mL dry DMF. For the work-up the solvent is removed in vacuo and the product is purified by chromatography on silica (DCM/MeOH gradient). Yield: 2.45 g (71%, approximately 80% pure).

A-39) 5-Ethynyl-4-(4-methanesulfonyl-phenyl)-6-methyl-pyrimidin-2-ylamine

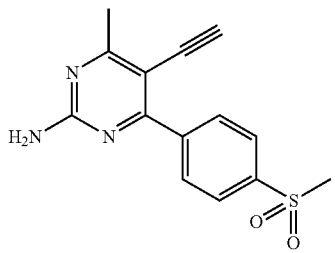 [SMILES: C#Cc1c(C)nc(N)nc1-c1ccc(S(C)(=O)=O)cc1]

The title compound is synthesized according to general procedure GP3 starting from 2.7 g (6.0 mmol) 4-(4-methanesulfonyl-phenyl)-6-methyl-5-trimethylsilanylethynyl-pyrimidin-2-ylamine (A-36) and 415 mg (3.0 mmol) potassium carbonate in 40 mL MeOH. After stirring for 2 h at 0° C. the precipitated product is filtered off and dried over night at 40° C. The product is treated with water, filtered off and dried again. Yield: 1.8 g (83%).

A-40) [3-(2-Amino-6-methyl-pyrimidin-4-yl)-5-trifluoromethyl-phenyl]-carbamic acid tert-butyl ester

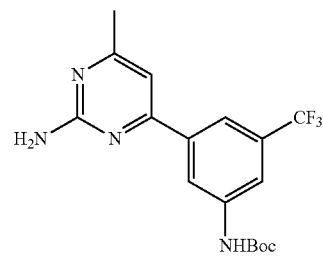 [SMILES: Cc1cc(-c2cc(NC(=O)OC(C)(C)C)cc(C(F)(F)F)c2)nc(N)n1]

The title compound is synthesized according to general procedure GP4 (A) starting from 215 mg (1.5 mmol) 2-amino-4-chloro-6-methylpyrimidine and 2.7 g (14 mmol) 5-trifluoromethyl-3-(tert-butyl-oxyxcarbonyl)aminophenyl boronic acid (GP2). The product is precipitated from the reaction mixture by addition of water. Yield after drying at 40° C.: 550 mg (100%).

A-41) [3-(2-Amino-5-iodo-6-methyl-pyrimidin-4-yl)-5-trifluoromethyl-phenyl]-carbamic acid tert-butyl ester

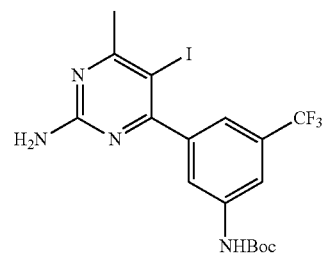 [SMILES: Cc1nc(N)nc(-c2cc(NC(=O)OC(C)(C)C)cc(C(F)(F)F)c2)c1I]

The title compound is synthesized according to general procedure GP1 starting from 550 mg (1.5 mmol) [3-(2-amino-6-methyl-pyrimidin-4-yl)-5-trifluoromethyl-phenyl]-carbamic acid tert-butyl ester (GP40) and 336 mg (1.5 mmol) NIS. Yield: 733 mg (99%).

A-42) {3-[2-Amino-5-(6-amino-pyridin-3-ylethynyl)-6-methyl-pyrimidin-4-yl]-5-trifluoromethyl-phenyl}-carbamic acid tert-butyl ester

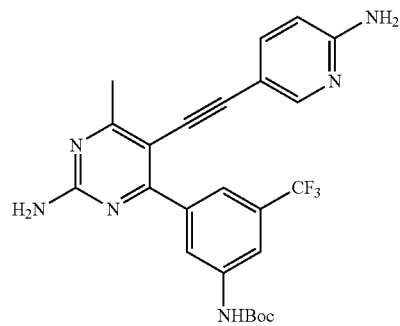 [SMILES: Cc1nc(N)nc(-c2cc(NC(=O)OC(C)(C)C)cc(C(F)(F)F)c2)c1C#Cc1ccc(N)nc1]

The title compound is synthesized according to general procedure GP2 starting from 733 mg (1.5 mmol) [3-(2-amino-5-iodo-6-methyl-pyrimidin-4-yl)-5-trifluoromethyl-phenyl]-carbamic acid tert-butyl ester (A-41) and 262 mg (2.2 mmol) 2-amino-5-ethynyl-pyridine (A-15) using 28 mg (0.15 mmol) CuI, 104 mg (0.15 mmol) PdCl$_2$(PPh$_3$)$_2$ and 2 mL (15 mmol) triethylamine in 14 mL dry DMF. For the work-up the solvent is removed in vacuo and the product is purified by chromatography on silica gel (DCM/MeOH gradient). Yield: 632 mg (88%).

A-43) 5-(6-Amino-pyridin-3-ylethynyl)-4-(3-amino-5-trifluoromethyl-phenyl)-6-methyl-pyrimidin-2-ylamine

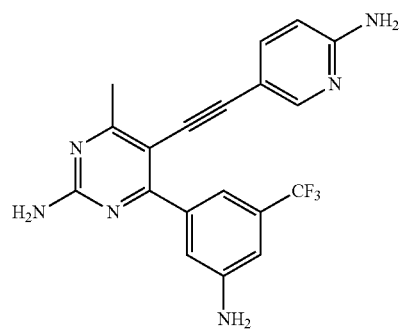 [SMILES: Cc1nc(N)nc(-c2cc(N)cc(C(F)(F)F)c2)c1C#Cc1ccc(N)nc1]

The title compound is synthesized starting from 632 mg (1.3 mmol) {3-[2-amino-5-(6-amino-pyridin-3-ylethynyl)-6-methyl-pyrimidin-4-yl]-5-trifluoromethyl-phenyl}-carbamic acid tert-butyl ester (A-42) by treatment with a 4 M solution of HCl in dioxane. After completion of the reaction the solvent is removed in vacuo followed by extraction with DCM and a saturated aqueous solution of NaHCO$_3$. Yield: 310 mg (62%).

A-44) 3-(2-Amino-4-chloro-6-methyl-pyrimidin-5-ylethynyl)-phenol

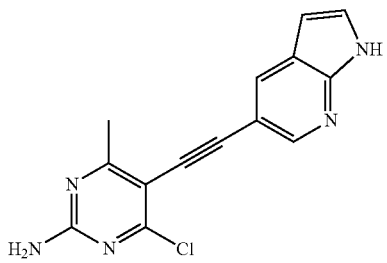 [SMILES: Cc1nc(N)nc(Cl)c1C#Cc1cnc2[nH]ccc2c1]

The title compound is synthesized according to general procedure GP2 starting from 500 mg (1.9 mmol) 4-chloro-5-iodo-6-methyl-pyrimidin-2-ylamine (GP3) and 396 mg (2.8 mmol) 5-ethynyl-1H-pyrrolo[2,3-b]pyridine (A-20) using 35 mg (0.19 mmol) CuI, 130 mg (0.19 mmol) PdCl$_2$(PPh$_3$)$_2$ and 2.6 mL (19 mmol) triethylamine in 6 mL dry DMF. The product precipitates from the reaction mixture, is filtered off and washed with DMF. Yield: 436 mg (75%).

A-45) 4-Chloro-6-methyl-5-(3-methyl-3H-imidazol-4-ylethynyl)-pyrimidin-2-ylamine

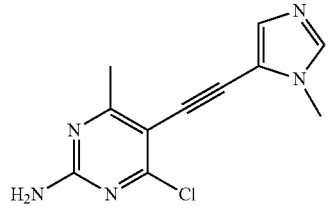 [SMILES: Cc1nc(N)nc(Cl)c1C#Cc1cncn1C]

The title compound is synthesized according to general procedure GP2 starting from 1.4 g (5.3 mmol) 4-chloro-5-iodo-6-methyl-pyrimidin-2-ylamine (A-3) and 900 mg (8.5 mmol) 5-ethynyl-1-methyl-1H-imidazole using 10 mg (0.05 mmol) CuI, 112 mg (0.03 mmol) PdCl$_2$(PPh$_3$)$_2$, 5.3 mL (5.3 mmol) of 9-methoxy-9-BBN and 1.3 mL (9.5 mmol) triethylamine in 125 mL degassed and dry acetonitril. The product precipitates from the reaction mixture and is filtered off. Yield: 780 mg (54%).

EXAMPLES 1-86

Examples 1 to 86 are synthesized according to the general procedures GP2 (Sonogashira reaction), GP4 (Suzuki coupling) or GP6 (nucleophilic displacement) as outlined above. The appropriate halides required for synthesis can be deduced from the table of the examples.

| No. | Educt | Structure | [M + H]$^+$ | $t_{Ret}$ [min] |
|---|---|---|---|---|
| 1 | A-37 | 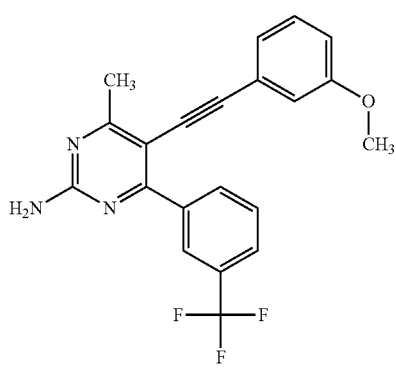 [SMILES: COc1cccc(C#Cc2c(C)nc(N)nc2-c2cccc(C(F)(F)F)c2)c1] | 384 | 2.40 |
| 2 | A-29 | 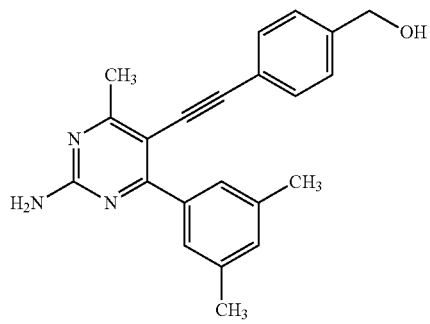 [SMILES: Cc1cc(C)cc(-c2nc(N)nc(C)c2C#Cc2ccc(CO)cc2)c1] | 344 | 1.98 |

| No. | Educt | Structure | [M + H]⁺ | t$_{Ret}$ [min] |
|---|---|---|---|---|
| 3 | A-27 | 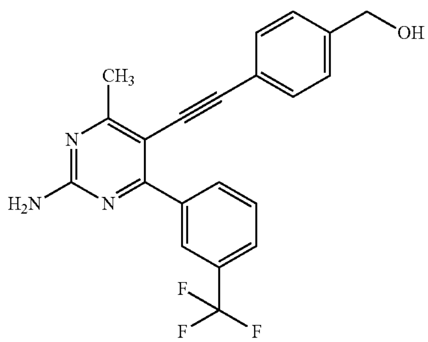 [SMILES: Cc1nc(N)nc(-c2cccc(C(F)(F)F)c2)c1C#Cc1ccc(CO)cc1] | 384 | 2.06 |
| 4 | A-27 | 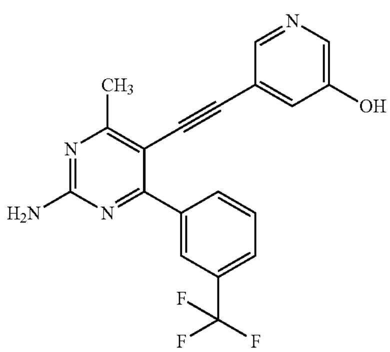 [SMILES: Cc1nc(N)nc(-c2cccc(C(F)(F)F)c2)c1C#Cc1cncc(O)c1] | 371 | 1.32 |
| 5 | A-43 | 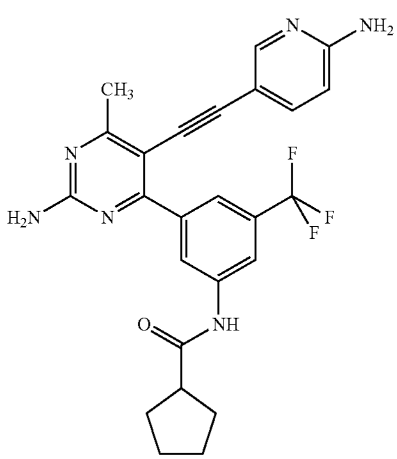 [SMILES: Cc1nc(N)nc(-c2cc(NC(=O)C3CCCC3)cc(C(F)(F)F)c2)c1C#Cc1ccc(N)nc1] | 481 | 1.04 |
| 6 | A-43 | 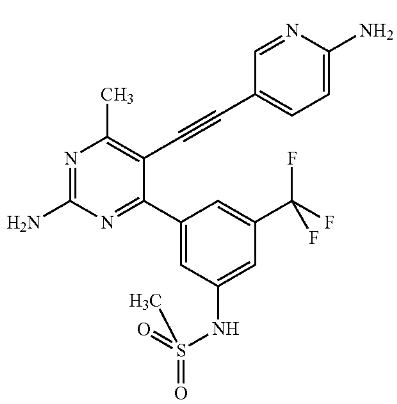 [SMILES: Cc1nc(N)nc(-c2cc(NS(C)(=O)=O)cc(C(F)(F)F)c2)c1C#Cc1ccc(N)nc1] | 463 | 1.36 |

-continued
| No. | Educt | Structure | [M + H]+ | $t_{Ret}$ [min] |
|---|---|---|---|---|
| 7 | A-28 | 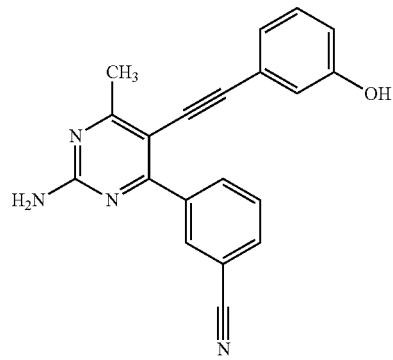 [SMILES: Cc1nc(N)nc(-c2cccc(C#N)c2)c1C#Cc1cccc(O)c1] | 327 | 1.67 |
| 8 | A-29 | 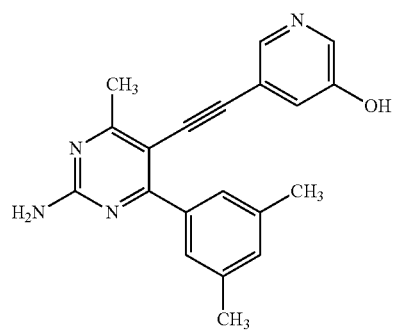 [SMILES: Cc1cc(C)cc(-c2nc(N)nc(C)c2C#Cc2cncc(O)c2)c1] | 331 | 1.22 |
| 9 | A-27 | 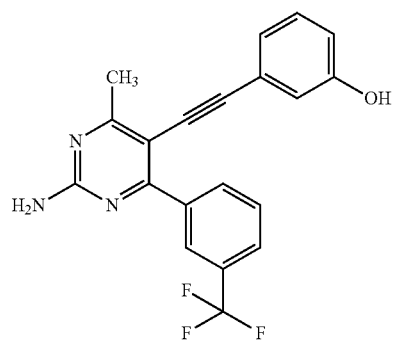 [SMILES: Cc1nc(N)nc(-c2cccc(C(F)(F)F)c2)c1C#Cc1cccc(O)c1] | 370 | 1.90 |
| 10 | A-37 | 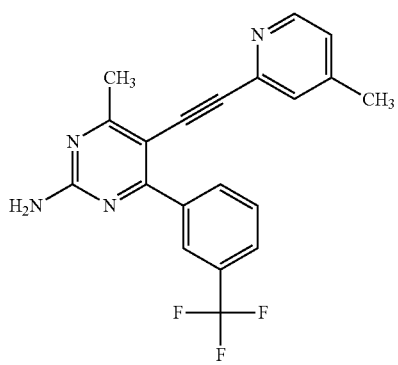 [SMILES: Cc1ccnc(C#Cc2c(C)nc(N)nc2-c2cccc(C(F)(F)F)c2)c1] | 369 | 2.14 |

-continued

| No. | Educt | Structure | [M + H]⁺ | t$_{Ret}$ [min] |
|---|---|---|---|---|
| 11 | A-28 | 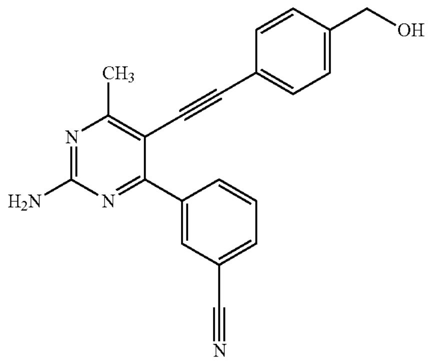 [SMILES: Cc1nc(N)nc(-c2cccc(C#N)c2)c1C#Cc1ccc(CO)cc1] | 341 | 1.79 |
| 12 | A-28 | 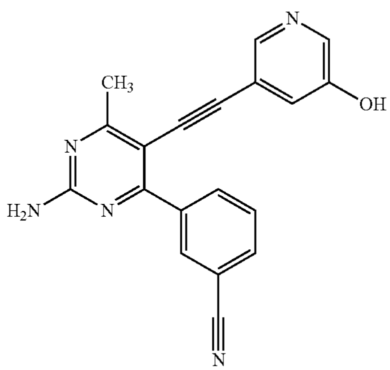 [SMILES: Cc1nc(N)nc(-c2cccc(C#N)c2)c1C#Cc1cncc(O)c1] | 328 | 1.11 |
| 13 | A-43 | 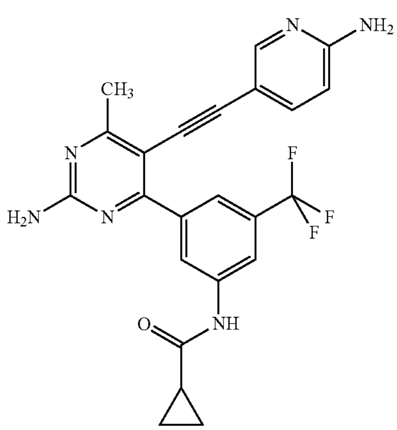 [SMILES: Cc1nc(N)nc(-c2cc(NC(=O)C3CC3)cc(C(F)(F)F)c2)c1C#Cc1ccc(N)nc1] | 453 | 1.87 |
| 14 | A-39 | 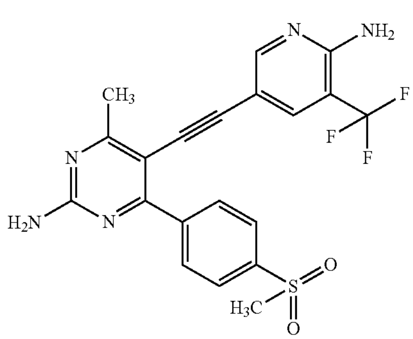 [SMILES: Cc1nc(N)nc(-c2ccc(S(C)(=O)=O)cc2)c1C#Cc1cnc(N)c(C(F)(F)F)c1] | 448 | 1.84 |

| No. | Educt | Structure | [M + H]+ | t_Ret [min] |
|---|---|---|---|---|
| 15 | A-30 | (structure) | 394 | 1.66 |
| 16 | A-39 | (structure) | 379 | 1.69 |
| 17 | A-30 | (structure) | 405 | 1.59 |
| 18 | A-32 | (structure) | 305 | 1.06 |

-continued
| No. | Educt | Structure | [M + H]⁺ | t$_{Ret}$ [min] |
|---|---|---|---|---|
| 19 | A-32 | 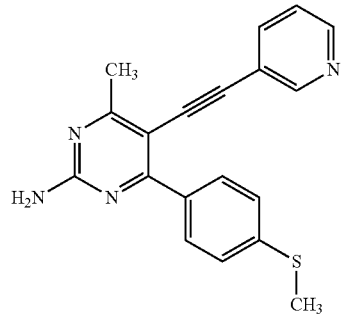 | 333 | 1.10 |
| 20 | A-45 | 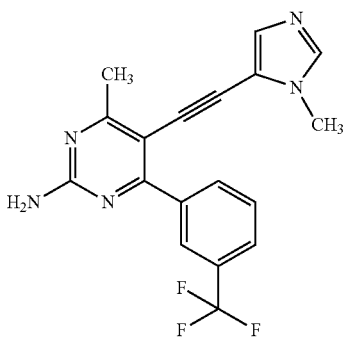 [SMILES: Cc1nc(N)nc(-c2cccc(C(F)(F)F)c2)c1C#Cc1cncn1C] | 358 | 1.04 |
| 21 | A-32 | 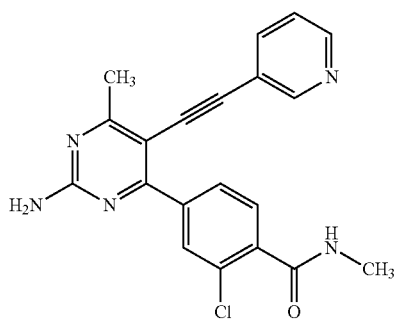 [SMILES: CNC(=O)c1ccc(-c2nc(N)nc(C)c2C#Cc2cccnc2)cc1Cl] | 378/379 | 0.94 |
| 22 | A-32 | 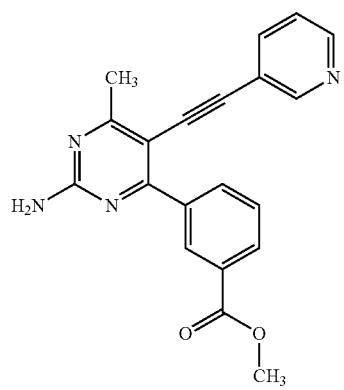 [SMILES: COC(=O)c1cccc(-c2nc(N)nc(C)c2C#Cc2cccnc2)c1] | 345 | 1.05 |

-continued

| No. | Educt | Structure | [M + H]+ | t_Ret [min] |
|---|---|---|---|---|
| 23 | A-32 | 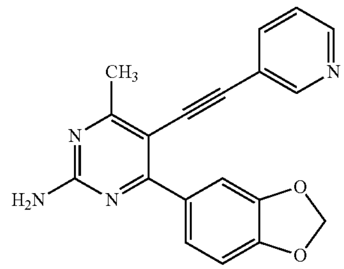 [SMILES: Cc1nc(N)nc(-c2ccc3c(c2)OCO3)c1C#Cc1cccnc1] | 331 | 1.03 |
| 24 | A-45 | 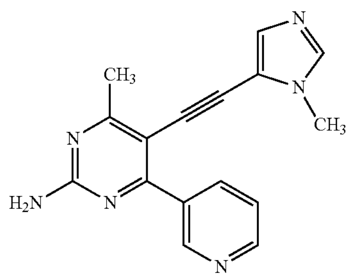 [SMILES: Cc1nc(N)nc(-c2cccnc2)c1C#Cc1cncn1C] | 291 | 0.80 |
| 25 | A-45 | 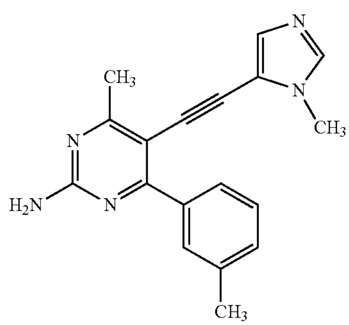 [SMILES: Cc1cccc(-c2nc(N)nc(C)c2C#Cc2cncn2C)c1] | 304 | 0.98 |
| 26 | A-45 | 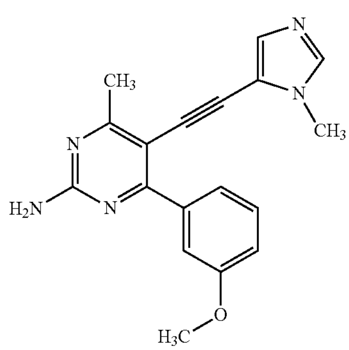 [SMILES: COc1cccc(-c2nc(N)nc(C)c2C#Cc2cncn2C)c1] | 320 | 0.94 |
| 27 | A-45 | 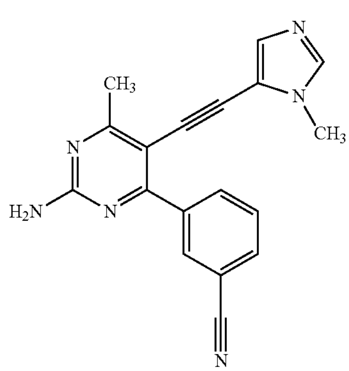 [SMILES: Cc1nc(N)nc(-c2cccc(C#N)c2)c1C#Cc1cncn1C] | 315 | 0.92 |

-continued

| No. | Educt | Structure | [M + H]+ | t_Ret [min] |
|---|---|---|---|---|
| 28 | A-45 | 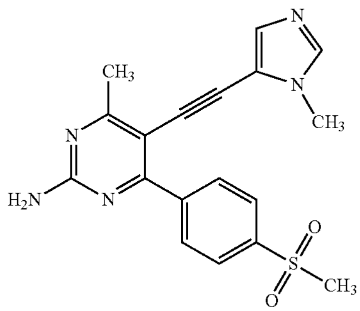 [SMILES: Cc1nc(N)nc(-c2ccc(S(C)(=O)=O)cc2)c1C#Cc1cncn1C] | 368 | 0.86 |
| 29 | A-32 | 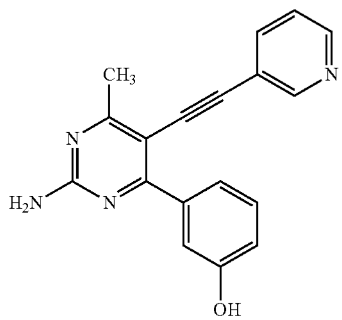 [SMILES: Cc1nc(N)nc(-c2cccc(O)c2)c1C#Cc1cccnc1] | 303 | 0.81 |
| 30 | A-32 | 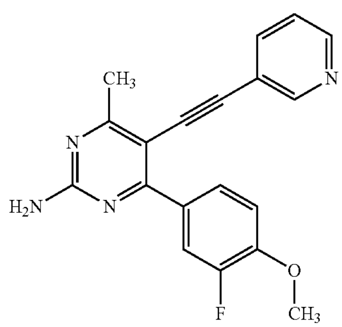 [SMILES: COc1ccc(-c2nc(N)nc(C)c2C#Cc2cccnc2)cc1F] | 335 | 1.06 |
| 31 | A-32 | 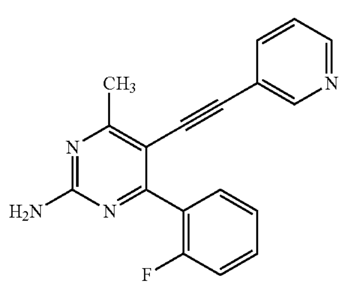 [SMILES: Cc1nc(N)nc(-c2ccccc2F)c1C#Cc1cccnc1] | 305 | 1.01 |
| 32 | A-32 | 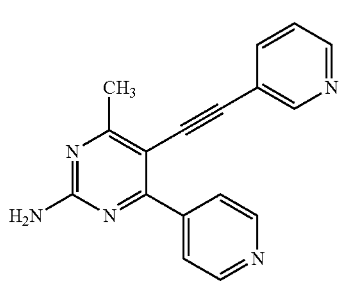 [SMILES: Cc1nc(N)nc(-c2ccncc2)c1C#Cc1cccnc1] | 288 | 0.89 |

-continued

| No. | Educt | Structure | [M + H]+ | t_{Ret} [min] |
|-----|-------|-----------|----------|---------------|
| 33 | A-32 | 2-amino-4-methyl-6-(3-acetamidophenyl)-5-(pyridin-3-ylethynyl)pyrimidine | 344 | 0.92 |
| 34 | A-32 | 2-amino-4-methyl-6-(3-aminophenyl)-5-(pyridin-3-ylethynyl)pyrimidine | 302 | 0.92 |
| 35 | A-32 | 2-amino-4-methyl-6-[3-(2-carboxyvinyl)phenyl]-5-(pyridin-3-ylethynyl)pyrimidine | 357 | 0.73 |
| 36 | A-32 | 2-amino-4-methyl-6-(4-vinylphenyl)-5-(pyridin-3-ylethynyl)pyrimidine | 313 | 1.11 |

-continued

| No. | Educt | Structure | [M + H]+ | $t_{Ret}$ [min] |
|---|---|---|---|---|
| 37 | A-32 | 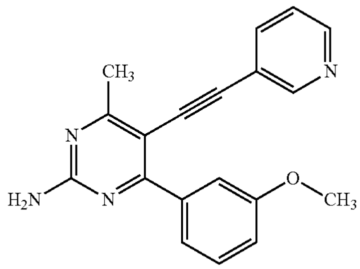 [SMILES: COc1cccc(-c2nc(N)nc(C)c2C#Cc2cccnc2)c1] | 317 | 1.80 |
| 38 | A-32 | 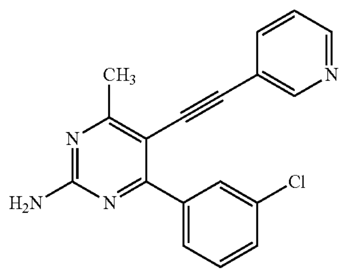 [SMILES: Cc1nc(N)nc(-c2cccc(Cl)c2)c1C#Cc1cccnc1] | 321 | 1.96 |
| 39 | A-32 | 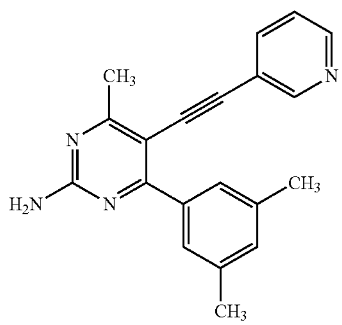 [SMILES: Cc1cc(C)cc(-c2nc(N)nc(C)c2C#Cc2cccnc2)c1] | 315 | 1.99 |
| 40 | A-32 | 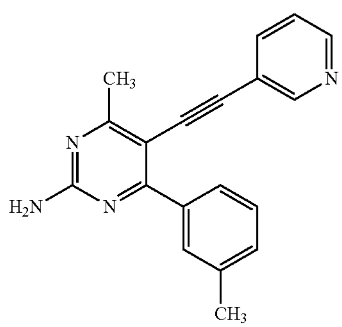 [SMILES: Cc1cccc(-c2nc(N)nc(C)c2C#Cc2cccnc2)c1] | 301 | 1.89 |
| 41 | A-30 | 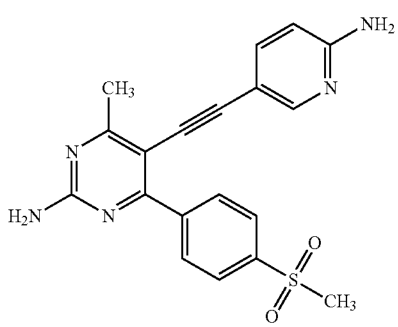 [SMILES: Cc1nc(N)nc(-c2ccc(S(C)(=O)=O)cc2)c1C#Cc1ccc(N)nc1] | 380 | 1.52 |

| No. | Educt | Structure | [M + H]⁺ | $t_{Ret}$ [min] |
|---|---|---|---|---|
| 42 | A-33 | 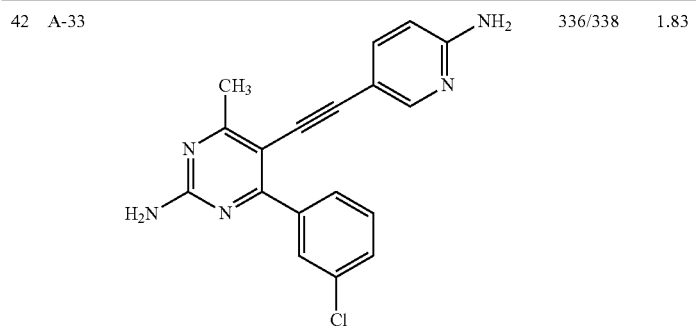 | 336/338 | 1.83 |
| 43 | A-33 | 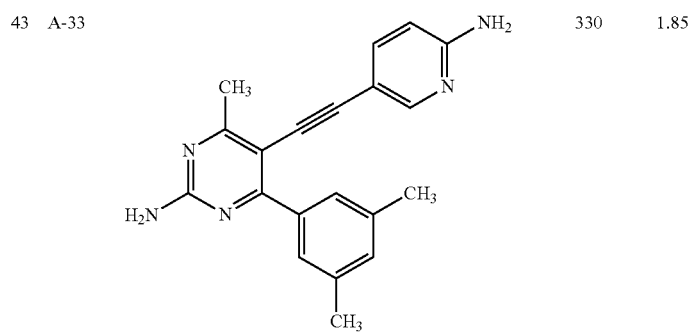 | 330 | 1.85 |
| 44 | A-33 | 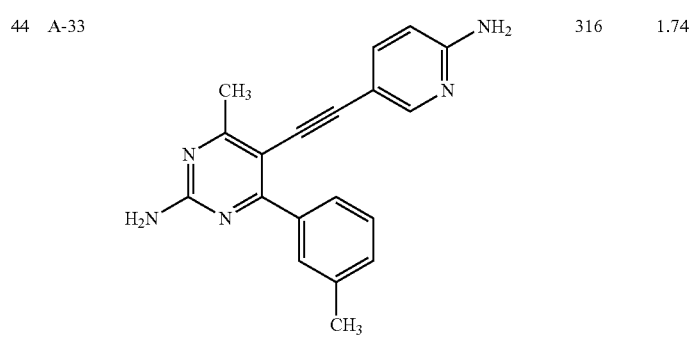 | 316 | 1.74 |
| 45 | A-33 | 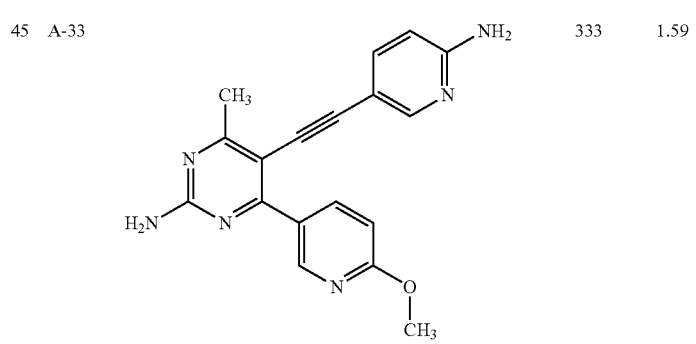 | 333 | 1.59 |

| No. | Educt | Structure | [M + H]⁺ | $t_{Ret}$ [min] |
|---|---|---|---|---|
| 46 | A-28 | (structure) | 327 | 1.65 |
| 47 | A-27 | (structure) | 355 | 2.04 |
| 48 | A-30 | (structure) | 365 | 1.60 |
| 49 | A-32 | (structure) | 312 | 1.77 |
| 50 | A-32 | (structure) | 288 | 1.50 |

-continued
| No. | Educt | Structure | [M + H]⁺ | $t_{Ret}$ [min] |
|---|---|---|---|---|
| 51 | A-33 | 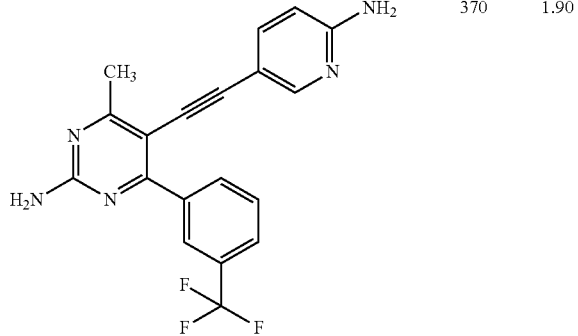 | 370 | 1.90 |
| 52 | A-44 | 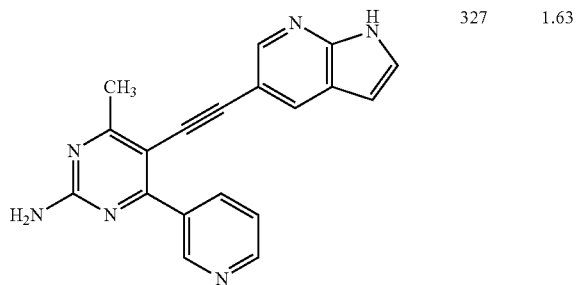 | 327 | 1.63 |
| 53 | A-44 | 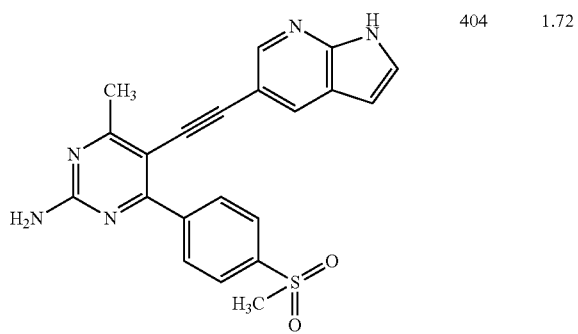 | 404 | 1.72 |
| 54 | A-32 | 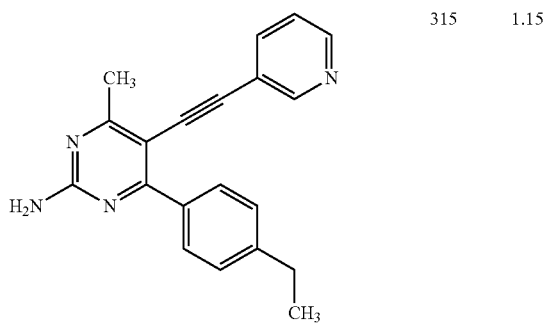 | 315 | 1.15 |

-continued
| No. | Educt | Structure | [M + H]+ | t_Ret [min] |
|---|---|---|---|---|
| 55 | A-32 | 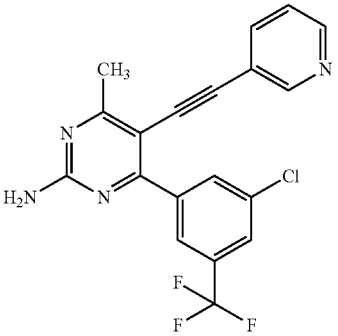 [SMILES: Cc1nc(N)nc(-c2cc(Cl)cc(C(F)(F)F)c2)c1C#Cc1cccnc1] | 389/391 | 1.23 |
| 56 | A-32 | 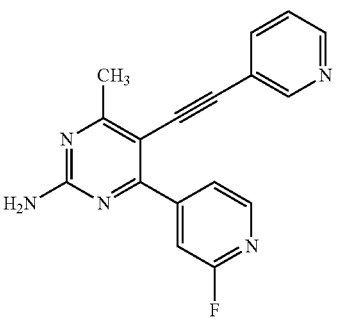 [SMILES: Cc1nc(N)nc(-c2ccnc(F)c2)c1C#Cc1cccnc1] | 306 | 0.96 |
| 57 | A-32 | 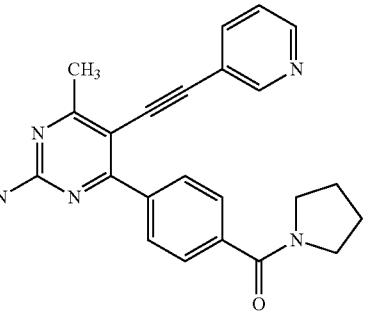 | 384 | 0.97 |
| 58 | A-31 | 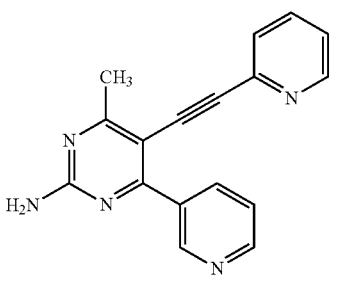 [SMILES: Cc1nc(N)nc(-c2cccnc2)c1C#Cc1ccccn1] | 288 | 0.89 |
| 59 | A-31 | 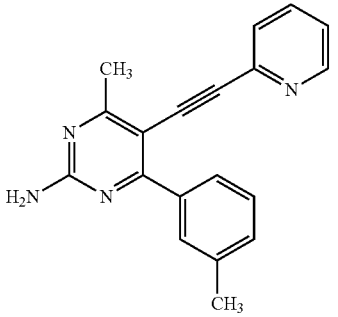 [SMILES: Cc1cccc(-c2nc(N)nc(C)c2C#Cc2ccccn2)c1] | 301 | 1.09 |

| No. | Educt | Structure | [M + H]+ | $t_{Ret}$ [min] |
|---|---|---|---|---|
| 60 | A-31 | 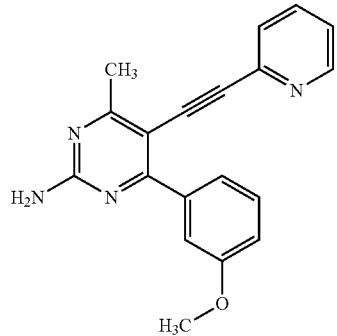 [SMILES: COc1cccc(-c2nc(N)nc(C)c2C#Cc2ccccn2)c1] | 317 | 1.04 |
| 61 | A-31 | 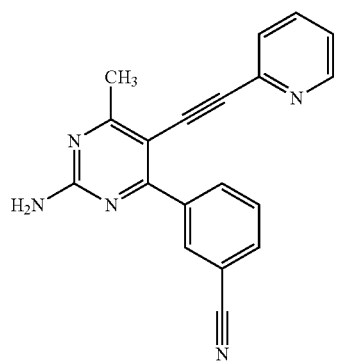 [SMILES: Cc1nc(N)nc(-c2cccc(C#N)c2)c1C#Cc1ccccn1] | 312 | 1.02 |
| 62 | A-31 | 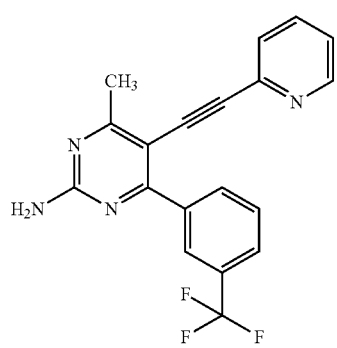 [SMILES: Cc1nc(N)nc(-c2cccc(C(F)(F)F)c2)c1C#Cc1ccccn1] | 355 | 1.14 |
| 63 | A-31 | 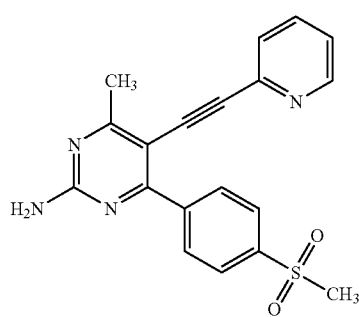 | 365 | 2.92 |

-continued
| No. | Educt | Structure | [M + H]+ | $t_{Ret}$ [min] |
|---|---|---|---|---|
| 64 | A-32 | 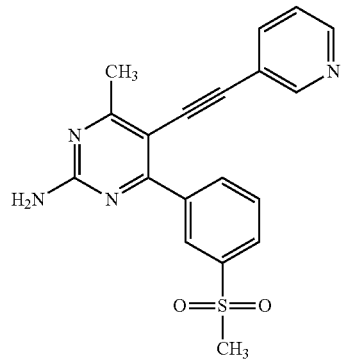 [SMILES: Cc1nc(N)nc(-c2cccc(S(C)(=O)=O)c2)c1C#Cc1cccnc1] | 365 | 0.95 |
| 65 | A-32 | 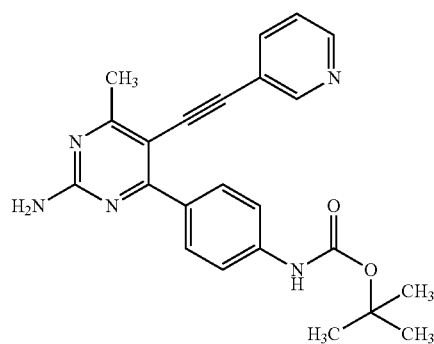 [SMILES: Cc1nc(N)nc(-c2ccc(NC(=O)OC(C)(C)C)cc2)c1C#Cc1cccnc1] | 402 | 1.12 |
| 66 | A-32 | 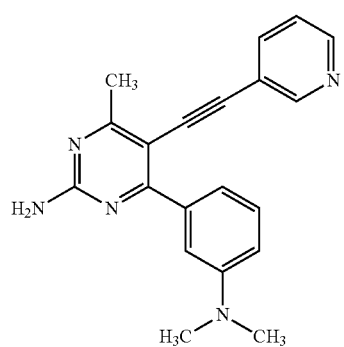 [SMILES: Cc1nc(N)nc(-c2cccc(N(C)C)c2)c1C#Cc1cccnc1] | 330 | 1.06 |
| 67 | A-32 | 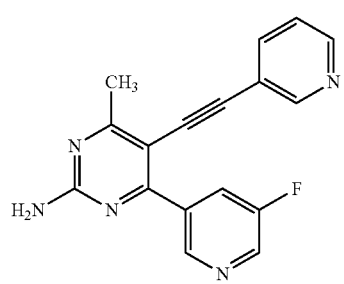 [SMILES: Cc1nc(N)nc(-c2cncc(F)c2)c1C#Cc1cccnc1] | 306 | 0.95 |

-continued
| No. | Educt | Structure | [M + H]+ | $t_{Ret}$ [min] |
|---|---|---|---|---|
| 68 | A-32 | 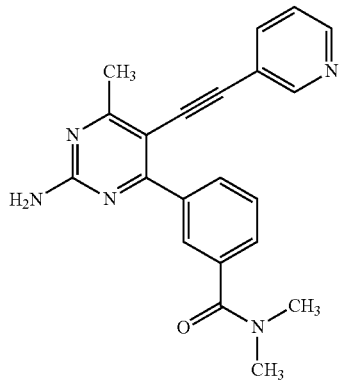 [SMILES: Cc1nc(N)nc(-c2cccc(C(=O)N(C)C)c2)c1C#Cc1cccnc1] | 358 | 0.93 |
| 69 | A-32 | 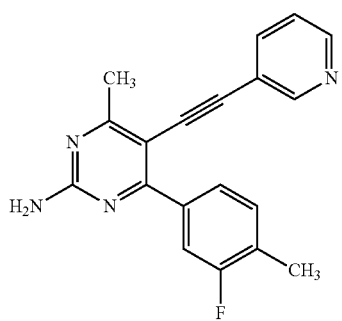 | 319 | 1.11 |
| 70 | A-32 | 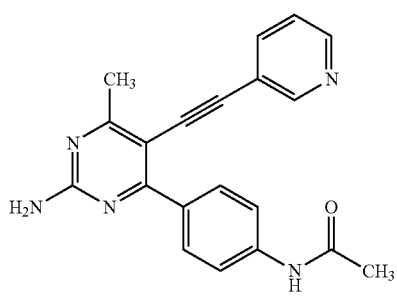 [SMILES: CC(=O)Nc1ccc(-c2nc(N)nc(C)c2C#Cc2cccnc2)cc1] | 344 | 0.91 |
| 71 | A-32 | 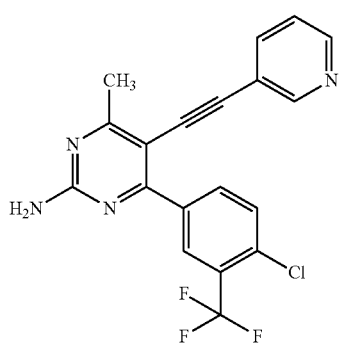 [SMILES: Cc1nc(N)nc(-c2ccc(Cl)c(C(F)(F)F)c2)c1C#Cc1cccnc1] | 389/391 | 1.20 |

-continued
| No. | Educt | Structure | [M + H]+ | t_Ret [min] |
|---|---|---|---|---|
| 72 | A-32 | 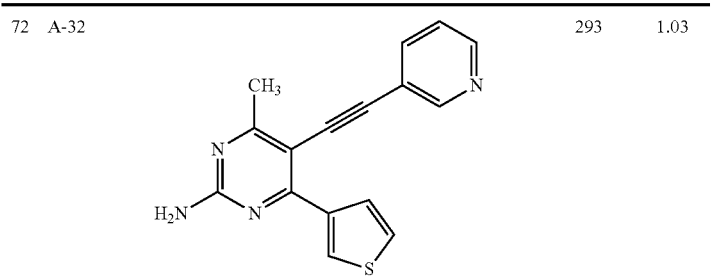 | 293 | 1.03 |
| 73 | A-32 | 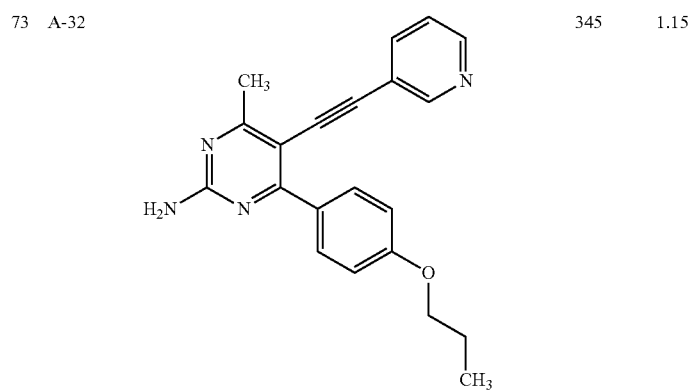 | 345 | 1.15 |
| 74 | A-32 | 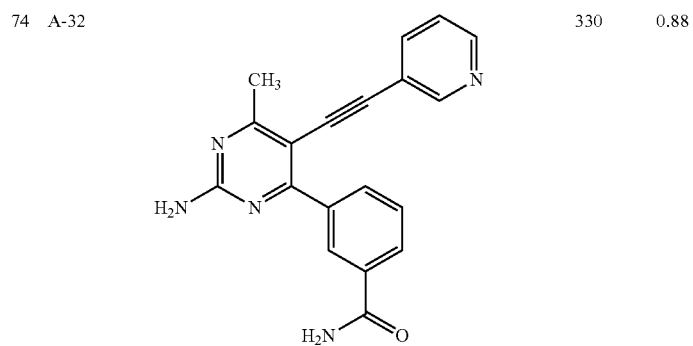 | 330 | 0.88 |
| 75 | A-32 | 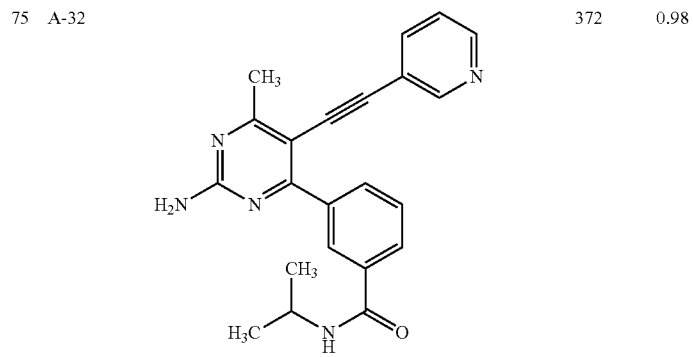 | 372 | 0.98 |

-continued

| No. | Educt | Structure | [M + H]+ | t$_{Ret}$ [min] |
|---|---|---|---|---|
| 76 | A-32 | 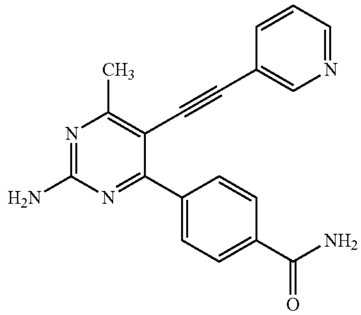 [SMILES: Cc1nc(N)nc(-c2ccc(C(N)=O)cc2)c1C#Cc1cccnc1] | 330 | 0.87 |
| 77 | A-32 | 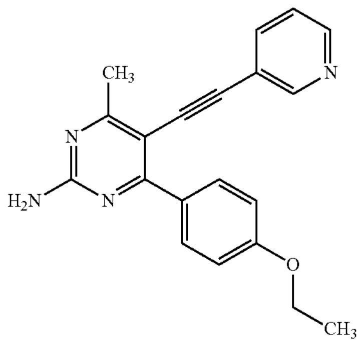 [SMILES: CCOc1ccc(-c2nc(N)nc(C)c2C#Cc2cccnc2)cc1] | 331 | 1.09 |
| 78 | A-32 | 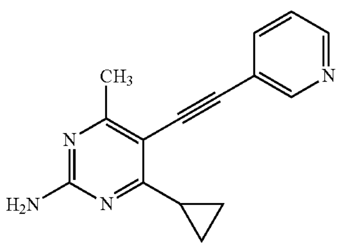 [SMILES: Cc1nc(N)nc(C2CC2)c1C#Cc1cccnc1] | 251 | 1.00 |
| 79 | A-32 | 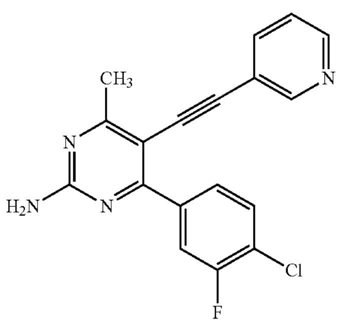 [SMILES: Cc1nc(N)nc(-c2ccc(Cl)c(F)c2)c1C#Cc1cccnc1] | 339/341 | 1.14 |
| 80 | A-32 | 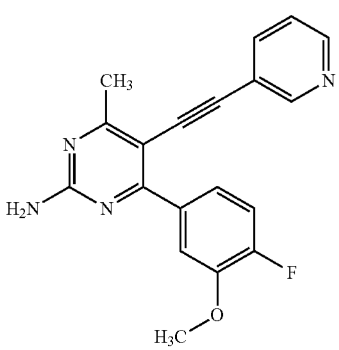 [SMILES: COc1cc(-c2nc(N)nc(C)c2C#Cc2cccnc2)ccc1F] | 335 | 1.06 |

-continued
| No. | Educt | Structure | [M + H]⁺ | $t_{Ret}$ [min] |
|---|---|---|---|---|
| 81 | A-32 | 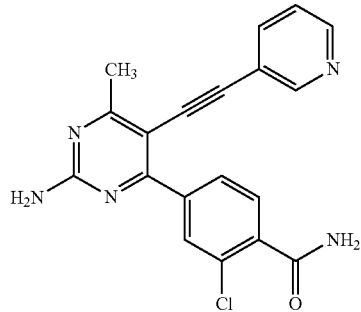 [SMILES: Cc1nc(N)nc(-c2ccc(C(N)=O)c(Cl)c2)c1C#Cc1cccnc1] | 364/366 | 0.90 |
| 82 | A-32 | 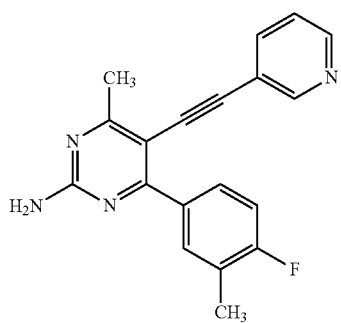 [SMILES: Cc1cc(-c2nc(N)nc(C)c2C#Cc2cccnc2)ccc1F] | 319 | 1.10 |
| 83 | A-32 | 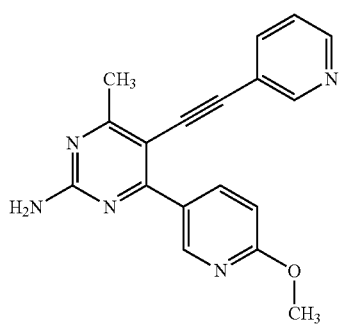 [SMILES: COc1ccc(-c2nc(N)nc(C)c2C#Cc2cccnc2)cn1] | 318 | 0.99 |
| 84 | A-30 | 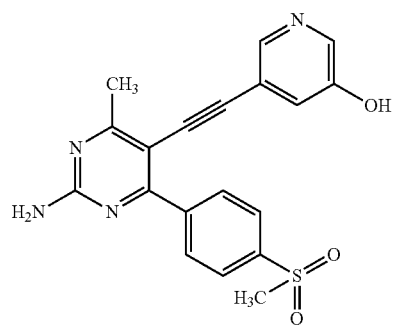 [SMILES: Cc1nc(N)nc(-c2ccc(S(C)(=O)=O)cc2)c1C#Cc1cncc(O)c1] | 381 | 0 |

-continued

| No. | Educt | Structure | [M + H]⁺ | $t_{Ret}$ [min] |
|---|---|---|---|---|
| 85 | A-30 | 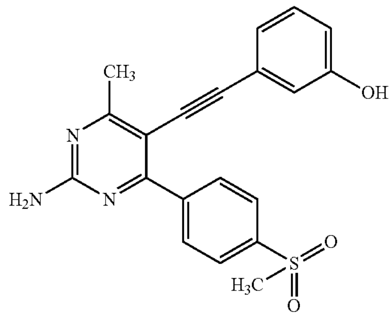 [SMILES: Cc1nc(N)nc(-c2ccc(S(C)(=O)=O)cc2)c1C#Cc1cccc(O)c1] | 380 | 1.50 |

INTERMEDIATES B

B-1) 6-Chloro-5-iodo-pyrimidine-2,4-diamine

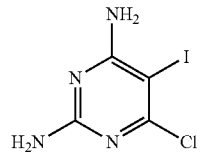

The title compound is synthesized according to general procedure GP1 starting from 25 g (173 mmol) 6-chloro-pyrimidine-2,4-diamine and 39 g (173 mmol) NIS. Yield after precipitation of the product from water: 38.8 g (83%).

B-2) 6-Chloro-5-pyridin-3-ylethynyl-pyrimidine-2,4-diamine

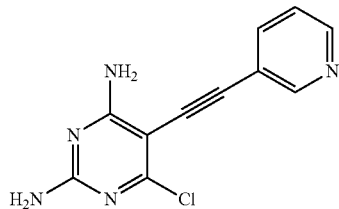 [SMILES: Nc1nc(N)c(C#Cc2cccnc2)c(Cl)n1]

The title compound is synthesized according to general procedure GP2 starting from 1.0 g (3.7 mmol) 6-chloro-5-iodo-pyrimidine-2,4-diamine, 494 g (4.79 mmol) 3-ethynylpyridine, 70 mg (0.37 mmol) CuI, 259 mg (0.37 mmol) PdCl$_2$(PPh$_3$)$_2$ and 85 mL triethylamine in 60 mL dry DMF. Yield after purification by chromatography on silica gel: 800 mg (88%).

B-3) 5-(6-Amino-pyridin-3-ylethynyl)-6-chloro-pyrimidine-2,4-diamine

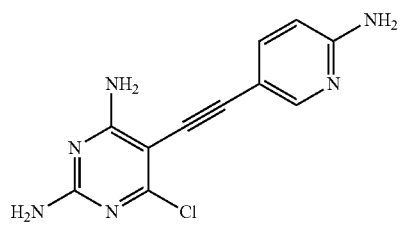 [SMILES: Nc1ccc(C#Cc2c(N)nc(N)nc2Cl)cn1]

The title compound is synthesized according to general procedure GP2 starting from 850 mg (3.1 mmol) 6-chloro-5-iodo-pyrimidine-2,4-diamine, 2.2 g (19 mmol) 5-ethynyl-2-amino-pyridine, 59 mg (0.31 mmol) CuI, 218 mg (0.31 mmol) PdCl$_2$(PPh$_3$)$_2$ and 21 mL triethylamine in 25 mL dry DMF. Yield after purification by RP-HPLC: 720 mg (88%).

B-4) 3-(2,4-Diamino-6-chloro-pyrimidin-5-ylethynyl)-phenol

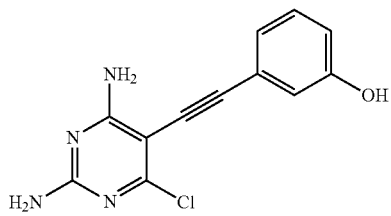 [SMILES: Nc1nc(N)c(C#Cc2cccc(O)c2)c(Cl)n1]

The title compound is synthesized according to general procedure GP2 starting from 500 mg (1.8 mmol) 6-chloro-5-iodo-pyrimidine-2,4-diamine, 827 mg (7.0 mmol) 3-ethynyl-phenol, 35 mg (0.19 mmol) CuI, 129 mg (0.19 mmol) PdCl$_2$(PPh$_3$)$_2$ and 4.1 mL triethylamine in 4 mL dry DMF. Yield after purification by RP-HPLC: 511 mg (100%).

B-5) 6-(3-Trifluoromethyl-phenyl)-pyrimidine-2,4-diamine

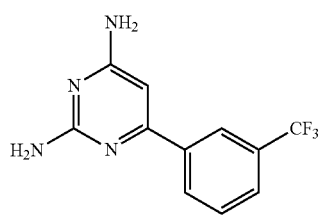 [SMILES: Nc1cc(-c2cccc(C(F)(F)F)c2)nc(N)n1]

The title compound is synthesized according to general procedure GP4 (A) starting from 1.3 g (9.0 mmol) 6-chloro-pyrimidine-2,4-diamine, 2.2 g (12 mmol) 3-trifluorophenyl boronic acid, 260 mg Pd(PPh3)4 and 7.7 mL 2 M aqueous solution of K$_2$CO$_3$ and 26 mL dimethoxyethane. Yield after chromatography by RP-HPLC: 1.25 g (55%).

B-6) 5-Iodo-6-(3-trifluoromethyl-phenyl)-pyrimidine-2,4-diamine

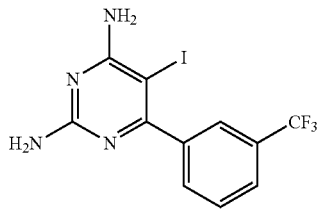 [SMILES: Nc1nc(N)c(I)c(-c2cccc(C(F)(F)F)c2)n1]

The title compound is synthesized according to general procedure GP1 starting from 1.8 g (7.1 mmol) 6-(3-trifluoromethyl-phenyl)-pyrimidine-2,4-diamine and 1.8 g (7.8 mmol) NIS. Yield: 2.0 g (74%).

B-7) 2-Methylsulfanyl-6-(3-trifluoromethyl-phenyl)-pyrimidin-4-ylamine

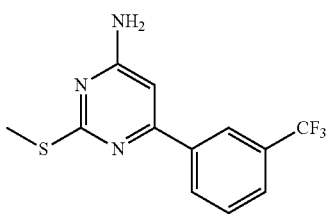 [SMILES: CSc1nc(N)cc(-c2cccc(C(F)(F)F)c2)n1]

The title compound is synthesized according to general procedure GP4 (C) starting from 1.0 g (5.7 mmol) 6-chloro-2-methylsulfanyl-pyrimidin-4-ylamine, 1.4 g (7.4 mmol) 3-trifluorophenylboronic acid, 164 mg Pd(PPh$_3$)$_4$ and 1.6 g (11 mmol) K$_2$CO$_3$ in a DME/water mixture 16/5 v/v). The solvent is removed under reduced pressure, the crude product separated between water and ethyl acetate. The organic layer is separated, dried over NGP$_2$SO$_4$ and filtered off. The solvent is removed under reduced pressure. The crude product is used without further purification. Yield: 2.14 g (100%).

B-8) 5-Iodo-2-methylsulfanyl-6-(3-trifluoromethyl-phenyl)-pyrimidin-4-ylamine

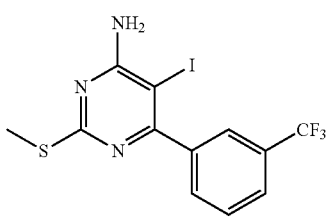 [SMILES: CSc1nc(N)c(I)c(-c2cccc(C(F)(F)F)c2)n1]

The title compound is synthesized according to general procedure GP2 starting from 2.0 g (7.0 mmol) 2-methylsulfanyl-6-(3-trifluoromethyl-phenyl)-pyrimidin-4-ylamine and 1.6 g (7.0 mmol) NIS. Yield after precipitation: 1.9 g (66%).

B-9) 5-(6-Amino-pyridin-3-ylethynyl)-2-methylsulfanyl-6-(3-trifluoromethyl-phenyl)-pyrimidin-4-ylamine

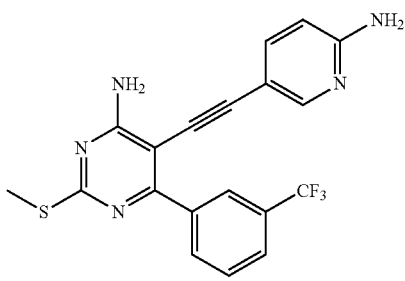 [SMILES: CSc1nc(N)c(C#Cc2ccc(N)nc2)c(-c2cccc(C(F)(F)F)c2)n1]

The title compound is synthesized according to general procedure GP2 starting from 850 mg (2.1 mmol) 5-iodo-2-methylsulfanyl-6-(3-trifluoromethyl-phenyl)-pyrimidin-4-ylamine, 1.5 g (12.4 mmol) 5-ethynyl-2-amino-pyridine, 39 mg (0.21 mmol) CuI, 145 mg (0.21 mmol) PdCl$_2$(PPh$_3$)$_2$ and 2.9 mL triethylamine in 15 mL dry DMF. Yield after purification by RP-HPLC: 427 mg (52%).

B-10) 5-(6-Amino-pyridin-3-ylethynyl)-2-methanesulfonyl-6-(3-trifluoromethyl-phenyl)-pyrimidin-4-ylamine

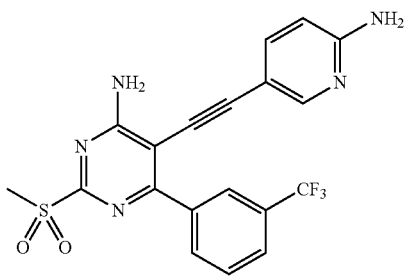 [SMILES: CS(=O)(=O)c1nc(N)c(C#Cc2ccc(N)nc2)c(-c2cccc(C(F)(F)F)c2)n1]

m-CPBA (859 mg, 5.0 mmol) is added to a solution of 1.0 g (2.5 mmol) 5-(6-amino-pyridin-3-ylethynyl)-2-methylsulfanyl-6-(3-trifluoromethyl-phenyl)-pyrimidin-4-ylamine in 100 mL DCM. After stirring for 48 h at RT additional 215 mg m-CPBA are added and the mixture is stirred for additional 24 h. A mixture of sulfone and sulfoxide is formed. The precipitate is filtered off and washed with DCM (510 mg). Additional product is isolated from the liquid phase after extraction with water and removal of the solvent from the organic phase. Yield: 1.1 g (100%).

EXAMPLES 86-139

Examples 86-139 are synthesized according to the general procedures GP2 (Sonogashira reaction), GP4 (Suzuki coupling) or GP6 (nucleophilic displacement) outlined above. The appropriate halides required for synthesis can be deduced from the table of examples.

| No. | Educt | Structure | [M + H]⁺ | t$_{Ret}$ [min] |
|---|---|---|---|---|
| 86 | B-2 | 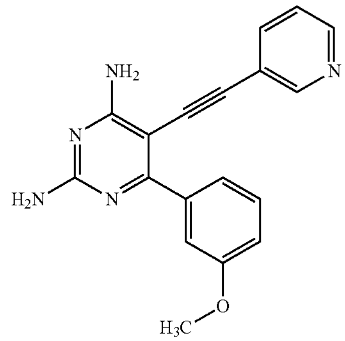 [SMILES: COc1cccc(-c2nc(N)nc(N)c2C#Cc2cccnc2)c1] | 318 | 0.96 |
| 87 | B-2 | 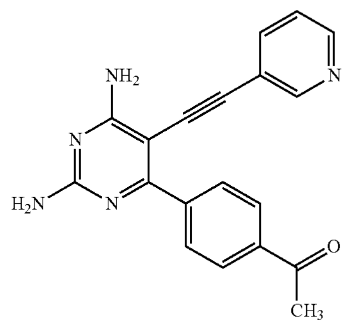 [SMILES: CC(=O)c1ccc(-c2nc(N)nc(N)c2C#Cc2cccnc2)cc1] | 330 | 0.91 |
| 88 | B-2 | 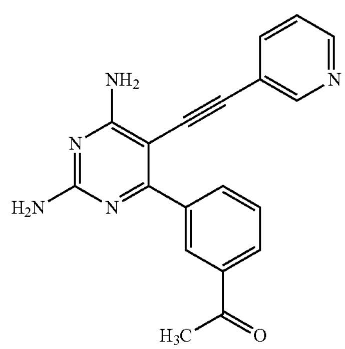 | 330 | 0.91 |
| 89 | B-6 | 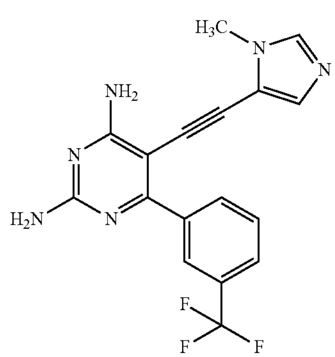 [SMILES: Cn1cncc1C#Cc1c(N)nc(N)nc1-c1cccc(C(F)(F)F)c1] | 359 | 0.97 |

| No. | Educt | Structure | [M + H]⁺ | t$_{Ret}$ [min] |
|---|---|---|---|---|
| 90 | B-6 | 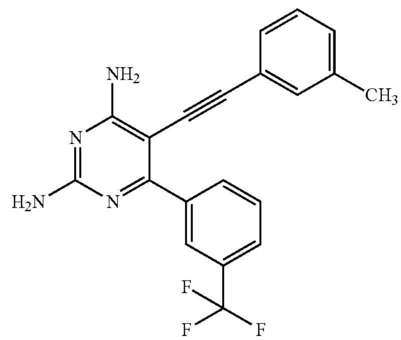 [SMILES: Cc1cccc(C#Cc2c(N)nc(N)nc2-c2cccc(C(F)(F)F)c2)c1] | 369 | 1.25 |
| 91 | B-4 | 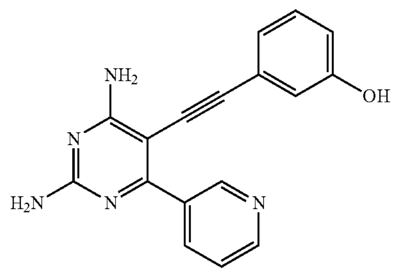 [SMILES: Nc1nc(N)c(C#Cc2cccc(O)c2)c(-c2cccnc2)n1] | 304 | 1.41 |
| 92 | B-2 | 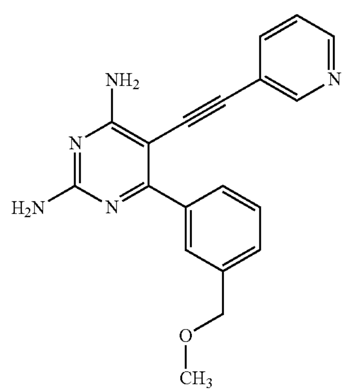 [SMILES: COCc1cccc(-c2nc(N)nc(N)c2C#Cc2cccnc2)c1] | 332 | 0.92 |
| 93 | B-2 | 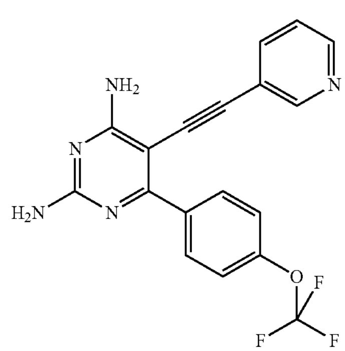 [SMILES: Nc1nc(N)c(C#Cc2cccnc2)c(-c2ccc(OC(F)(F)F)cc2)n1] | 372 | 1.09 |

-continued

| No. | Educt | Structure | [M + H]⁺ | t_Ret [min] |
|---|---|---|---|---|
| 94 | B-2 | 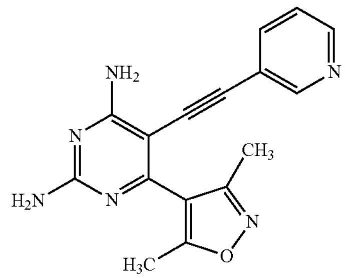 [SMILES: Cc1noc(C)c1-c1nc(N)nc(N)c1C#Cc1cccnc1] | 307 | 0.85 |
| 95 | B-10 | 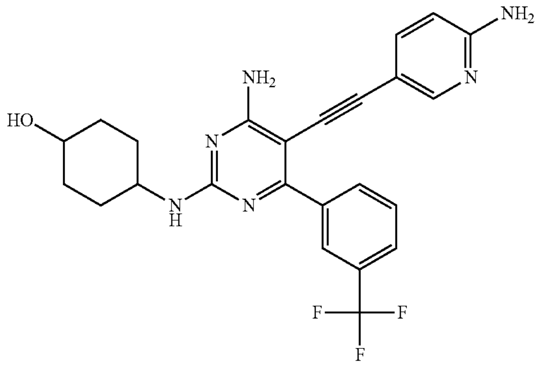 [SMILES: Nc1ccc(C#Cc2c(N)nc(NC3CCC(O)CC3)nc2-c2cccc(C(F)(F)F)c2)cn1] | 469 | 1.89 |
| 96 | B-2 | 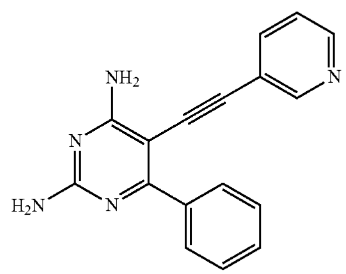 [SMILES: Nc1nc(N)c(C#Cc2cccnc2)c(-c2ccccc2)n1] | 288 | 1.55 |
| 97 | B-2 | 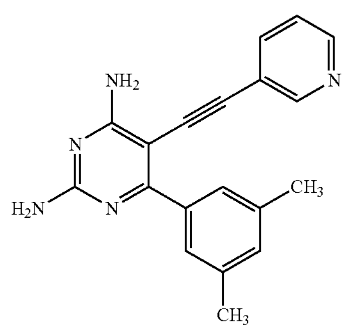 | 316 | 1.04 |
| 98 | B-2 | 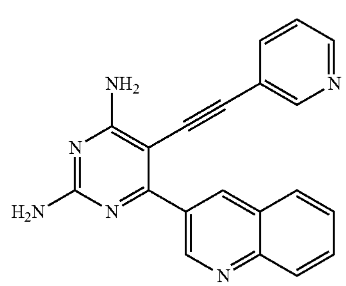 [SMILES: Nc1nc(N)c(C#Cc2cccnc2)c(-c2cnc3ccccc3c2)n1] | 339 | 0.94 |

-continued

| No. | Educt | Structure | [M + H]+ | t_Ret [min] |
|---|---|---|---|---|
| 99 | B-4 | 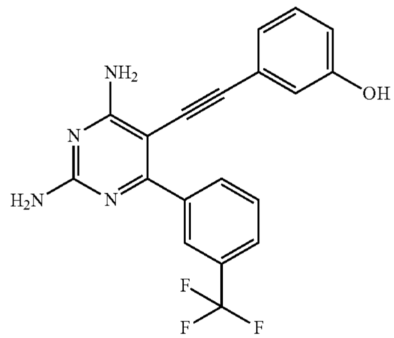 | 371 | 1.93 |
| 100 | B-3 | 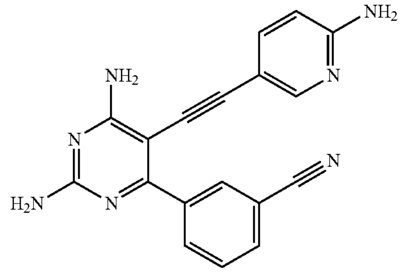 [SMILES: N#Cc1cccc(-c2nc(N)nc(N)c2C#Cc2ccc(N)nc2)c1] | 328 | 1.49 |
| 101 | B-2 | 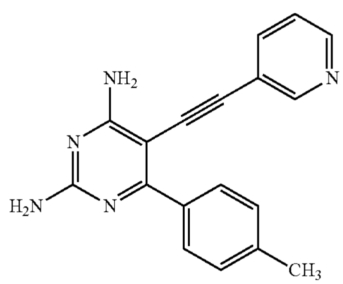 [SMILES: Cc1ccc(-c2nc(N)nc(N)c2C#Cc2cccnc2)cc1] | 302 | 1.00 |
| 102 | B-6 | 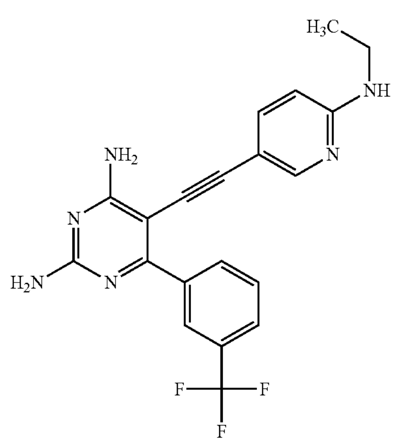 [SMILES: CCNc1ccc(C#Cc2c(N)nc(N)nc2-c2cccc(C(F)(F)F)c2)cn1] | 399 | 2.00 |

| No. | Educt | Structure | [M + H]+ | t_Ret [min] |
|---|---|---|---|---|
| 103 | B-6 | 4-amino-2-amino-5-(pyridin-3-ylethynyl)-6-(3-(trifluoromethyl)phenyl)pyrimidine | 356 | 1.86 |
| 104 | B-2 | 4-amino-2-amino-6-(3-isopropoxyphenyl)-5-(pyridin-3-ylethynyl)pyrimidine | 346 | 1.05 |
| 105 | B-2 | 4-amino-2-amino-6-(4-phenoxyphenyl)-5-(pyridin-3-ylethynyl)pyrimidine | 380 | 1.12 |
| 106 | B-2 | 4-amino-2-amino-6-(quinolin-6-yl)-5-(pyridin-3-ylethynyl)pyrimidine | 339 | 0.88 |

| No. | Educt | Structure | [M + H]⁺ | t_Ret [min] |
|---|---|---|---|---|
| 107 | B-2 | (4-amino-2-amino-6-(4-methoxyphenyl)pyrimidin-5-yl)ethynyl-pyridin-3-yl | 318 | 0.96 |
| 108 | B-6 | 5-(cyclopentylethynyl)-6-(3-(trifluoromethyl)phenyl)pyrimidine-2,4-diamine | 347 | 1.24 |
| 109 | B-6 | 5-((1-hydroxycyclopentyl)ethynyl)-6-(3-(trifluoromethyl)phenyl)pyrimidine-2,4-diamine | 363 | 1.11 |
| 110 | B-6 | 5-(phenylethynyl)-6-(3-(trifluoromethyl)phenyl)pyrimidine-2,4-diamine | 355 | 2.50 |

| No. | Educt | Structure | [M + H]+ | t_Ret [min] |
|---|---|---|---|---|
| 111 | B-4 | (structure) | 334 | 1.62 |
| 112 | B-2 | (structure) | 313 | 1.60 |
| 113 | B-6 | (structure) | 371 | 1.76 |
| 114 | B-10 | (structure) | 427 | 2.28 |

-continued
| No. | Educt | Structure | [M + H]+ | t_Ret [min] |
|---|---|---|---|---|
| 115 | B-10 | 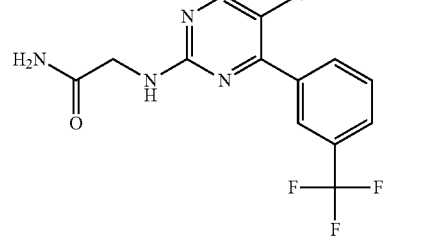 | 428 | 1.68 |
| 116 | B-10 | 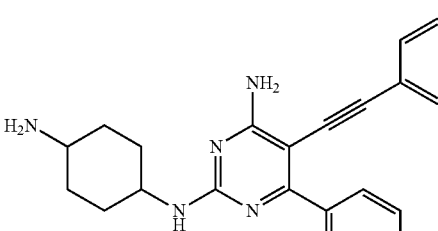 | 468 | 1.91 |
| 117 | B-10 | 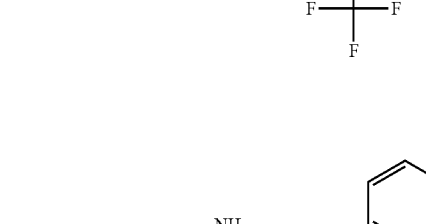 | 415 | 1.76 |
| 118 | B-2 | 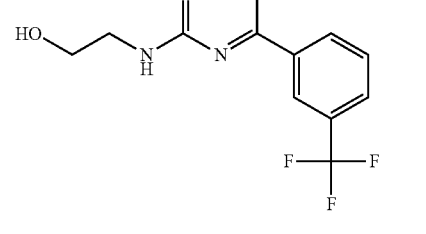 | 313 | 0.94 |

| No. | Educt | Structure | [M + H]+ | t_Ret [min] |
|---|---|---|---|---|
| 129 | B-2 | 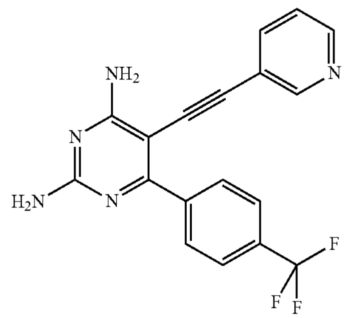 [SMILES: Nc1nc(N)c(C#Cc2cccnc2)c(-c2ccc(C(F)(F)F)cc2)n1] | 356 | 1.08 |
| 120 | B-2 | 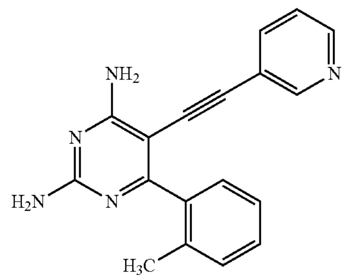 [SMILES: Cc1ccccc1-c1nc(N)nc(N)c1C#Cc1cccnc1] | 302 | 0.95 |
| 121 | B-4 | 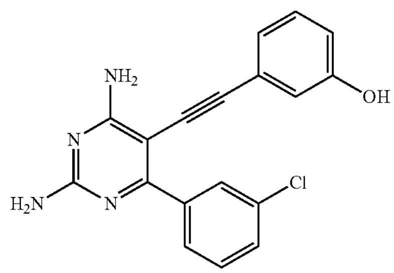 [SMILES: Nc1nc(N)c(C#Cc2cccc(O)c2)c(-c2cccc(Cl)c2)n1] | 337 | 1.85 |
| 122 | B-4 | 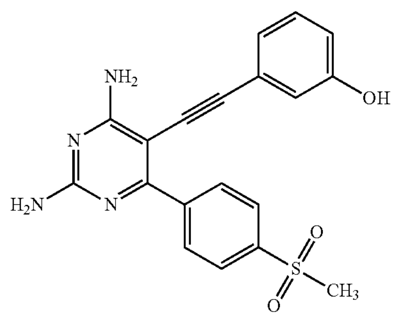 [SMILES: CS(=O)(=O)c1ccc(-c2nc(N)nc(N)c2C#Cc2cccc(O)c2)cc1] | 381 | 1.52 |
| 123 | B-10 | 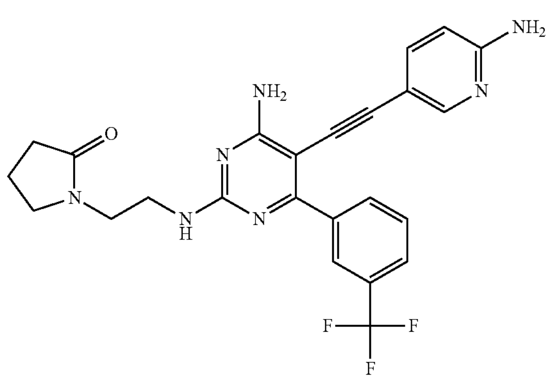 [SMILES: Nc1ccc(C#Cc2c(N)nc(NCCN3CCCC3=O)nc2-c2cccc(C(F)(F)F)c2)cn1] | 482 | 1.85 |

-continued
| No. | Educt | Structure | [M + H]⁺ | t_Ret [min] |
|-----|-------|-----------|----------|-------------|
| 124 | B-6 | 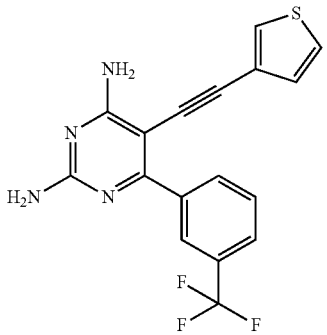 [SMILES: Nc1nc(N)c(C#Cc2ccsc2)c(-c2cccc(C(F)(F)F)c2)n1] | 361 | 1.19 |
| 125 | B-4 | 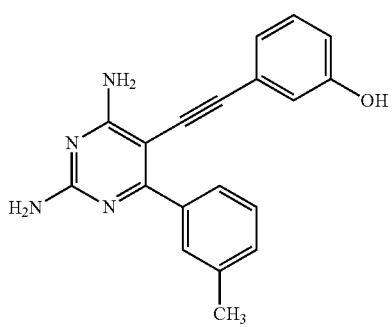 [SMILES: Cc1cccc(-c2nc(N)nc(N)c2C#Cc2cccc(O)c2)c1] | 317 | 1.79 |
| 126 | B-2 | 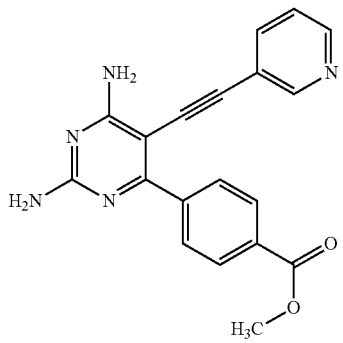 [SMILES: COC(=O)c1ccc(-c2nc(N)nc(N)c2C#Cc2cccnc2)cc1] | 346 | 0.96 |
| 127 | B-4 | 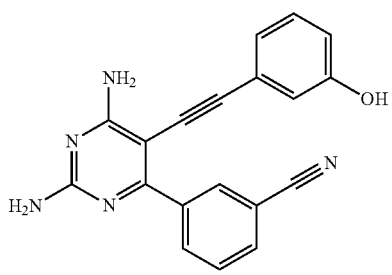 [SMILES: N#Cc1cccc(-c2nc(N)nc(N)c2C#Cc2cccc(O)c2)c1] | 328 | 1.68 |
| 128 | B-4 | 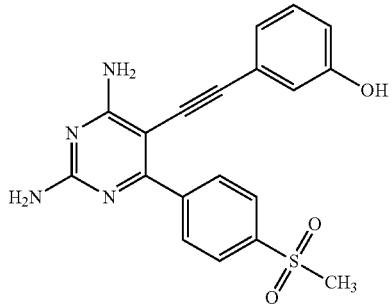 [SMILES: CS(=O)(=O)c1ccc(-c2nc(N)nc(N)c2C#Cc2cccc(O)c2)cc1] | 381 | 1.31 |

| No. | Educt | Structure | [M + H]⁺ | t$_{Ret}$ [min] |
|---|---|---|---|---|
| 129 | B-6 | 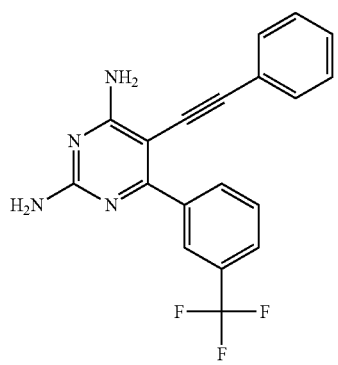 [SMILES: Nc1nc(N)c(C#Cc2ccccc2)c(-c2cccc(C(F)(F)F)c2)n1] | 355 | 2.10 |
| 130 | B-2 | 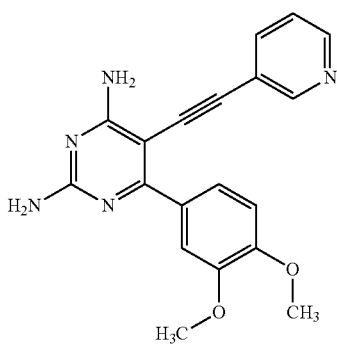 [SMILES: COc1ccc(-c2nc(N)nc(N)c2C#Cc2cccnc2)cc1OC] | 348 | 0.91 |
| 131 | B-2 | 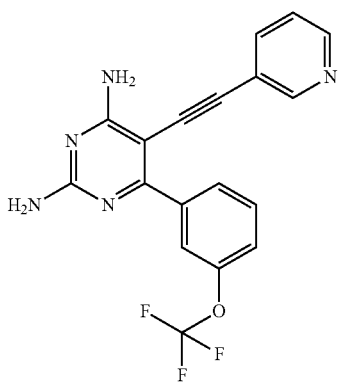 [SMILES: Nc1nc(N)c(C#Cc2cccnc2)c(-c2cccc(OC(F)(F)F)c2)n1] | 372 | 1.08 |
| 132 | B-2 | 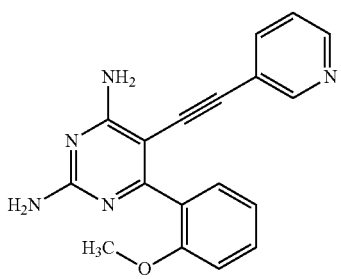 [SMILES: COc1ccccc1-c1nc(N)nc(N)c1C#Cc1cccnc1] | 318 | 0.91 |

| No. | Educt | Structure | [M + H]⁺ | $t_{Ret}$ [min] |
|---|---|---|---|---|
| 133 | B-6 | 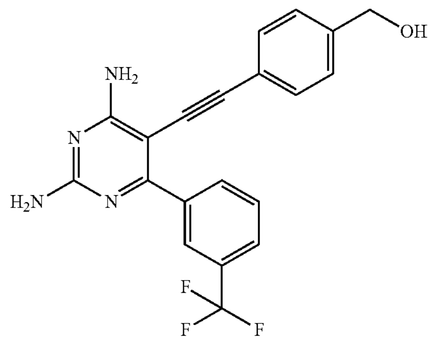 [SMILES: Nc1nc(N)c(C#Cc2ccc(CO)cc2)c(-c2cccc(C(F)(F)F)c2)n1] | 385 | 1.06 |
| 134 | B-6 | 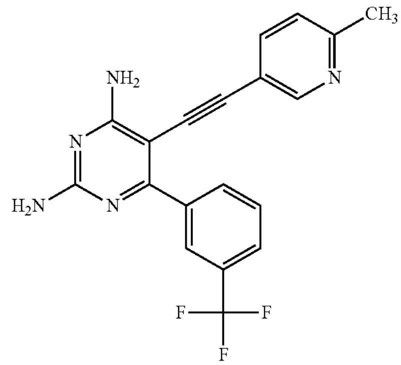 | 370 | 1.94 |
| 135 | B-10 | 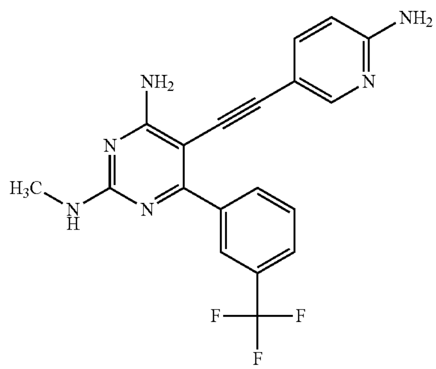 [SMILES: CNc1nc(N)c(C#Cc2ccc(N)nc2)c(-c2cccc(C(F)(F)F)c2)n1] | 385 | 1.94 |
| 136 | B-2 | 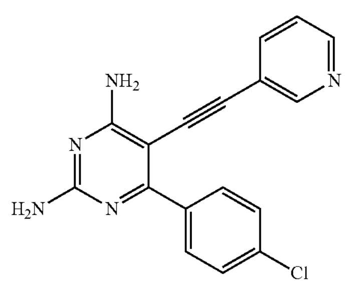 [SMILES: Nc1nc(N)c(C#Cc2cccnc2)c(-c2ccc(Cl)cc2)n1] | 322/324 | 1.03 |

-continued

| No. | Educt | Structure | [M + H]⁺ | $t_{Ret}$ [min] |
|---|---|---|---|---|
| 137 | B-2 | 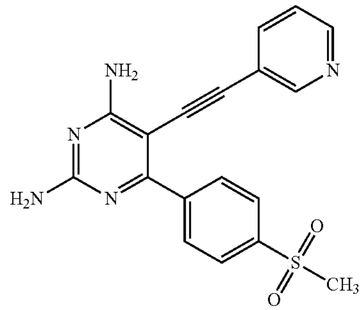 [SMILES: CS(=O)(=O)c1ccc(-c2nc(N)nc(N)c2C#Cc2cccnc2)cc1] | 366 | 0.86 |
| 138 | B-4 | 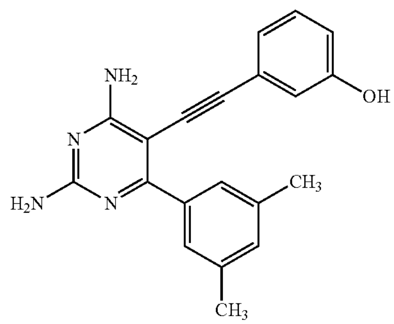 [SMILES: Cc1cc(C)cc(-c2nc(N)nc(N)c2C#Cc2cccc(O)c2)c1] | 331 | 1.88 |
| 139 | B-6 | 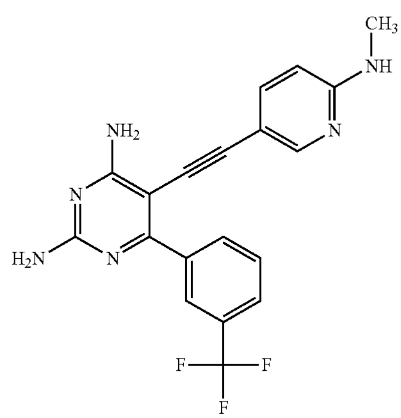 [SMILES: CNc1ccc(C#Cc2c(N)nc(N)nc2-c2cccc(C(F)(F)F)c2)cn1] | 385 | 1.88 |

140) 5-(6-Amino-pyridin-3-ylethynyl)-6-(3-trifluoromethyl-phenyl)-pyrimidin-4-ylamine

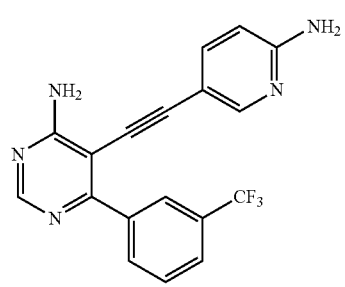 [SMILES: Nc1ccc(C#Cc2c(N)ncnc2-c2cccc(C(F)(F)F)c2)cn1]

To a solution of 60 mg (0.080 mmol) 5-(6-amino-pyridin-3-ylethynyl)-2-methanesulfonyl-6-(3-trifluoromethyl-phenyl)-pyrimidin-4-ylamine (B-10) and 15.7 mg (0.42 mmol) sodiumborohydride in 1 mL EtOH is stirred at 80° C. for 60 minutes. The title compound is purified from the crude reaction mixture by RP-HPLC (ACN/H₂O gradient). Yield: 1.4 mg (5%).

EXAMPLES 141-212

Examples 141 to 212 are synthesized according to the general procedures GP2 (Sonogashira reaction) and GP6 (nucleophilic displacement) outlined above. The appropriate halides required for synthesis can be deduced from the table of examples.

| No. | Educt | Structure | [M + H]⁺ | $t_{Ret}$ [min] |
|---|---|---|---|---|
| 141 | A-32 | 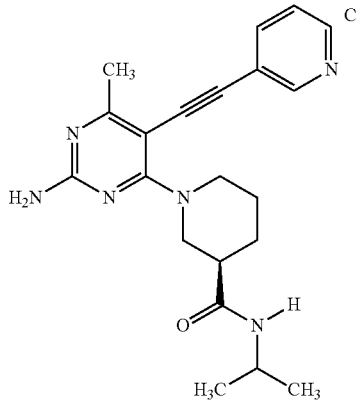 Chiral | 379 | 1.63 |
| 142 | A-32 | 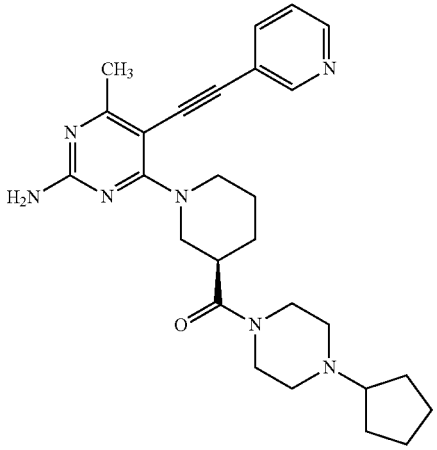 Chiral | 474 | 1.84 |
| 143 | A-32 | 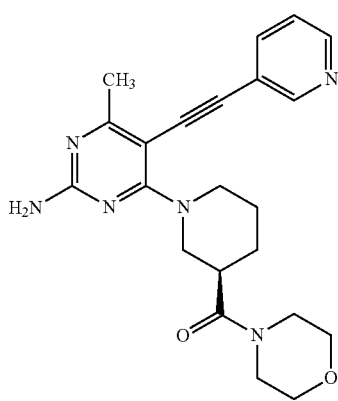 Chiral | 407 | 1.56 |
| 144 | A-32 | 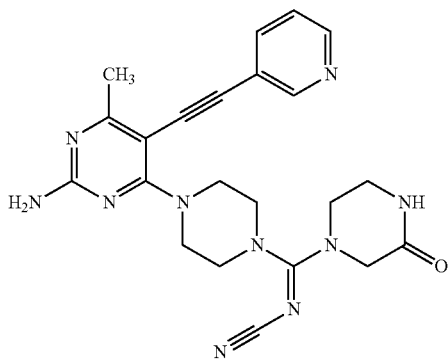 [SMILES: Cc1nc(N)nc(N2CCN(/C(=N\C#N)N3CCNC(=O)C3)CC2)c1C#Cc1cccnc1] | 445 | 1.42 |

| No. | Educt | Structure | [M + H]⁺ | t_Ret [min] |
|---|---|---|---|---|
| 145 | A-32 | (Chiral) Pyrimidine with 2-amino, 6-methyl, 5-(pyridin-3-ylethynyl), 4-[(3R)-3-(pyrrolidin-1-ylcarbonyl)piperidin-1-yl] | 391 | 1.67 |
| 146 | A-32 | (Chiral) Pyrimidine with 2-amino, 6-methyl, 5-(pyridin-3-ylethynyl), 4-[(3R)-3-(N,N-dimethylcarbamoyl)piperidin-1-yl] | 365 | 1.57 |
| 147 | A-32 | Pyrimidine with 2-amino, 6-methyl, 5-(pyridin-3-ylethynyl), 4-[4-[(cyanoimino)(4-methylpiperazin-1-yl)methyl]piperazin-1-yl] | 445 | 1.53 |
| 148 | A-32 | Pyrimidine with 2-amino, 6-methyl, 5-(pyridin-3-ylethynyl), 4-[4-[(cyanoimino)[[2-(2-oxoimidazolidin-1-yl)ethyl]amino]methyl]piperazin-1-yl] | 474 | 1.44 |

-continued
| No. | Educt | Structure | [M + H]+ | t_Ret [min] |
|-----|-------|-----------|----------|-------------|
| 149 | A-32 | 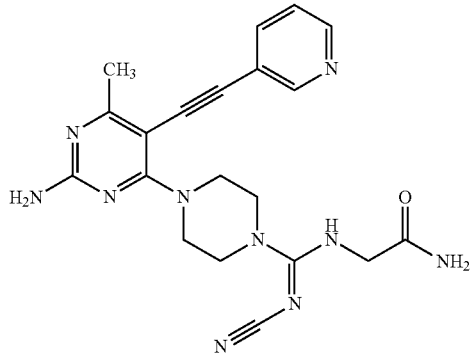 [SMILES: Cc1nc(N)nc(N2CCN(/C(=N\C#N)NCC(N)=O)CC2)c1C#Cc1cccnc1] | 419 | 1.37 |
| 150 | A-34 | Chiral 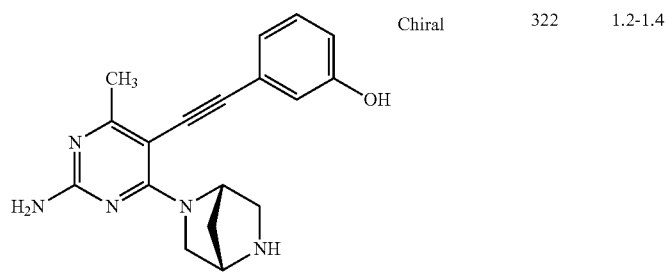 | 322 | 1.2-1.4 |
| 151 | A-34 | 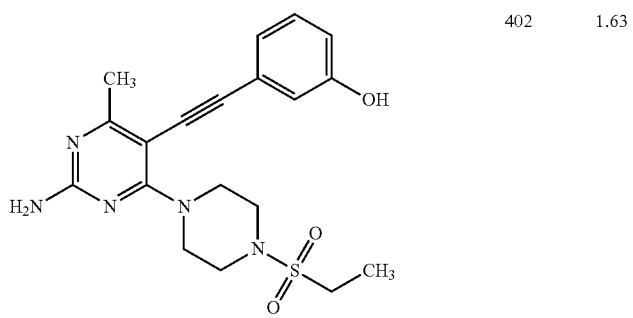 | 402 | 1.63 |
| 152 | A-32 | 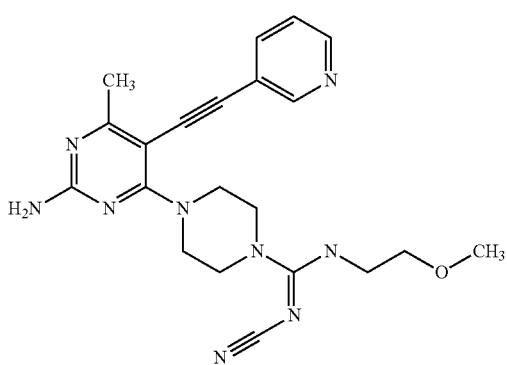 [SMILES: COCCN/C(=N/C#N)N1CCN(c2nc(N)nc(C)c2C#Cc2cccnc2)CC1] | 420 | 1.54 |

-continued
| No. | Educt | Structure | [M + H]⁺ | t$_{Ret}$ [min] |
|---|---|---|---|---|
| 153 | A-32 | 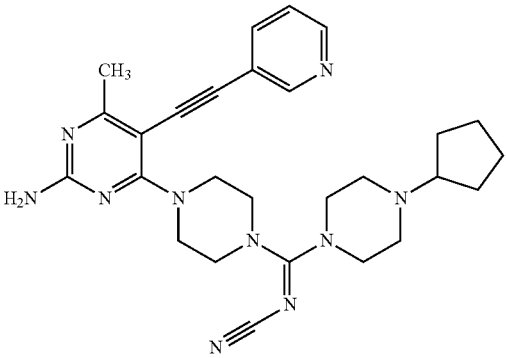 [SMILES: Cc1nc(N)nc(N2CCN(/C(=N\C#N)N3CCN(C4CCCC4)CC3)CC2)c1C#Cc1cccnc1] | 499 | 1.80 |
| 154 | A-32 | 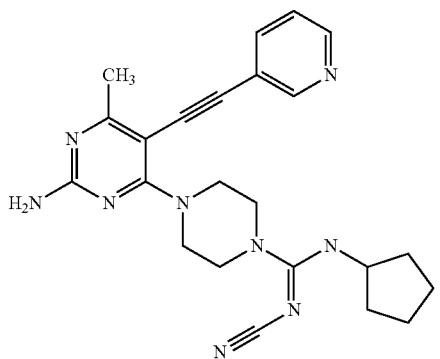 [SMILES: Cc1nc(N)nc(N2CCN(/C(=N\C#N)NC3CCCC3)CC2)c1C#Cc1cccnc1] | 402 | 1.57 |
| 155 | A-32 | 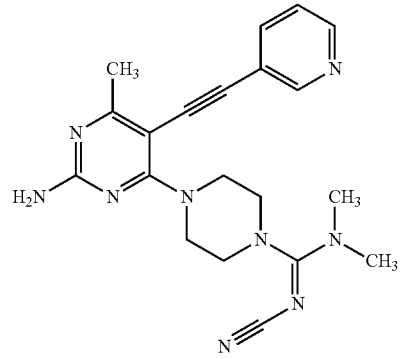 [SMILES: Cc1nc(N)nc(N2CCN(/C(=N\C#N)N(C)C)CC2)c1C#Cc1cccnc1] | 390 | 1.54 |
| 156 | A-32 | 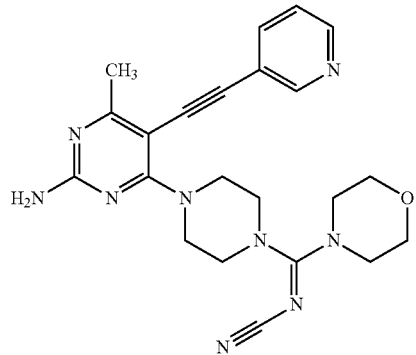 [SMILES: Cc1nc(N)nc(N2CCN(/C(=N\C#N)N3CCOCC3)CC2)c1C#Cc1cccnc1] | 432 | 1.53 |

-continued

| No. | Educt | Structure | [M + H]+ | t_Ret [min] |
|---|---|---|---|---|
| 157 | A-34 | 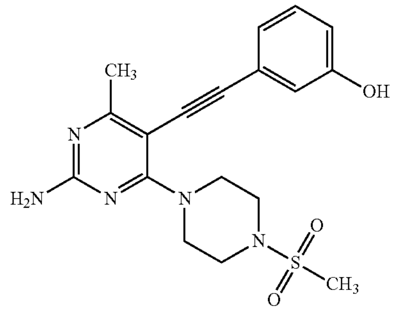 [SMILES: Cc1nc(N)nc(N2CCN(S(C)(=O)=O)CC2)c1C#Cc1cccc(O)c1] | 388 | 1.53 |
| 158 | A-34 | 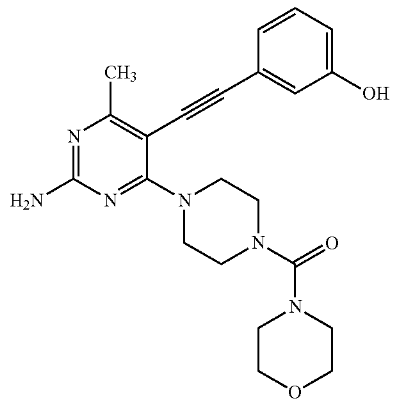 [SMILES: Cc1nc(N)nc(N2CCN(C(=O)N3CCOCC3)CC2)c1C#Cc1cccc(O)c1] | 423 | |
| 159 | A-34 | 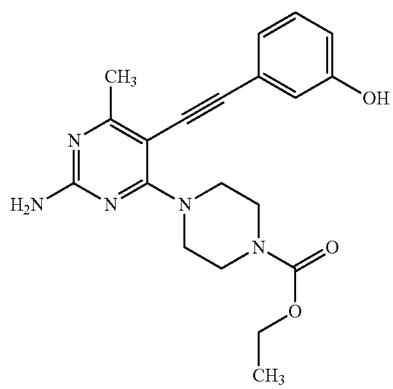 [SMILES: CCOC(=O)N1CCN(c2nc(N)nc(C)c2C#Cc2cccc(O)c2)CC1] | 382 | 1.74 |
| 160 | A-34 | 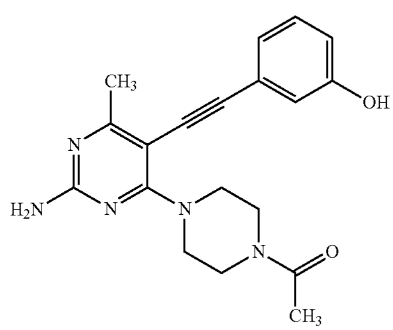 [SMILES: CC(=O)N1CCN(c2nc(N)nc(C)c2C#Cc2cccc(O)c2)CC1] | 352 | 1.42 |

-continued
| No. | Educt | Structure | [M + H]⁺ | $t_{Ret}$ [min] |
|---|---|---|---|---|
| 161 | A-34 | 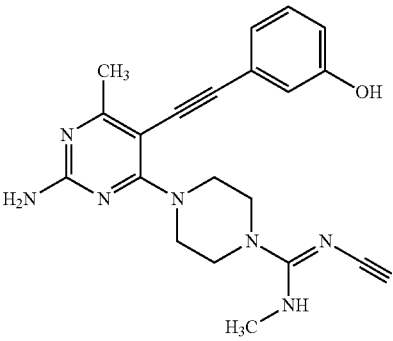 | 391 | 1.45 |
| 162 | A-33 | 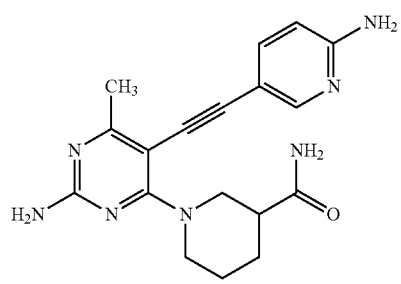 [SMILES: Cc1nc(N)nc(N2CCCC(C(N)=O)C2)c1C#Cc1ccc(N)nc1] | 352 | 1.33 |
| 163 | A-34 | 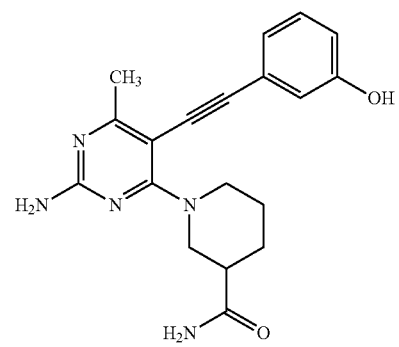 [SMILES: Cc1nc(N)nc(N2CCCC(C(N)=O)C2)c1C#Cc1cccc(O)c1] | 352 | 1.38 |
| 164 | A-33 | 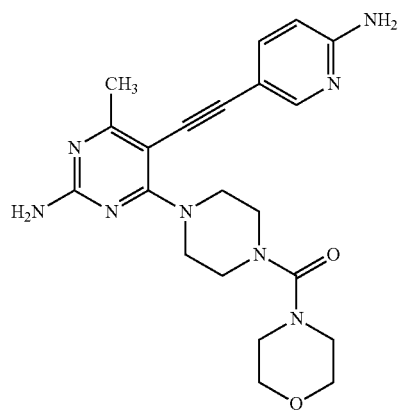 [SMILES: Cc1nc(N)nc(N2CCN(C(=O)N3CCOCC3)CC2)c1C#Cc1ccc(N)nc1] | 423 | 1.47 |

-continued

| No. | Educt | Structure | [M + H]⁺ | t$_{Ret}$ [min] |
|---|---|---|---|---|
| 165 | A-33 | 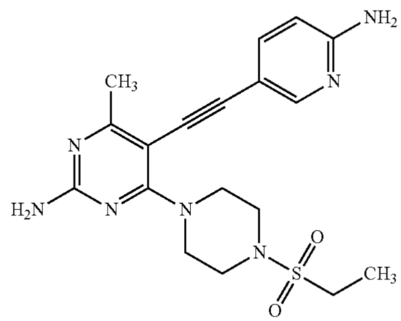 [SMILES: CCS(=O)(=O)N1CCN(c2nc(N)nc(C)c2C#Cc2ccc(N)nc2)CC1] | 402 | 1.54 |
| 166 | A-33 | 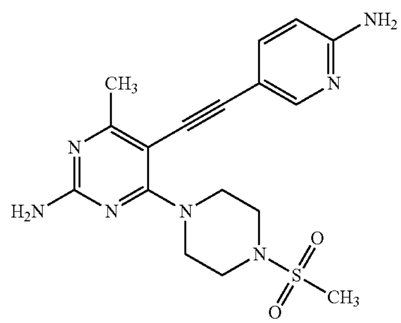 [SMILES: Cc1nc(N)nc(N2CCN(S(C)(=O)=O)CC2)c1C#Cc1ccc(N)nc1] | 388 | 1.49 |
| 167 | A-33 | 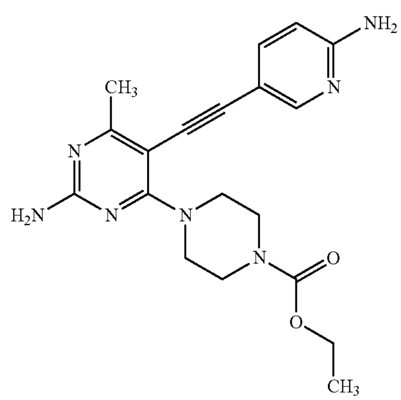 [SMILES: CCOC(=O)N1CCN(c2nc(N)nc(C)c2C#Cc2ccc(N)nc2)CC1] | 382 | 1.65 |
| 168 | A-33 | 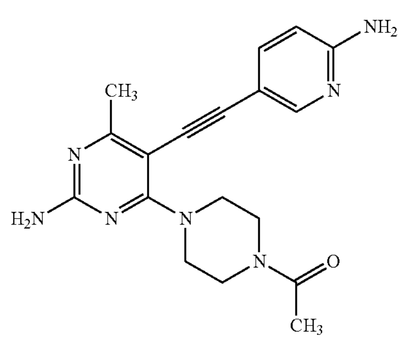 [SMILES: CC(=O)N1CCN(c2nc(N)nc(C)c2C#Cc2ccc(N)nc2)CC1] | 352 | 1.41 |

-continued

| No. | Educt | Structure | [M + H]+ | t_Ret [min] |
|---|---|---|---|---|
| 169 | A-32 | 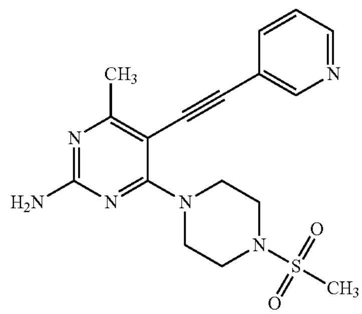 [SMILES: Cc1nc(N)nc(N2CCN(S(C)(=O)=O)CC2)c1C#Cc1cccnc1] | 373 | 1.56 |
| 170 | A-32 | 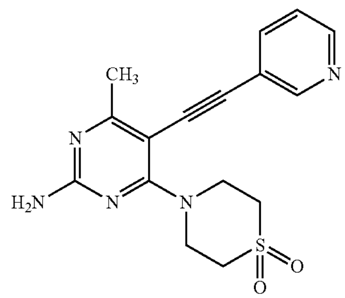 [SMILES: Cc1nc(N)nc(N2CCS(=O)(=O)CC2)c1C#Cc1cccnc1] | 344 | 1.69 |
| 171 | A-32 | 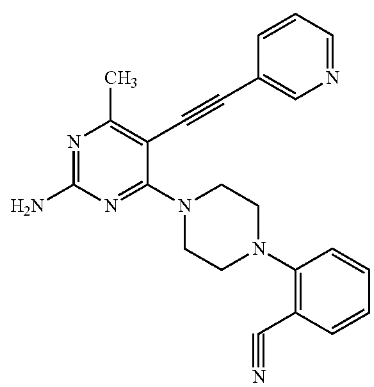 [SMILES: Cc1nc(N)nc(N2CCN(c3ccccc3C#N)CC2)c1C#Cc1cccnc1] | 396 | 2.24 |
| 172 | A-32 | 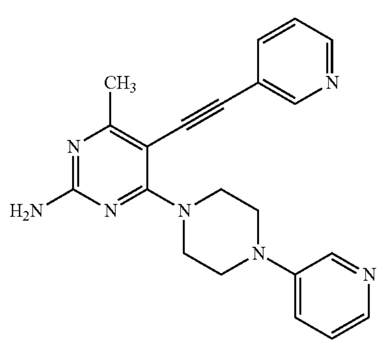 [SMILES: Cc1nc(N)nc(N2CCN(c3cccnc3)CC2)c1C#Cc1cccnc1] | 372 | 1.61 |

-continued

| No. | Educt | Structure | [M + H]⁺ | t$_{Ret}$ [min] |
|---|---|---|---|---|
| 173 | A-32 | 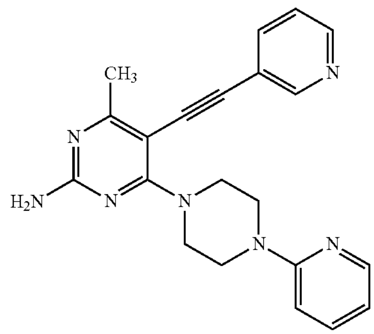 [SMILES: Cc1nc(N)nc(N2CCN(c3ccccn3)CC2)c1C#Cc1cccnc1] | 372 | 1.63 |
| 174 | A-32 | 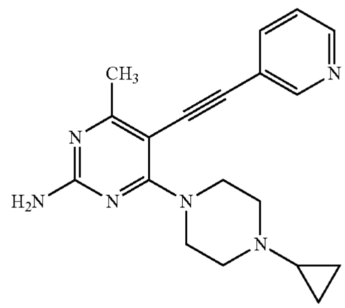 [SMILES: Cc1nc(N)nc(N2CCN(C3CC3)CC2)c1C#Cc1cccnc1] | 335 | 1.42 |
| 175 | A-32 | 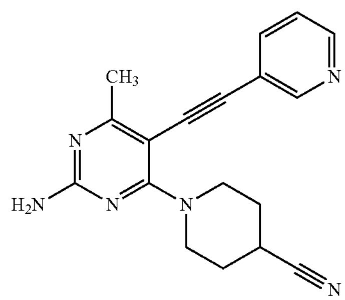 [SMILES: Cc1nc(N)nc(N2CCC(C#N)CC2)c1C#Cc1cccnc1] | 319 | 2.34 |
| 176 | A-32 | 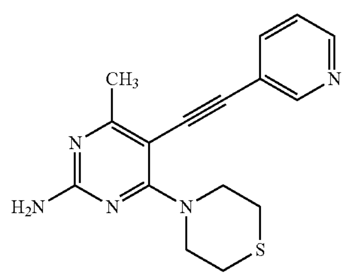 [SMILES: Cc1nc(N)nc(N2CCSCC2)c1C#Cc1cccnc1] | 312 | 2.45 |
| 177 | A-32 | 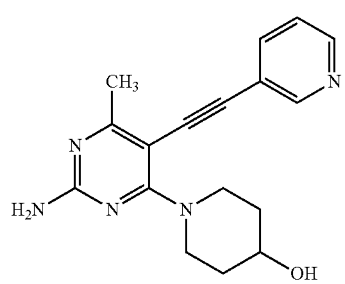 [SMILES: Cc1nc(N)nc(N2CCC(O)CC2)c1C#Cc1cccnc1] | 310 | 2.13 |

-continued

| No. | Educt | Structure | [M + H]+ | t_Rel [min] |
|---|---|---|---|---|
| 178 | A-32 | (structure) | 308 | 2.69 |
| 179 | A-32 | (structure) | 266 | 2.25 |
| 180 | A-32 | (structure) | 296 | 2.21 |
| 181 | A-32 | (structure) | 363 | 2.02 |
| 182 | A-32 | (structure) | 280 | 1.91 |

-continued
| No. | Educt | Structure | [M + H]+ | t_Ret [min] |
|---|---|---|---|---|
| 183 | A-32 | 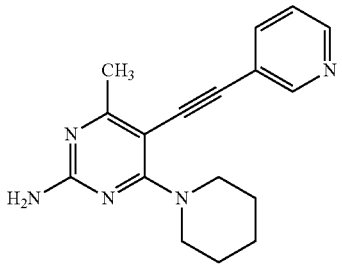 [SMILES: Cc1nc(N)nc(N2CCCCC2)c1C#Cc1cccnc1] | 294 | 1.86 |
| 184 | A-32 | 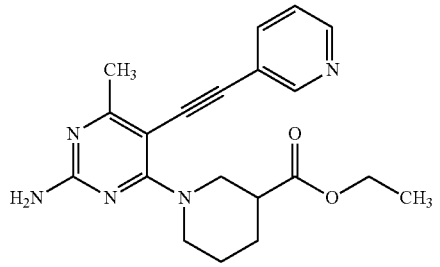 [SMILES: CCOC(=O)C1CCCN(c2nc(N)nc(C)c2C#Cc2cccnc2)C1] | 366 | 1.88 |
| 185 | A-32 | 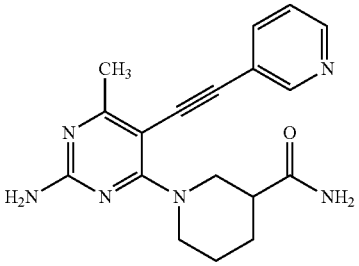 [SMILES: Cc1nc(N)nc(N2CCCC(C(N)=O)C2)c1C#Cc1cccnc1] | 337 | 1.39 |
| 186 | A-32 | 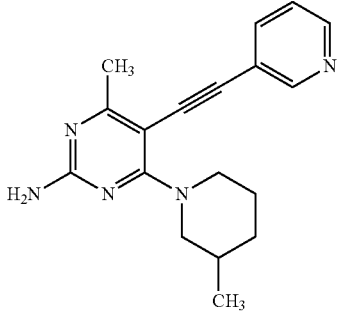 [SMILES: Cc1nc(N)nc(N2CCCC(C)C2)c1C#Cc1cccnc1] | 308 | 1.98 |
| 187 | A-32 | 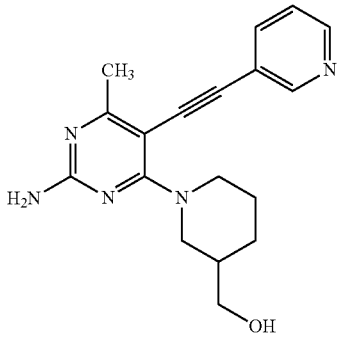 [SMILES: Cc1nc(N)nc(N2CCCC(CO)C2)c1C#Cc1cccnc1] | 324 | 1.57 |

-continued

| No. | Educt | Structure | [M + H]⁺ | t$_{Ref}$ [min] |
|-----|-------|-----------|----------|-----------------|
| 188 | A-32 | 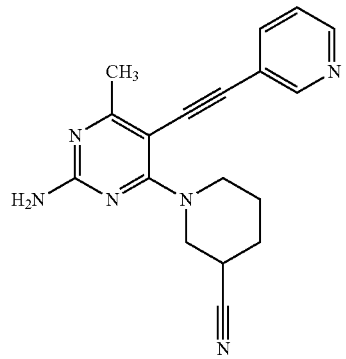 [SMILES: Cc1nc(N)nc(N2CCCC(C#N)C2)c1C#Cc1cccnc1] | 319 | 1.64 |
| 189 | A-32 | 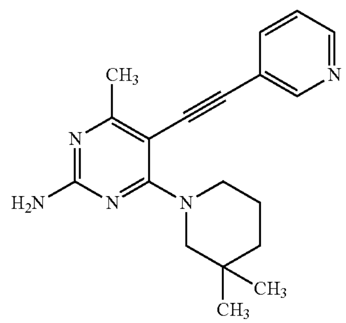 [SMILES: Cc1nc(N)nc(N2CCCC(C)(C)C2)c1C#Cc1cccnc1] | 322 | 2.04 |
| 190 | A-33 | 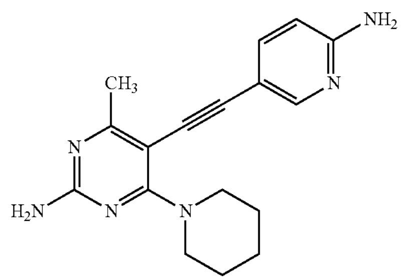 [SMILES: Cc1nc(N)nc(N2CCCCC2)c1C#Cc1ccc(N)nc1] | 309 | 1.72 |
| 191 | A-32 | 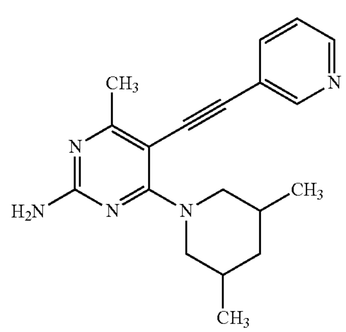 [SMILES: Cc1nc(N)nc(N2CC(C)CC(C)C2)c1C#Cc1cccnc1] | 322 | 2.06/2.09 |

| No. | Educt | Structure | [M + H]+ | t_Ret [min] |
|---|---|---|---|---|
| 192 | A-32 | 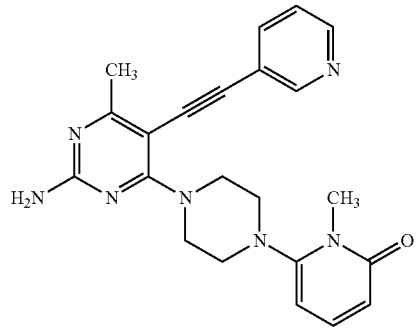 [SMILES: Cc1nc(N)nc(N2CCN(c3cccc(=O)n3C)CC2)c1C#Cc1cccnc1] | 402 | 1.63 |
| 193 | A-32 | 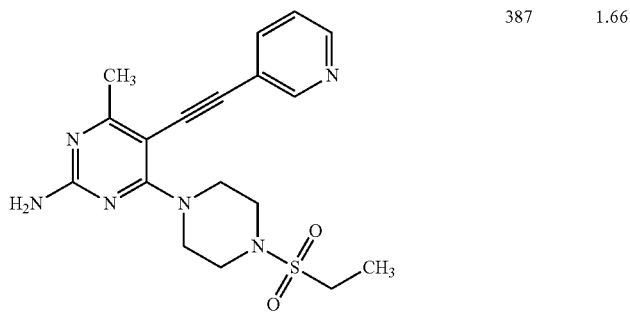 | 387 | 1.66 |
| 194 | A-32 | 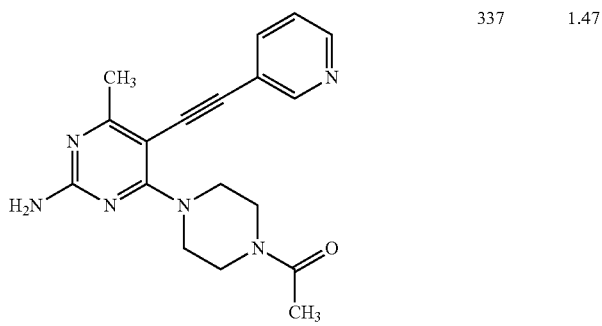 | 337 | 1.47 |
| 195 | A-32 | 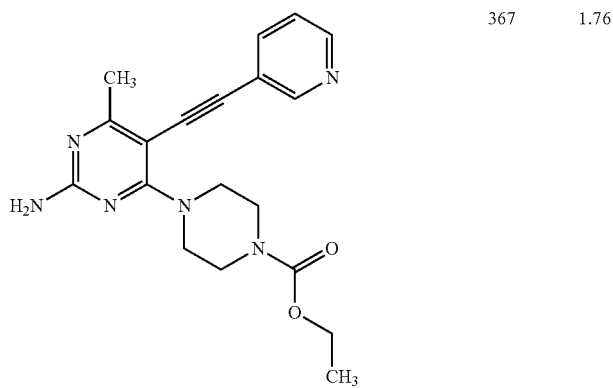 | 367 | 1.76 |

-continued

| No. | Educt | Structure | [M + H]⁺ | $t_{Ret}$ [min] |
|---|---|---|---|---|
| 196 | A-32 | 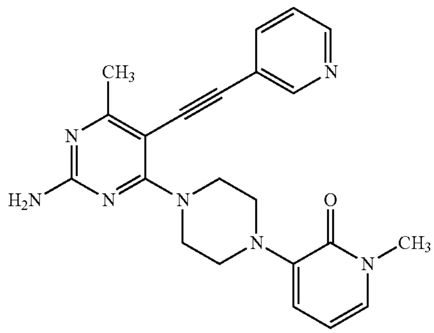 [SMILES: Cc1nc(N)nc(N2CCN(c3cccn(C)c3=O)CC2)c1C#Cc1cccnc1] | 402 | 1.64 |
| 197 | A-32 | 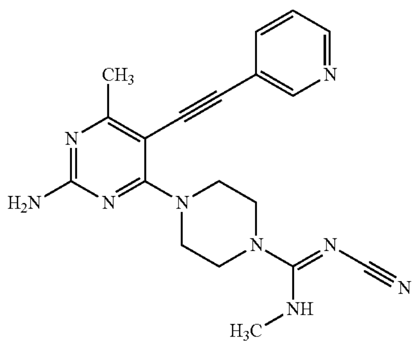 [SMILES: CN/C(=N\C#N)N1CCN(c2nc(N)nc(C)c2C#Cc2cccnc2)CC1] | 376 | 1.49 |
| 198 | B-2 | 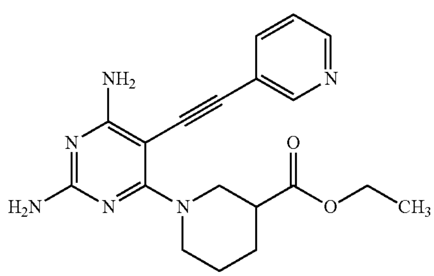 [SMILES: CCOC(=O)C1CCCN(c2nc(N)nc(N)c2C#Cc2cccnc2)C1] | 367 | 1.74 |
| 199 | B-4 | 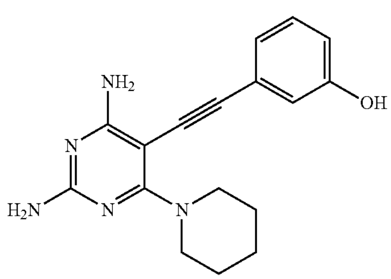 [SMILES: Nc1nc(N)c(C#Cc2cccc(O)c2)c(N2CCCCC2)n1] | 310 | 1.81 |
| 200 | B-2 | 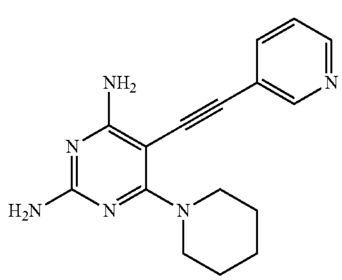 | 295 | 1.71 |

-continued

| No. | Educt | Structure | [M + H]⁺ | t_Ref [min] |
|-----|-------|-----------|----------|-------------|
| 201 | A-32 | 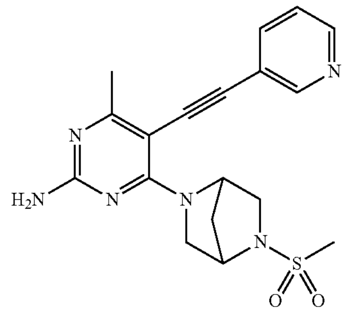 [SMILES: Cc1nc(N)nc(N2CC3CC2CN3S(C)(=O)=O)c1C#Cc1cccnc1] | 385 | |
| 202 | A-32 | 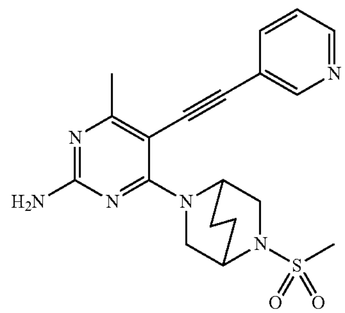 [SMILES: Cc1nc(N)nc(N2CC3CCC2CN3S(C)(=O)=O)c1C#Cc1cccnc1] | 399 | |
| 203 | A-32 | 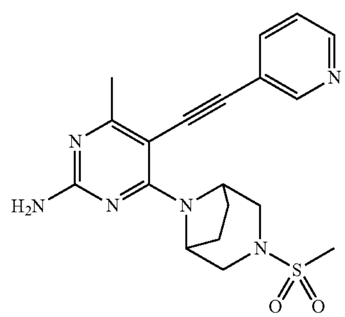 [SMILES: Cc1nc(N)nc(N2C3CCC2CN(S(C)(=O)=O)C3)c1C#Cc1cccnc1] | 399 | |
| 204 | A-32 | 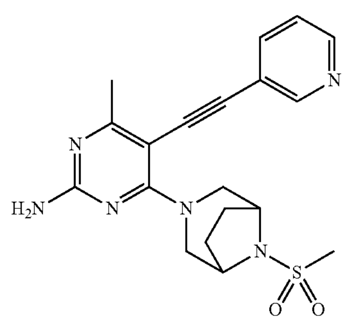 [SMILES: Cc1nc(N)nc(N2CC3CCC(C2)N3S(C)(=O)=O)c1C#Cc1cccnc1] | 399 | |
| 205 | A-32 | 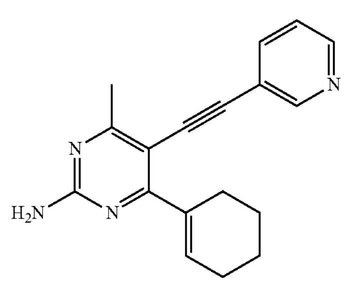 [SMILES: Cc1nc(N)nc(C2=CCCCC2)c1C#Cc1cccnc1] | 291 | |

-continued
| No. | Educt | Structure | [M + H]+ | t_Ref [min] |
|---|---|---|---|---|
| 206 | A-32 | 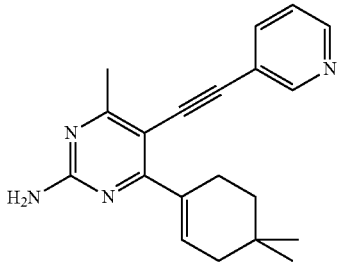 [SMILES: Cc1nc(N)nc(C2=CCC(C)(C)CC2)c1C#Cc1cccnc1] | 319 | |
| 207 | A-32 | 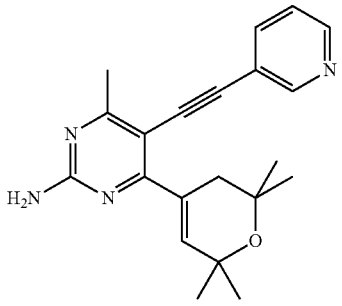 [SMILES: Cc1nc(N)nc(C2=CC(C)(C)OC(C)(C)C2)c1C#Cc1cccnc1] | 349 | |
| 208 | A-32 | 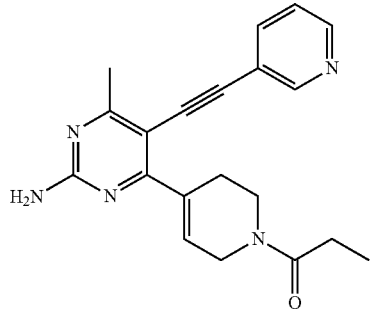 [SMILES: CCC(=O)N1CC=C(c2nc(N)nc(C)c2C#Cc2cccnc2)CC1] | 348 | |
| 209 | A-32 | 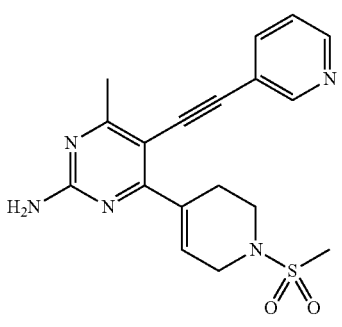 [SMILES: Cc1nc(N)nc(C2=CCN(S(C)(=O)=O)CC2)c1C#Cc1cccnc1] | 370 | |
| 210 | A-32 | 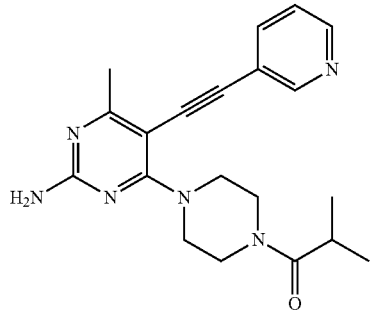 [SMILES: Cc1nc(N)nc(N2CCN(C(=O)C(C)C)CC2)c1C#Cc1cccnc1] | 365 | |

| No. | Educt | Structure | [M + H]⁺ | $t_{Ret}$ [min] |
|---|---|---|---|---|
| 211 | A-32 | 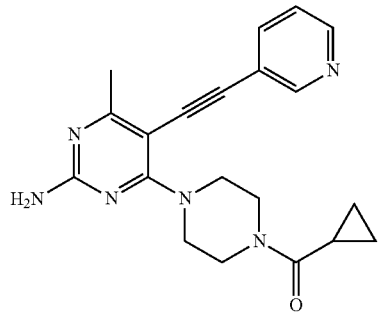 [SMILES: Cc1nc(N)nc(N2CCN(C(=O)C3CC3)CC2)c1C#Cc1cccnc1] | 363 | |
| 212 | A-32 | 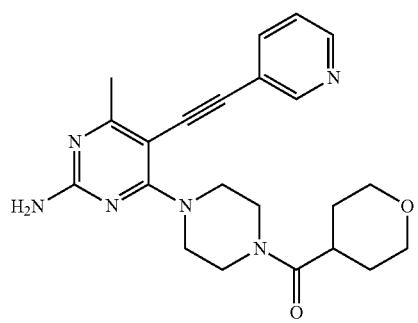 [SMILES: Cc1nc(N)nc(N2CCN(C(=O)C3CCOCC3)CC2)c1C#Cc1cccnc1] | 407 | |

INTERMEDIATES C

C-46) 4-Chloro-6-methyl-5-(6-methyl-pyridin-3-ylethynyl)-pyrimidin-2-ylamine

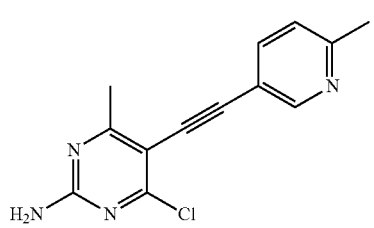 [SMILES: Cc1ccc(C#Cc2c(C)nc(N)nc2Cl)cn1]

The title compound is synthesized according to general procedure GP2 starting from 1.0 g (3.7 mmol) 4-chloro-6-methyl-5iodo-pyrimidin-2-ylamine using 570 mg (3.7 mmol) 5-ethynyl-2-methyl-pyridine, 71 mg (0.37 mmol) CuI, 260 mg (0.37 mmol) bis-(triphenylphoshine)palladium (II) chloride, 5.1 mL (27 mmol) triethylamine in 40 mL DMF. The reaction mixture is stirred over night at 55° C. After removal of the solvent under reduced pressure, the product is purified by chromatography on silica gel using a DCM/MeOH gradient (100:0->85:15, 30 min). Yield: 270 mg (28%).

C-47) 4-[2-Amino-6-methyl-5-(6-methyl-pyridin-3-ylethynyl)-pyrimidin-4-yl]-2-chloro-benzoic acid methyl ester

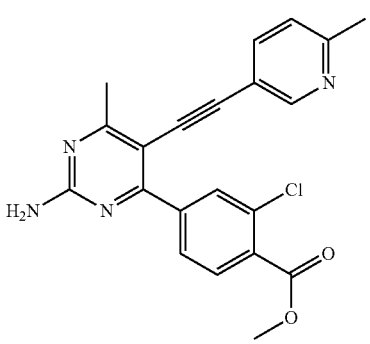 [SMILES: COC(=O)c1ccc(-c2nc(N)nc(C)c2C#Cc2ccc(C)nc2)cc1Cl]

The title compound is synthesized according to general procedure GP4 starting from 200 mg (0.77 mmol) 4-chloro-6-methyl-5-(6-methyl-pyridin-3-ylethynyl)-pyrimidin-2-ylamine using 249 mg (1.16 mmol) 3-chloro-4-methoxycarbonylphenyl boronic acid, 24 mg (0.16 mmol) Pd(PPh₃)₄, 205 mg (1.47 mmol) K₂CO₃ in 3 mL dioxane/H₂O (3:1 v/v). The product precipitates from the reaction mixture, is filtered off and can be used without further purification. Yield: 235 mg (77%).

C-48) 4-[2-Amino-6-methyl-5-(6-methyl-pyridin-3-ylethynyl)-pyrimidin-4-yl]-2-chloro-benzoic acid

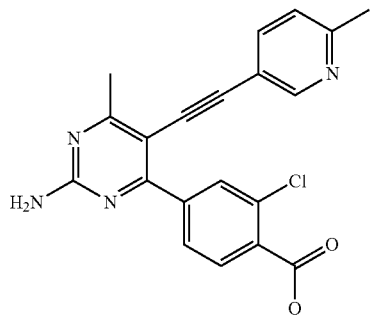 [SMILES: Cc1ccc(C#Cc2c(C)nc(N)nc2-c2ccc(C(=O)O)c(Cl)c2)cn1]

The title compound is synthesized according to general procedure GP8 starting from 235 mg (0.6 mmol) 4-[2-amino-6-methyl-5-(6-methyl-pyridin-3-ylethynyl)-pyrimidin-4-yl]-2-chloro-benzoic acid using 0.9 mL (0.9 mmol) 1 N NaOH in THF.

Yield: 130 mg (57%).

C-49) 4-Chloro-6-ethyl-5-iodo-pyrimidin-2-ylamine

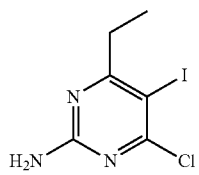

The title compound is synthesized according to general procedure GP1 starting from 2.5 g (16 mmol) 4-chloro-6-ethyl-pyrimidin-2-ylamine and 3.7 g (16 mmol) NIS. Yield after precipitation from the reaction mixture: 3.83 g (85%).

C-50) 4-Chloro-6-ethyl-5-(6-methyl-pyridin-3-yl-ethynyl)-pyrimidin-2-ylamine

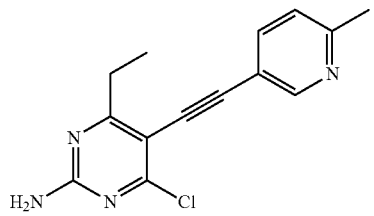 [SMILES: CCc1nc(N)nc(Cl)c1C#Cc1ccc(C)nc1]

The title compound is synthesized according to general procedure GP2 starting from 300 mg (1.1 mmol) 4-chloro-6-ethyl-5-iodo-pyrimidin-2-ylamine using 160 mg (1.1 mmol) 5-ethynyl-2-methyl-pyridine hydrochloride, 20 mg (0.11 mmol) CuI, 74 mg (0.11 mmol) bis-(triphenylphoshine)palladium (II) chloride, 1.5 mL (10.6 mmol) triethylamine in 11 mL DMF. The reaction mixture is stirred over night at 60° C. After removal of the solvent under reduced pressure, the product is purified by PR-HPLC. Yield: 130 mg (45%).

C-51) 4-[2-Amino-6-ethyl-5-(6-methyl-pyridin-3-ylethynyl)-pyrimidin-4-yl]-2-fluoro-benzoic acid methyl ester

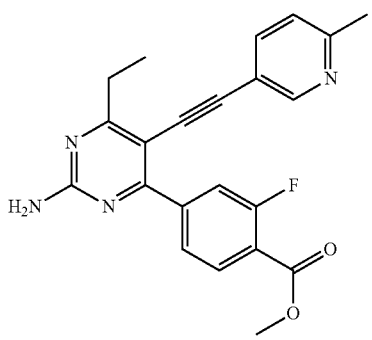 [SMILES: CCc1nc(N)nc(-c2ccc(C(=O)OC)c(F)c2)c1C#Cc1ccc(C)nc1]

The title compound is synthesized according to general procedure GP4 starting from 130 mg (0.48 mmol) 4-chloro-6-ethyl-5-(6-methyl-pyridin-3-ylethynyl)-pyrimidin-2-ylamine using 142 mg (0.7 mmol) 3-fluoro-4-methoxycarbonylphenyl boronic acid, 14 mg (0.01 mmol) Pd(PPh$_3$)$_4$, 133 mg (1.0 mmol) K$_2$CO$_3$ in 2.25 mL DME/H$_2$O (10:1 v/v). The product precipitates from the reaction mixture, is filtered off and can be used without further purification. Yield: 125 mg (67%).

C-52) 4-[2-Amino-6-ethyl-5-(6-methyl-pyridin-3-ylethynyl)-pyrimidin-4-yl]-2-fluoro-benzoic acid

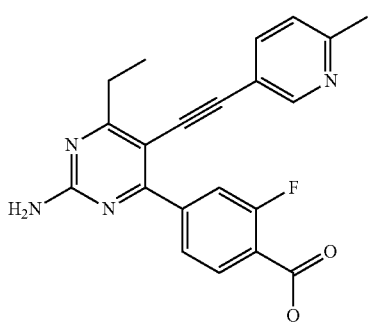 [SMILES: CCc1nc(N)nc(-c2ccc(C(=O)O)c(F)c2)c1C#Cc1ccc(C)nc1]

The title compound is synthesized according to general procedure GP8 starting from 130 mg (0.47 mmol) 4-[2-amino-6-ethyl-5-(6-methyl-pyridin-3-ylethynyl)-pyrimidin-4-yl]-2-fluoro-benzoic acid methyl ester using 470 µL (0.47 mmol) 1 N NaOH in 3 mL THF. The product precipitates from the reaction mixture and is isolated by filtration.

Yield: 77 mg (62%).

C-53) 5-(6-Amino-pyridin-3-ylethynyl)-4-chloro-6-ethyl-pyrimidin-2-ylamine

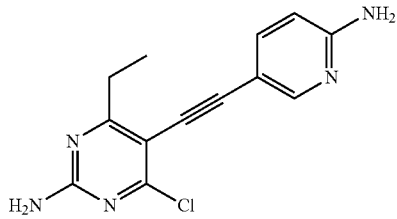 [SMILES: CCc1nc(N)nc(Cl)c1C#Cc1ccc(N)nc1]

The title compound is synthesized according to general procedure GP2 starting from 3.0 g (10.6 mmol) 4-chloro-6-ethyl-5-iodo-pyrimidin-2-ylamine using 1.37 mg (12 mmol) 5-ethynyl-2-amino-pyridine, 200 mg (1.1 mmol) CuI, 740 mg (1.1 mmol) bis-(triphenylphoshine)palladium (II) chloride, 15 mL (106 mmol) triethylamine in 60 mL DMF. The reaction mixture is stirred over night at 65° C. Small amounts of water are added to the reaction mixture, the precipitated product is filtered off and washed subsequently with DMF, $H_2O$ and diethylether. The crude product is re-crystallized from DMF (Yield: 1.65 g). Additional product is isolated from the mother liquid by RP-HPLC. (Yield: 325 mg). Overall yield: 1.97 g (68%).

C-54) 4-[2-Amino-5-(6-amino-pyridin-3-ylethynyl)-6-ethyl-pyrimidin-4-yl]-3-fluoro-benzoic acid ethyl ester

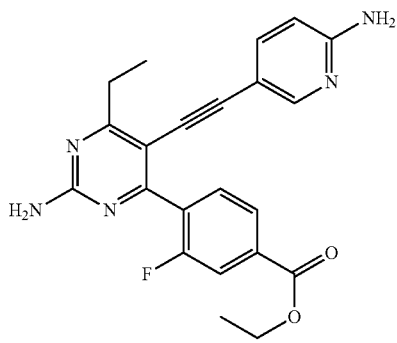 [SMILES: CCOC(=O)c1ccc(-c2nc(N)nc(CC)c2C#Cc2ccc(N)nc2)c(F)c1]

The title compound is synthesized according to general procedure GP4 starting from 300 mg (1.1 mmol) 4-chloro-6-ethyl-5-(6-amino-pyridin-3-ylethynyl)-pyrimidin-2-ylamine using 349 mg (1.6 mmol) 2-fluoro-4-ethoxycarbonylphenyl boronic acid, 34 mg (0.22 mmol) Pd(PPh$_3$)$_4$, 291 mg (2.1 mmol) K$_2$CO$_3$ in 5 mL DME/H$_2$O (5:2 v/v). After stirring twice for 60 min at 130° C. under microwave irradiation, conversion of the starting material is about 75%, an about 1:1 mixture of the desired product and the saponified ester is formed. The product precipitates from the reaction mixture, is filtered off and is washed with water and diethylether. Yield: 155 mg (35%).

The mother liquid contains the corresponding carboxylic acid which can be isolated together with acid obtained from the saponification of the ester.

C-55) 4-[2-Amino-5-(6-amino-pyridin-3-ylethynyl)-6-ethyl-pyrimidin-4-yl]-3-fluoro-benzoic acid

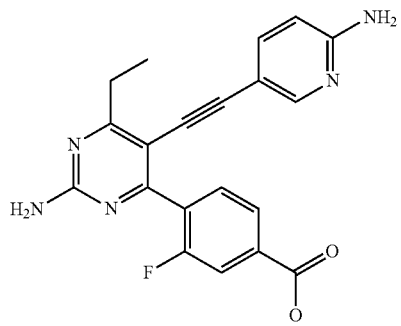 [SMILES: CCc1nc(N)nc(-c2ccc(C(=O)O)cc2F)c1C#Cc1ccc(N)nc1]

The title compound is synthesized according to general procedure GP8 starting from 200 mg (0.54 mmol) 4-[2-amino-5-(6-amino-pyridin-3-ylethynyl)-6-ethyl-pyrimidin-4-yl]-3-fluoro-benzoic acid methyl ester using 0.81 mL (0.81 mmol) 1 N NaOH in 4 mL THF. After completion of the reaction, the reaction mixture is combined with the mother liquid from the proceeding Suzuki coupling. The pH is adjusted to 4-5 (using 1 N HCl) upon which the product precipitates from the reaction mixture and is isolated by filtration. Yield: 240 mg (58% over two steps).

C-56) 4-[2-Amino-5-(6-amino-pyridin-3-ylethynyl)-6-ethyl-pyrimidin-4-yl]-2-fluoro-benzoic acid methyl ester

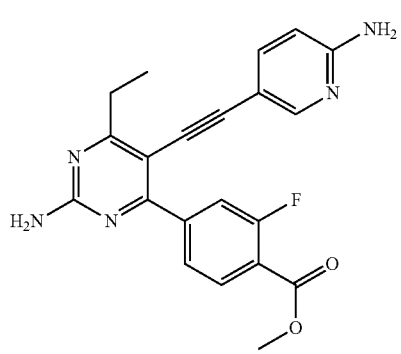 [SMILES: CCc1nc(N)nc(-c2ccc(C(=O)OC)c(F)c2)c1C#Cc1ccc(N)nc1]

The title compound is synthesized according to general procedure GP4 starting from 500 mg (1.8 mmol) 4-chloro-6-ethyl-5-(6-amino-pyridin-3-ylethynyl)-pyrimidin-2-ylamine using 542 mg (2.7 mmol) 3-Fluoro-4-methoxycarbonylphenyl boronic acid, 56 mg (0.37 mmol) Pd(PPh$_3$)$_4$, 611 mg (4.4 mmol) K$_2$CO$_3$ in 10 mL DME/H$_2$O (9:1 v/v). After stirring twice for 60 min at 130° C. under microwave irradiation, conversion of the starting material is about 75%, an about 1:4 mixture of the desired product and the saponified ester is formed. The product precipitates from the reaction mixture, is filtered off and is washed with water and diethylether. Yield: 537 mg (75%).

C-57) 4-[2-Amino-5-(6-amino-pyridin-3-ylethynyl)-6-ethyl-pyrimidin-4-yl]-2-fluoro-benzoic acid

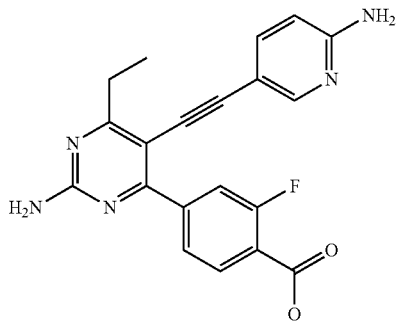

The title compound is synthesized according to general procedure GP8 starting from 630 mg (1.6 mmol) 4-[2-amino-5-(6-amino-pyridin-3-ylethynyl)-6-ethyl-pyrimidin-4-yl]-2-fluoro-benzoic acid methyl ester using 1.6 mL (1.6 mmol) 1 N NaOH in 10 mL THF. The precipitate is collected by filtration and washed with THF. Yield: 580 mg (96%).

C-58) 4-[2-Amino-5-(6-amino-pyridin-3-ylethynyl)-6-ethyl-pyrimidin-4-yl]-benzoic acid methyl ester

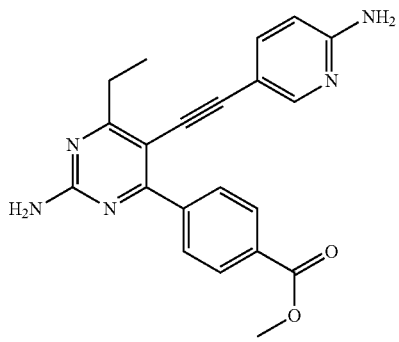 [SMILES: CCc1nc(N)nc(-c2ccc(C(=O)OC)cc2)c1C#Cc1ccc(N)nc1]

The title compound is synthesized according to general procedure GP4 starting from 300 mg (1.1 mmol) 4-chloro-6-ethyl-5-(6-amino-pyridin-3-ylethynyl)-pyrimidin-2-ylamine using 296 mg (1.6 mmol) 4-methoxycarbonylphenyl boronic acid, 34 mg (0.22 mmol) Pd(PPh$_3$)$_4$, 290 mg (2.1 mmol) K$_2$CO$_3$ in 5 mL DME/H$_2$O (5:2 v/v). The product precipitates from the reaction mixture, is filtered off and is washed with water and diethylether. Yield: 120 mg (29%).

The mother liquid contains the corresponding carboxylic acid which can be isolated together with acid obtained from the saponification of the ester.

C-59) 4-[2-Amino-5-(6-amino-pyridin-3-ylethynyl)-6-ethyl-pyrimidin-4-yl]-benzoic acid

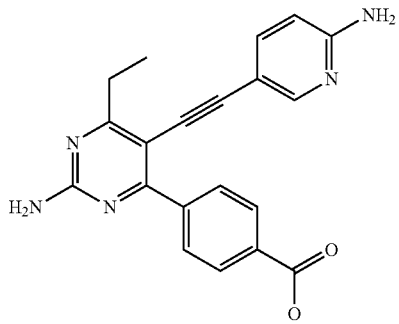 [SMILES: CCc1nc(N)nc(-c2ccc(C(=O)O)cc2)c1C#Cc1ccc(N)nc1]

The title compound is synthesized according to general procedure GP8 starting from 120 mg (0.32 mmol) 4-[2-amino-5-(6-amino-pyridin-3-ylethynyl)-6-ethyl-pyrimidin-4-yl]-benzoic acid methyl ester using 0.48 mL (0.48 mmol) 1 N NaOH in 3 mL THF.

For the work-up the reaction mixture is combined with the mother liquid from the proceeding Suzuki coupling (contains additional amounts of the product), the pH is adjusted to pH 4-5 (using 1 N HCl) upon which the product precipitates and is isolated by filtration. The product is washed with water and diethylether. Yield: 400 mg (>100% over 2 steps).

C-60) 4-[2-Amino-5-(6-amino-pyridin-3-ylethynyl)-6-ethyl-pyrimidin-4-yl]-2-chloro-benzoic acid methyl ester

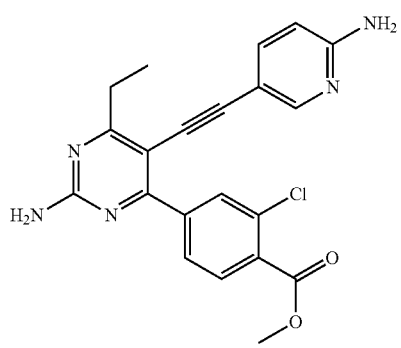 [SMILES: CCc1nc(N)nc(-c2ccc(C(=O)OC)c(Cl)c2)c1C#Cc1ccc(N)nc1]

The title compound is synthesized according to general procedure GP4 starting from 700 mg (2.6 mmol) 4-chloro-6-ethyl-5-(6-amino-pyridin-3-ylethynyl)-pyrimidin-2-ylamine using 822 mg (3.8 mmol) 3-Chloro-4-methoxycarbonylphenyl boronic acid, 80 mg (0.37 mmol) Pd(PPh$_3$)$_4$, 678 mg (4.8 mmol) K$_2$CO$_3$ in 9 mL DME/H$_2$O (7:2 v/v). The product precipitates from the reaction mixture, is filtered off and is washed with water, diethylether, isopropanol and again diethylether. Yield: 951 mg (91%).

C-61) 4-[2-Amino-5-(6-amino-pyridin-3-ylethynyl)-6-ethyl-pyrimidin-4-yl]-2-chloro-benzoic acid

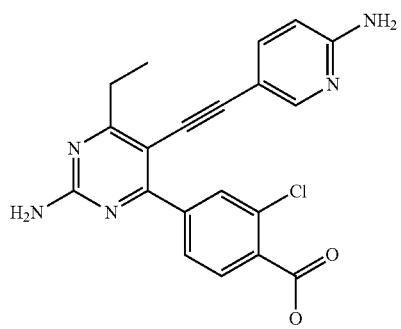 [SMILES: CCc1nc(N)nc(-c2ccc(C(=O)O)c(Cl)c2)c1C#Cc1ccc(N)nc1]

The title compound is synthesized according to general procedure GP8 starting from 951 mg (2.3 mmol) 4-[2-amino-5-(6-amino-pyridin-3-ylethynyl)-6-ethyl-pyrimidin-4-yl]-2-chloro-benzoic acid methyl ester using 3.5 mL (3.5 mmol) 1 N NaOH in 16 mL THF. The product precipitates from the reaction mixture and is isolated by filtration. The product is washed with THF and diethylether. Yield: 345 mg (38%).

C-62) 4-Chloro-6-ethyl-5-(6-methylamino-pyridin-3-ylethynyl)-pyrimidin-2-ylamine

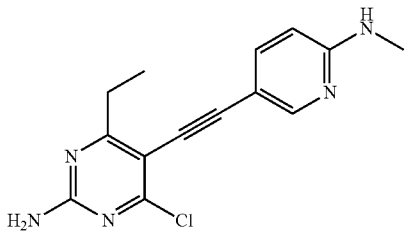 [SMILES: CCc1nc(N)nc(Cl)c1C#Cc1ccc(NC)nc1]

The title compound is synthesized according to general procedure GP2 starting from 3.0 g (10.6 mmol) 4-chloro-6-ethyl-5-iodo-pyrimidin-2-ylamine using 1.5 g (11.6 mmol) 5-ethynyl-2-aminomethyl-pyridine, 201 mg (1.1 mmol) CuI, 743 mg (1.1 mmol) bis-(triphenylphoshine)palladium (II) chloride, 15 mL (106 mmol) triethylamine in 25 mL DMF. The reaction mixture is stirred for 3 days at 55° C. The reaction mixture is concentrated under reduced pressure and the product is isolated by chromatography on silica gel. Yield: 1.54 g (51%).

C-63) 4-[2-Amino-6-ethyl-5-(6-methylamino-pyridin-3-ylethynyl)-pyrimidin-4-yl]-2-fluoro-benzoic acid methyl ester

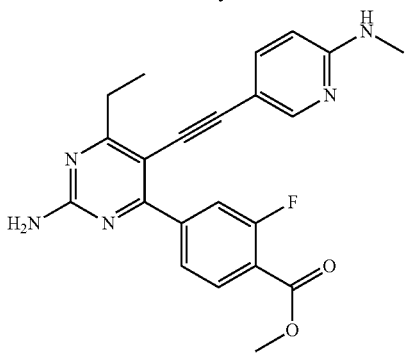

The title compound is synthesized according to general procedure GP4 starting from 330 mg (1.2 mmol) 4-chloro-6-ethyl-5-(6-aminomethyl-pyridin-3-ylethynyl)-pyrimidin-2-ylamine using 344 mg (1.7 mmol) 3-fluoro-4-methoxycarbonylphenyl boronic acid, 36 mg (0.23 mmol) Pd(PPh$_3$)$_4$, 307 mg (2.2 mmol) K$_2$CO$_3$ in 7 mL DME/H$_2$O (5:2 v/v). After stirring for 60 min at 130° C. under microwave irradiation, an about 1:1 mixture of the desired product and the saponified ester is formed. The product precipitates from the reaction mixture, is filtered off and is washed with water and diethylether.
Yield: 238 mg (51%).
The mother liquid contains the corresponding carboxylic acid which can be isolated together with acid obtained from the saponification of the ester.

C-64) 4-[2-Amino-6-ethyl-5-(6-methylamino-pyridin-3-ylethynyl)-pyrimidin-4-yl]-2-fluoro-benzoic acid

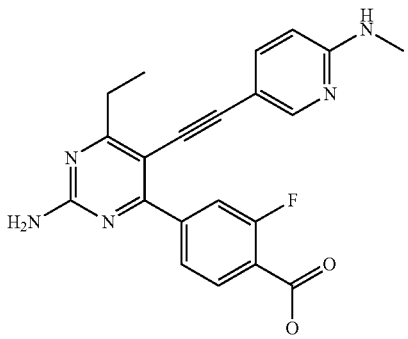 [SMILES: CCc1nc(N)nc(-c2ccc(C(=O)O)c(F)c2)c1C#Cc1ccc(NC)nc1]

The title compound is synthesized according to general procedure GP8 starting from 238 mg (0.59 mmol) 4-[2-amino-6-ethyl-5-(6-methylamino-pyridin-3-ylethynyl)-pyrimidin-4-yl]-2-fluoro-benzoic acid methyl ester using 0.88 mL (0.88 mmol) 1 N NaOH in 3 mL THF.

For the work-up the reaction mixture is combined with the mother liquid from the proceeding Suzuki coupling (contains additional amounts of the product), the pH is adjusted to pH 4-5 (using 1 N HCl) upon which the product precipitates and is isolated by filtration. The product is washed with water and diethylether. Yield: 517 mg (114% over 2 steps).

C-65) 4-Chloro-6-methyl-5-(6-methylamino-pyridin-3-ylethynyl)-pyrimidin-2-ylamine

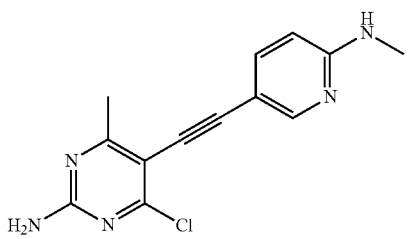 [SMILES: CNc1ccc(C#Cc2c(C)nc(N)nc2Cl)cn1]

The title compound is synthesized according to general procedure GP2 starting from 3.0 g (10.6 mmol) 4-chloro-6-ethyl-5-iodo-pyrimidin-2-ylamine using 1.5 g (11.6 mmol) 5-ethynyl-2-aminomethyl-pyridine, 201 mg (1.1 mmol) CuI, 743 mg (1.1 mmol) bis-(triphenylphoshine)palladium (II) chloride, 15 mL (106 mmol) triethylamine in 25 mL DMF. The reaction mixture is stirred for 3 days at 55° C. The reaction mixture is concentrated under reduced pressure and the product is isolated by chromatography on silica gel. Yield: 1.54 g (51%).

C-66) 4-[2-Amino-6-methyl-5-(6-methylamino-pyridin-3-ylethynyl)-pyrimidin-4-yl]-2-chloro-benzoic acid methyl ester

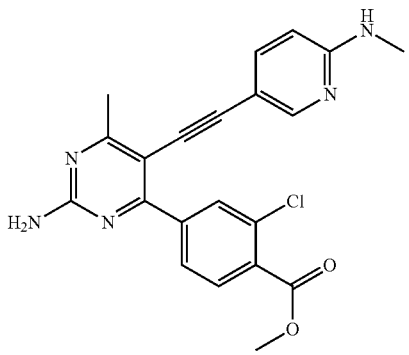 [SMILES: CNc1ccc(C#Cc2c(C)nc(N)nc2-c2ccc(C(=O)OC)c(Cl)c2)cn1]

The title compound is synthesized according to general procedure GP4 starting from 500 mg (1.8 mmol) 4-chloro-6-methyl-5-(6-aminomethyl-pyridin-3-ylethynyl)-pyrimidin-2-ylamine using 587 mg (2.7 mmol) 3-chloro-4-methoxycarbonylphenyl boronic acid, 56 mg (0.23 mmol) Pd(PPh$_3$)$_4$, 5100 mg (3.7 mmol) K$_2$CO$_3$ in 6 mL DME/H$_2$O (5:1 v/v). The product precipitates from the reaction mixture, is filtered off and is washed with water. Yield: 740 mg (99%).

C-67) 4-[2-Amino-6-methyl-5-(6-methylamino-pyridin-3-ylethynyl)-pyrimidin-4-yl]-2-chloro-benzoic acid

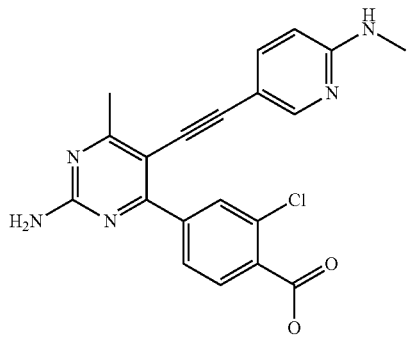 [SMILES: CNc1ccc(C#Cc2c(C)nc(N)nc2-c2ccc(C(=O)O)c(Cl)c2)cn1]

The title compound is synthesized according to general procedure GP8 starting from 700 mg (1.7 mmol) 4-[2-amino-6-methyl-5-(6-methylamino-pyridin-3-ylethynyl)-pyrimidin-4-yl]-2-chloro-benzoic acid methyl ester using 2.6 mL (2.6 mmol) 1 N NaOH in 10 mL THF. The product precipitates and is isolated by filtration. The product is washed with water and used without further purification. Yield: 370 mg (55%).

C-68) 4-[2-Amino-6-methyl-5-(6-methylamino-pyridin-3-ylethynyl)-pyrimidin-4-yl]-3-fluoro-benzoic acid ethyl ester

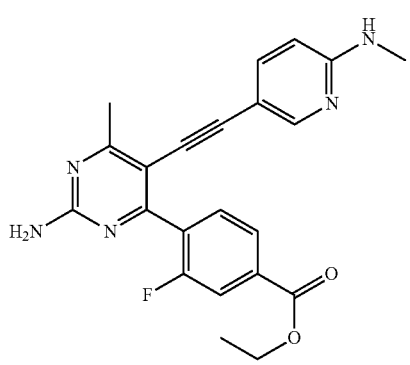 [SMILES: CCOC(=O)c1ccc(-c2nc(N)nc(C)c2C#Cc2ccc(NC)nc2)c(F)c1]

The title compound is synthesized according to general procedure GP4 starting from 500 mg (1.8 mmol) 4-chloro-6-methyl-5-(6-aminomethyl-pyridin-3-ylethynyl)-pyrimidin-2-ylamine using 581 mg (2.7 mmol) 2-fluoro-4-ethoxycarbonylphenyl boronic acid, 56 mg (0.37 mol) Pd(PPh$_3$)$_4$, 510 (3.7 mmol) K$_2$CO$_3$ in 6 mL DME/H$_2$O (5:1 v/v). After stirring for 2×30 min at 120° C. under microwave irradiation, the product precipitates from the reaction mixture, is filtered off and is washed with DMF, MeOH, water and diethylether. Yield: 637 mg (86%).

C-69) 4-[2-Amino-6-methyl-5-(6-methylamino-pyridin-3-ylethynyl)-pyrimidin-4-yl]-3-fluoro-benzoic acid

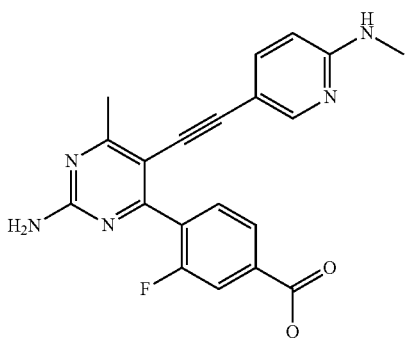 [SMILES: CNc1ccc(C#Cc2c(C)nc(N)nc2-c2ccc(C(=O)O)cc2F)cn1]

The title compound is synthesized according to general procedure GP8 starting from 640 mg (1.6 mmol) 4-[2-amino-6-methyl-5-(6-methylamino-pyridin-3-ylethynyl)-pyrimidin-4-yl]-2-chloro-benzoic acid ethyl ester using 2.4 mL (2.4 mmol) 1 N NaOH in 10 mL THF. The product precipitates and is isolated by filtration. The product is washed with water. Yield: 620 mg (104%, contains some starting material from the preceding Suzuki coupling).

C-70) 4-[2-Amino-5-(6-amino-pyridin-3-ylethynyl)-6-methyl-pyrimidin-4-yl]-benzoic acid methyl ester

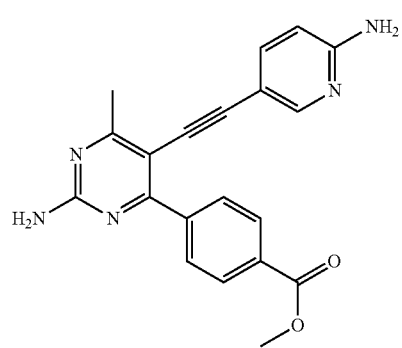 [SMILES: COC(=O)c1ccc(-c2nc(N)nc(C)c2C#Cc2ccc(N)nc2)cc1]

The title compound is synthesized according to general procedure GP4 starting from 2.0 g (7.7 mmol) 4-chloro-6-methyl-5-(6-amino-pyridin-3-ylethynyl)-pyrimidin-2-ylamine using 2.1 g (11.6 mmol) 4-methoxycarbonylphenyl boronic acid, 240 mg (1.5 mmol) Pd(PPh$_3$)$_4$, 2.2 g (15.4 mmol) K$_2$CO$_3$ in 20 mL DME/H$_2$O (4:1 v/v). The product precipitates from the reaction mixture, is filtered off and is washed with water and diethylether.

Yield: 2.3 g (98%).

C-71) 4-[2-Amino-5-(6-amino-pyridin-3-ylethynyl)-6-methyl-pyrimidin-4-yl]-benzoic acid

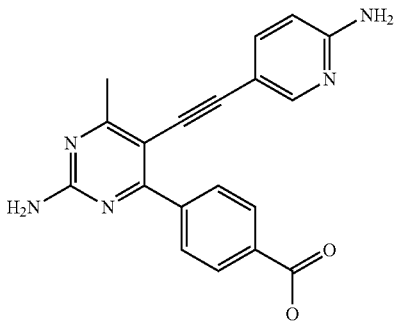 [SMILES: Cc1nc(N)nc(-c2ccc(C(=O)O)cc2)c1C#Cc1ccc(N)nc1]

The title compound is synthesized according to general procedure GP8 starting from 2.3 g (6.4 mmol) 4-[2-amino-5-(6-amino-pyridin-3-ylethynyl)-6-methyl-pyrimidin-4-yl]-benzoic acid methyl ester using 9.6 mL (9.6 mmol) 1 N NaOH in 20 mL THF. The product precipitates and is isolated by filtration and is washed with water. Yield: 2.2 g (99%).

C-72) 4-[2-Amino-5-(6-amino-pyridin-3-ylethynyl)-6-methyl-pyrimidin-4-yl]-2-chloro benzoic acid methyl ester

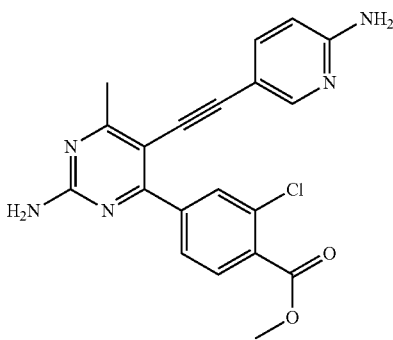 [SMILES: COC(=O)c1ccc(-c2nc(N)nc(C)c2C#Cc2ccc(N)nc2)cc1Cl]

The title compound is synthesized according to general procedure GP4 starting from 1.0 mg (3.9 mmol) 4-chloro-6-methyl-5-(6-amino-pyridin-3-ylethynyl)-pyrimidin-2-ylamine using 1.2 g (5.8 mmol) 2-chloro-4-methoxycarbonylphenyl boronic acid, 120 mg (0.77 mmol) Pd(PPh$_3$)$_4$, 1.0 g (7.3 mmol) K$_2$CO$_3$ in 12 mL DME/H$_2$O (5:1 v/v). The product precipitates from the reaction mixture, is filtered off and is washed with water and diethylether. Yield: 1.24 g (82%).

C-73) 4-[2-Amino-5-(6-amino-pyridin-3-ylethynyl)-6-methyl-pyrimidin-4-yl]-2-chloro benzoic acid

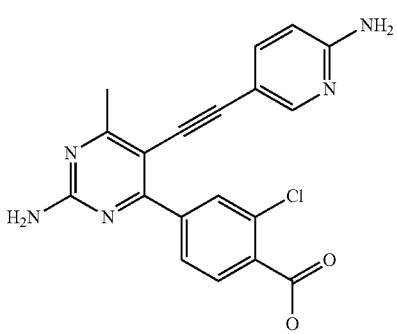 [SMILES: Cc1nc(N)nc(-c2ccc(C(=O)O)c(Cl)c2)c1C#Cc1ccc(N)nc1]

The title compound is synthesized according to general procedure GP8 starting from 1.24 g (3.1 mmol) 4-[2-amino-5-(6-amino-pyridin-3-ylethynyl)-6-methyl-pyrimidin-4-yl]-2-chloro-benzoic acid methyl ester using 4.7 mL (4.7 mmol) 1 N NaOH in 22 mL THF. The product precipitates and is isolated by filtration. The product is washed with THF and diethylether. Yield: 1.13 g (95%).

C-74) 4-[2-Amino-5-(6-amino-pyridin-3-ylethynyl)-6-methyl-pyrimidin-4-yl]-2-fluoro benzoic acid methyl ester

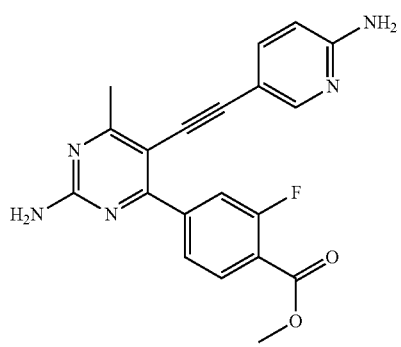 [SMILES: COC(=O)c1ccc(-c2nc(N)nc(C)c2C#Cc2ccc(N)nc2)cc1F]

The title compound is synthesized according to general procedure GP4 starting from 2.0 g (7.7 mmol) 4-chloro-6-methyl-5-(6-amino-pyridin-3-ylethynyl)-pyrimidin-2-ylamine using 2.3 g (11.6 mmol) 2-fluoro-4-methoxycarbonylphenyl boronic acid, 240 mg (1.5 mmol) Pd(PPh$_3$)$_4$, 2.6 g (18.5 mmol) K$_2$CO$_3$ in 24 mL DME/H$_2$O (5:1 v/v). The product precipitates from the reaction mixture, is filtered off and is washed with water and diethylether. Yield: 2.9 g (100%).

C-75) 4-[2-Amino-5-(6-amino-pyridin-3-ylethynyl)-6-methyl-pyrimidin-4-yl]-2-fluoro benzoic acid

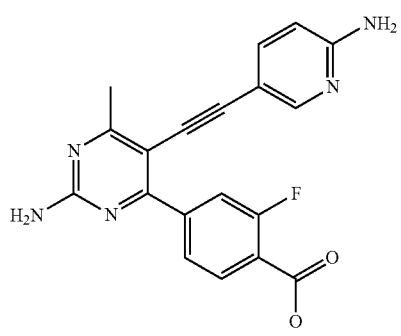 [SMILES: Cc1nc(N)nc(-c2ccc(C(=O)O)c(F)c2)c1C#Cc1ccc(N)nc1]

The title compound is synthesized according to general procedure GP8 starting from 3.0 g (8.0 mmol) 4-[2-amino-5-(6-amino-pyridin-3-ylethynyl)-6-methyl-pyrimidin-4-yl]-2-fluorobenzoic acid methyl ester using 12 mL (12 mmol) 1 N NaOH in 30 mL THF. The product precipitates and is isolated by filtration. The product is washed with water. Yield: 2.2 g (76%).

C-76) 5-[2-Amino-5-(6-amino-pyridin-3-ylethynyl)-6-methyl-pyrimidin-4-yl]-2-fluoro-benzoic acid methyl ester

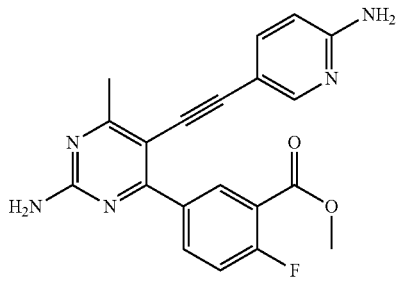

The title compound is synthesized according to general procedure GP4 starting from 1.5 g (5.8 mmol) 4-chloro-6-methyl-5-(6-amino-pyridin-3-ylethynyl)-pyrimidin-2-ylamine using 1.7 g (8.7 mmol) (4-fluoro-3-methoxycarbonyl)phenyl boronic acid, 67 mg (0.58 mmol) Pd(PPh$_3$)$_4$, 2.6 g (18.5 mmol) K$_2$CO$_3$ in 18 mL DME/H$_2$O/ethanol (10:5:1 v/v/v). The product precipitates from the reaction mixture, is filtered off and is washed with water and diethylether yielding 1.95 g (5.2 mmol) of the desired product, which is used without further purification.

C-77) 5-[2-Amino-5-(6-amino-pyridin-3-ylethynyl)-6-methyl-pyrimidin-4-yl]-2-fluoro-benzoic acid

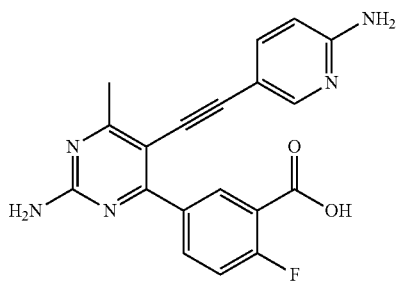

The title compound is synthesized according to general procedure GP8 starting from 1.95 g (5.1 mmol) 5-[2-amino-5-(6-amino-pyridin-3-ylethynyl)-6-methyl-pyrimidin-4-yl]-2-fluoro-benzoic acid methyl ester using 500 mg (11.9 mmol) LiOH in 40 mL THF and 10 mL water. The product precipitates and is isolated by filtration. The product is washed with MeOH yielding 1.76 g (4.48 mmol) of the desired product.

C-78) 5-[2-Amino-5-(6-amino-pyridin-3-ylethynyl)-6-methyl-pyrimidin-4-yl]-2-chloro-benzoic acid methyl ester

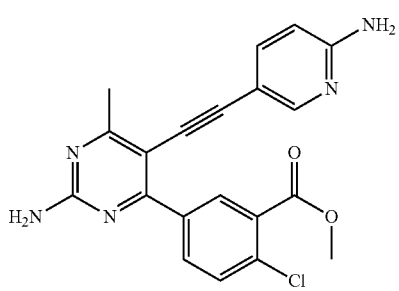 [SMILES: COC(=O)c1cc(-c2nc(N)nc(C)c2C#Cc2ccc(N)nc2)ccc1Cl]

The title compound is synthesized according to general procedure GP4 starting from 1.5 g (5.8 mmol) 4-chloro-6-methyl-5-(6-amino-pyridin-3-ylethynyl)-pyrimidin-2-ylamine using 1.36 g (6.35 mmol) (4-chloro-3-methoxycarbonyl)phenyl boronic acid, 202 mg (0.29 mmol) Pd(PPh$_3$)$_4$, 2.6 g (18.5 mmol) K$_2$CO$_3$ in 16 mL DME/H$_2$O (5:1 v/v). The product precipitates from the reaction mixture, is filtered off and is washed with water and diethylether yielding 1.76 g (4.4 mmol) desired product, which is used without further purification.

C-79) 5-[2-Amino-5-(6-amino-pyridin-3-ylethynyl)-6-methyl-pyrimidin-4-yl]-2-chloro-benzoic acid

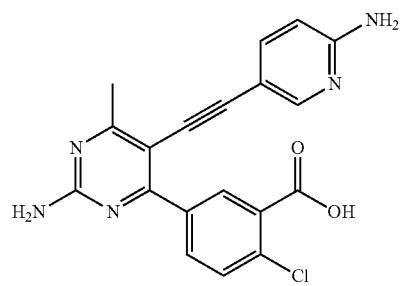 [SMILES: Cc1nc(N)nc(-c2ccc(Cl)c(C(=O)O)c2)c1C#Cc1ccc(N)nc1]

The title compound is synthesized according to general procedure GP8 starting from 2.28 g (5.78 mmol) 5-[2-amino-5-(6-amino-pyridin-3-ylethynyl)-6-methyl-pyrimidin-4-yl]-2-chloro-benzoic acid methyl ester using 347 mg (14.4 mmol.) LiOH in 20 mL THF and 1 mL water. The product precipitates and is isolated by filtration. The product is washed with water/acetonitrile (1:1 v/v) yielding 1.30 g (3.44 mmol) desired product, which is used without further purification.

C-84) 4-[2-Amino-5-(6-amino-pyridin-3-ylethynyl)-6-methyl-pyrimidin-4-yl]-piperazine-1-carboxylic acid tert-butyl ester

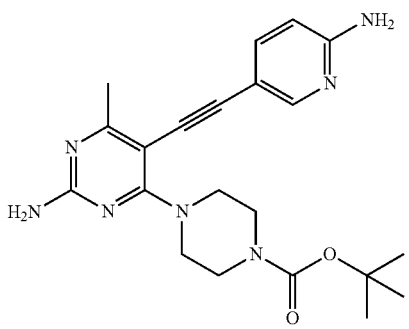 [SMILES: Cc1nc(N)nc(N2CCN(C(=O)OC(C)(C)C)CC2)c1C#Cc1ccc(N)nc1]

The title compound is synthesized according to general procedure GP7 starting from 5.0 g (19.3 mmol) 4-chloro-6-methyl-5-(6-amino-pyridin-3-ylethynyl)-pyrimidin-2-ylamine and 3.94 g (21.2 mmol) N-Boc-piperazine using 2.94 mL (21.2 mmol) triethylamine in 30 mL NMP. Work up is performed by addition of 500 mL water to the reaction mixture and stirring for 30 min. The solid material is filtered off, washed with water (50 mL three times) yielding 7.25 g (17.7 mmol) of the desired product with sufficient purity.

C-85) 5-(6-Amino-pyridin-3-ylethynyl)-4-methyl-6-piperazin-1-yl-pyrimidin-2-ylamine

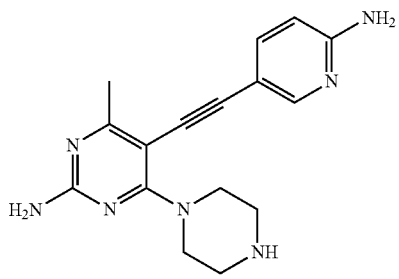 [SMILES: Cc1nc(N)nc(N2CCNCC2)c1C#Cc1ccc(N)nc1]

7.1 g (17.3 mmol) of 4-[2-amino-5-(6-amino-pyridin-3-ylethynyl)-6-methyl-pyrimidin-4-yl]-piperazine-1-carboxylic acid tert-butyl ester are dissolved in DCM (400 mL) and 40 mL TFA are added. The reaction mixture is stirred over night at RT. The reaction mixture is adjusted to neutral pH using concentrated aqueous $Na_2CO_3$ solution and the DCM is evaporated at reduced pressure. The residue is washed with water, taken up in acetonitrile and freeze dried yielding 4.0 g (13.0 mmol) of the desired product which is used for the next step without further purification.

C-86) 1-[2-Amino-5-(6-amino-pyridin-3-ylethynyl)-6-methyl-pyrimidin-4-yl]-piperidine-4-carboxylic acid ethyl ester

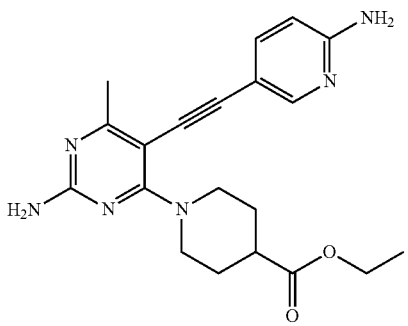 [SMILES: CCOC(=O)C1CCN(c2nc(N)nc(C)c2C#Cc2ccc(N)nc2)CC1]

The title compound is synthesized according to general procedure GP7 starting from 2.0 g (7.7 mmol) 4-chloro-6-methyl-5-(6-amino-pyridin-3-ylethynyl)-pyrimidin-2-ylamine and 1.33 g (8.47 mmol) piperidine-4-carboxylic acid ethyl ester using 1.18 mL (8.5 mmol) triethylamine in 12 mL NMP. Work up is performed by addition of 50 mL water to the reaction mixture and stirring for 30 min. The solid material is filtered off, washed with water (50 mL three times) yielding 1.58 g (4.15 mmol) of the desired product with sufficient purity.

C-87) 1-[2-Amino-5-(6-amino-pyridin-3-ylethynyl)-6-methyl-pyrimidin-4-yl]-piperidine-4-carboxylic acid

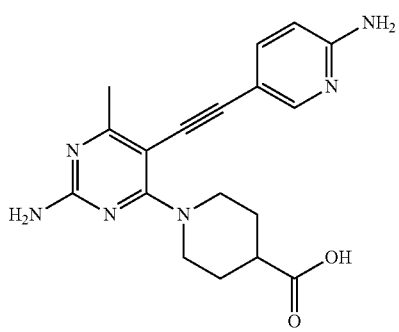 [SMILES: Cc1nc(N)nc(N2CCC(C(=O)O)CC2)c1C#Cc1ccc(N)nc1]

The title compound is synthesized according to general procedure GP8 starting from 1.0 g (2.63 mmol) 1-[2-amino-5-(6-amino-pyridin-3-ylethynyl)-6-methyl-pyrimidin-4-yl]-piperidine-4-carboxylic acid ethyl ester and 126 mg (5.26 mmol) LiOH in 80 mL THF and 20 ml water. Yielding 772 mg (2.19 mmol) of the desired product.

C-88) 4-[2-Amino-5-(6-amino-pyridin-3-ylethynyl)-6-methyl-pyrimidin-4-yl]-3,6-dihydro-2H-pyridine-1-carboxylic acid tert-butyl ester

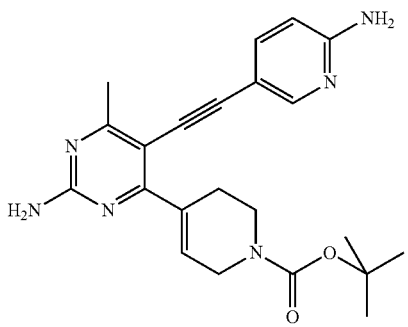 [SMILES: Cc1nc(N)nc(C2=CCN(C(=O)OC(C)(C)C)CC2)c1C#Cc1ccc(N)nc1]

A mixture of 500 mg (1.9 mmol) 4-chloro-6-methyl-5-(6-amino-pyridin-3-ylethynyl)-pyrimidin-2-ylamine, 1.2 g (3.9 mmol) 4-(4,4,5,5-tetramethyl-[1,3,2]-dioxaborolan-2-yl)-3,6-dihydro-2H-pyridine-1-carboxylic acid tert-butyl ester, 135 mg (1.9 mmol) $Pd(PPh_3)_2Cl_2$, 40 mL 1 M aqueous $Na_2CO_3$ solution and 244 mg LiCl (5.78 mmol) in 100 mL toluene/ethanol (4:1 v/v) is kept over 2 days at reflux. After cooling the solvent is evaporated, water is added and the aqueous suspension is extracted 4 times with ethyl acetate (200 mL each). The organic layer is dried over MgSO4 and the solvent is removed under reduced pressure. The residue is purified using flash column chromatography yielding 635 mg (1.56 mmol) of the desired product which is used without further purification in the next step.

C-89) 5-(6-Amino-pyridin-3-ylethynyl)-4-methyl-6-(1,2,3,6-tetrahydro-pyridin-4-yl)-pyrimidin-2-ylamine

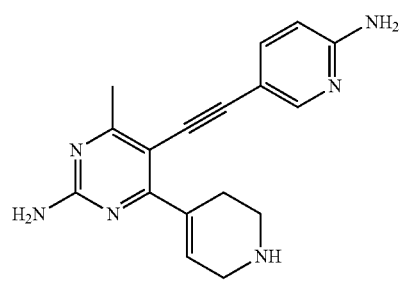 [SMILES: Cc1nc(N)nc(C2=CCNCC2)c1C#Cc1ccc(N)nc1]

630 mg (1.5 mmol) of 4-[2-amino-5-(6-amino-pyridin-3-ylethynyl)-6-methyl-pyrimidin-4-yl]-3,6-dihydro-2H-pyridine-1-carboxylic acid tert-butyl ester are dissolved in DCM (40 mL) and 2 mL TFA are added. The reaction mixture is stirred for 3 h, concentrated aqueous $Na_2CO_3$ solution is added until pH 7 is reached and DCM is evaporated at reduced pressure. The residue is washed with water, taken up in acetonitrile and freeze dried yielding 253 mg (0.83 mmol) of the desired product which is used for the next step without further purification.

C-90) {1-[2-Amino-5-(6-amino-pyridin-3-ylethynyl)-6-methyl-pyrimidin-4-yl]-piperidin-3-yl}-carbamic acid tert-butyl ester

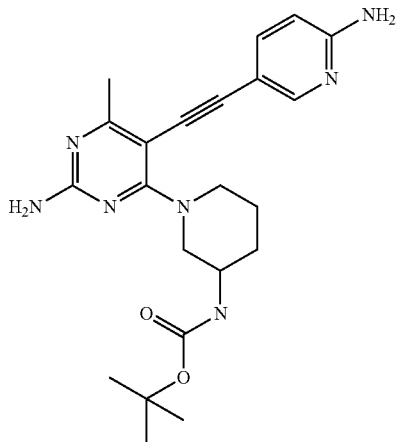 [SMILES: Cc1nc(N)nc(N2CCCC(NC(=O)OC(C)(C)C)C2)c1C#Cc1ccc(N)nc1]

The title compound is synthesized according to general procedure GP7 starting from 2.0 g (7.7 mmol) 4-chloro-6-methyl-5-(6-amino-pyridin-3-ylethynyl)-pyrimidin-2-ylamine and 2.0 g (10.0 mmol) piperidin-3-yl-carbamic acid tert-butyl ester using 1.29 mL (9.2 mmol) triethylamine in 5 mL NMP and 5 mL DMSO. 200 mL ethyl acetate and 100 mL half concentrated aqueous $Na_2CO_3$ solution are added and the phases are separated. The aqueous phase is extracted 2 times with ethyl acetate (100 mL each). The combined organic layers are dried over sodium sulfate and the solvent is removed under reduced pressure. The crude product is used without further purification in the next step.

C-91) 4-(3-Amino-piperidin-1-yl)-5-(6-amino-pyridin-3-ylethynyl)-6-methyl-pyrimidin-2-ylamine

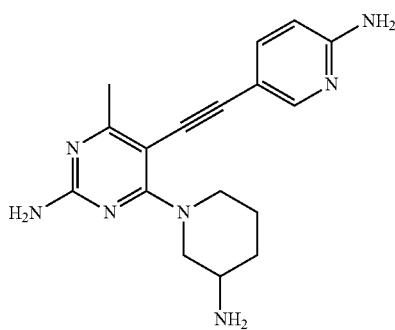 [SMILES: Cc1nc(N)nc(N2CCCC(N)C2)c1C#Cc1ccc(N)nc1]

3.3 g (7.8 mmol) of {1-[2-amino-5-(6-amino-pyridin-3-ylethynyl)-6-methyl-pyrimidin-4-yl]-piperidin-3-yl}-carbamic acid tert-butyl ester are dissolved in DCM (50 mL) and 26 mL TFA are added. The reaction mixture is stirred over night at RT. The reaction mixture is adjusted to neutral pH using concentrated aqueous $Na_2CO_3$ solution and the DCM is evaporated at reduced pressure. The residue is washed with water, taken up in acetonitrile and freeze dried. The crude product is used without further purification in the next step.

C-92) {1-[2-Amino-5-(6-amino-pyridin-3-ylethynyl)-6-methyl-pyrimidin-4-yl]-piperidin-4-yl}-carbamic acid tert-butyl ester

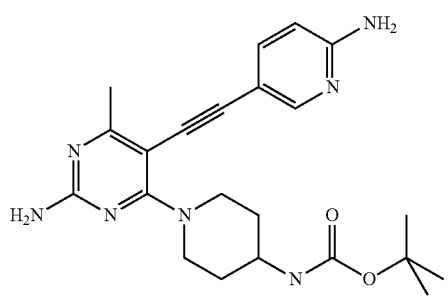 [SMILES: Cc1nc(N)nc(N2CCC(NC(=O)OC(C)(C)C)CC2)c1C#Cc1ccc(N)nc1]

The title compound is synthesized according to general procedure GP7 starting from 2.0 g (7.7 mmol) 4-chloro-6-methyl-5-(6-amino-pyridin-3-ylethynyl)-pyrimidin-2-ylamine and 1.7 g (8.47 mmol) piperidin-4-yl-carbamic acid tert-butyl ester using 1.07 ml (7.7 mmol) triethylamine in 3 mL NMP and 12 mL DMSO. 200 mL ethyl acetate and 100 mL half concentrated aqueous $Na_2CO_3$ solution are added and the phases are separated. The aqueous phase is extracted 2 times with ethyl acetate (100 mL each). The combined organic layers are dried over sodium sulfate and the solvent is removed under reduced pressure. The crude product is used without further purification in the next step.

C-93) 4-(4-Amino-piperidin-1-yl)-5-(6-amino-pyridin-3-ylethynyl)-6-methyl-pyrimidin-2-ylamine

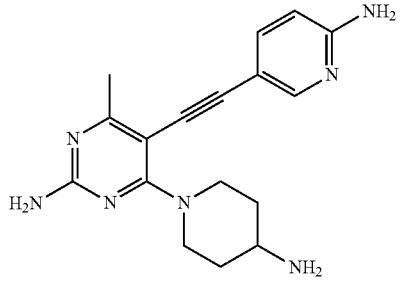 [SMILES: Cc1nc(N)nc(N2CCC(N)CC2)c1C#Cc1ccc(N)nc1]

3.2 g (7.6 mmol) of {1-[2-amino-5-(6-amino-pyridin-3-ylethynyl)-6-methyl-pyrimidin-4-yl]-piperidin-4-yl}-carbamic acid tert-butyl ester are dissolved in DCM (50 mL) and 26 mL TFA are added. The reaction mixture is stirred over night at RT. The reaction mixture is adjusted to neutral pH using concentrated aqueous $Na_2CO_3$ solution and the DCM is evaporated at reduced pressure. The residue is washed with water, taken up in acetonitrile and freeze dried. The crude product is used without further purification in the next step.

EXAMPLES 213-418

| No. | Structure | Starting Material | MW | MS [M + H]+ | HPLC t$_{Ret}$ |
|-----|-----------|-------------------|------|-------------|----------------|
| 213 | 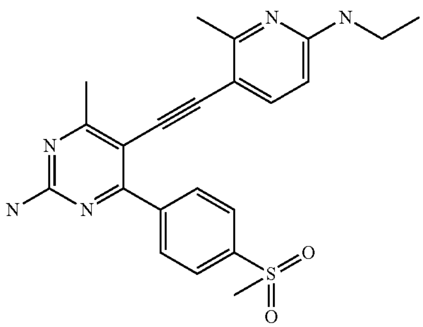 [SMILES: CCNc1ccc(C#Cc2c(C)nc(N)nc2-c2ccc(S(C)(=O)=O)cc2)c(C)n1] | A-39 | 421.5 | 422 | 1.58 |
| 214 | 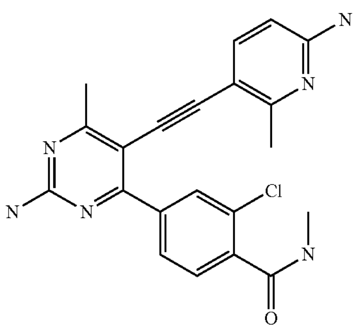 [SMILES: CNC(=O)c1ccc(-c2nc(N)nc(C)c2C#Cc2ccc(N)nc2C)cc1Cl] | | 406.9 | 407 | 1.19 |
| 215 | 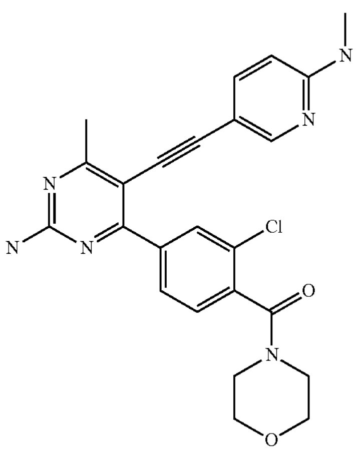 [SMILES: CNc1ccc(C#Cc2c(C)nc(N)nc2-c2ccc(C(=O)N3CCOCC3)c(Cl)c2)cn1] | | 462.9 | 463 | 1.45 |
| 216 | 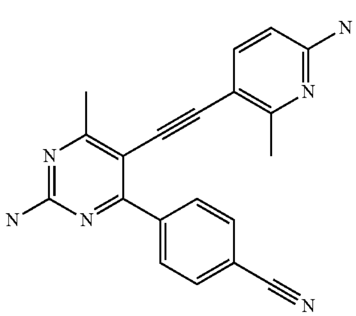 [SMILES: Cc1nc(N)ccc1C#Cc1c(C)nc(N)nc1-c1ccc(C#N)cc1] | | 340.4 | 341 | 1.39 |

-continued

| No. | Structure | Starting Material | MW | MS [M + H]+ | HPLC t_Ret |
|---|---|---|---|---|---|
| 217 | 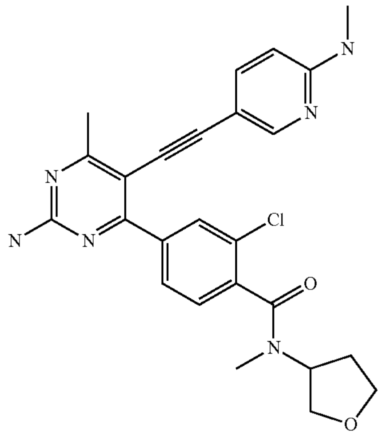 [SMILES: CNc1ccc(C#Cc2c(C)nc(N)nc2-c2ccc(C(=O)N(C)C3CCOC3)c(Cl)c2)cn1] | C-67 | 477 | 477/479 | 1.50 |
| 218 | 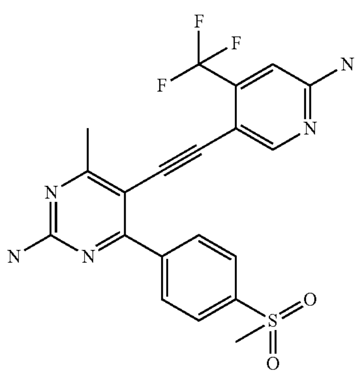 [SMILES: Cc1nc(N)nc(-c2ccc(S(C)(=O)=O)cc2)c1C#Cc1cnc(N)cc1C(F)(F)F] | A-39 | 447.4 | 448 | 1.47 |
| 219 | 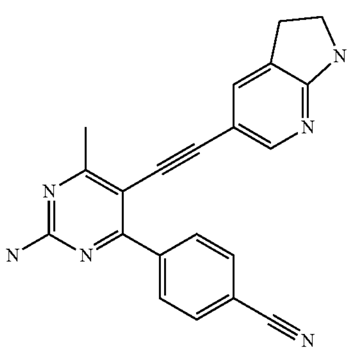 [SMILES: Cc1nc(N)nc(-c2ccc(C#N)cc2)c1C#Cc1cnc2c(c1)CCN2] | | 352.4 | 353 | 1.49 |

-continued
| No. | Structure | Starting Material | MW | MS [M + H]+ | HPLC t$_{Ret}$ |
|---|---|---|---|---|---|
| 220 | 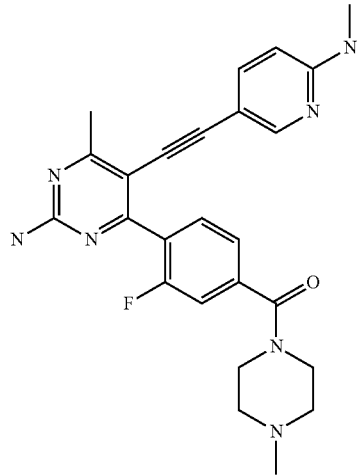 [SMILES: CNc1ccc(C#Cc2c(C)nc(N)nc2-c2ccc(C(=O)N3CCN(C)CC3)cc2F)cn1] | C-69 | 459.5 | 460 | 1.33 |
| 221 | 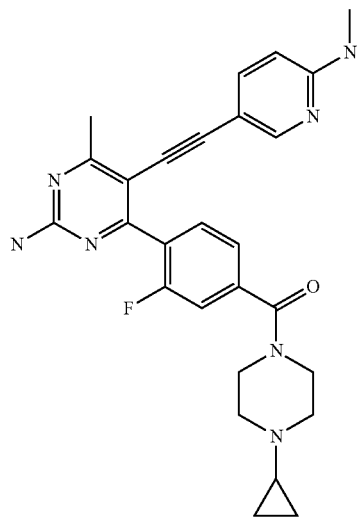 [SMILES: CNc1ccc(C#Cc2c(C)nc(N)nc2-c2ccc(C(=O)N3CCN(C4CC4)CC3)cc2F)cn1] | C-69 | 485.6 | 486 | 1.67 |
| 222 | 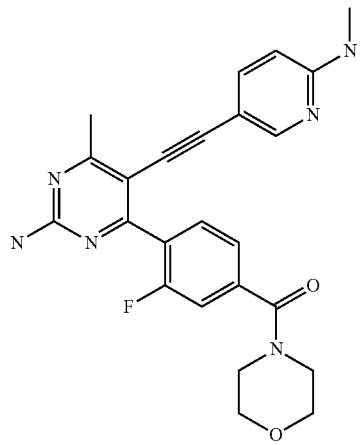 [SMILES: CNc1ccc(C#Cc2c(C)nc(N)nc2-c2ccc(C(=O)N3CCOCC3)cc2F)cn1] | C-69 | 446.5 | 447 | 1.37 |

-continued

| No. | Structure | Starting Material | MW | MS [M + H]+ | HPLC t_Ret |
|---|---|---|---|---|---|
| 223 | 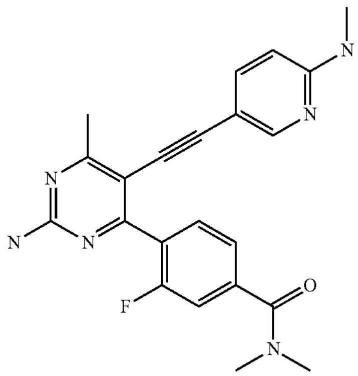 [SMILES: CNc1ccc(C#Cc2c(C)nc(N)nc2-c2ccc(C(=O)N(C)C)cc2F)cn1] | C-69 | 404.4 | 405 | 1.34 |
| 224 | 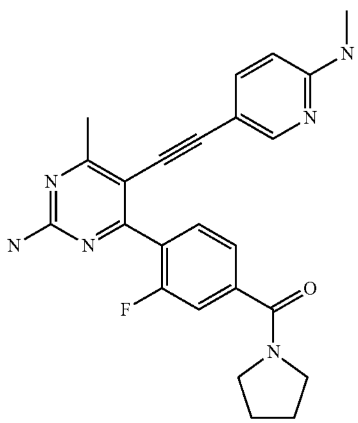 [SMILES: CNc1ccc(C#Cc2c(C)nc(N)nc2-c2ccc(C(=O)N3CCCC3)cc2F)cn1] | C-69 | 430.5 | 431 | 1.60 |
| 225 | 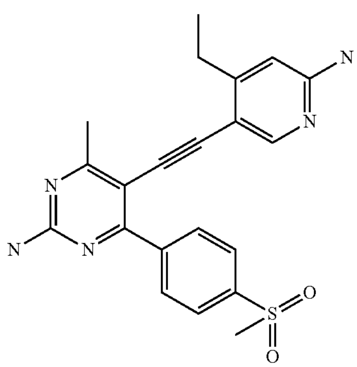 [SMILES: CCc1cc(N)ncc1C#Cc1c(C)nc(N)nc1-c1ccc(S(C)(=O)=O)cc1] | A-39 | 407.5 | 408 | 1.43 |
| 226 | 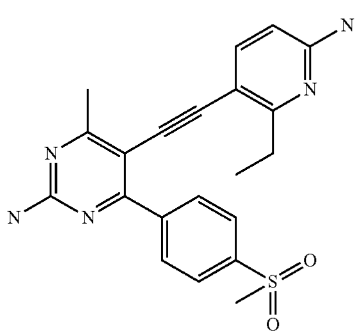 [SMILES: CCc1nc(N)ccc1C#Cc1c(C)nc(N)nc1-c1ccc(S(C)(=O)=O)cc1] | A-39 | 407.5 | 408 | 1.47 |

-continued

| No. | Structure | Starting Material | MW | MS [M + H]+ | HPLC t_Ret |
|---|---|---|---|---|---|
| 227 | 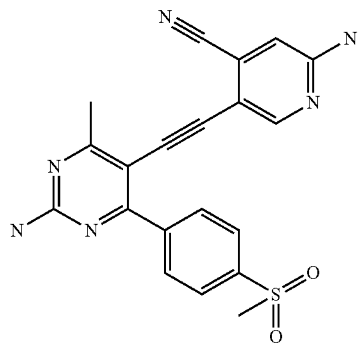 [SMILES: Cc1nc(N)nc(-c2ccc(S(C)(=O)=O)cc2)c1C#Cc1cnc(N)cc1C#N] | A-39 | 404.5 | M − H = 403 | |
| 228 | 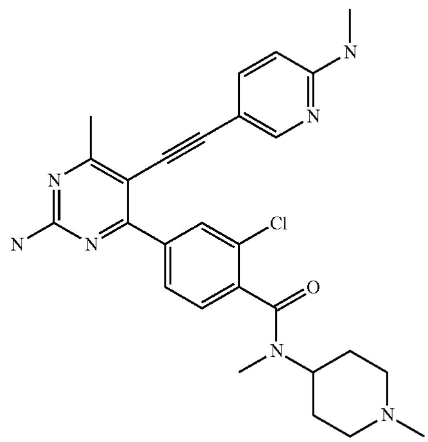 [SMILES: CNc1ccc(C#Cc2c(C)nc(N)nc2-c2ccc(C(=O)N(C)C3CCN(C)CC3)c(Cl)c2)cn1] | C-67 | 504 | 504/506 | 1.48 |
| 229 | 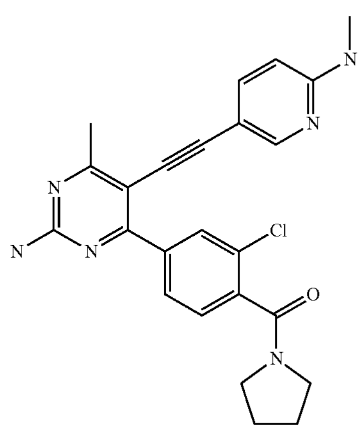 [SMILES: CNc1ccc(C#Cc2c(C)nc(N)nc2-c2ccc(C(=O)N3CCCC3)c(Cl)c2)cn1] | C-67 | 446.9 | 447/449 | 1.56 |
| 230 | 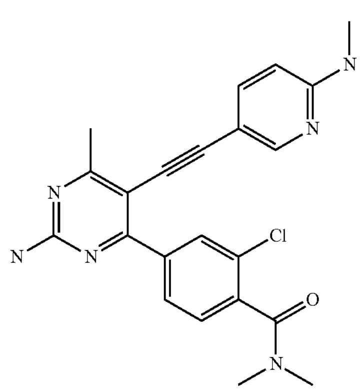 [SMILES: CNc1ccc(C#Cc2c(C)nc(N)nc2-c2ccc(C(=O)N(C)C)c(Cl)c2)cn1] | C-67 | 420.9 | 421 | 1.49 |

-continued

| No. | Structure | Starting Material | MW | MS [M + H]+ | HPLC t_Ret |
|---|---|---|---|---|---|
| 231 | 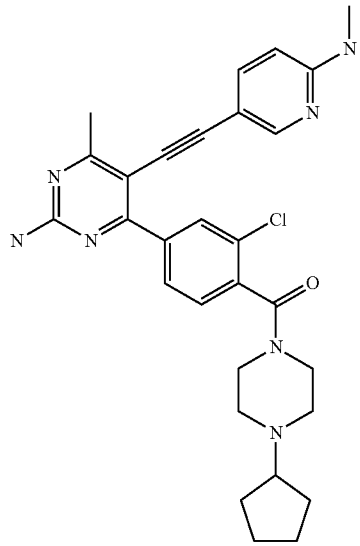 [SMILES: CNc1ccc(C#Cc2c(C)nc(N)nc2-c2ccc(C(=O)N3CCN(C4CCCC4)CC3)c(Cl)c2)cn1] | C-67 | 530.1 | 530/532 | 1.75 |
| 232 | 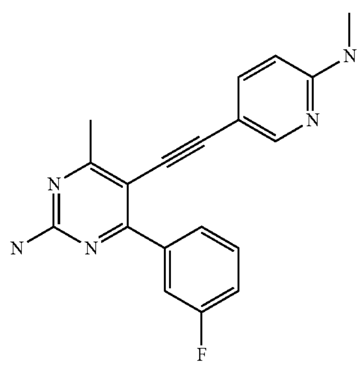 [SMILES: CNc1ccc(C#Cc2c(C)nc(N)nc2-c2cccc(F)c2)cn1] | C-65 | 333.4 | 334 | 1.61 |
| 233 | 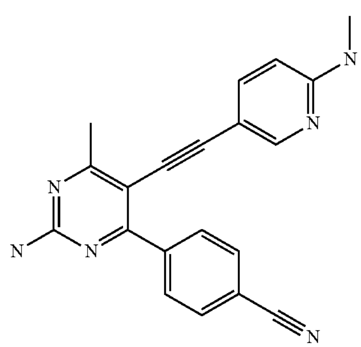 [SMILES: CNc1ccc(C#Cc2c(C)nc(N)nc2-c2ccc(C#N)cc2)cn1] | C-65 | 340.4 | 341 | 1.55 |

-continued

| No. | Structure | Starting Material | MW | MS [M + H]+ | HPLC $t_{Ret}$ |
|---|---|---|---|---|---|
| 234 | 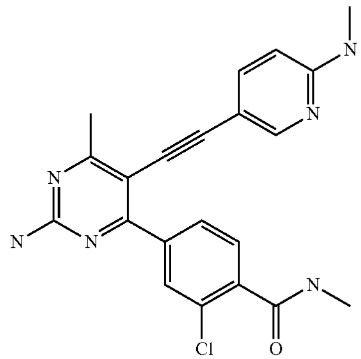 [SMILES: CNC(=O)c1ccc(-c2nc(N)nc(C)c2C#Cc2ccc(NC)nc2)cc1Cl] | C-65 | 406.9 | 407 | 1.40 |
| 235 | 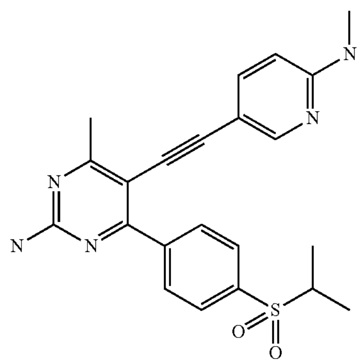 [SMILES: CNc1ccc(C#Cc2c(C)nc(N)nc2-c2ccc(S(=O)(=O)C(C)C)cc2)cn1] | C-65 | 421.5 | 422 | 1.55 |
| 236 | 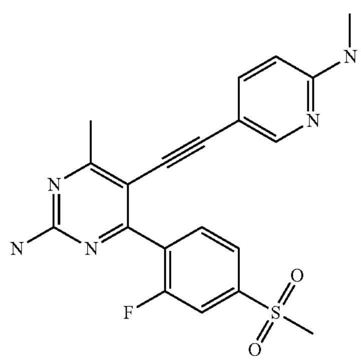 [SMILES: CNc1ccc(C#Cc2c(C)nc(N)nc2-c2ccc(S(C)(=O)=O)cc2F)cn1] | C-65 | 411.5 | 412 | |
| 237 | 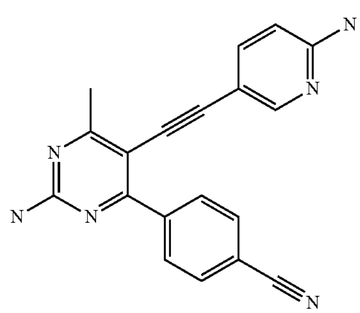 [SMILES: Cc1nc(N)nc(-c2ccc(C#N)cc2)c1C#Cc1ccc(N)nc1] | A-33 | 326.4 | 327 | 1.40 |

-continued
| No. | Structure | Starting Material | MW | MS [M + H]+ | HPLC t<sub>Ret</sub> |
|---|---|---|---|---|---|
| 238 | 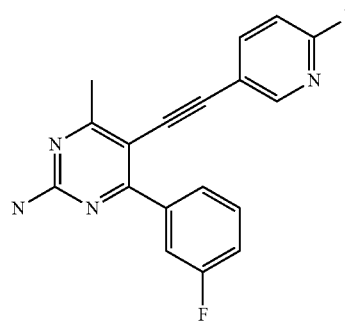 | A-33 | 319.3 | 320 | 1.26 |
| 239 | 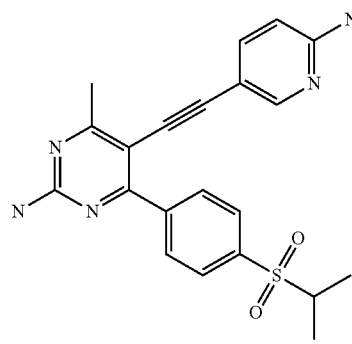 | A-33 | 407.5 | 408 | 1.42 |
| 240 | 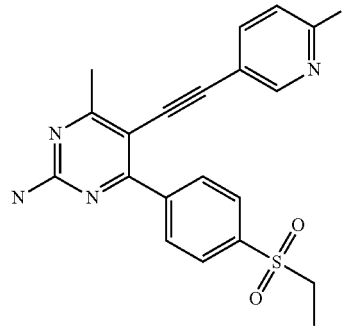 | A-33 | 393.5 | 394 | 1.34 |
| 241 | 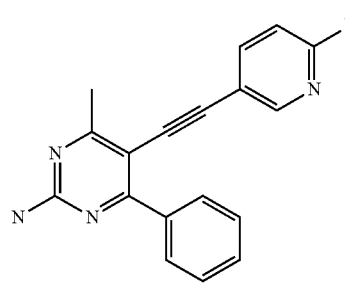 | A-33 | 301.4 | 302 | 1.39 |

-continued

| No. | Structure | Starting Material | MW | MS [M + H]+ | HPLC t_Ret |
|---|---|---|---|---|---|
| 242 | 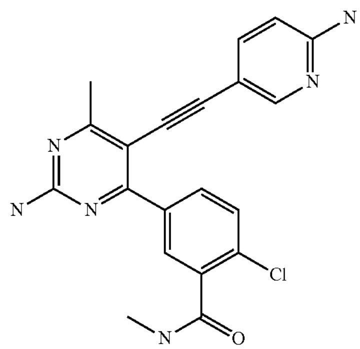 [SMILES: CNC(=O)c1cc(-c2nc(N)nc(C)c2C#Cc2ccc(N)nc2)ccc1Cl] | A-33 | 392.8 | 393 | 1.27 |
| 243 | 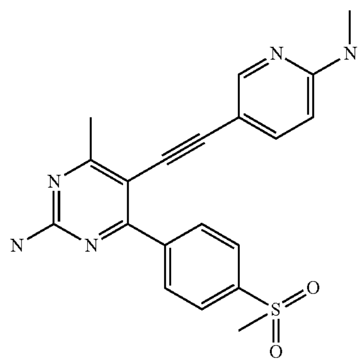 [SMILES: CNc1ccc(C#Cc2c(C)nc(N)nc2-c2ccc(S(C)(=O)=O)cc2)cn1] | A-30 | 393.5 | 394 | 1.50 |
| 244 | 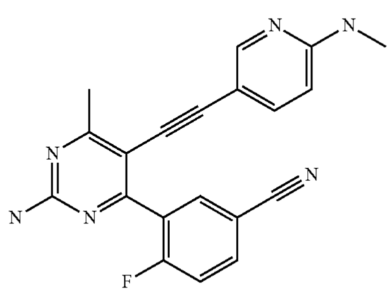 [SMILES: CNc1ccc(C#Cc2c(C)nc(N)nc2-c2cc(C#N)ccc2F)cn1] | A-30 | 358.4 | 359 | 1.52 |
| 245 | 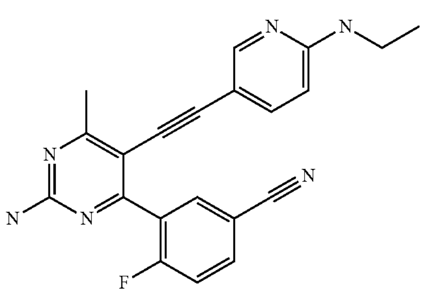 [SMILES: CCNc1ccc(C#Cc2c(C)nc(N)nc2-c2cc(C#N)ccc2F)cn1] | | 372.4 | 373 | 1.64 |
| 246 | 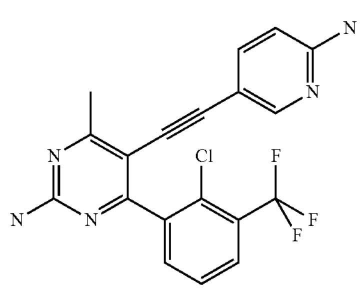 [SMILES: Cc1nc(N)nc(-c2cccc(C(F)(F)F)c2Cl)c1C#Cc1ccc(N)nc1] | A-33 | 403.8 | 404 | 1.59 |

-continued
| No. | Structure | Starting Material | MW | MS [M + H]+ | HPLC t$_{Ret}$ |
|---|---|---|---|---|---|
| 247 | 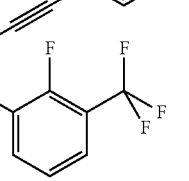 | A-33 | 387.3 | 388 | 1.56 |
| 248 | 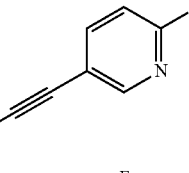 | A-33 | 376.4 | 377 | 1.28 |
| 249 | 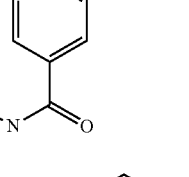 | A-33 | 368.4 | 369 | 1.51 |
| 250 | 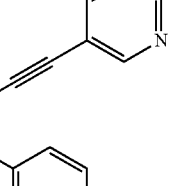 | A-33 | 399.4 | 400 | 1.64 |
| 251 | 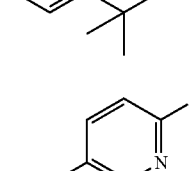 | A-33 | 399.4 | 400 | 1.63 |

-continued
| No. | Structure | Starting Material | MW | MS [M + H]+ | HPLC t_Ret |
|---|---|---|---|---|---|
| 252 | 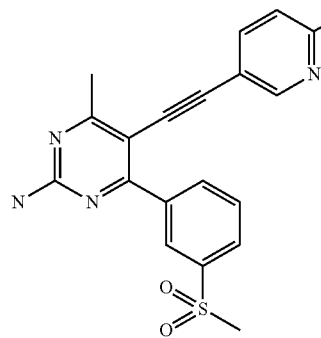 | A-33 | 379.4 | 380 | 1.26 |
| 253 | 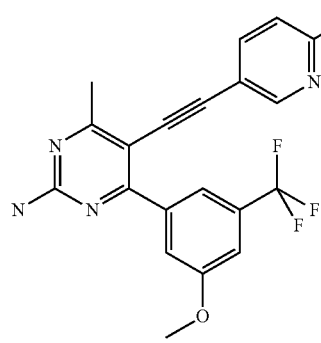 | A-33 | 399.4 | 400 | 1.68 |
| 254 | 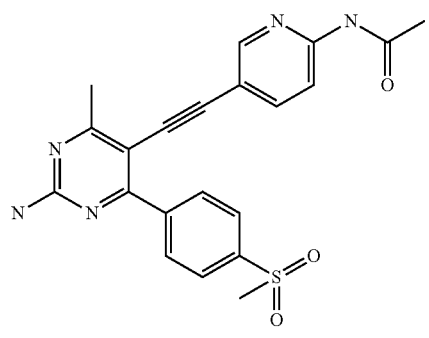 [SMILES: CC(=O)Nc1ccc(C#Cc2c(C)nc(N)nc2-c2ccc(S(C)(=O)=O)cc2)cn1] | A-39 | 421.5 | 422 | |
| 255 | 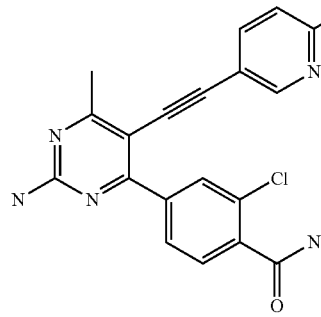 | A-33 | 378.8 | 379 | |

-continued

| No. | Structure | Starting Material | MW | MS [M + H]⁺ | HPLC $t_{Ret}$ |
|---|---|---|---|---|---|
| 256 | 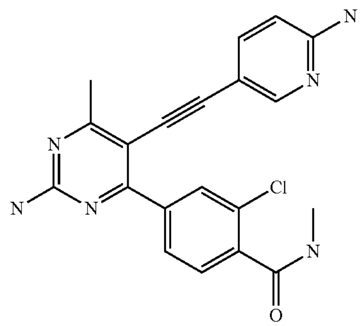 [SMILES: CNC(=O)c1ccc(-c2nc(N)nc(C)c2C#Cc2ccc(N)nc2)cc1Cl] | A-33 | 392.8 | 393 | |
| 257 | 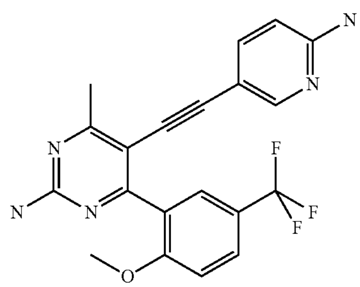 [SMILES: COc1ccc(C(F)(F)F)cc1-c1nc(N)nc(C)c1C#Cc1ccc(N)nc1] | A-33 | 399.4 | 400 | 1.54 |
| 258 | 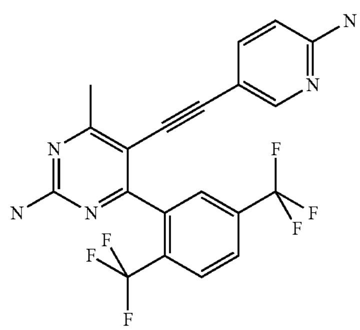 [SMILES: Cc1nc(N)nc(-c2cc(C(F)(F)F)ccc2C(F)(F)F)c1C#Cc1ccc(N)nc1] | A-33 | 437.3 | 438 | 1.65 |
| 259 | 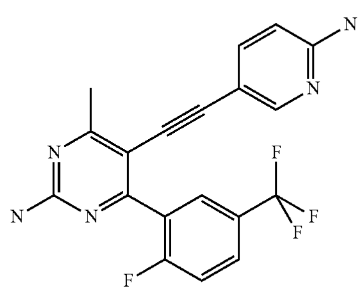 [SMILES: Cc1nc(N)nc(-c2cc(C(F)(F)F)ccc2F)c1C#Cc1ccc(N)nc1] | A-33 | 387.3 | 388 | 1.60 |
| 260 | 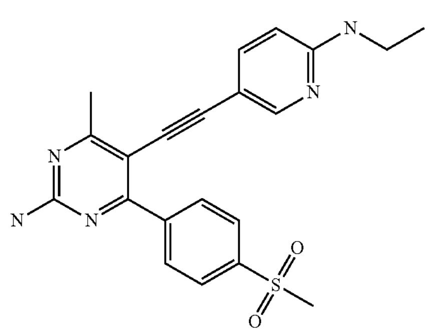 [SMILES: CCNc1ccc(C#Cc2c(C)nc(N)nc2-c2ccc(S(C)(=O)=O)cc2)cn1] | A-39 | 407.5 | 408 | 1.53 |

-continued

| No. | Structure | Starting Material | MW | MS [M + H]+ | HPLC t_Ret |
|---|---|---|---|---|---|
| 261 | 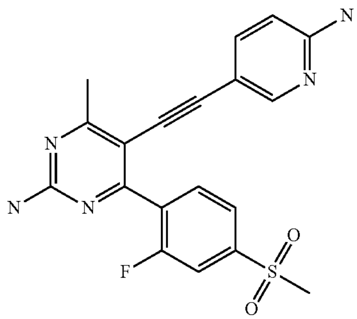 [SMILES: Cc1nc(N)nc(-c2ccc(S(C)(=O)=O)cc2F)c1C#Cc1ccc(N)nc1] | A-33 | 397.4 | 398 | 1.29 |
| 262 | 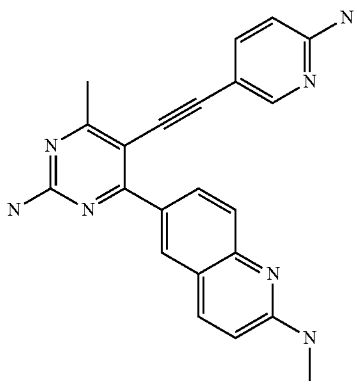 [SMILES: CNc1ccc2cc(-c3nc(N)nc(C)c3C#Cc3ccc(N)nc3)ccc2n1] | A-33 | 381.4 | 382 | 1.42 |
| 263 | 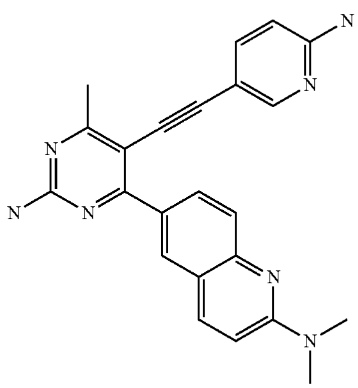 [SMILES: Cc1nc(N)nc(-c2ccc3nc(N(C)C)ccc3c2)c1C#Cc1ccc(N)nc1] | A-33 | 395.5 | 396 | 1.62 |
| 264 | 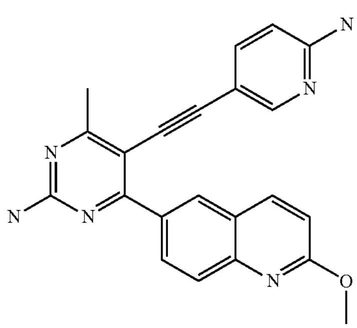 [SMILES: COc1ccc2cc(-c3nc(N)nc(C)c3C#Cc3ccc(N)nc3)ccc2n1] | A-33 | 382.4 | 383 | 1.65 |

-continued

| No. | Structure | Starting Material | MW | MS [M + H]+ | HPLC t_Ret |
|---|---|---|---|---|---|
| 265 | 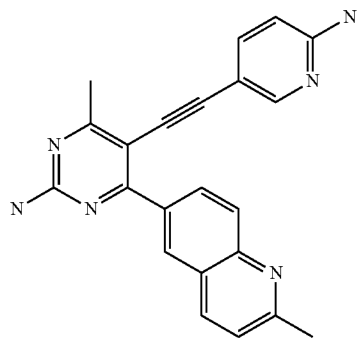 [SMILES: Cc1ccc2cc(-c3nc(N)nc(C)c3C#Cc3ccc(N)nc3)ccc2n1] | A-33 | 366.4 | 367 | 1.48 |
| 266 | 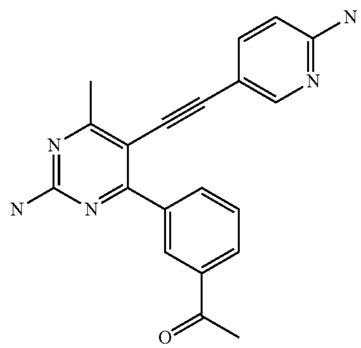 [SMILES: CC(=O)c1cccc(-c2nc(N)nc(C)c2C#Cc2ccc(N)nc2)c1] | A-33 | 343.4 | 344 | 1.29 |
| 267 | 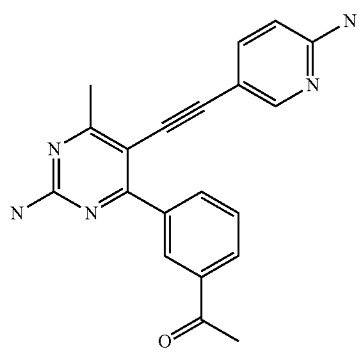 [SMILES: CC(=O)c1cccc(-c2nc(N)nc(C)c2C#Cc2ccc(N)nc2)c1] | A-33 | 343.4 | 344 | |
| 268 | 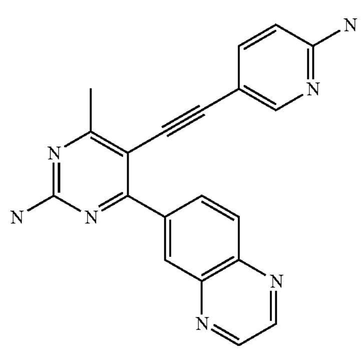 [SMILES: Cc1nc(N)nc(-c2ccc3nccnc3c2)c1C#Cc1ccc(N)nc1] | A-33 | 353.4 | 354 | 1.21 |

-continued
| No. | Structure | Starting Material | MW | MS [M + H]+ | HPLC t$_{Ret}$ |
|---|---|---|---|---|---|
| 269 | 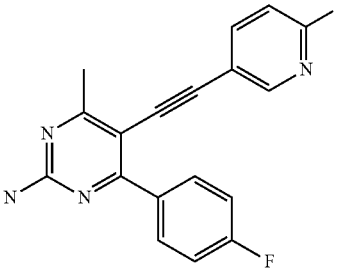 | A-33 | 319.3 | 320 | |
| 270 | 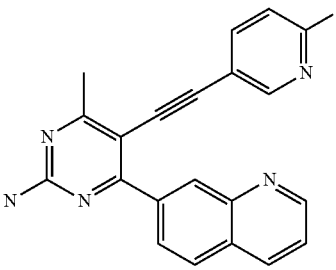 | A-33 | 352.4 | 353 | 1.28 |
| 271 | 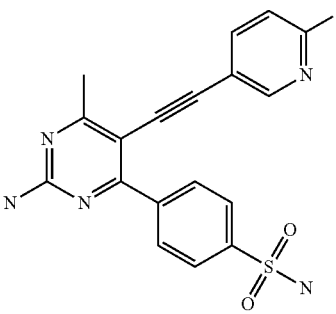 | A-33 | 380.4 | | |
| 272 | 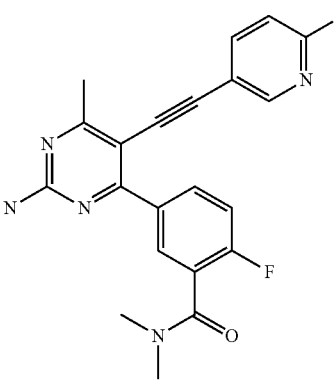 | A-33 | 390.4 | 391 | 1.23 |
| 273 | 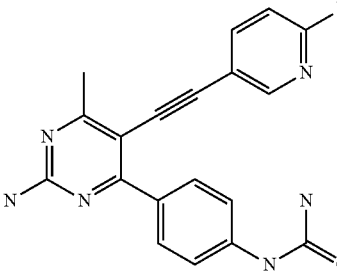 | A-33 | 359.4 | 360 | 1.01 |

-continued
| No. | Structure | Starting Material | MW | MS [M + H]+ | HPLC $t_{Ret}$ |
|---|---|---|---|---|---|
| 274 | 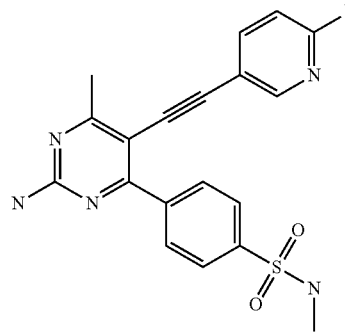 | A-33 | 394.5 | 395 | |
| 275 | 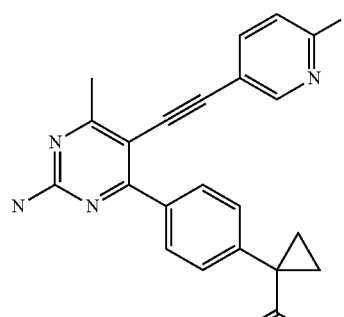 | A-33 | 385.4 | 386 | |
| 276 | 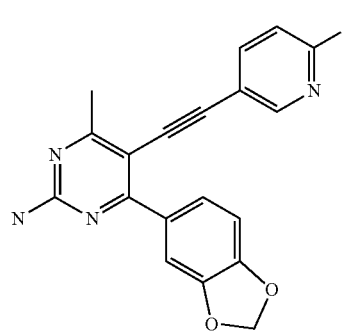 | A-33 | 345.4 | 346 | |
| 278 | 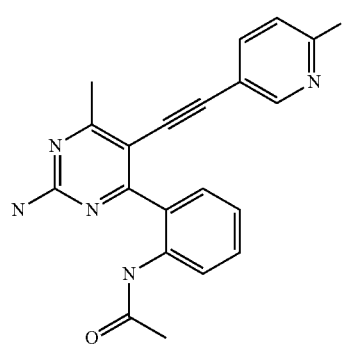 | A-33 | 358.4 | 359 | |

-continued

| No. | Structure | Starting Material | MW | MS [M + H]+ | HPLC t_Ret |
|---|---|---|---|---|---|
| 279 | 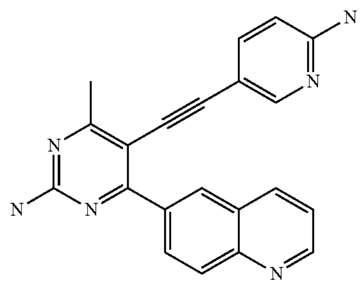 [SMILES: Cc1nc(N)nc(-c2ccc3ncccc3c2)c1C#Cc1ccc(N)nc1] | A-33 | 352.4 | 353 | 1.25 |
| 280 | 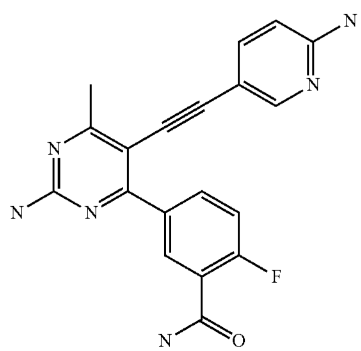 [SMILES: Cc1nc(N)nc(-c2ccc(F)c(C(N)=O)c2)c1C#Cc1ccc(N)nc1] | A-33 | 362.4 | 363 | 1.08 |
| 281 | 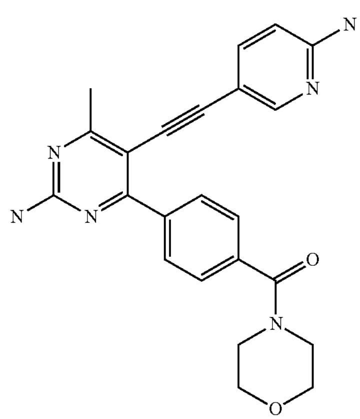 [SMILES: Cc1nc(N)nc(-c2ccc(C(=O)N3CCOCC3)cc2)c1C#Cc1ccc(N)nc1] | C-71 | 414.5 | 415 | 1.39 |
| 282 | 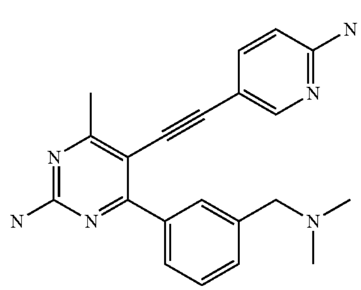 [SMILES: Cc1nc(N)nc(-c2cccc(CN(C)C)c2)c1C#Cc1ccc(N)nc1] | A-33 | 358.4 | 359 | |

| No. | Structure | Starting Material | MW | MS [M + H]+ | HPLC $t_{Ret}$ |
|---|---|---|---|---|---|
| 283 | 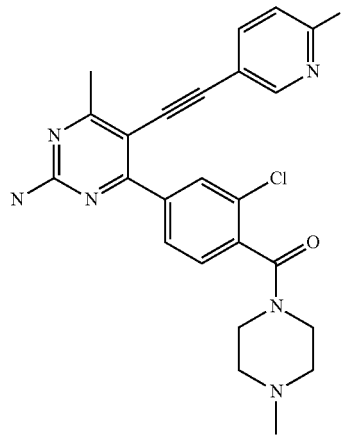 | C-73 | 462 | 462/464 | 1.44 |
| 284 | 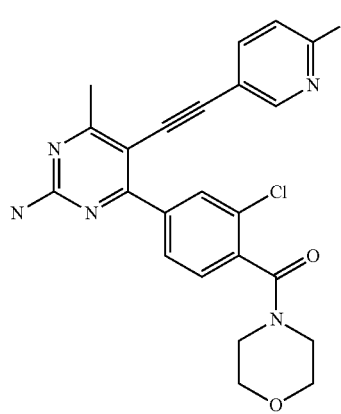 | C-73 | 448.9 | 449 | 1.42 |
| 285 | 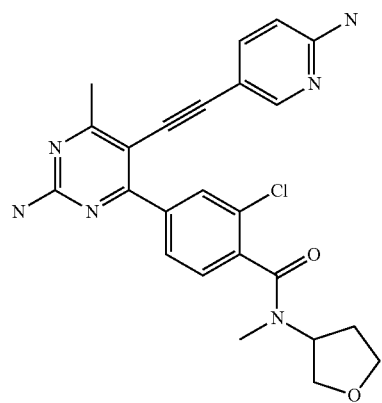 [SMILES: Cc1nc(N)nc(-c2ccc(C(=O)N(C)C3CCOC3)c(Cl)c2)c1C#Cc1ccc(N)nc1] | C-73 | 462.9 | 463/465 | 1.47 |

| No. | Structure | Starting Material | MW | MS [M + H]+ | HPLC $t_{Ret}$ |
|---|---|---|---|---|---|
| 286 | 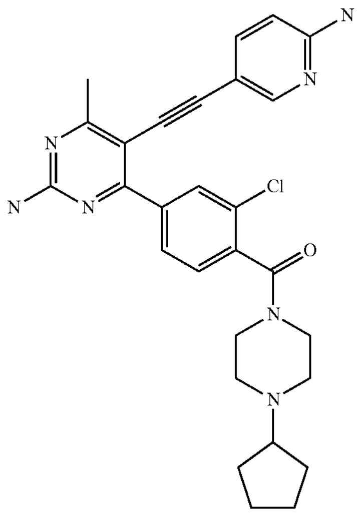 [SMILES: Cc1nc(N)nc(-c2ccc(C(=O)N3CCN(C4CCCC4)CC3)c(Cl)c2)c1C#Cc1ccc(N)nc1] | C-73 | 516 | 516/518 | 1.76 |
| 287 | 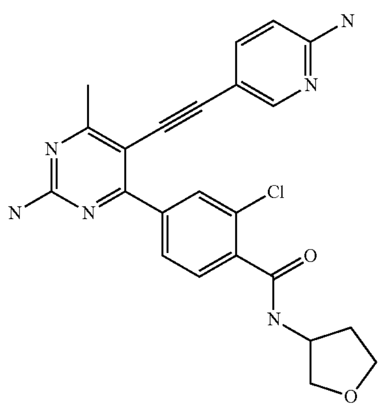 [SMILES: Cc1nc(N)nc(-c2ccc(C(=O)NC3CCOC3)c(Cl)c2)c1C#Cc1ccc(N)nc1] | C-73 | 448.9 | 449 | 1.40 |
| 288 | 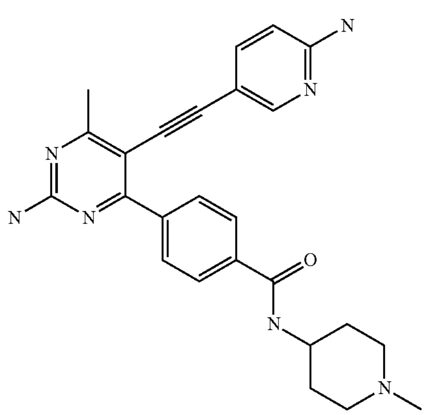 [SMILES: Cc1nc(N)nc(-c2ccc(C(=O)NC3CCN(C)CC3)cc2)c1C#Cc1ccc(N)nc1] | C-71 | 441.5 | 442 | 1.36 |

-continued

| No. | Structure | Starting Material | MW | MS [M + H]+ | HPLC t_Ret |
|---|---|---|---|---|---|
| 289 | 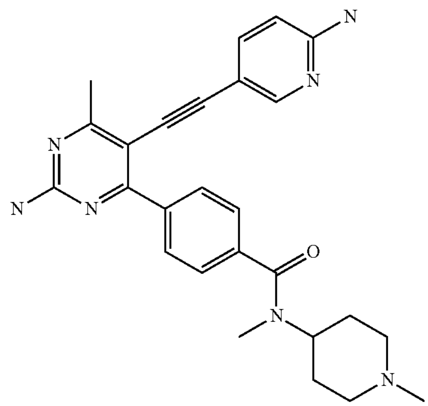 [SMILES: Cc1nc(N)nc(-c2ccc(C(=O)N(C)C3CCN(C)CC3)cc2)c1C#Cc1ccc(N)nc1] | C-71 | 455.6 | 456 | 1.40 |
| 290 | 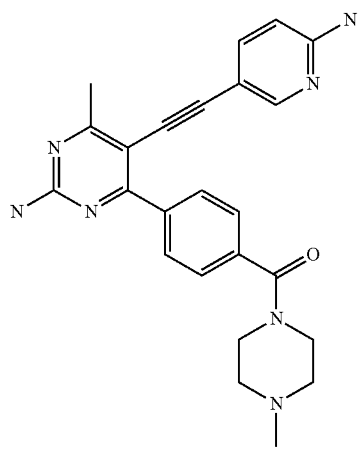 [SMILES: Cc1nc(N)nc(-c2ccc(C(=O)N3CCN(C)CC3)cc2)c1C#Cc1ccc(N)nc1] | C-71 | 427.5 | 428 | 1.35 |
| 291 | 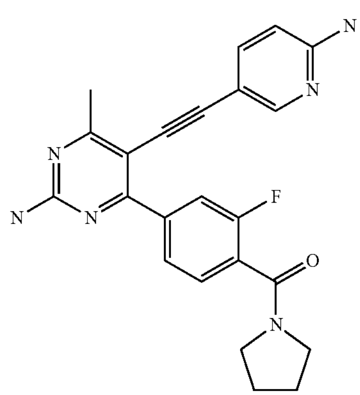 [SMILES: Cc1nc(N)nc(-c2ccc(C(=O)N3CCCC3)c(F)c2)c1C#Cc1ccc(N)nc1] | C-75 | 416.5 | 417 | 1.49 |

-continued
| No. | Structure | Starting Material | MW | MS [M + H]+ | HPLC t_Ret |
|---|---|---|---|---|---|
| 292 | 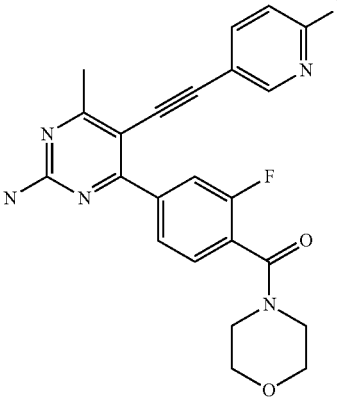 | C-75 | 432.5 | 433 | 1.38 |
| 293 | 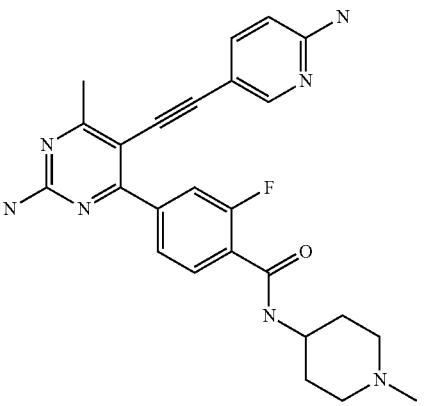 [SMILES: Cc1nc(N)nc(-c2ccc(C(=O)NC3CCN(C)CC3)c(F)c2)c1C#Cc1ccc(N)nc1] | C-75 | 459.5 | 460 | 1.45 |
| 294 | 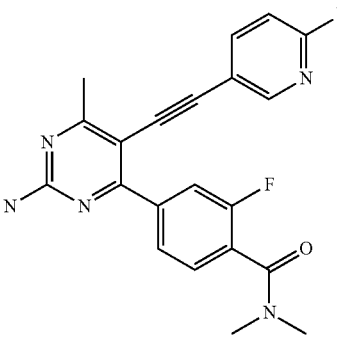 | C-75 | 390.4 | 391 | 1.40 |

-continued
| No. | Structure | Starting Material | MW | MS [M + H]+ | HPLC t_Ret |
|---|---|---|---|---|---|
| 295 | 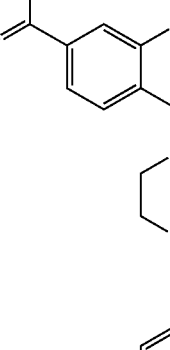 | C-75 | 445.5 | 446 | 1.40 |
| 296 | 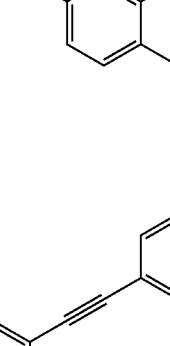 | C-73 | 418.9 | 419 | |
| 297 | 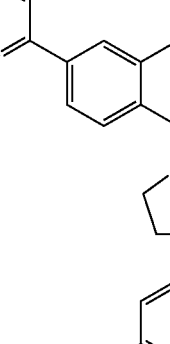 | C-73 | 432.9 | 433/435 | 1.55 |
| 298 | 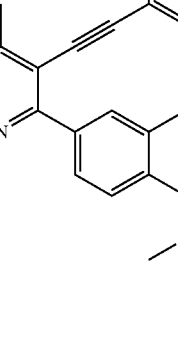 | C-73 | 406.9 | 407/409 | 1.45 |

-continued

| No. | Structure | Starting Material | MW | MS [M + H]+ | HPLC t_Ret |
|---|---|---|---|---|---|
| 299 | 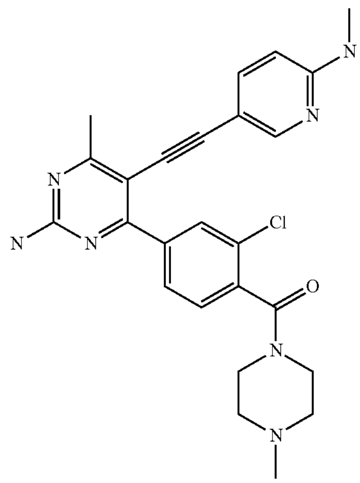 [SMILES: CNc1ccc(C#Cc2c(C)nc(N)nc2-c2ccc(C(=O)N3CCN(C)CC3)c(Cl)c2)cn1] | C-67 | 476 | 476 | 1.58 |
| 300 | 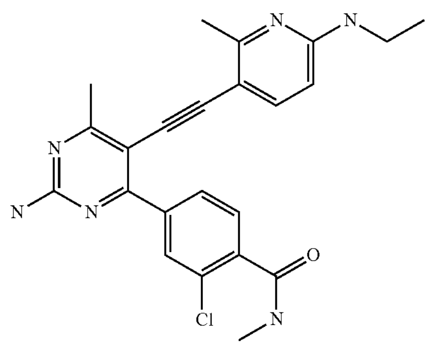 [SMILES: CCNc1ccc(C#Cc2c(C)nc(N)nc2-c2ccc(C(=O)NC)c(Cl)c2)c(C)n1] | | 434.9 | 435/437 | 1.71 |
| 301 | 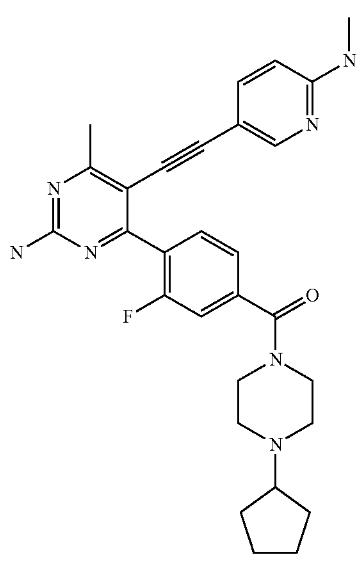 [SMILES: CNc1ccc(C#Cc2c(C)nc(N)nc2-c2ccc(C(=O)N3CCN(C4CCCC4)CC3)cc2F)cn1] | C-69 | 513.6 | 514 | 1.79 |

-continued
| No. | Structure | Starting Material | MW | MS [M + H]+ | HPLC t_Ret |
|---|---|---|---|---|---|
| 302 | 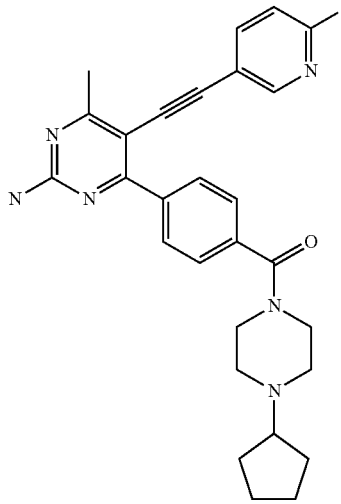 | C-71 | 481.6 | 482 | 1.65 |
| 303 | 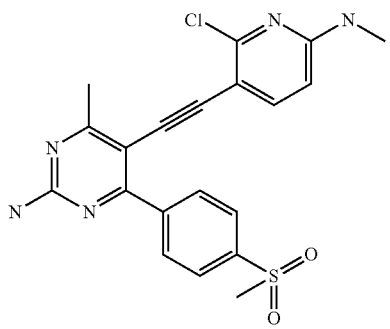 [SMILES: CNc1ccc(C#Cc2c(C)nc(N)nc2-c2ccc(S(C)(=O)=O)cc2)c(Cl)n1] | A-39 | 427.9 | 428/430 | 1.86 |
| 304 | 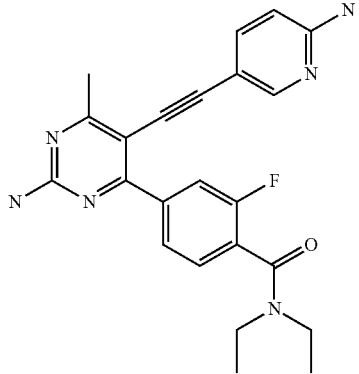 [SMILES: CCN(CC)C(=O)c1ccc(-c2nc(N)nc(C)c2C#Cc2ccc(N)nc2)cc1F] | C-75 | 418.5 | 419 | 1.58 |

-continued

| No. | Structure | Starting Material | MW | MS [M + H]+ | HPLC t_Ret |
|---|---|---|---|---|---|
| 305 | 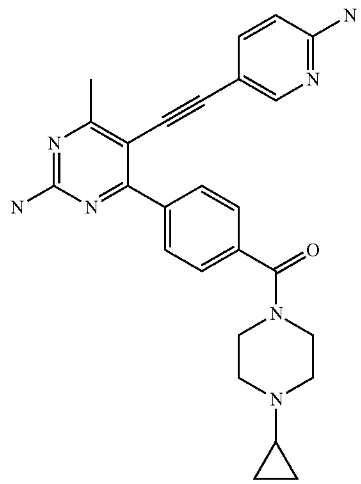 [SMILES: Cc1nc(N)nc(-c2ccc(C(=O)N3CCN(C4CC4)CC3)cc2)c1C#Cc1ccc(N)nc1] | C-71 | 453.5 | 454 | 1.54 |
| 306 | 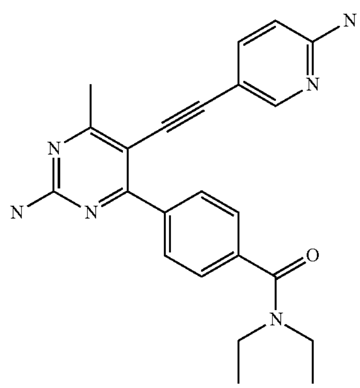 [SMILES: CCN(CC)C(=O)c1ccc(-c2nc(N)nc(C)c2C#Cc2ccc(N)nc2)cc1] | C-71 | 400.5 | 401 | 1.52 |
| 307 | 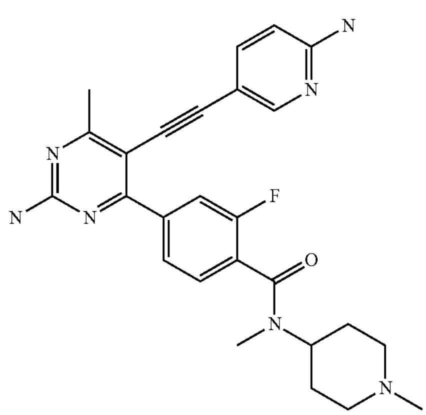 [SMILES: Cc1nc(N)nc(-c2ccc(C(=O)N(C)C3CCN(C)CC3)c(F)c2)c1C#Cc1ccc(N)nc1] | C-75 | 473.6 | 474 | 1.46 |

-continued
| No. | Structure | Starting Material | MW | MS [M + H]+ | HPLC t_Ret |
|---|---|---|---|---|---|
| 308 | 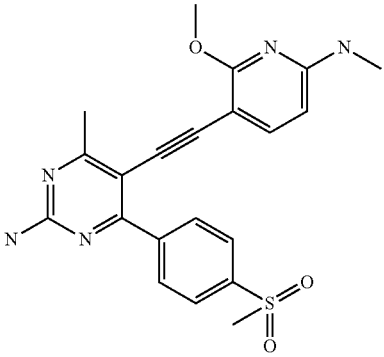 [SMILES: CNc1ccc(C#Cc2c(C)nc(N)nc2-c2ccc(S(C)(=O)=O)cc2)c(OC)n1] | A-39 | 423.5 | 424 | 1.92 |
| 309 | 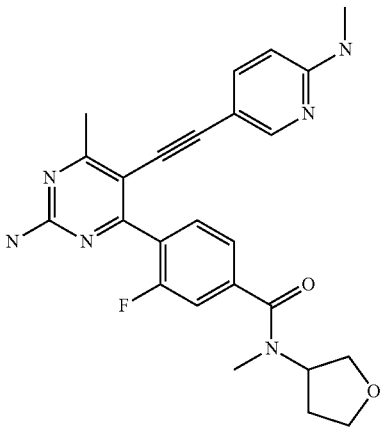 [SMILES: CNc1ccc(C#Cc2c(C)nc(N)nc2-c2ccc(C(=O)N(C)C3CCOC3)cc2F)cn1] | C-69 | 460.1 | 461 | |
| 310 | 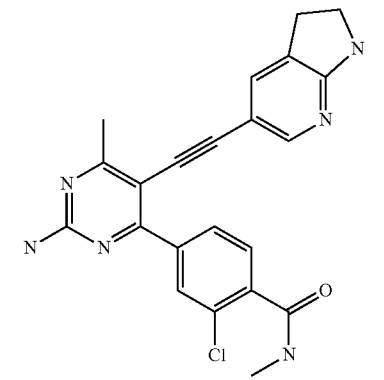 [SMILES: CNC(=O)c1ccc(-c2nc(N)nc(C)c2C#Cc2cnc3c(c2)CCN3)cc1Cl] | | 418.9 | 419 | 1.53 |
| 311 | 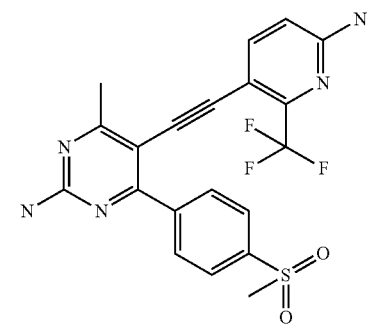 [SMILES: Cc1nc(N)nc(-c2ccc(S(C)(=O)=O)cc2)c1C#Cc1ccc(N)nc1C(F)(F)F] | A-39 | 447.4 | M − H = 446 (571) | 1.61 |

-continued

| No. | Structure | Starting Material | MW | MS [M + H]+ | HPLC t$_{Ret}$ |
|---|---|---|---|---|---|
| 312 | 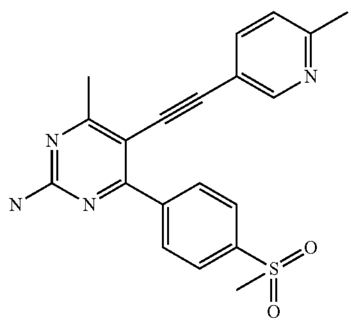 [SMILES: Cc1ccc(C#Cc2c(C)nc(N)nc2-c2ccc(S(C)(=O)=O)cc2)cn1] | A-30 | 378.5 | 379 | 1.72 |
| 313 | 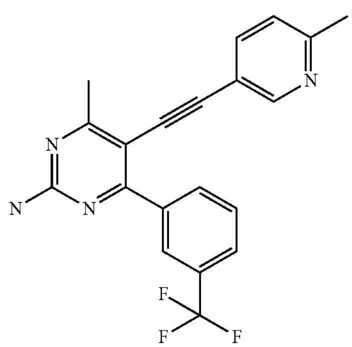 [SMILES: Cc1ccc(C#Cc2c(C)nc(N)nc2-c2cccc(C(F)(F)F)c2)cn1] | A-27 | 368.4 | 369 | 2.13 |
| 314 | 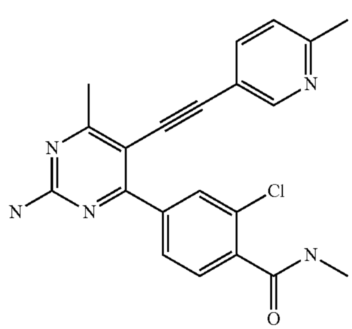 [SMILES: CNC(=O)c1ccc(-c2nc(N)nc(C)c2C#Cc2ccc(C)nc2)cc1Cl] | C-46 | 391.9 | 392/394 | 1.51 |
| 315 | 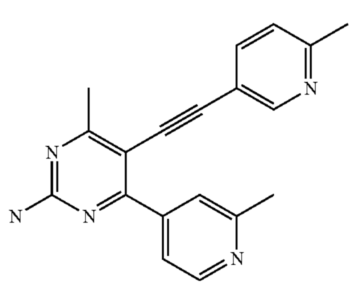 [SMILES: Cc1ccc(C#Cc2c(C)nc(N)nc2-c2ccnc(C)c2)cn1] | C-46 | 315.4 | 316 | 1.46 |

-continued
| No. | Structure | Starting Material | MW | MS [M + H]+ | HPLC t_Ret |
|---|---|---|---|---|---|
| 316 | 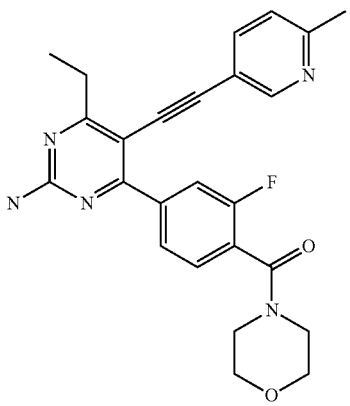 [SMILES: CCc1nc(N)nc(-c2ccc(C(=O)N3CCOCC3)c(F)c2)c1C#Cc1ccc(C)nc1] | C-52 | 445.5 | 446 | 1.65 |
| 317 | 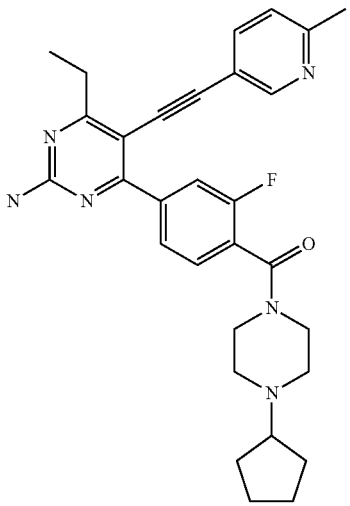 [SMILES: CCc1nc(N)nc(-c2ccc(C(=O)N3CCN(C4CCCC4)CC3)c(F)c2)c1C#Cc1ccc(C)nc1] | C-52 | 512.6 | 513 | 1.95 |
| 318 | 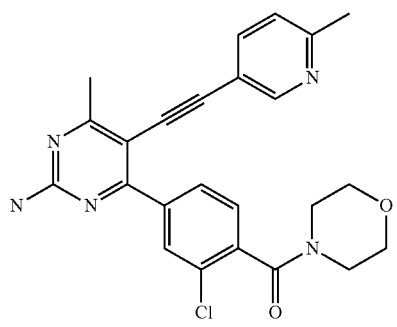 [SMILES: Cc1ccc(C#Cc2c(C)nc(N)nc2-c2ccc(C(=O)N3CCOCC3)c(Cl)c2)cn1] | C-48 | 447.9 | 448/450 | 1.57 |
| 319 | 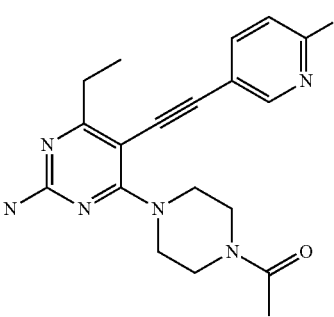 | C-53 | 365.4 | 366 | |

-continued
| No. | Structure | Starting Material | MW | MS [M + H]+ | HPLC t_Ret |
|---|---|---|---|---|---|
| 320 | 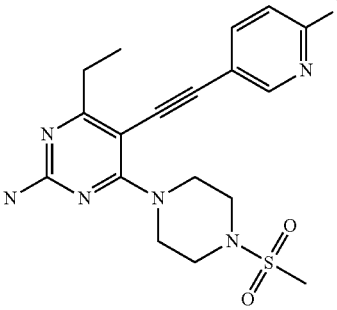 | C-53 | 401.5 | 402 | 1.33 |
| 321 | 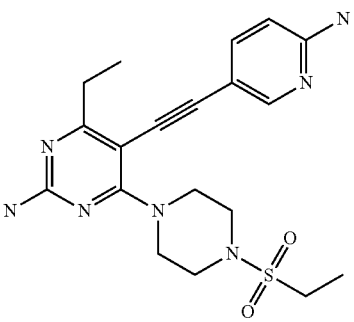 [SMILES: CCc1nc(N)nc(N2CCN(S(=O)(=O)CC)CC2)c1C#Cc1ccc(N)nc1] | C-53 | 415.5 | 416 | |
| 322 | 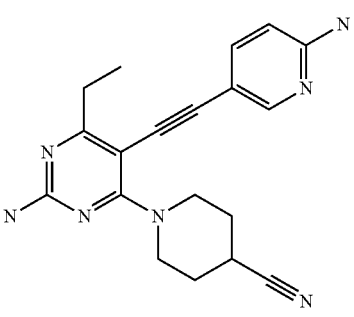 [SMILES: CCc1nc(N)nc(N2CCC(C#N)CC2)c1C#Cc1ccc(N)nc1] | C-53 | 347.4 | 348 | 1.39 |
| 323 | 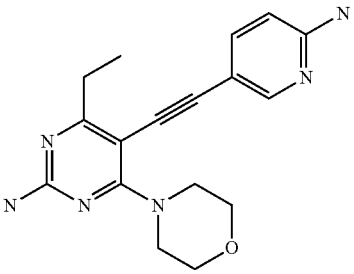 [SMILES: CCc1nc(N)nc(N2CCOCC2)c1C#Cc1ccc(N)nc1] | C-53 | 324.4 | 325 | 1.32 |

-continued

| No. | Structure | Starting Material | MW | MS [M + H]+ | HPLC t_Ret |
|---|---|---|---|---|---|
| 324 | 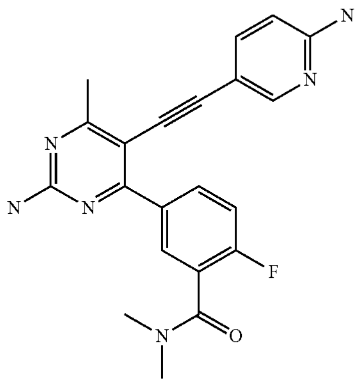 [SMILES: Cc1nc(N)nc(-c2ccc(F)c(C(=O)N(C)C)c2)c1C#Cc1ccc(N)nc1] | A-33 | 390.4 | 391 | 1.23 |
| 325 | 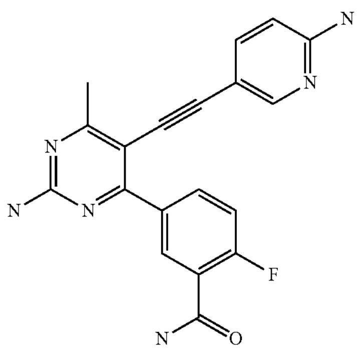 [SMILES: Cc1nc(N)nc(-c2ccc(F)c(C(N)=O)c2)c1C#Cc1ccc(N)nc1] | A-33 | 362.4 | 363 | 1.08 |
| 326 | 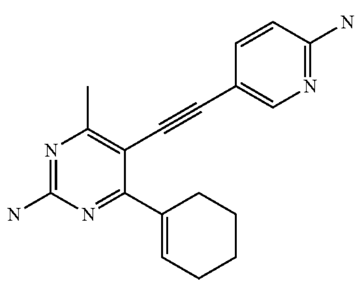 [SMILES: Cc1nc(N)nc(C2=CCCCC2)c1C#Cc1ccc(N)nc1] | A-33 | 305.4 | 306 | 1.58 |
| 327 | 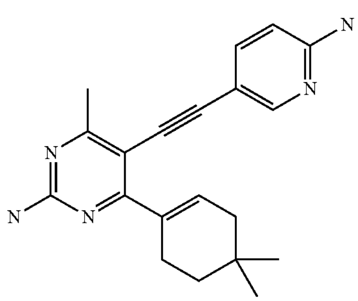 [SMILES: Cc1nc(N)nc(C2=CCC(C)(C)CC2)c1C#Cc1ccc(N)nc1] | A-33 | 333.4 | 334 | 1.78 |

-continued

| No. | Structure | Starting Material | MW | MS [M + H]+ | HPLC $t_{Ret}$ |
|---|---|---|---|---|---|
| 328 | 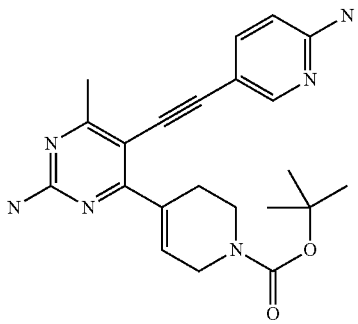 [SMILES: Cc1nc(N)nc(C2=CCN(C(=O)OC(C)(C)C)CC2)c1C#Cc1ccc(N)nc1] | | 406.5 | 407 | 1.69 |
| 329 | 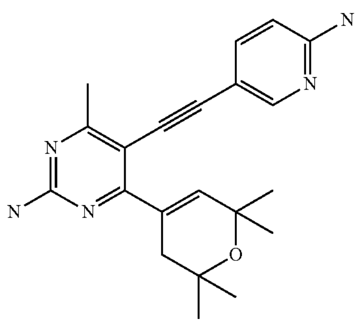 [SMILES: Cc1nc(N)nc(C2=CC(C)(C)OC(C)(C)C2)c1C#Cc1ccc(N)nc1] | A-33 | 363.5 | 364 | 1.61 |
| 330 | 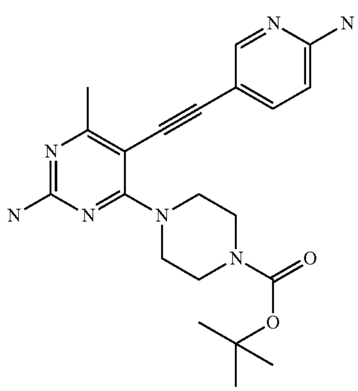 [SMILES: Cc1nc(N)nc(N2CCN(C(=O)OC(C)(C)C)CC2)c1C#Cc1ccc(N)nc1] | | 409.5 | 410 | 1.70 |
| 331 | 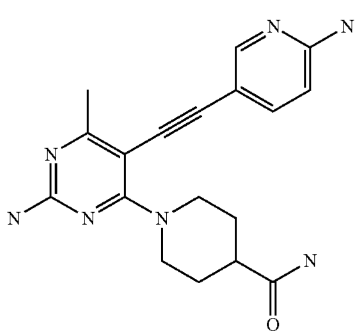 [SMILES: Cc1nc(N)nc(N2CCC(C(N)=O)CC2)c1C#Cc1ccc(N)nc1] | A-33 | 351.4 | 352 | |

-continued

| No. | Structure | Starting Material | MW | MS [M + H]+ | HPLC $t_{Ret}$ |
|---|---|---|---|---|---|
| 332 | 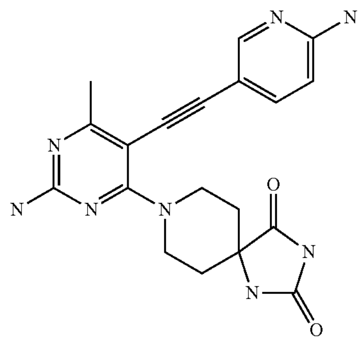 [SMILES: Cc1nc(N)nc(N2CCC3(CC2)NC(=O)NC3=O)c1C#Cc1ccc(N)nc1] | A-33 | 392.4 | 393 | |
| 333 | 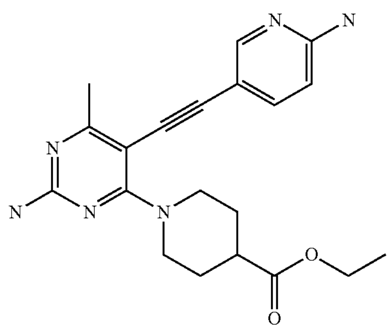 [SMILES: CCOC(=O)C1CCN(c2nc(N)nc(C)c2C#Cc2ccc(N)nc2)CC1] | A-33 | 380.4 | 381 | |
| 334 | 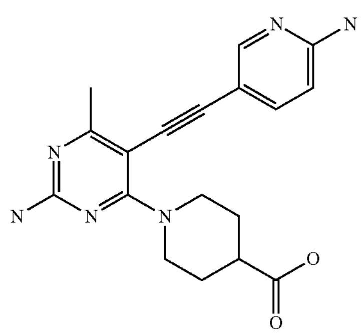 [SMILES: Cc1nc(N)nc(N2CCC(C(=O)O)CC2)c1C#Cc1ccc(N)nc1] | | 352.4 | 353 | 0.62 |
| 335 | 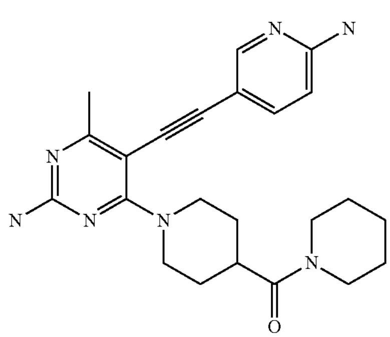 [SMILES: Cc1nc(N)nc(N2CCC(C(=O)N3CCCCC3)CC2)c1C#Cc1ccc(N)nc1] | C-87 | 419.5 | 420 | |

-continued

| No. | Structure | Starting Material | MW | MS [M + H]+ | HPLC t_Ret |
|---|---|---|---|---|---|
| 336 | 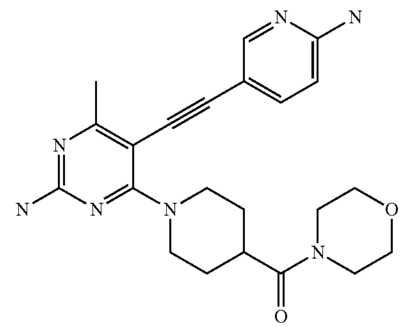 [SMILES: Cc1nc(N)nc(N2CCC(C(=O)N3CCOCC3)CC2)c1C#Cc1ccc(N)nc1] | C-87 | 421.5 | 422 | |
| 337 | 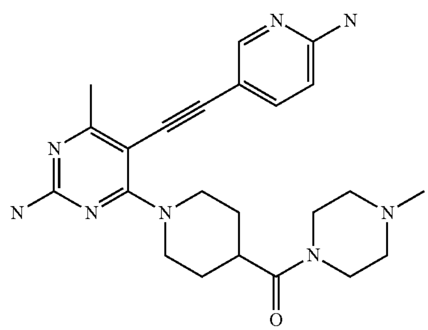 [SMILES: Cc1nc(N)nc(N2CCC(C(=O)N3CCN(C)CC3)CC2)c1C#Cc1ccc(N)nc1] | C-87 | 434.6 | 435 | |
| 338 | 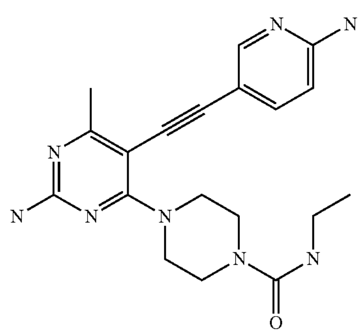 [SMILES: CCNC(=O)N1CCN(c2nc(N)nc(C)c2C#Cc2ccc(N)nc2)CC1] | C-85 | 380.5 | 381 | |
| 339 | 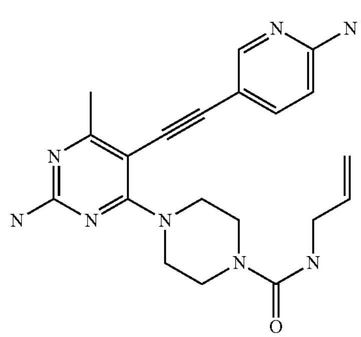 [SMILES: C=CCNC(=O)N1CCN(c2nc(N)nc(C)c2C#Cc2ccc(N)nc2)CC1] | C-85 | 392.5 | 393 | 0.15 |

-continued
| No. | Structure | Starting Material | MW | MS [M + H]+ | HPLC t$_{Ret}$ |
|---|---|---|---|---|---|
| 340 | 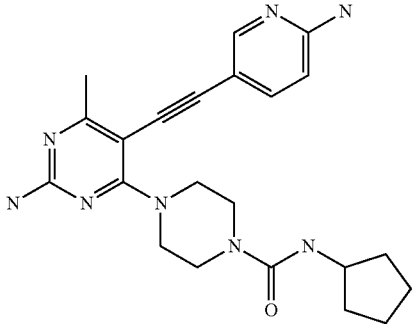 [SMILES: Cc1nc(N)nc(N2CCN(C(=O)NC3CCCC3)CC2)c1C#Cc1ccc(N)nc1] | C-85 | 420.5 | 421 | 1.28 |
| 341 | 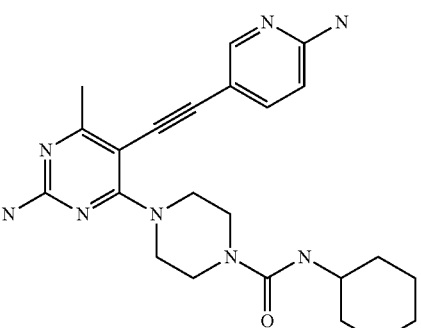 | C-85 | 434.6 | 435 | 1.43 |
| 342 | 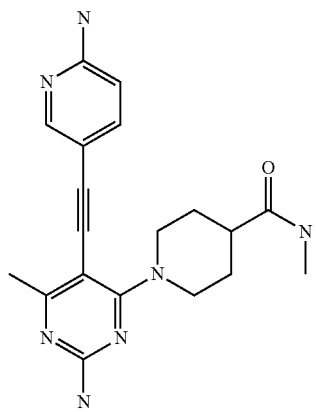 | C-87 | 365.4 | 366 | 1.18 |
| 343 | 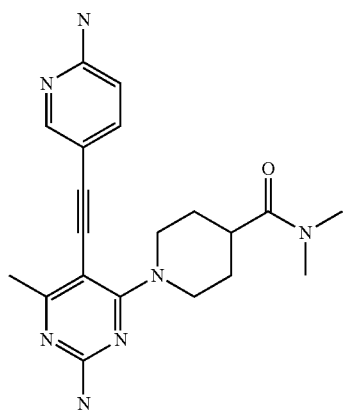 | C-87 | 379.5 | 380 | |

-continued

| No. | Structure | Starting Material | MW | MS [M + H]+ | HPLC t_Ret |
|---|---|---|---|---|---|
| 344 | 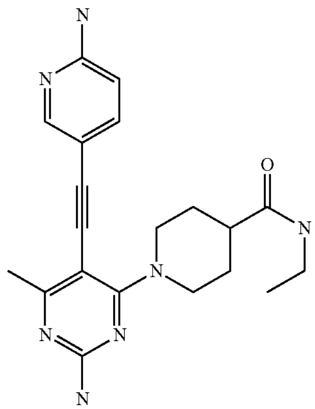 [SMILES: CCNC(=O)C1CCN(c2nc(N)nc(C)c2C#Cc2ccc(N)nc2)CC1] | C-87 | 379.5 | 380 | 1.26 |
| 345 | 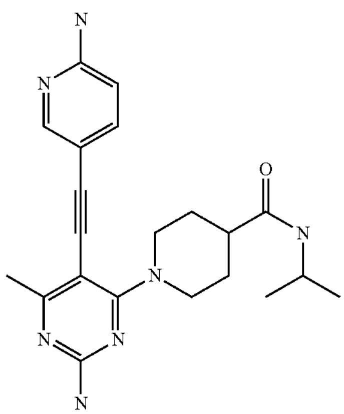 [SMILES: Cc1nc(N)nc(N2CCC(C(=O)NC(C)C)CC2)c1C#Cc1ccc(N)nc1] | C-87 | 393.5 | 394 | 1.35 |
| 346 | 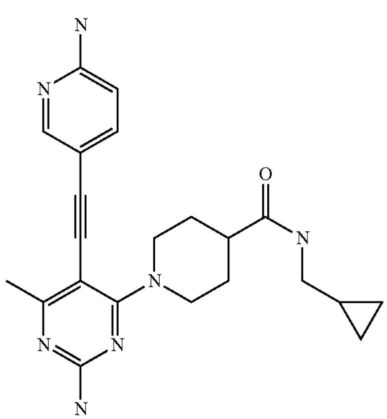 [SMILES: Cc1nc(N)nc(N2CCC(C(=O)NCC3CC3)CC2)c1C#Cc1ccc(N)nc1] | C-87 | 405.5 | 406 | |

-continued

| No. | Structure | Starting Material | MW | MS [M + H]+ | HPLC t_Ret |
|---|---|---|---|---|---|
| 347 | 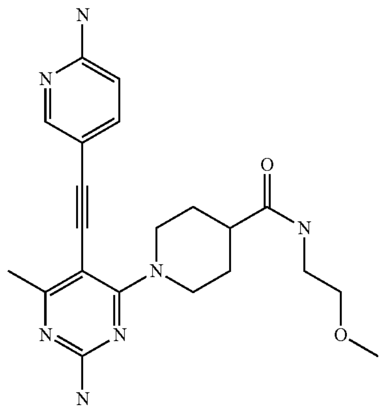 | C-87 | 409.5 | 410 | |
| 348 | 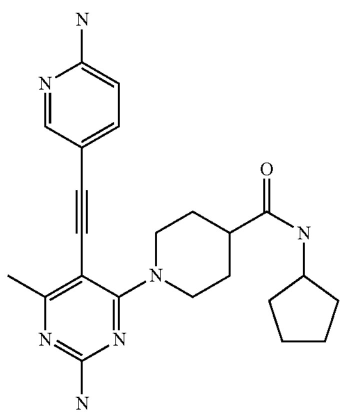 [SMILES: Cc1nc(N)nc(N2CCC(C(=O)NC3CCCC3)CC2)c1C#Cc1ccc(N)nc1] | C-87 | 419.5 | 420 | |
| 349 | 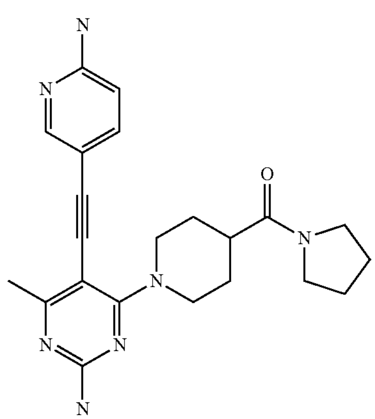 [SMILES: Cc1nc(N)nc(N2CCC(C(=O)N3CCCC3)CC2)c1C#Cc1ccc(N)nc1] | C-87 | 405.5 | 406 | 1.41 |

-continued

| No. | Structure | Starting Material | MW | MS [M + H]+ | HPLC t_Ret |
|---|---|---|---|---|---|
| 350 | 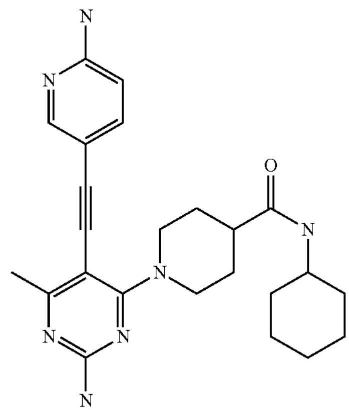 [SMILES: Cc1nc(N)nc(N2CCC(C(=O)NC3CCCCC3)CC2)c1C#Cc1ccc(N)nc1] | C-87 | 433.6 | 434 | 1.58 |
| 351 | 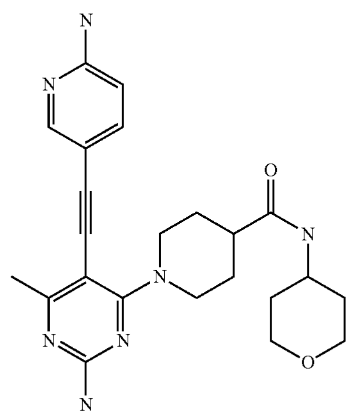 [SMILES: Cc1nc(N)nc(N2CCC(C(=O)NC3CCOCC3)CC2)c1C#Cc1ccc(N)nc1] | C-87 | 435.5 | 436 | 1.26 |
| 352 | 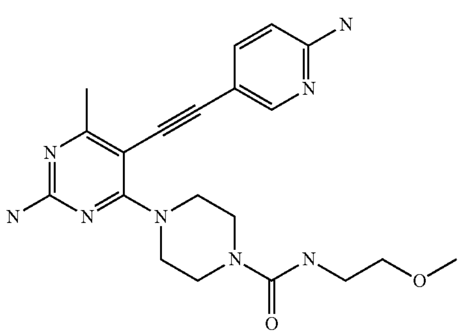 [SMILES: COCCNC(=O)N1CCN(c2nc(N)nc(C)c2C#Cc2ccc(N)nc2)CC1] | C-85 | 410.5 | 411 | 1.23 |
| 353 | 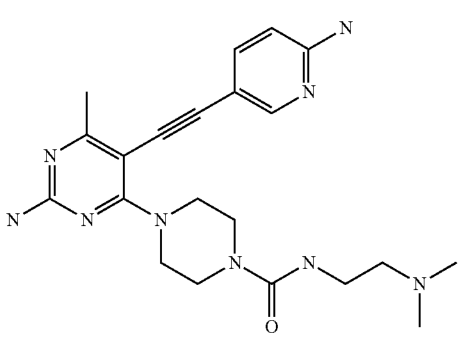 [SMILES: Cc1nc(N)nc(N2CCN(C(=O)NCCN(C)C)CC2)c1C#Cc1ccc(N)nc1] | C-85 | 423.5 | 424 | 1.28 |

-continued

| No. | Structure | Starting Material | MW | MS [M + H]+ | HPLC $t_{Ret}$ |
|---|---|---|---|---|---|
| 354 | 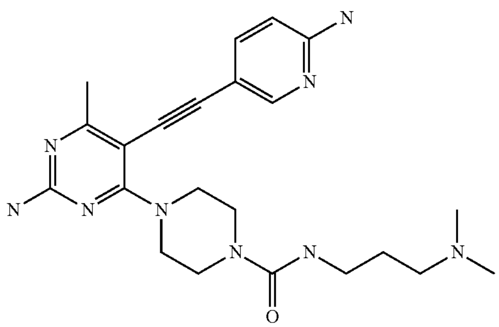 [SMILES: Cc1nc(N)nc(N2CCN(C(=O)NCCCN(C)C)CC2)c1C#Cc1ccc(N)nc1] | C-85 | 437.5 | 438 | 1.35 |
| 355 | 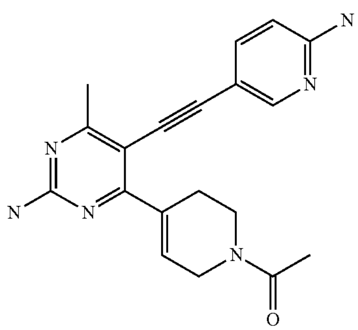 [SMILES: CC(=O)N1CC=C(c2nc(N)nc(C)c2C#Cc2ccc(N)nc2)CC1] | C-85 | 348.4 | 349 | |
| 356 | 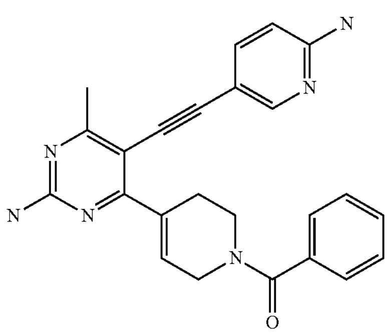 [SMILES: Cc1nc(N)nc(C2=CCN(C(=O)c3ccccc3)CC2)c1C#Cc1ccc(N)nc1] | C-89 | 410.5 | 411 | 1.44 |
| 357 | 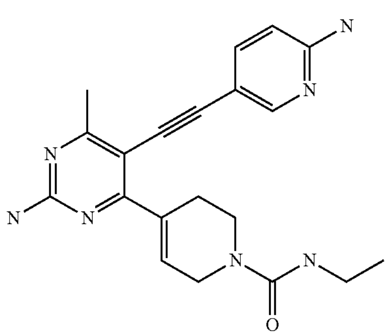 [SMILES: CCNC(=O)N1CC=C(c2nc(N)nc(C)c2C#Cc2ccc(N)nc2)CC1] | C-89 | 377.4 | 378 | |

-continued

| No. | Structure | Starting Material | MW | MS [M + H]+ | HPLC $t_{Ret}$ |
|---|---|---|---|---|---|
| 358 | 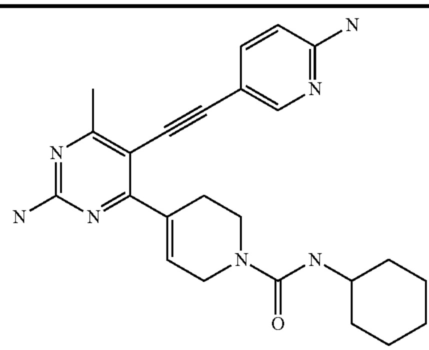 | C-89 | 431.5 | 432 | |
| 359 | 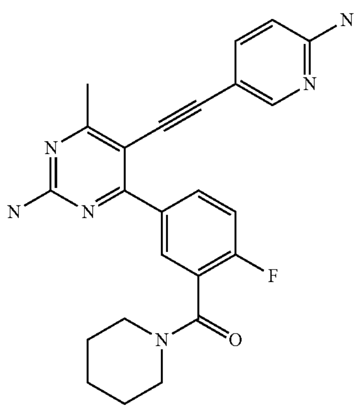 [SMILES: Cc1nc(N)nc(-c2ccc(F)c(C(=O)N3CCCCC3)c2)c1C#Cc1ccc(N)nc1] | A-33 | 430.5 | 431 | |
| 360 | 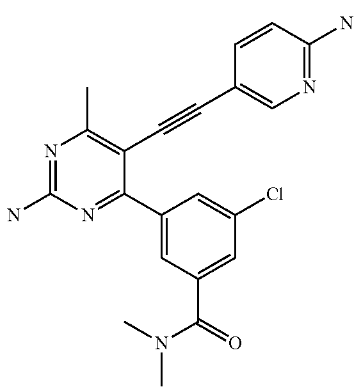 [SMILES: Cc1nc(N)nc(-c2cc(Cl)cc(C(=O)N(C)C)c2)c1C#Cc1ccc(N)nc1] | A-33 | 406.9 | 407 | |
| 361 | 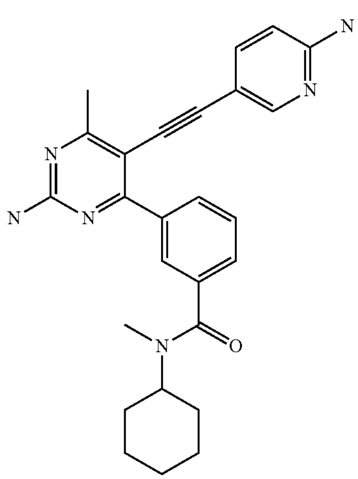 [SMILES: Cc1nc(N)nc(-c2cccc(C(=O)N(C)C3CCCCC3)c2)c1C#Cc1ccc(N)nc1] | A-33 | 440.5 | 441 | |

-continued

| No. | Structure | Starting Material | MW | MS [M + H]+ | HPLC t_Ret |
|---|---|---|---|---|---|
| 362 | 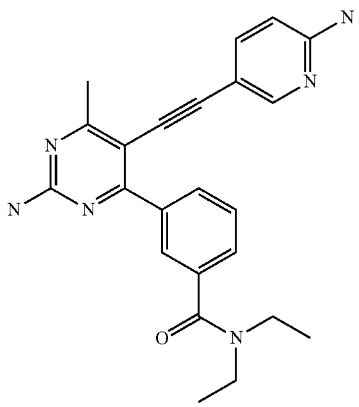 [SMILES: CCN(CC)C(=O)c1cccc(-c2nc(N)nc(C)c2C#Cc2ccc(N)nc2)c1] | A-33 | 400.5 | 401 | |
| 363 | 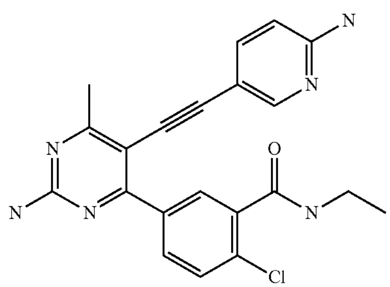 [SMILES: CCNC(=O)c1cc(-c2nc(N)nc(C)c2C#Cc2ccc(N)nc2)ccc1Cl] | A-33 | 406.9 | 407 | |
| 364 | 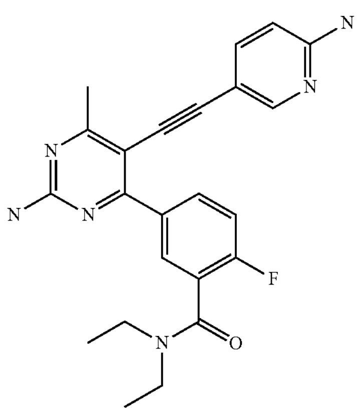 [SMILES: CCN(CC)C(=O)c1cc(-c2nc(N)nc(C)c2C#Cc2ccc(N)nc2)ccc1F] | A-33 | 418.5 | 419 | |
| 365 | 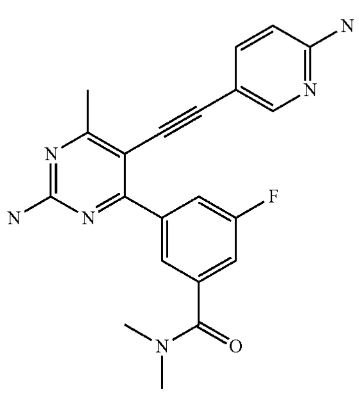 [SMILES: Cc1nc(N)nc(-c2cc(F)cc(C(=O)N(C)C)c2)c1C#Cc1ccc(N)nc1] | A-33 | 390.4 | 391 | |

-continued

| No. | Structure | Starting Material | MW | MS [M + H]+ | HPLC t$_{Ret}$ |
|---|---|---|---|---|---|
| 366 | 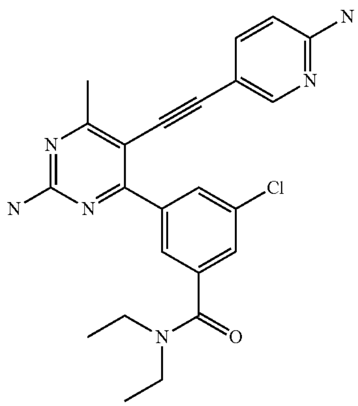 [SMILES: CCN(CC)C(=O)c1cc(Cl)cc(-c2nc(N)nc(C)c2C#Cc2ccc(N)nc2)c1] | A-33 | 434.9 | 435 | |
| 367 | 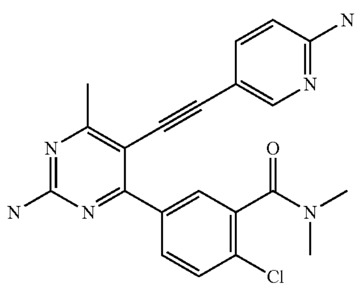 [SMILES: Cc1nc(N)nc(-c2ccc(Cl)c(C(=O)N(C)C)c2)c1C#Cc1ccc(N)nc1] | A-33 | 406.9 | 407 | |
| 368 | 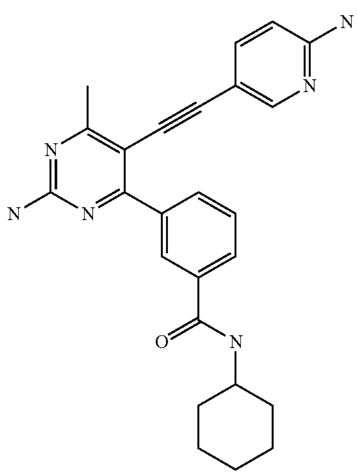 [SMILES: Cc1nc(N)nc(-c2cccc(C(=O)NC3CCCCC3)c2)c1C#Cc1ccc(N)nc1] | A-33 | 426.5 | 427 | |
| 369 | 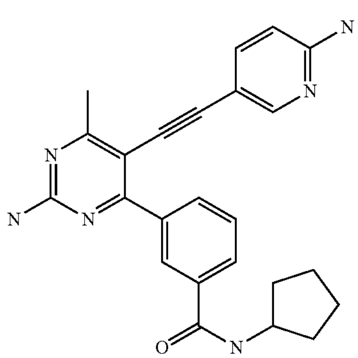 [SMILES: Cc1nc(N)nc(-c2cccc(C(=O)NC3CCCC3)c2)c1C#Cc1ccc(N)nc1] | A-33 | 412.5 | 414 | |

-continued
| No. | Structure | Starting Material | MW | MS [M + H]+ | HPLC t_Ret |
|---|---|---|---|---|---|
| 370 | 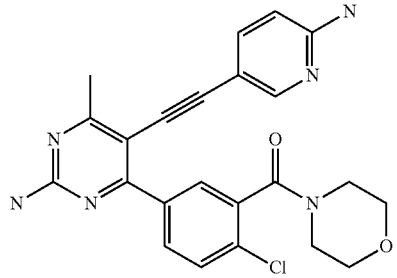 [SMILES: Cc1nc(N)nc(-c2ccc(Cl)c(C(=O)N3CCOCC3)c2)c1C#Cc1ccc(N)nc1] | A-33 | 448.9 | 449 | |
| 371 | 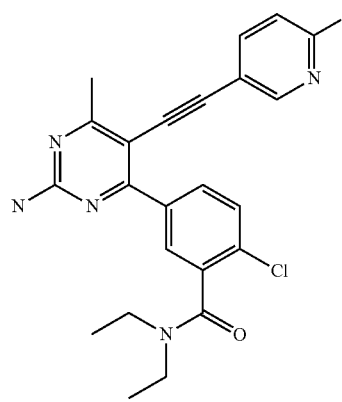 | A-33 | 434.9 | 435 | |
| 372 | 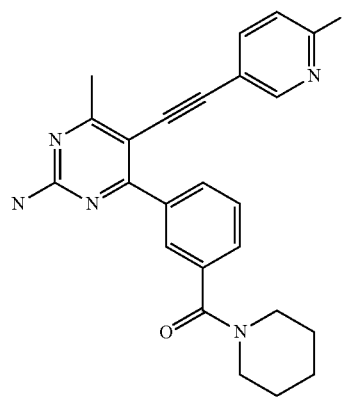 | A-33 | 412.5 | 413 | 1.48 |
| 373 | 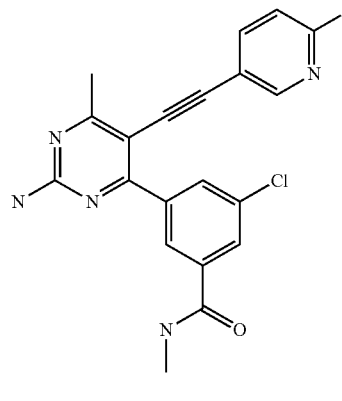 | A-33 | 392.8 | 393 | |

| No. | Structure | Starting Material | MW | MS [M + H]+ | HPLC t_Ret |
|---|---|---|---|---|---|
| 374 | 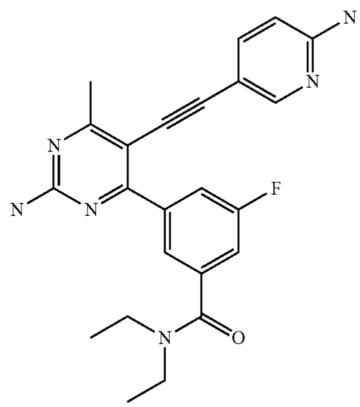 [SMILES: CCN(CC)C(=O)c1cc(F)cc(-c2nc(N)nc(C)c2C#Cc2ccc(N)nc2)c1] | A-33 | 418.5 | 419 | 1.53 |
| 375 | 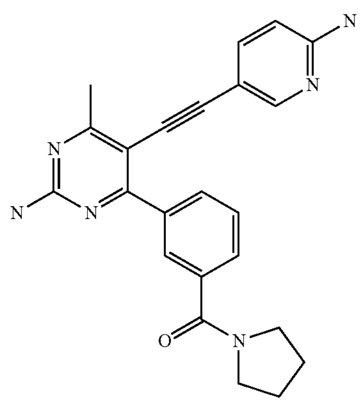 [SMILES: Cc1nc(N)nc(-c2cccc(C(=O)N3CCCC3)c2)c1C#Cc1ccc(N)nc1] | A-33 | 398.5 | 399 | 1.37 |
| 376 | 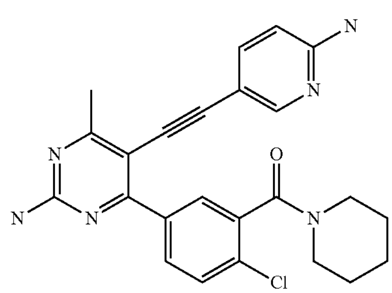 [SMILES: Cc1nc(N)nc(-c2ccc(Cl)c(C(=O)N3CCCCC3)c2)c1C#Cc1ccc(N)nc1] | A-33 | 446.9 | 447 | |
| 377 | 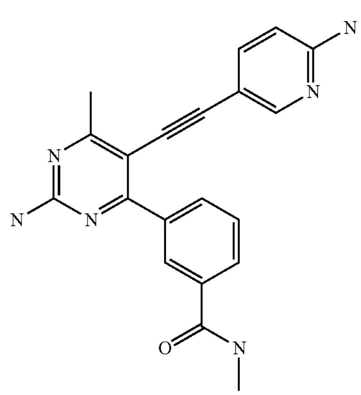 [SMILES: CNC(=O)c1cccc(-c2nc(N)nc(C)c2C#Cc2ccc(N)nc2)c1] | A-33 | 358.4 | 359 | |

-continued

| No. | Structure | Starting Material | MW | MS [M + H]+ | HPLC t_Ret |
|---|---|---|---|---|---|
| 378 | 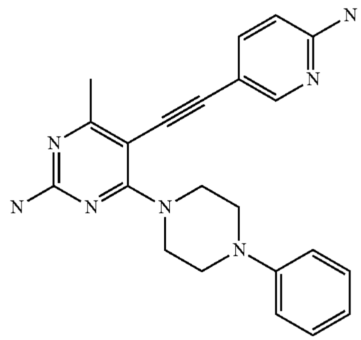 [SMILES: Cc1nc(N)nc(N2CCN(c3ccccc3)CC2)c1C#Cc1ccc(N)nc1] | A-33 | 385.5 | 386 | 1.66 |
| 379 | 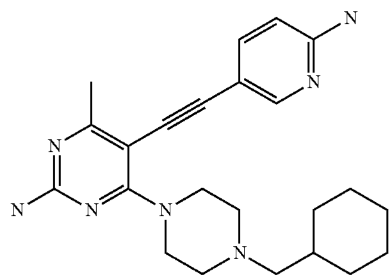 [SMILES: Cc1nc(N)nc(N2CCN(CC3CCCCC3)CC2)c1C#Cc1ccc(N)nc1] | A-33 | 405.5 | 406 | 1.91 |
| 380 | 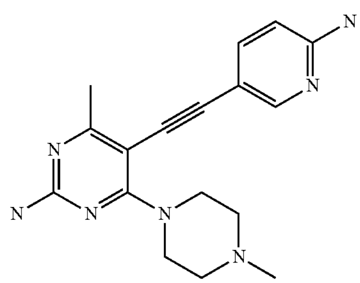 [SMILES: Cc1nc(N)nc(N2CCN(C)CC2)c1C#Cc1ccc(N)nc1] | A-33 | 323.4 | 324 | 1.22 |
| 381 | 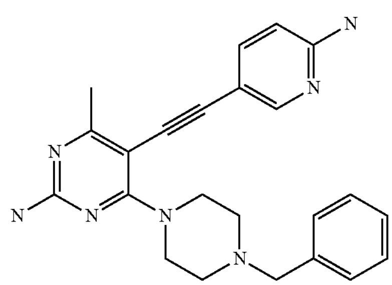 [SMILES: Cc1nc(N)nc(N2CCN(Cc3ccccc3)CC2)c1C#Cc1ccc(N)nc1] | A-33 | 399.5 | 400 | 1.64 |
| 382 | 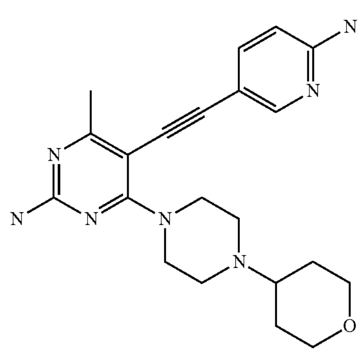 [SMILES: Cc1nc(N)nc(N2CCN(C3CCOCC3)CC2)c1C#Cc1ccc(N)nc1] | A-33 | 393.5 | 394 | 1.28 |

-continued

| No. | Structure | Starting Material | MW | MS [M + H]+ | HPLC t_Ret |
|---|---|---|---|---|---|
| 383 | 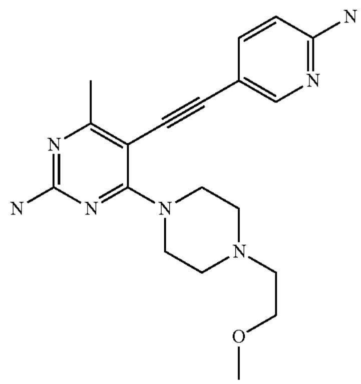 [SMILES: COCCN1CCN(c2nc(N)nc(C)c2C#Cc2ccc(N)nc2)CC1] | A-33 | 367.5 | 368 | 1.27 |
| 384 | 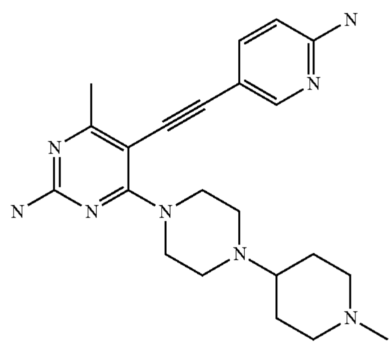 [SMILES: Cc1nc(N)nc(N2CCN(C3CCN(C)CC3)CC2)c1C#Cc1ccc(N)nc1] | A-33 | 406.5 | 407 | 1.36 |
| 385 | 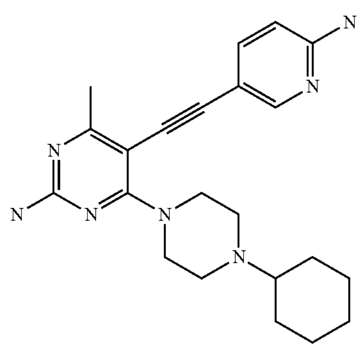 [SMILES: Cc1nc(N)nc(N2CCN(C3CCCCC3)CC2)c1C#Cc1ccc(N)nc1] | A-33 | 391.5 | 392 | 1.68 |
| 386 | 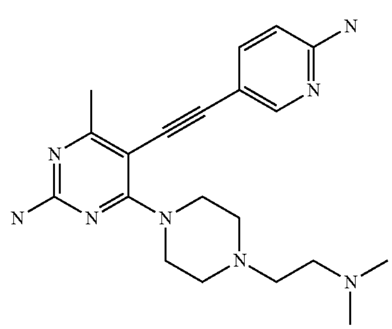 [SMILES: Cc1nc(N)nc(N2CCN(CCN(C)C)CC2)c1C#Cc1ccc(N)nc1] | A-33 | 380.5 | 381 | 1.30 |

-continued

| No. | Structure | Starting Material | MW | MS [M + H]+ | HPLC t_Ret |
|---|---|---|---|---|---|
| 387 | 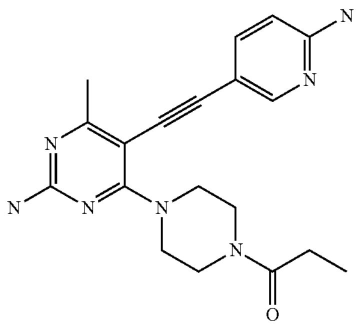 [SMILES: CCC(=O)N1CCN(c2nc(N)nc(C)c2C#Cc2ccc(N)nc2)CC1] | A-33 | 365.4 | 366 | 1.25 |
| 388 | 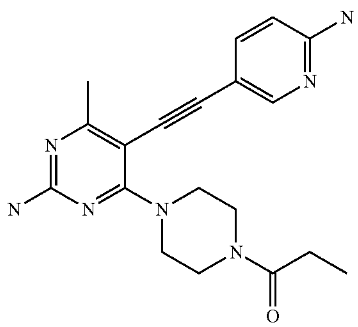 [SMILES: CCC(=O)N1CCN(c2nc(N)nc(C)c2C#Cc2ccc(N)nc2)CC1] | A-33 | 419.5 | 420 | 1.57 |
| 389 | 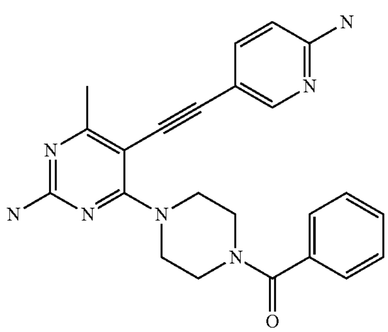 [SMILES: Cc1nc(N)nc(N2CCN(C(=O)c3ccccc3)CC2)c1C#Cc1ccc(N)nc1] | A-33 | 413.5 | 414 | 1.42 |
| 390 | 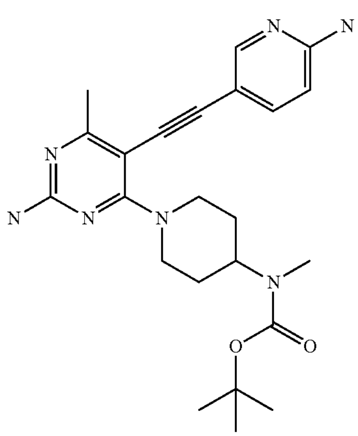 [SMILES: Cc1nc(N)nc(N2CCC(N(C)C(=O)OC(C)(C)C)CC2)c1C#Cc1ccc(N)nc1] | | 437.5 | 438 | 1.71 |

-continued

| No. | Structure | Starting Material | MW | MS [M + H]+ | HPLC t_Ret |
|---|---|---|---|---|---|
| 391 | 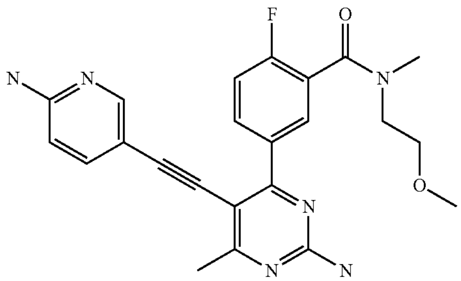 [SMILES: COCCN(C)C(=O)c1cc(-c2nc(N)nc(C)c2C#Cc2ccc(N)nc2)ccc1F] | C-77 | 434.5 | 435 | 1.38 |
| 392 | 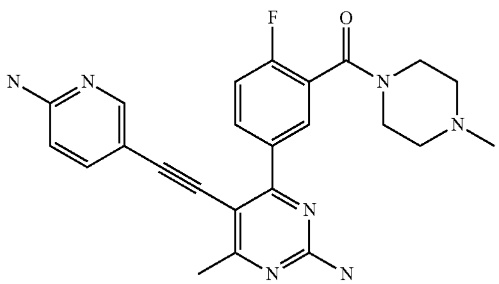 [SMILES: Cc1nc(N)nc(-c2ccc(F)c(C(=O)N3CCN(C)CC3)c2)c1C#Cc1ccc(N)nc1] | C-77 | 445.5 | 446 | 1.33 |
| 393 | 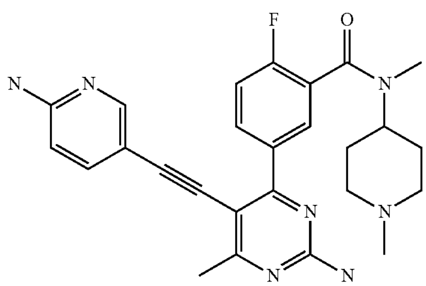 [SMILES: Cc1nc(N)nc(-c2ccc(F)c(C(=O)N(C)C3CCN(C)CC3)c2)c1C#Cc1ccc(N)nc1] | C-77 | 473.6 | 474 | 1.40 |
| 394 | 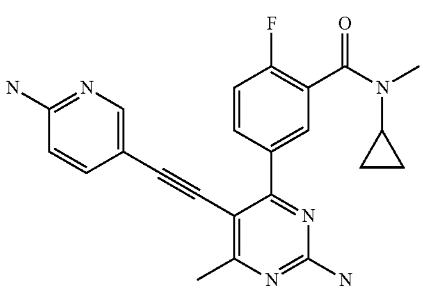 [SMILES: Cc1nc(N)nc(-c2ccc(F)c(C(=O)N(C)C3CC3)c2)c1C#Cc1ccc(N)nc1] | C-77 | 416.5 | 417 | 1.46 |
| 395 | 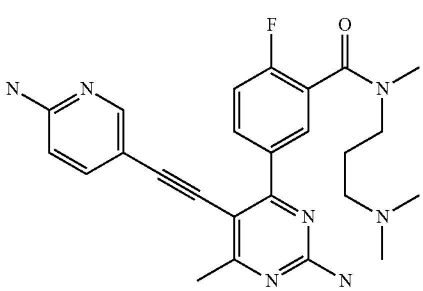 [SMILES: Cc1nc(N)nc(-c2ccc(F)c(C(=O)N(C)CCCN(C)C)c2)c1C#Cc1ccc(N)nc1] | C-77 | 461.5 | 462 | 1.43 |

-continued
| No. | Structure | Starting Material | MW | MS [M + H]+ | HPLC t_Ret |
|---|---|---|---|---|---|
| 396 | 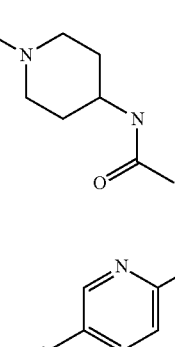 | C-93 | 365.4 | 366 | 1.14 |
| 397 | 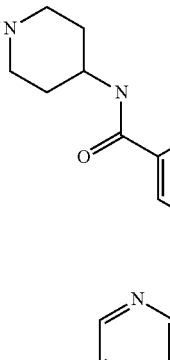 | C-93 | 427.5 | 428 | 1.45 |
| 398 | 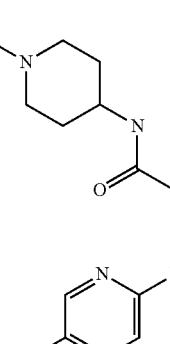 | C-93 | 379.5 | 380 | 1.22 |
| 399 | 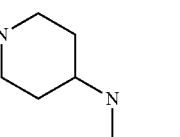 | C-93 | 441.5 | 442 | 1.45 |

-continued

| No. | Structure | Starting Material | MW | MS [M + H]⁺ | HPLC t$_{Ret}$ |
|---|---|---|---|---|---|
| 400 | 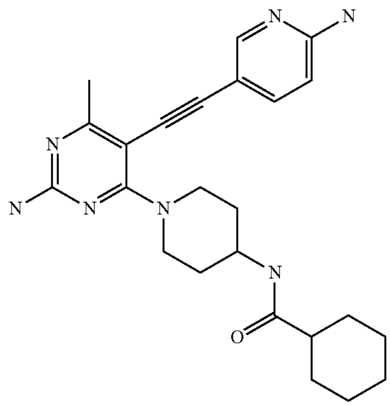 [SMILES: Cc1nc(N)nc(N2CCC(NC(=O)C3CCCCC3)CC2)c1C#Cc1ccc(N)nc1] | C-93 | 433.6 | 434 | 1.54 |
| 401 | 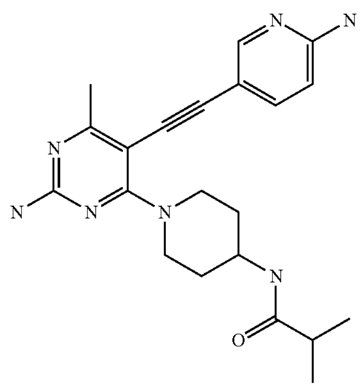 [SMILES: Cc1nc(N)nc(N2CCC(NC(=O)C(C)C)CC2)c1C#Cc1ccc(N)nc1] | C-93 | 393.5 | 394 | 1.31 |
| 402 | 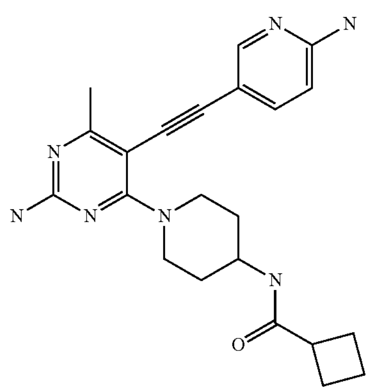 [SMILES: Cc1nc(N)nc(N2CCC(NC(=O)C3CCC3)CC2)c1C#Cc1ccc(N)nc1] | C-93 | 405.5 | 406 | 1.36 |
| 403 | 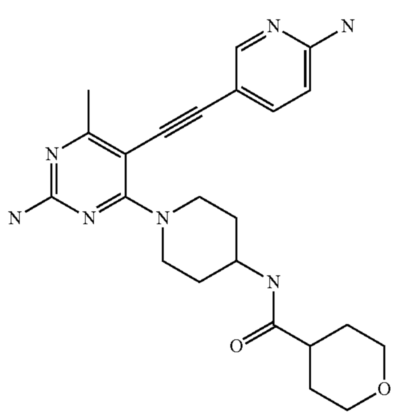 [SMILES: Cc1nc(N)nc(N2CCC(NC(=O)C3CCOCC3)CC2)c1C#Cc1ccc(N)nc1] | C-93 | 435.5 | 436 | 1.23 |

| No. | Structure | Starting Material | MW | MS [M + H]+ | HPLC $t_{Ret}$ |
|---|---|---|---|---|---|
| 404 | 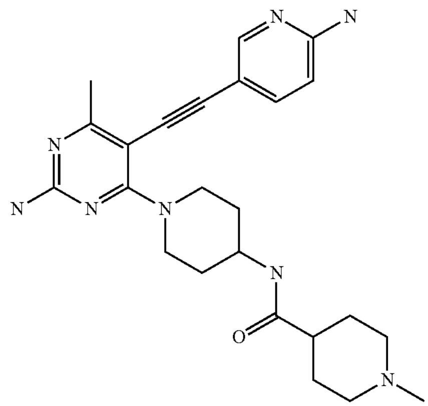 [SMILES: Cc1nc(N)nc(N2CCC(NC(=O)C3CCN(C)CC3)CC2)c1C#Cc1ccc(N)nc1] | C-93 | 448.6 | 449 | 1.29 |
| 405 | 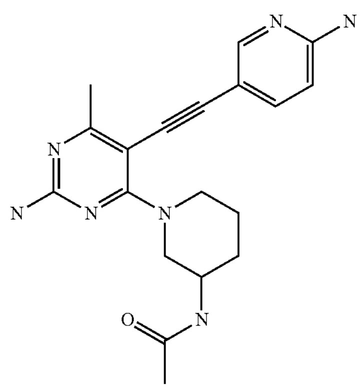 [SMILES: CC(=O)NC1CCCN(c2nc(N)nc(C)c2C#Cc2ccc(N)nc2)C1] | C-91 | 365.4 | 366 | 1.17 |
| 406 | 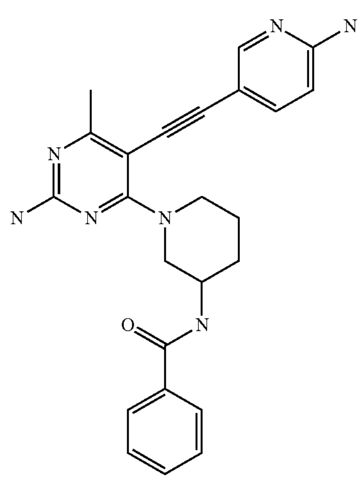 [SMILES: Cc1nc(N)nc(N2CCCC(NC(=O)c3ccccc3)C2)c1C#Cc1ccc(N)nc1] | C-91 | 427.5 | 428 | 1.44 |

-continued

| No. | Structure | Starting Material | MW | MS [M + H]⁺ | HPLC t$_{Ret}$ |
|---|---|---|---|---|---|
| 407 | 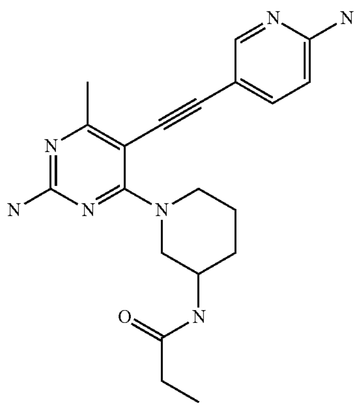 [SMILES: CCC(=O)NC1CCCN(c2nc(N)nc(C)c2C#Cc2ccc(N)nc2)C1] | C-91 | 379.5 | 380 | 1.24 |
| 408 | 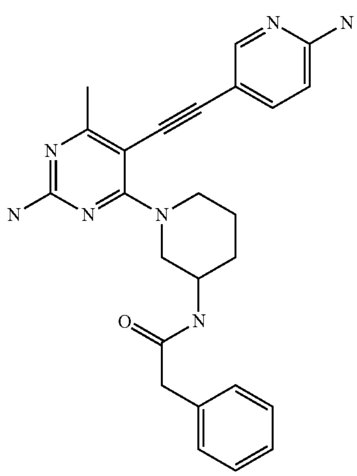 [SMILES: Cc1nc(N)nc(N2CCCC(NC(=O)Cc3ccccc3)C2)c1C#Cc1ccc(N)nc1] | C-91 | 441.5 | 442 | 1.44 |
| 409 | 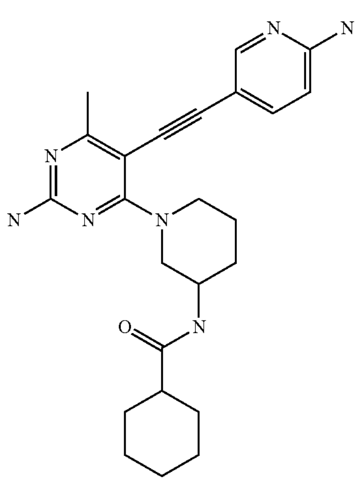 [SMILES: Cc1nc(N)nc(N2CCCC(NC(=O)C3CCCCC3)C2)c1C#Cc1ccc(N)nc1] | C-91 | 433.6 | 434 | 1.54 |

-continued
| No. | Structure | Starting Material | MW | MS [M + H]+ | HPLC t<sub>Ret</sub> |
|---|---|---|---|---|---|
| 410 | 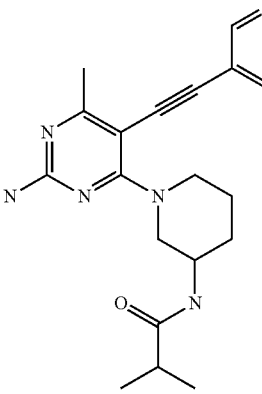 | C-91 | 393.5 | 394 | 1.33 |
| 411 | 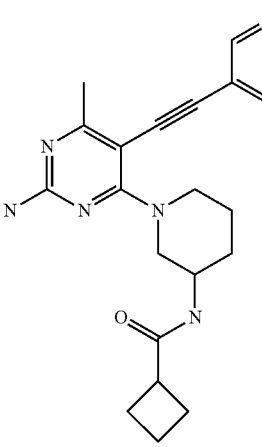 | C-91 | 405.5 | 406 | 1.37 |
| 412 | 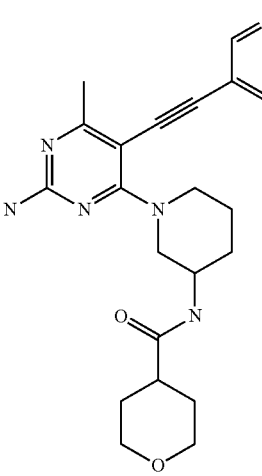 | C-91 | 435.5 | 436 | 1.25 |

| No. | Structure | Starting Material | MW | MS [M + H]+ | HPLC $t_{Ret}$ |
|---|---|---|---|---|---|
| 413 | 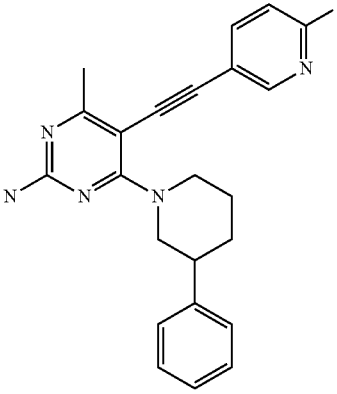 | A-33 | 384.5 | 385 | 1.78 |
| 414 | 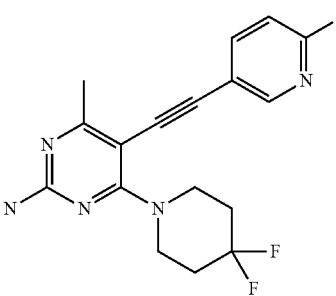 | A-33 | 344.4 | 345 | 1.49 |
| 415 | 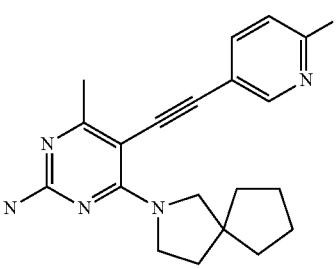 | A-33 | 348.5 | 349 | 1.72 |
| 416 | 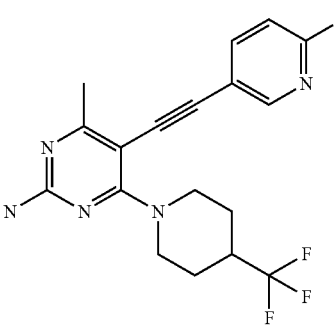 | A-33 | 376.4 | 377 | 1.60 |

-continued

| No. | Structure | Starting Material | MW | MS [M + H]⁺ | HPLC t_Ret |
|-----|-----------|-------------------|------|-------------|------------|
| 417 | 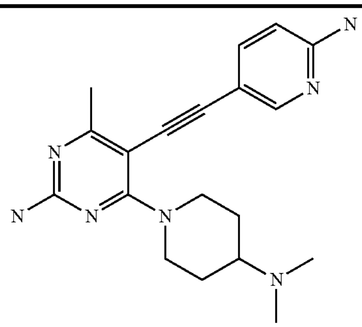 | A-33 | 351.5 | 352 | 1.35 |
| 418 | 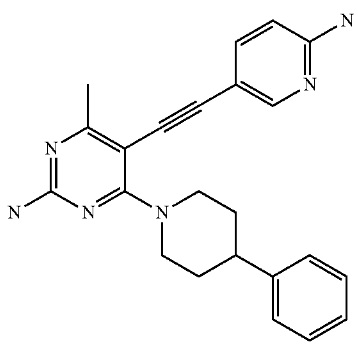 | A-33 | 384.5 | 385 | |

In order to prepare compounds bearing one or more deuterium instead of hydrogen may prepared as outlined above. The following examples have been prepared using building blocks from commercial vendors (identified via e.g. ACD-Finder or SciFinder) using GP4 (Suzuki coupling) or GP9 (Formation of amides):

| No. | Structure | Starting Material | MW | MS [M + H]⁺ | HPLC t_ret |
|-----|-----------|-------------------|------|-------------|------------|
| 419 | 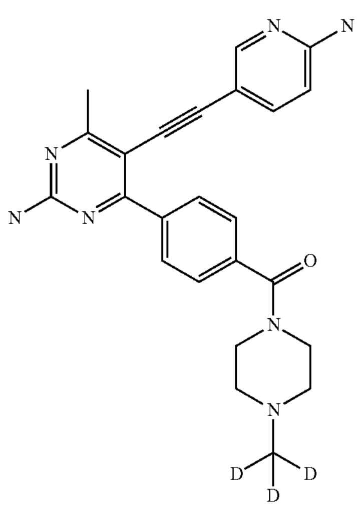 [SMILES: [2H]C([2H])([2H])N1CCN(C(=O)c2ccc(-c3nc(N)nc(C)c3C#Cc3ccc(N)nc3)cc2)CC1] | C-71 | 430.5 | 431 | 1.24 |

| No. | Structure | Starting Material | MW | MS [M + H]+ | HPLC $t_{ret}$ |
|---|---|---|---|---|---|
| 420 | 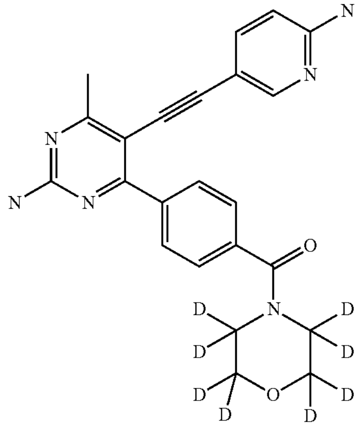 [SMILES: [2H]C1([2H])OC([2H])([2H])C([2H])([2H])N(C(=O)c2ccc(-c3nc(N)nc(C)c3C#Cc3ccc(N)nc3)cc2)C1([2H])[2H]] | C-71 | 422.5 | 423 | 1.22 |
| 421 | 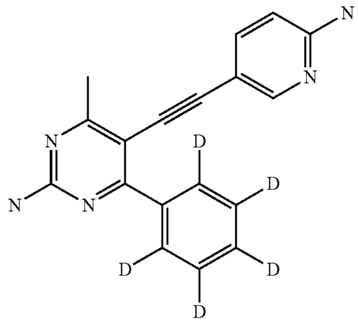 [SMILES: [2H]c1c([2H])c([2H])c(-c2nc(N)nc(C)c2C#Cc2ccc(N)nc2)c([2H])c1[2H]] | A-33 | 306.4 | 307 | |

Analytical Method 1
HPLC: Agilent 1100 Series
MS: Agilent LC/MSD SL
column: Phenomenex, Mercury Gemini C18, 3 μm, 2.0×20 mm,
  Part. No. 00M-4439-B0-CE
solvent A: 5 mM $NH_4HCO_3$/20 mM $NH_3$
  B: acetonitrile HPLC grade
detection: MS: Positive and negative
  mass range: 120-700 m/z
  fragmentor: 70
  gain EMV: 1
  threshold: 150
  stepsize: 0.25
  UV: 315 nm
  bandwidth: 170 nm
  reference: off
  range: 210-400 nm
  range step: 2.00 nm
  peakwidth: <0.01 min
  slit: 2 nm
injection: 5 μL
flow: 1.00 mL/min
column temperature: 40° C.
gradient:

| | | |
|---|---|---|
| 0.00 min | 5% B | |
| 0.00-2.50 min | 5% -> 95% B | |
| 2.50-2.80 min | 95% B | |
| 2.81-3.10 min | 95% -> 5% B | |

Analytical Method 2
Instrument: Agilent 1100-SL: incl. ELSD/DAD/MSD
Chromatography:
  Column: Phenomenex Gemini® C18, 50×2.0 mm,
Method "Acid"
  Eluent A: 0.1% formic acid in acetonitrile
  Eluent B: 0.1% formic acid in Water
  Linear Gradient program: $t_0$=2% A, $t_{3.5\ min}$=98% A, $t_{6\ min}$=98% A
  Flow: 1 mL/min
  Column oven temperature: 35° C.
Method "Base"
  Eluent A: 10 mM ammonia in acetonitrile
  Eluent B: 10 mM ammonia in water
  Linear Gradient program: $t_0$=2% A, $t_{3.5\ min}$=98% A, $t_{6\ min}$=98% A
  Flow: 1 mL/min
  Column oven temperature: 35° C.
Evaporative Light Scattering Detector (ELSD):
  Instrument: Polymer Laboratories PL-ELS 2100
  Nebuliser gas flow: 1.1 L/min $N_2$
  Nebuliser temp: 50° C.
  Evaporation temp: 80° C.
  Lamp: Blue LED 480 nm
Diode Array Detector (DAD):
  Instrument: Agilent G1316A
  Sample wavelength: 220-320 nm
  Reference wavelength: Off
Mass Spectroscopy (MSD):
  Instrument: Agilent LC/MSD-SL
  Ionisation: ESI (Positive & Negative)
  Mass range: 100-800

Abbreviations Used

| | |
|---|---|
| ACN | acetonitrile |
| bu | butyl |
| CDI | carbonyl diimidazole |
| d | day(s) |
| DC | thin layer chromatography |
| DCM | dichloromethane |
| DIPEA | diisopropylethyl amine |
| DMF | N,N-dimethylformamide |
| DMSO | dimethylsulphoxide |
| et | ethyl |
| h | hour(s) |
| HPLC | high performance liquid chromatography |
| iPr | isopropyl |
| LC | liquid chromatography |
| M | molar |
| me | methyl |
| min | minute(s) |
| mL | millilitre |
| MS | mass spectrometry |
| N | normal |
| NIS | N-iodosuccinimide |
| NMP | N-methylpyrrolindinone |
| NMR | nuclear resonance spectroscopy |
| NP | normal phase |
| ppm | part per million |
| Rf | retention factor |
| RP | reversed phase |
| prep | preparative |
| RT | room temperature |
| tert | tertiary |
| $t_{Ret}$ | retention time |
| THF | tetrahydrofuran |
| TMS | tetramethylsilanyl |

The Examples that follow describe the biological activity of the compounds according to the invention without restricting the invention to these Examples.

PC3 Proliferation Test

The test is based on measurement of cellular DNA content via fluorescent dye binding. Because cellular DNA content is highly regulated, it is closely proportional to cell number. The extent of proliferation is determined by comparing cell counts for samples treated with drugs with untreated controls.

PC3 (human prostate carcinoma cell line) cells are sown in microtitre plates and incubated overnight in culture medium at 37° C. and 5% $CO_2$. The test substances are diluted stepwise and added to the cells such that the total volume is 200 µL/well. Cells to which diluent, but not substance, is added serve as controls. After an incubation time of 3 days, the medium is replaced by 100 µL/well dye-binding solution and the cells are incubated at 37° C. in the dark for a further 60 min. For measuring the fluorescence, excitation takes place at a wavelength of 485 nm and the emission is measured at 530 nm.

$EC_{50}$ values are calculated using the GraphPad Prism program.

Most compounds of the Examples cited have an $EC_{50}$ (Proliferation PC3) of less than 1 µM.

P-AKT Measurement in PC3 Cells

P-AKT levels in PC3 cells are detected by cell-based ELISA. Cells are cultured in 96-well plates and treated with serial dilutions of test substances for 2 h. Cells to which diluent, but not substance, is added serve as controls. Subsequently, the cells are fixed rapidly to preserve protein modifications. Each well is then incubated with a primary antibody specific for Ser473-phosphorylated. AKT. Subsequent incubation with secondary HRP-conjugated antibody and developing solution provides a colorimetric readout at 450 nm. $EC_{50}$ values are calculated using the GraphPad Prism program.

Most compounds of the Examples cited have an $EC_{50}$ (P-AKT PC3) of less than 1 µM.

The substances of the present invention are PI3 kinase inhibitors. On account of their biological properties, the novel compounds of the general formula (1) and their isomers and their physiologically tolerated salts are suitable for treating diseases which are characterized by excessive or anomalous cell proliferation.

These diseases include, for example: viral infections (e.g. HIV and Kaposi's sarcoma); inflammation and autoimmune diseases (e.g. colitis, arthritis, Alzheimer's disease, glomerulonephritis and wound healing); bacterial, fungal and/or parasitic infections; leukaemias, lymphomas and solid tumours; skin diseases (e.g. psoriasis); bone diseases; cardiovascular diseases (e.g. restenosis and hypertrophy). In addition, the compounds are useful for protecting proliferating cells (e.g. hair cells, intestinal cells, blood cells and progenitor cells) from DNA damage due to irradiation, UV treatment and/or cytostatic treatment (Davis et al., 2001).

For example, the following cancer diseases can be treated with compounds according to the invention, without, however, being restricted thereto: brain tumours, such as acoustic neurinoma, astrocytomas such as piloid astrocytomas, fibrillary astrocytoma, protoplasmic astrocytoma, gemistocytic astrocytoma, anaplastic astrocytoma and glioblastomas, brain lymphomas, brain metastases, hypophyseal tumour such as prolactinoma, HGH (human growth hormone) producing tumour and ACTH-producing tumour (adrenocorticotrophic hormone), craniopharyngiomas, medulloblastomas, meningiomas and oligodendrogliomas; nerve tumours (neoplasms) such as tumours of the vegetative nervous system such as neuroblastoma sympathicum, ganglioneuroma, paraganglioma (phaeochromocytoma and chromaffinoma) and glomus caroticum tumour, tumours in the peripheral nervous system such as amputation neuroma, neurofibroma, neurinoma (neurilemoma, schwannoma) and malignant schwannoma, as well as tumours in the central nervous system such as brain and spinal cord tumours; intestinal cancer such as rectal carcinoma, colon carcinoma, anal carcinoma, small intestine tumours and duodenal tumours; eyelid tumours such as basalioma or basal cell carcinoma; pancreatic gland cancer or pancreatic carcinoma; bladder cancer or bladder carcinoma; lung cancer (bronchial carcinoma) such as small-cell bronchial carcinomas (oat cell carcinomas) and non-small-cell bronchial carcinomas such as squamous epithelium carcinomas, adenocarcinomas and large-cell bronchial carcinomas; breast cancer such as mammary carcinoma, such as infiltrating ductal carcinoma, colloid carcinoma, lobular invasive carcinoma, tubular carcinoma, adenoid cystic carcinoma, and papillary carcinoma; non-Hodgkin's lymphomas (NHL) such as Burkitt's lymphoma, low-malignancy non-Hodkgin's lymphomas (NHL) and mucosis fungoides; uterine cancer or endometrial carcinoma or corpus carcinoma; CUP syndrome (cancer of unknown primary); ovarian cancer or ovarian carcinoma such as mucinous, endometrial or serous cancer; gall bladder cancer; bile duct cancer such as Klatskin's tumour; testicular cancer such as seminomas and non-seminomas; lymphoma (lymphosarcoma) such as malignant lymphoma, Hodgkin's disease, non-Hodgkin's lymphomas (NHL) such as chronic lymphatic leukaemia, hair cell leukaemia, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as vocal cord tumours, supraglottal, glottal and subglottal laryngeal tumours; bone cancer such as osteochondroma, chondroma, chrondoblastoma, chondromyxoidfibroma, osteoma, osteoid-osteoma, osteoblastoma, eosinophilic granuloma, giant cell tumour, chondrosarcoma, osteosarcoma, Ewing's sarcoma, reticulo sarcoma, plasmocytoma, fibrous dysplasia, juvenile bone cyst and aneurysmatic bone cyst; head/neck tumours such as tumours of the lips, tongue, floor of the mouth, oral cavity, gingiva, pallet, salivary glands, pharynx, nasal cavities, paranasal sinuses, larynx and middle ear; liver cancer such as liver cell carcinoma or hepatocellular carcinoma (HCC); leukaemias, such as acute leukaemias, such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or stomach carcinoma such as papillary, tubular and mucinous adenocarcinoma, signet ring cell carcinoma, adenoid squamous cell carcinoma, small-cell carcinoma and undifferentiated carcinoma; melanomas such as superficially spreading, nodular malignant lentigo and acral lentiginous melanoma; renal cancer, such as kidney cell carcinoma or hypernephroma or Grawitz's tumour; oesophageal cancer or oesophageal carcinoma; cancer of the penis; prostate cancer; pharyngeal cancer or pharyngeal carcinomas such as nasopharyngeal carcinomas, oropharyngeal carcinomas and hypopharyngeal carcinomas; retinoblastoma; vaginal cancer or vaginal carcinoma; squamous epithelium carcinomas, adeno carcinomas, in situ carcinomas, malignant melanomas and sarcomas; thyroid gland carcinomas such as papillary, follicular and medullary thyroid gland carcinoma, and also anaplastic carcinomas; spinalioma, prickle cell carcinoma and squamous epithelium carcinoma of the skin; thymomas, urethral cancer and vulvar cancer.

The novel compounds can be used for the prevention or short-term or long-term treatment of the abovementioned diseases including, where appropriate, in combination with other state-of-the-art compounds such as other anti-tumour substances, cytotoxic substances, cell proliferation inhibitors, antiangiogenic substances, steroids or antibodies.

The compounds of the general formula (1) can be used on their own or in combination with other active compounds according to the invention and, where appropriate, in combination with other pharmacologically active compounds as well. Chemotherapeutic agents which can be administered in combination with the compounds according to the invention include, without being restricted thereto, hormones, hormone analogs and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone and octreotide), aromatase inhibitors (e.g. anastrozole, letrozole, liarozole, vorozole, exemestane and atamestane), LHRH agonists and antagonists (e.g. goserelin acetate and luprolide), inhibitors of growth factors (growth factors such as platelet-derived growth factor and hepatocyte growth factor, examples of inhibitors are growth factor antibodies, growth factor receptor antibodies and tyrosine kinase inhibitors, such as gefitinib, imatinib, lapatinib, Erbitux® and trastuzumab); antimetabolites (e.g. antifolates such as methotrexate and raltitrexed, pyrimidine analogs such as 5-fluorouracil, capecitabine and gemcitabine, purine and adenosine analogs such as mercaptopurine, thioguanine, cladribine and pentostatin, cytarabine and fludarabine); antitumour antibiotics (e.g. anthracyclines, such as doxorubicin, daunorubicin, epirubicin and idarubicin, mitomycin C, bleomycin, dactinomycin, plicamycin and streptozocin); platinum derivatives (e.g. cisplatin, oxaliplatin and carboplatin); alkylating agents (e.g. estramustine, meclorethamine, melphalan, chlorambucil, busulphan, dacarbazine, cyclophosphamide, ifosfamide and temozolomide, nitrosoureas such as carmustine and lomustine and thiotepa); antimitotic agents (e.g. vinca alkaloids such as vinblastine, vindesine, vinorelbine and vincristine; and taxans such as paclitaxel and docetaxel); topoisomerase inhibitors (e.g. epipodophyllotoxins such as etoposide and etopophos, teniposide, amsacrine, topotecan, irinotecan and mitoxantrone) and various chemotherapeutic agents such as amifostin, anagrelide, clodronate, filgrastin, interferon alpha, leucovorin, rituximab, procarbazine, levamisole, mesna, mitotan, pamidronate and porfimer.

Examples of suitable forms for use are tablets, capsules, suppositories, solutions, in particular solutions for injection (s.c., i.v., i.m.) and infusion, syrups, emulsions or dispersible powders. In this connection, the proportion of the pharmaceutically active compound(s) should in each case be in the range of 0.1-90% by weight, preferably 0.5-50% by weight, of the total composition, that is in quantities which are sufficient to achieve the dosage range which is specified below. If necessary, the doses mentioned can be given several times a day.

Appropriate tablets can be obtained, for example, by mixing the active compound(s) with known auxiliary substances, for example inert diluents, such as calcium carbonate, calcium phosphate or lactose, disintegrants, such as maize starch or alginic acid, binders, such as starch or gelatine, lubricants, such as magnesium stearate or talc, and/or agents for achieving a depot effect, such as carboxymethyl cellulose, cellulose acetate phthalate or polyvinyl acetate. The tablets can also comprise several layers.

Correspondingly, sugar-coated tablets can be produced by coating cores, which have been prepared in analogy with tablets, with agents which are customarily used in sugar coatings, for example collidone or shellac, gum arabic, talc, titanium dioxide or sugar. The core can also comprise several layers in order to achieve a depot effect or to avoid incompatibilities. In the same way, the sugar coating can also comprise several layers in order to achieve a depot effect, with it being possible to use the auxiliary substances which are mentioned above in the case of the tablets.

Syrups of the active compounds or active compound combinations according to the invention can additionally comprise a sweetening agent, such as saccharine, cyclamate, glycerol or sugar as well as a taste-improving agent, e.g. flavouring agents such as vanillin or orange extract. They can also comprise suspension aids or thickeners, such as sodium carboxymethyl cellulose, wetting agents, for example condensation products of fatty alcohols and ethylene oxide, or protectants such as p-hydroxybenzoates.

Injection and infusion solutions are produced in a customary manner, e.g. while adding isotonizing agents, preservatives, such as p-hydroxybenzoates, or stabilizers, such as alkali metal salts of ethylenediaminetetraacetic acid, where appropriate using emulsifiers and/or dispersants, with it being possible, for example, to employ, where appropriate, organic solvents as solubilizing agents or auxiliary solvents when using water as diluent, and aliquoted into injection bottles or ampoules or infusion bottles.

The capsules, which comprise one or more active compounds or active compound combinations, can, for example, be produced by mixing the active compounds with inert carriers, such as lactose or sorbitol, and encapsulating the mixture in gelatine capsules. Suitable suppositories can be produced, for example, by mixing with excipients which are envisaged for this purpose, such as neutral fats or polyethylene glycol, or their derivatives.

Auxiliary substances which may be mentioned by way of example are water, pharmaceutically unobjectionable organic solvents, such as paraffins (e.g. petroleum fractions), oils of vegetable origin (e.g. groundnut oil or sesame oil), monofunctional or polyfunctional alcohols (e.g. EtOH or glycerol), carrier substances such as natural mineral powders (e.g. kaolins, argillaceous earths, talc and chalk), synthetic mineral powders (e.g. highly disperse silicic acid and silicates), sugars (e.g. cane sugar, lactose and grape sugar), emulsifiers (e.g. lignin, sulphite waste liquors, methyl cellulose, starch and polyvinylpyrrolidone) and glidants (e.g. magnesium stearate, talc, stearic acid and sodium lauryl sulphate).

Administration is effected in a customary manner, preferably orally or transdermally, in particular and preferably orally. In the case of oral use, the tablets can naturally also comprise, in addition to the abovementioned carrier substances, additives such as sodium citrate, calcium carbonate and dicalcium phosphate together with a variety of further substances such as starch, preferably potato starch, gelatine and the like. It is furthermore also possible to use glidants, such as magnesium stearate, sodium lauryl sulphate and talc, for the tableting. In the case of aqueous suspensions, a variety of taste improvers or dyes can also be added to the active compounds in addition to the abovementioned auxiliary substances.

For parenteral administration, it is possible to employ solutions of the active compounds while using suitable liquid carrier materials. The dosage for intravenous administration is 1-1000 mg per hour, preferably between 5 and 500 mg per hour.

Despite this, it may be necessary, where appropriate, to diverge from the above-mentioned quantities, depending on the body weight or the nature of the route of administration, on the individual response to the medicament, on the nature of its formulation and on the time or interval at which the administration is effected. Thus, it may, in some cases, be sufficient to make do with less than the previously mentioned lowest quantity whereas, in other cases, the abovementioned upper limit has to be exceeded. When relatively large quantities are being administered, it may be advisable to divide these into several single doses which are given over the course of the day.

The following formulation examples illustrate the present invention without, however, restricting its scope:

Pharmaceutical Formulation Examples

| A) Tablets | per tablet |
| --- | --- |
| Active compound in accordance with formula (1) | 100 mg |
| Lactose | 140 mg |
| Maize starch | 240 mg |
| Polyvinylpyrrolidone | 15 mg |
| Magnesium stearate | 5 mg |
| | 500 mg |

The finely ground active compound, lactose and a part of the maize starch are mixed with each other. The mixture is sieved, after which it is moistened with a solution of polyvinylpyrrolidone in water, kneaded, wet-granulated and dried. The granular material, the remainder of the maize starch and the magnesium stearate are sieved and mixed with each other. The mixture is pressed into tablets of suitable shape and size.

| B) Tablets | per tablet |
| --- | --- |
| Active compound in accordance with formula (1) | 80 mg |
| Lactose | 55 mg |
| Maize starch | 190 mg |
| Microcrystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active compound, a part of the maize starch, the lactose, microcrystalline cellulose and polyvinylpyrrolidone are mixed with each other, after which the mixture is sieved and worked, together with the remainder of the maize starch and water, into a granular material, which is dried and sieved. The sodium carboxymethyl starch and the magnesium stearate are then added to the granular material and mixed with it, and the mixture is pressed into tablets of suitable size.

| C) Ampoule solution | |
| --- | --- |
| Active compound in accordance with formula (1) | 50 mg |
| Sodium chloride | 50 mg |
| Water for injection | 5 mL |

The active compound is dissolved, either at its intrinsic pH or, where appropriate, at pH 5.5-6.5, in water after which sodium chloride is added as isotonizing agent. The resulting solution is rendered pyrogen-free by filtration and the filtrate is aliquoted, under aseptic conditions, into ampoules, which are then sterilized and sealed by melting. The ampoules contain 5 mg, 25 mg and 50 mg of active compound.

The invention claimed is:

1. A compound of formula (1),

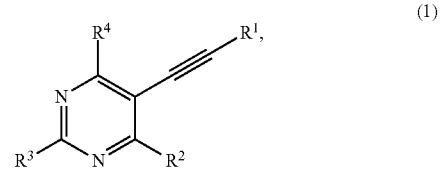

wherein
$R^1$ denotes a group selected from among $C_{3-8}$cycloalkyl, $C_{6-10}$aryl and 5-12 membered heteroaryl, optionally substituted by one or more identical or different $R^5$; and
$R^2$ denotes a group selected from among $C_{3-8}$cycloalkyl, 3-8 membered heterocycloalkyl, $C_{6-10}$aryl and 5-12 membered heteroaryl, optionally substituted by one or more identical or different $R^5$ and
$R^3$ denotes a group selected from among halogen, —$OR^e$, —$NR^eR^e$, —$CF_3$, —CN, —NC, —$NO_2$ and $C_{1-6}$alkyl; and
$R^4$ denotes a group selected from among $C_{1-3}$alkyl, $C_{3-8}$cycloalkyl, 3-8 membered heterocycloalkyl, —$OR^e$, —$NR^eR^e$, —$CF_3$, —CN, —NC and —$NO_2$, and
each $R^5$ denotes a group selected from among $R^a$, $R^b$ and $R^a$ substituted by one or more identical or different $R^b$ and/or $R^c$; and
each $R^a$ independently of one another denotes hydrogen or a group optionally substituted by one or more identical or different $R^b$ and/or $R^e$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, each $R^b$ denotes a suitable group and is selected independently of one another from among =O, —$OR^c$, $C_{1-3}$haloalkyloxy, —$OCF_3$, =S, —$SR^c$, =$NR^c$, =$NOR^c$, =$NNR^cR^c$, =$NN(R^g)C(O)NR^cR^c$, —$NR^cR^c$, —$ONR^cR^c$, —$N(OR^c)R^c$, —$N(R^g)NR^cR^c$, halogen, —$CF_3$, —CN, —NC, —OCN, —SCN, —NO, —$NO_2$, =$N_2$, —$N_3$, —$S(O)R^c$, —$S(O)OR^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)NR^cR^c$, —$OS(O)_2NR^cR^c$, —$C(O)R^c$, —$C(O)OR^c$, —$C(O)SR^c$, —$C(O)NR^cR^c$, —$C(O)N(R^g)NR^cR^c$, —$C(O)N(R^g)OR^c$, —$C(NR^g)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^g)NR^cR^c$, —$SC(O)R^c$, —$SC(O)OR^c$, —$SC(O)NR^cR^c$, —$SC(NR^g)NR^cR^c$, —$N(R^g)C(O)R^c$, —$[C(O)R^c]_2$, —$N(OR^g)C(O)R^c$, —$N(R^g)C(NR^g)R^c$, —$N(R^g)N(R^g)C(O)R^c$, —$N[C(O)R^c]NR^cR^c$, —$N(R^g)C(S)R^c$, —$N(R^g)S(O)R^c$, —$N(R^g)S(O)OR^c$, —$N(R^g)S(O)_2R^c$, —$N[S(O)_2R^c]_2$, —$N(R^g)S(O)_{2OR}^c$, —$N(R^g)S(O)_2NR^cR^c$, —$N(R^g)[S(O)_2]_2R^c$, —$N(R^g)C(O)OR^c$, —$N(R^g)C(O)SR^c$, —$N(R^g)C(O)NR^cR^c$, —$N(R^g)C(O)NR^gNR^cR^c$, —$N(R^g)N(R^g)C(O)NR^cR^c$, —$N(R^g)C(S)NR^cR^c$, —$[N(R^g)C(O)]_2R^c$, —$N(R^g)[C(O)]_2R^c$, —$N\{[C(O)]_2R^c\}_2$, —$N(R^g)[C(O)]_2OR^c$, —$N(R^g)[C(O)]_2NR^cR^c$, —$N\{[C(O)]_2OR^c\}_2$, —$N\{[C(O)]_2NR^cR^c\}_2$, —$[N(R^g)C(O)]_2OR^c$, —$N(R^g)C(NR^g)OR^c$, —$N(R^g)C(NOH)R^c$, —$N(R^g)C(NR^g)SR^c$, —$N(R^g)C(NR^g)NR^cR^c$ and —N=$C(R^g)NR^cR^c$ and each $R^c$ independently of one another denotes hydrogen or a group optionally substituted by one or more identical or different $R^d$ and/or $R^e$, selected from among $C_{1-6}$alkyl, 2-6membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero-aryl, 6-18 membered heteroarylalkyl, 3-14 membered heterocycloalkyl and 4-14 membered heterocycloalkylalkyl, and each $R^d$ denotes a suitable group and is selected independently of one another from among =O, —$OR^e$, $C_{1-3}$haloalkyloxy, —$OCF_3$, =S, —$SR^e$, =$NR^e$, =$NOR^e$, =$NNR^eR^e$, =$NN(R^g)C(O)NR^eR^e$, —$NR^eR^e$, —$ONR^eR^e$, —$N(R^g)NR^eR^e$, halogen, —$CF_3$, —CN, —NC, —OCN, —SCN, —NO, —$NO_2$, =$N_2$, —$N_3$, —$S(O)R^e$, —$S(O)OR^e$, —$S(O)_2R^e$, —$S(O)_2OR^e$, —$S(O)NR^eR^e$, —$S(O)_2NR^eR^e$, —$OS(O)R^e$, —$OS(O)_2R^e$, —$OS(O)_2OR^e$, —$OS(O)NR^eR^e$, —$OS(O)_2NR^eR^e$, —$C(O)R^e$, —$C(O)OR^e$, —$C(O)SR^e$, —$C(O)NR^eR^e$, —$C(O)N(R^g)NR^eR^e$, —$C(O)N(R^g)OR^e$, —$C(NR^g)NR^eR^e$, —$C(NOH)R^e$, —$C(NOH)NR^eR^e$, —$OC(O)R^e$, —$OC(O)OR^e$, —$OC(O)SR^e$, —$OC(O)NR^eR^e$, —$OC(NR^g)NR^eR^e$, —$SC(O)R^e$, —$SC(O)OR^e$, —$SC(O)NR^eR^e$, —$SC(NR^g)NR^eR^e$, —$N(R^g)C(O)R^e$, —$N[C(O)R^e]_2$, —$N(OR^g)C(O)R^e$, —$N(R^g)C(NR^g)R^e$, —$N(R^g)N(R^g)C(O)R^e$, —$N[C(O)R^e]NR^eR^e$, —$N(R^g)C(S)R^e$, —$N(R^g)S(O)R^e$, —$N(R^g)S(O)OR^e$—$N(R^g)S(O)_2R^e$, —$N[S(O)_2R^e]_2$, —$N(R^g)S(O)_2OR^e$, —$N(R^g)S(O)_2NR^eR^e$, —$N(R^g)[S(O)_2]_2R^e$, —$N(R^g)C(O)OR^e$, —$N(R^g)C(O)SR^e$, —$N(R^g)C(O)NR^eR^e$, —$N(R^g)C(O)NR^gNR^eR^e$, —$N(R^g)N(R^g)C(O)NR^eR^e$, —$N(R^g)C(S)NR^eR^e$, —$[N(R^g)C(O)]_2R^e$, —$N(R^g)[C(O)]_2R^e$, —$N\{[C(O)]_2R^e\}_2$, —$N(R^g)[C(O)]_2OR^e$, —$N(R^g)[C(O)]_2NR^eR^e$, —$N\{[C(O)]_2OR^e\}_2$, —$N\{[C(O)]_2NR^eR^e\}_2$, —$[N(R^g)C(O)]_2OR^e$, —$N(R^g)C(NR^g)OR^e$, —$N(R^g)C(NOH)R^e$, —$N(R^g)C(NR^g)SR^e$, —$N(R^g)C(NR^g)NR^eR^e$ and —N=$C(R^g)NR^eR^e$ each $R^e$ independently of one another denotes hydrogen or a group optionally substituted by one or more identical or different $R^f$ and/or $R^g$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero-aryl, 6-18 membered heteroarylalkyl, 3-14 membered heterocycloalkyl and 4-14 membered heterocycloalkylalkyl, and each $R^f$ denotes a suitable group and in each case is selected independently of one another from among =O, —$OR^g$, $C_{1-3}$haloalkyloxy, —$OCF_3$, =S, —$SR^g$, =$NR^g$, =$NOR^g$, =$NNR^gR^g$, =$NN(R^h)C(O)NR^gR^g$, —$NR^gR^g$, —$ONR^gR^g$, —$N(R^h)NR^gR^g$, halogen, —$CF_3$, —CN, —NC, —OCN, —SCN, —NO, —$NO_2$, =$N_2$, —$N_3$, —$S(O)R^g$, —$S(O)OR^g$, —$S(O)_2R^g$, —$S(O)_2OR^g$, —$S(O)NR^gR^g$, —$S(O)_2NR^gR^g$, —$OS(O)R^g$, —$OS(O)_2R^g$, —$OS(O)_2OR^g$, —$OS(O)NR^gR^g$, —$OS(O)_2NR^gR^g$, —$C(O)R^g$, —$C(O)OR^g$, —$C(O)SR^g$, —$C(O)NR^gR^g$, —$C(O)N(R^h)NR^gR^g$, —$C(O)N(R^h)OR^g$, —$C(NR^h)NR^gR^g$, —$C(NOH)R^g$, —$C(NOH)NR^gR^g$, —$OC(O)R^g$, —$OC(O)OR^g$, —$OC(O)SR^g$, —$OC(O)NR^gR^g$, —$OC(NR^h)NR^gR^g$, —$SC(O)R^g$, —$SC(O)OR^g$, —$SC(O)NR^gR^g$, —$SC(NR^h)NR^gR^g$, —$N(R^h)C(O)R^g$, —$N[C(O)R^g]_2$, —$N(OR^h)C(O)R^g$, —$N(R^h)C(NR^h)R^g$, —$N(R^h)N(R^h)C(O)R^g$, —$N[C(O)R^g]NR^gR^g$, —$N(R^h)C(S)R^g$, —$N(R^h)S(O)R^g$, —$N(R^h)S(O)OR^g$, —$N(R^h)S(O)_2R^g$, —$N[S(O)_2R^g]_2$, —$N(R^h)S(O)_2OR^g$, —$N(R^h)S(O)_2NR^gR^g$, —$N(R^h)[S(O)_2]_2R^g$, —$N(R^h)C(O)OR^g$, —$N(R^h)C(O)SR^g$, —$N(R^h)C(O)NR^gR^g$, —$N(R^h)C(O)NR^hNR^gR^g$, —$N(R^h)N(R^h)C(O)NR^gR^g$, —$N(R^h)C(S)NR^gR^g$, —$[N(R^h)C(O)]_2R^g$, —$N(R^h)[C(O)]_2R^g$, —$N\{[C(O)]_2R^g\}_2$, —$N(R^h)[C(O)]_2OR^g$, —$N(R^h)[C(O)]_2NR^gR^g$, —$N\{[C(O)]_2OR^g\}_2$, —$N\{[C(O)]_2NR^gR^g\}_2$, —$[N(R^h)C(O)]_2OR^g$, —$N(R^h)C(NR^h)OR^g$, —$N(R^h)C(NOH)R^g$, —$N(R^h)C(NR^h)SR^g$, —$N(R^h)C(NR^h)NR^gR^g$; and —N=$C(R^h)NR^hR^h$; and each $R^g$ independently of one another denotes hydrogen or a group optionally substituted by one or more identical or different $R^h$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero-aryl, 6-18 membered heteroarylalkyl, 3-14 membered heterocycloalkyl and 4-14 membered heterocycloalkylalkyl; and each $R^h$ is selected independently of one another from among hydrogen, $C_{1-6}$alkyl, 2-6 membered heteroalkyl, $C_{1-6}$haloalkyl, $C_{3-10}$cycloalkyl, $C_{4-16}$cycloalkylalkyl, $C_{61-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl, or a prodrug, a tautomer, a racemate, an enantiomer, a diastereomer or mixtures thereof, or a pharmacologically acceptable salt thereof.

2. The compound according to claim 1, wherein $R^4$ denotes —$CH_3$ or —$C_2H_5$.

3. The compound according to claim 1, wherein $R^3$ denotes —$NR^eR^e$.

4. The compound according to claim 3, wherein $R^3$ denotes —$NH_2$.

5. The compound according to claim 1, wherein $R^2$ denotes phenyl or pyridyl, optionally substituted by one or more identical or different $R^5$.

6. The compound according to claim 1, wherein $R^2$ denotes heterocycloalkyl, optionally substituted by one or more identical or different $R^5$.

7. The compound according to claim 1, wherein $R^1$ denotes phenyl, pyridyl or pyrimidinyl, optionally substituted by one or more identical or different $R^5$.

* * * * *